US006875884B1

(12) United States Patent
Padia et al.

(10) Patent No.: US 6,875,884 B1

(45) Date of Patent: Apr. 5, 2005

(54) UREA DERIVATIVES AS INHIBITORS FOR CCR-3 RECEPTOR

(75) Inventors: Janak Padia, Tucson, AZ (US); Michael Hocker, Tucson, AZ (US); Tsuyoshi Nishitoba, Gunma-ken (JP); Hirohi Ohashi, Gunma-ken (JP); Eiji Sawa, Gunma-ken (JP)

(73) Assignee: Kirin Beer Kabushiki Kaisha, Tokyo (JP)

(*) Notice: Subject to any disclaimer, the term of this patent is extended or adjusted under 35 U.S.C. 154(b) by 0 days.

(21) Appl. No.: 10/019,652

(22) PCT Filed: Jul. 28, 2000

(86) PCT No.: PCT/US00/17868

§ 371 (c)(1), (2), (4) Date: Jul. 2, 2002

(87) PCT Pub. No.: WO01/09088

PCT Pub. Date: Feb. 8, 2001

Related U.S. Application Data

(60) Provisional application No. 60/191,094, filed on Mar. 22, 2000, and provisional application No. 60/146,216, filed on Jul. 28, 1999.

(51) Int. Cl.[7] .................... C07C 205/00; C07C 229/00; C07C 327/00; C07D 215/38; C07D 233/61

(52) U.S. Cl. .......................... 560/21; 560/34; 560/169; 562/435; 562/27; 562/28; 562/50; 562/52; 562/56; 546/175; 546/334; 548/253; 548/335.5; 548/504; 548/566; 549/434; 549/77; 549/484

(58) Field of Search .......................... 560/21, 34, 169; 562/435, 27, 28, 50, 52, 56

(56) References Cited

U.S. PATENT DOCUMENTS 4,880,802 A 11/1989 Schohe et al. ........... 514/222.2

5,849,732 A * 12/1998 Suzuki et al. .......... 514/217.11

FOREIGN PATENT DOCUMENTS

| | | |
|---|---|---|
| DE | 888699 | 9/1953 |
| EP | 0432442 | 6/1991 |
| EP | 0903349 | 3/1999 |
| JP | 9-278737 | 10/1997 |
| WO | WO 00/41685 | 7/2000 |
| WO | WO 00/53172 | 9/2000 |
| WO | WO 01/09088 | 2/2001 |
| WO | WO 02/059081 | 8/2002 |

OTHER PUBLICATIONS

Nakao, Kazuya et al. "Quantitative Structure—Activity Analyses of Novel Hydroxyphenylurea Derivatives as Antioxidants," *Bioorganic & Medicinal Chemistry* (1998), vol. 6, pp. 849–868.

O'Brien, Patrick M. et al. "Inhibitors of Acyl–CoA:Cholesterol O–Acyl Transferase (ACAT) as Hypocholesterolemic Agents. B.[1] Incorporation of Amide or Amine Functionalities into a Series of Disubstituted Ureas and Carbamates. Effects on ACAT Inhibition in Vitro and Efficacy in Vivo[2]", *J. med. Chem.* (1994), vol. 37, No. 12, pp. 1810–1822, American Chemical Society.

Rost, William J. et al. "N–Aralkyl–N–methylaminoethyl Carbanilates as Hypocholesteremic Agents," *Journal of Pharmaceutical Sciences* (1967), vol. 56, No. 12, pp. 1598–1603.

* cited by examiner

*Primary Examiner*—D. Margaret Seaman

(74) *Attorney, Agent, or Firm*—Foley & Lardner LLP

(57) ABSTRACT

Urea and thiourea derivatives inhibit cell function of the chemokine receptor CCR-3. These compounds offer an effective means for treating a range of diseases thought to be mediated by the CCR-3 receptor. A variety of useful urea and thiourea derivatives can be synthesized using liquid and solid phase synthesis protocols.

25 Claims, 5 Drawing Sheets

UREA DERIVATIVES AS INHIBITORS FOR CCR-3 RECEPTOR

This application is a 371 of PCT/US00/17868 filed Jul. 28, 2000 which claims benefit of Provisional No. 60/191,094 filed Mar. 22, 2000.

BACKGROUND OF THE INVENTION

The present invention relates to certain urea derivatives that are inhibitors of CCR-3 receptor activity, methods for preparing these compounds, pharmaceutical compositions containing such compounds and methods for their use.

Chemokines are chemotactic cytokines that are produced by a variety of cells to attract leukocytes to sites of inflammation or lymphoid tissue. CCR-3 is a chemokine receptor that is expressed in a variety of cells, including, but not limited to, eosinophils, basophils, T cells and dendritic cells. See Ponath, P. D. et al., *J. Exp. Med.* (1996) 183, 2437–2448; Yamada, H. et al., *Biochem. Biophys. Res. Comm.* (1997) 231, 365–368; Sallusto, F. et al., *Science* (1997) 277, 2005–2007; Sato, K. et al., *Blood* (1999) 93, 34–42. CCR-3 is also known as a co-receptor to HIV virus infection. See He, J. et al., *Nature* (1997) 385, 645–649. Several chemokines including eotaxin, eotaxin-2, RANTES, MCP-2, MCP-3, MCP4 bind to CCR-3 and activate cell functions such as intracellular $Ca^{2+}$ mobilization, chemotactic response, superoxide anion generation and cell aggregation. See Forssmann, U. et al., *J. Exp. Med.* (1997) 185, 2171–2176; Heath, H. et al., *J. Clin. Invest.* (1997) 99, 178–184; Uguccioni, M. et al., *J. Exp. Med.* (1996) 183, 2379–2384; Tenscher, K. et al., *Blood* (1996) 88, 3195–3199; Sato, K. et al., *Blood* (1999) 93, 34–42. In particular, eotaxin exhibits a potent and specific chemotactic activity for eosinophils via binding to CCR-3, in vitro and in vivo. See Ponath, P. D. et al., *J. Clin. Invest.* (1996) 97, 604–612.

Tissue eosinophilia is observed in a number of pathological conditions such as asthma, rhinitis, eczema, inflammatory bowel diseases and parasitic infections. See Bousquest J. et al., *N. Eng. J. Med.* 323, 1033–1039; Middleton, Jr., E. et al., Chapter 42, Allergy Principles and Practice $4^{th}$ ed. vol.2 Mosby-Year Book, Inc. 1993 U.S.A. In asthma, the airways of patients are infiltrated by a large numbers of eosinophils, and eotaxin production in bronchial mucosa and bronchoalveolar lavage (BALF) is increased. Several studies have suggested a strong correlation between the number of eosinophils in BALF, the eotaxin level in BALF and the clinical parameters of disease severity. See Walker, C. et al., *J. Allergy Clin. Immunol.* (1991) 88, 935–942; Ying, S. et al., *Eur. J. Immunol.* (1997) 27 3507–3516. Furthermore, pretreatment with a CCR-3-antibody has been shown to block chemotaxis and $Ca^{2+}$ influx induced by eotaxin, RANTES, MCP-3 or MCP4, suggesting that most of the eosinophilic response to these chemokines in allergic and eosinophilic patients is mediated through CCR-3. See Heath, H. et al., *J. Clin. Invest.* (1997) 99, 178–184. Similarly, it has recently been disclosed that certain cyclic amine derivatives are antagonistic to CCR-3 and may be useful for treating eosinophil-mediated allergic diseases. See EP 0903349A2. Also, CCR-3 expression on human Th2 type T-cells and human cultured dendritic cells mediates cell functions such as chemotactic response. See Sallusto, F. et al., *Science* (1997) 277, 2005–2007; Sato, K. et al., *Blood* (1999) 93, 34–42. In addition, anti-CCR-3 antibody has been shown to inhibit aggregation of T-cells and dendritic cells, suggesting CCR-3 may regulate the interaction of these cells during the process of antigen presentation. See Sato, K. et al., *Blood* (1999) 93, 34–42. Therefore, CCR-3 inhibitors may also be useful for regulating immune responses.

These examples suggest that CCR-3 mediated diseases may be treated using compounds that inhibit CCR-3 activity. Because CCR-3 is present on many cell types, however, and is responsible for a variety of disease states, an arsenal of compounds which inhibit CCR-3 activity is required to treat CCR-3 mediated diseases effectively.

SUMMARY OF THE INVENTION

It is therefore one object of the present invention to provide compounds which inhibit CCR-3 receptor activity.

It is another object of the present invention to provide a method of treating CCR-3 mediated diseases.

In accomplishing these and other objects of the invention, there is provided, in accordance with one aspect of the present invention, a compound having the following Formula:

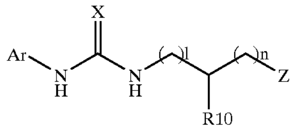

or a salt, hydrate, or complex thereof, wherein:

1 and n are independently 0, 1, 2, 3, 4 or 5;

(1+n) is 1, 2, 3, 4 or 5;

X is O or S;

R10 is selected from the group consisting of hydrogen, hydroxy, $C_{3-7}$cycloalkyloxy, acyloxy, carboxy, carbamoyl, acyl, amino, alkylamino, arylamino, acylamino, $C_{1-5}$alkyl, aryl, $C_{1-5}$alkoxy, aryloxy, alkylcarbamoyl, arylcarbamoyl, alkyloxycarbonyl,
- Wherein the $C_{1-5}$alkyl, aryl, $C_{1-5}$alkoxy, aryloxy, alkylcarbamoyl, arylcarbamoyl or alkyloxycarbonyl is optionally substituted with one or more groups independently selected from the group consisting of carboxy, carbamoyl, alkylcarbamoyl, arylcarbamoyl, alkylsulfonylcarbamoyl, arylsulfonylcarbamoyl, alkyloxycarbonyl, sulfonyl, alkylsulfonyl, arylsulfonyl, sulfamoyl, alkylsulfmoyl, arylsulfamoyl, alkylsulfonamide, arylsulfonamide, alkylthio, halogen, hydroxy, acyloxy, $C_{1-5}$alkoxy, aryloxy, heteroaryloxy, nitro, amino, acylamino, alkylarino, arylamino, cyano, aryl, heteroaryl
  - Wherein the aryl or heteroaryl is optionally substituted with one or more groups independently selected from the group consisting of $C_{1-5}$alkyl or $C_{1-5}$alkoxy, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, sulfonyl, alklylsulfonyl, arylsulfonyl, sulfamoyl, alkylsulfamoyl, arylsulfamoyl, alkylsulfonamide, arylsulfonamide, alkylthio, acyl, acyloxy, hydroxy, and halogen;

Ar is aryl or heteroaryl
- optionally substituted with one or more groups independently selected from the group consisting of hydroxy, halogen, trihalomethyl, trihalomethoxy, $C_{1-5}$alkyl, $C_{1-5}$alkoxy, cyano, nitro, amino, carboxy, alkyloxycarbonyl, arylmethyloxycarbonyl, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryloxy optionally substituted with one or more groups independently selected from the group consisting of hydroxy, halogen, trihalomethyl, $C_{1-5}$alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino, and heteroaryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Z is:

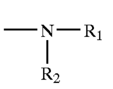

or

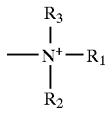

wherein $R_1$ is:

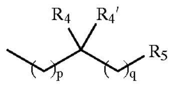

or

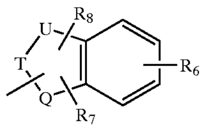

or

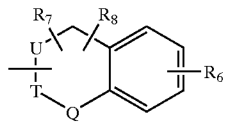

or

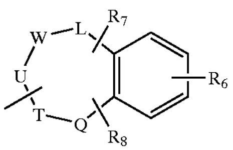

p is 0, 1 or 2;

q is 0, 1 or 2;

$R_4$ and R4' are independently selected from the group consisting of hydrogen, halogen, $C_{1-5}$ alkyl, aryl, heteroaryl wherein the aryl or heteroaryl is optionally substituted with one or more groups independently selected from the group of consisting of hydrogen, hydroxy, halogen, trihalomethyl, $C_{1-5}$ alkyl, $C_{1-5}$alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

and $COR_9$; wherein $R_9$ is hydroxy, $C_{1-5}$alkyl, $C_{1-5}$alkoxy, amino, alkylamino or arylamino;

$R_5$ is aryl or heteroaryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylufamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_6$ is selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, and aryloxy optionally substituted with one or more groups independently selected from the group consisting of hydroxy, halogen, trihalomethyl. $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_7$ and $R_8$ are independently selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfonyl, arylsulfonyl, alkylthio, alkylsulfonamide, arylsulfonamide, hydrazino, acylamino, alkylamino, hydroxyamino, amidino, guanidino, and cyanoguanidino;

Q, T, U, W and L are independently selected from the group of atoms consisting of C, N, O and S; wherein adjacent atoms U-T, T-Q, U-W, W-L may form one or more double bonds;

$R_2$ and $R_3$ are independently selected from the group consisting of $C_{1-8}$ alkyl, $C_{1-8}$ alkenyl and $C_{1-8}$ alkynyl optionally substituted with one or more groups independently selected from the group consisting of carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, halogen, acyloxy, hydroxy, nitro, amino, acylamino, alkylamino, cyano, aryl optionally substituted with one or more groups independently selected from the group consisting of $C_{1-5}$ alkyl or $C_{1-5}$ alkoxy, wherein the alkyl or alkoxy may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, aryloxy, arylmethyloxy, hydrazino, hydroxyamino, amidino, guanidino, cyanoguanidino, hydroxy, and halogen, heteroaryl optionally substituted with one or more groups independently selected from the group consisting of $C_{1-5}$ alkyl or $C_{1-5}$ alkoxy which may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, $C_{1-5}$ alkoxy optionally substituted with one or more groups independently selected from the group consisting of $C_{1-5}$ alkyl or $C_{1-5}$ alkoxy which may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, arylmethyloxy optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfmoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, $C_{3-7}$ cycloalkyl optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, and heterocycle;

provided that none of $R_1$, $R_2$, and $R_3$ bond together;

further provided that Ar is not 2-hydroxy-5-methoxyphenyl, and further provided that when Ar is phenyl, Z is

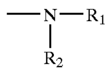

and $R_2$ is methyl, then $R_1$ is not

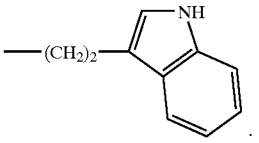

In another embodiment of the present invention, there is provided a pharmaceutical composition comprising one or more the disclosed compounds.

In yet another embodiment, there is provided a method of treating CCR-3 mediated diseases in a patient, comprising administering to the patient an effective amount of a pharmaceutical composition comprising one or more of the inventive compounds of the present invention.

In another embodiment, a kit is provided for treating CCR3 mediated diseases in a patient, comprising:

(A) a pharmaceutical composition comprising one or more of the inventive compounds of the present invention;

(B) reagents to effect administration of the pharmaceutical composition to the patient; and (C) instruments to effect administration of the pharmaceutical composition to the patient.

Other objects, features and advantages of the present invention will become apparent from the following detailed description. It should be understood that examples are given by way of illustration only, since various changes and modifications within the spirit and scope of the invention will become apparent to those skilled in the art.

BRIEF DESCRIPTION OF THE DRAWINGS

Scheme 1 provides a schematic representation of the synthesis of N-Phenylcarbamoyl-N'-[2-(4-chlorophenyl) ethyl]-N'-ethyl-1,3-diaminopropane (Compound No. 1).

Scheme 2 provides a schematic representation of the synthesis of N-Phenylcarbamoyl-N'-[2-(4-chlorophenyl) ethyl]-N'-propyl-1,3-diaminopropane (Compound No. 10).

Scheme 3 depicts the synthesis of Methyl 4-[[3-(4-bromophenylureido)propyl](1,2,3,4-tetrahydro-1-naphthyl) amino]butylate (Compound No. 29).

Scheme 4 depicts the synthesis of 4-[[3-(4-Bromophenylureido)propyl](1,2,3,4-tetrahydro-1-naphthyl) amino]butanoic acid (Compound No.60).

Scheme 5 depicts the synthesis of [3-(Phenylureido) propyl][2-(4-chlorophenyl)ethyl]-diethylammonium iodide (Compound No.91).

Scheme 6 depicts the synthesis of Active Compounds by Solid Phase Synthesis.

Scheme 7 depicts the synthesis of N-phenylcarbamoyl-N'-[2-(4-chlorophenyl)ethyl]-N'-ethyl 2-hydroxy-1,3-diaminopropane (Compound No.163).

Scheme 8 depicts the synthesis of 4[[3-(4-chlorophenylthioureido)propyl](1,2,3,4-tetrahydro-1-naphthyl)amino]butanoic acid (Compound No.164).

Scheme 9 depicts the synthesis of 4[[(3S)-3-(4-bromophenylureido)-3-(tert-butoxycarbonyl)propyl](1,2,3,4-tetrahydro-1-naphthyl)amino]butanoic acid (Compound Nos.165 and 166).

Scheme 10 depicts the synthesis of 4-[[3-(4-bromophenylureido)-2-hydroxypropyl](1,2,3,4-tetrahydro-1-naphthyl)amino]butanoic acid (Compound No. 167).

Scheme 11 depicts the synthesis of 4[[3-(4-Bromophenylureido)propyl](1,2,3,4-tetrahydro-1-naphthyl) amino]butanamide (Compound No.193).

Scheme 12 depicts the synthesis of 3-[[3-(4-Bromophenylureido)propyl](1,2,3,4-tetrahydro-1-naphthyl) amino]-1-[(phenylsulfonyl)carbamoyl]propane (Compound No.196).

Scheme 13 depicts the synthesis of 4[[3-(4-Bromophenylureido)propyl](1,2,3,4-tetrahydro-1-naphthyl) amino]-1-butanol (Compound No.203).

Scheme 14 depicts the synthesis of 3-[[3-(4-Bromophenylureido)propyl](1,2,3,4-tetrahydro-1-naphthyl) amino]-1-(1H-tetrazol-5-yl)propane (Compound No.218).

Scheme 15 depicts the synthesis of Methyl 4-[[3-[4-(carboxy)phenylureido]propyl](1,2,3,4-tetrahydro-1-naphthyl)amino]butylate (Compound No.225).

Scheme 16 depicts the synthesis of 4[[3-[4-(Ethoxycarbonyl)phenylureido]propyl](1,2,3,4-tetrahydro-1-naphthyl)amino]butanoic acid (Compound No.228).

Scheme 17 depicts the synthesis of [3-(Phenylureido) propyl]bis[2-(4-chlorophenyl)ethyl]amine (Compound No.238).

Scheme 18 depicts the synthesis of 4-[[(3S)-3-(4-Bromophenylureido)-3-(isopropylcarbamoyl)propyl](1,2,3,4-tetrahydro-1-naphthyl)amino]butanoic acid (Compound No.286).

Scheme 19 depicts the synthesis of [3-(Phenylureido) propyl][2-(4-chlorophenyl)ethyl]bis(4-methylbenzyl) ammonium iodide (Compound No.296).

Scheme 20 depicts the synthesis of [3-(4-Bromophenylureido)propyl][(1S)-1-phenylethyl][3-(carboxy)propyl]ethylammonium trifluoroacetate (Compound No.315).

Scheme 21 depicts the synthesis of [3-(Phenylureido) propyl][2-(4-chlorophenyl)ethyl][4-(carboxy)benzyl] ethylammonium iodide (Compound No.322).

Figure 1A:
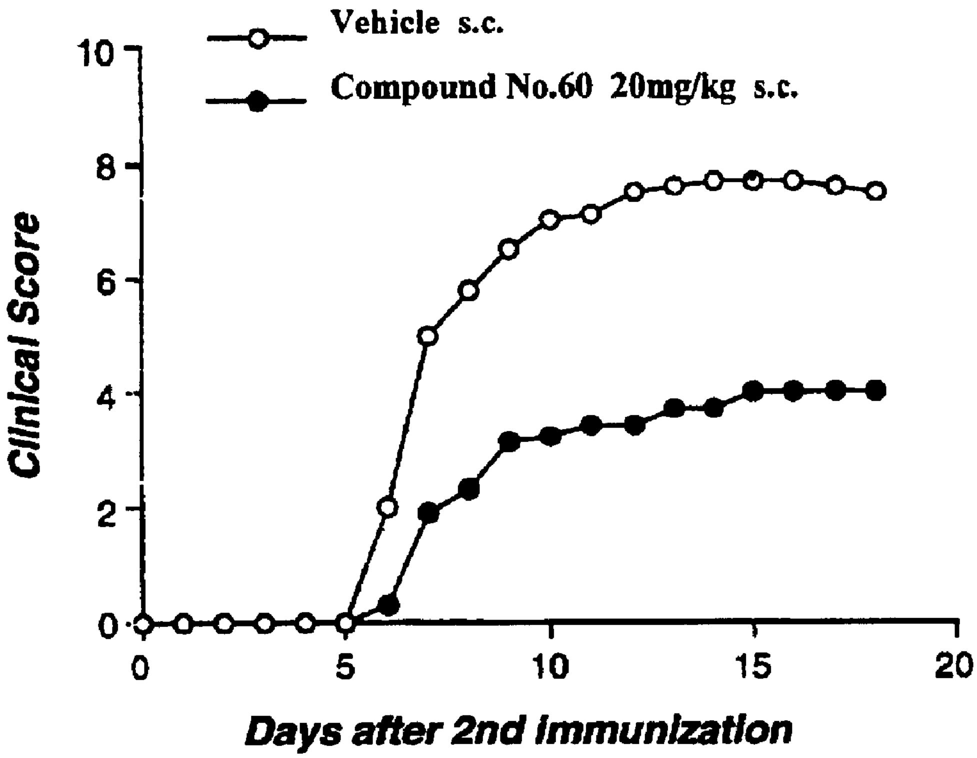

FIG. 1A demonstrates the inhibitory effects of Compound No. 60 on collagen-induced arthritis.

Figure 1B:
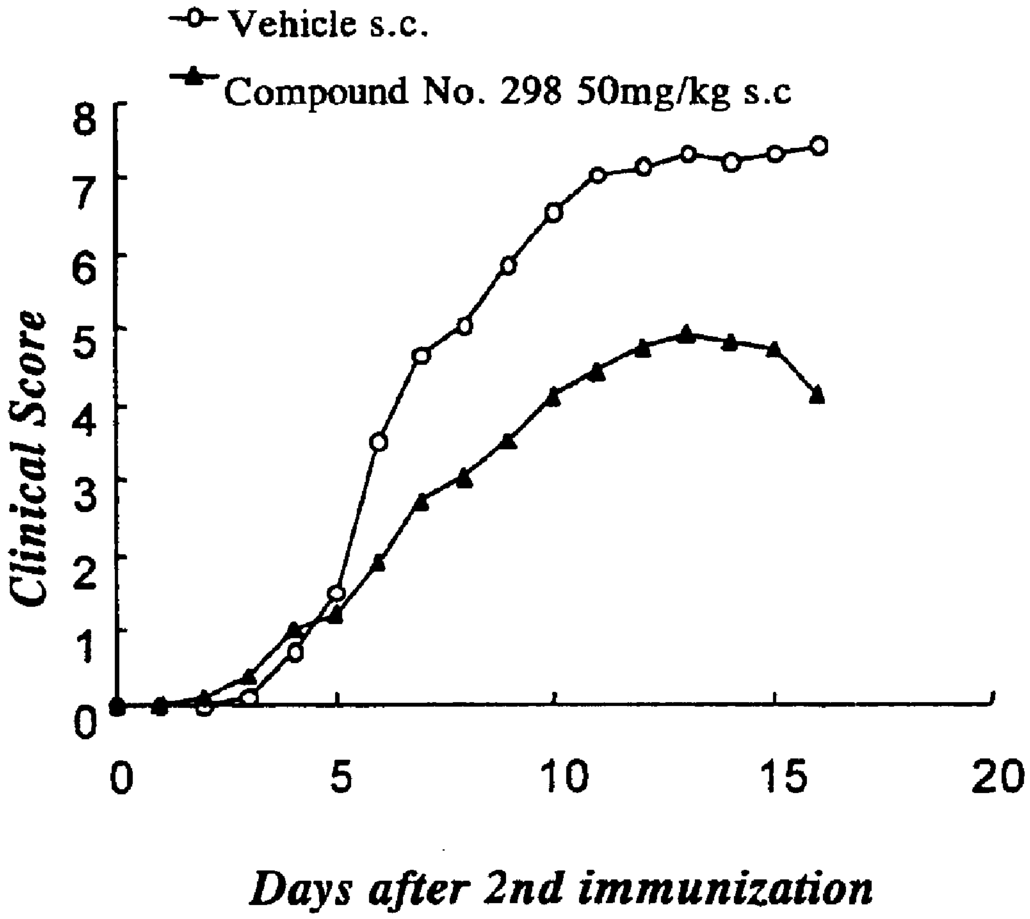

FIG. 1B demonstrates the inhibitory effects of Compound No. 298 on collagen-induced arthritis.

Figure 2A:
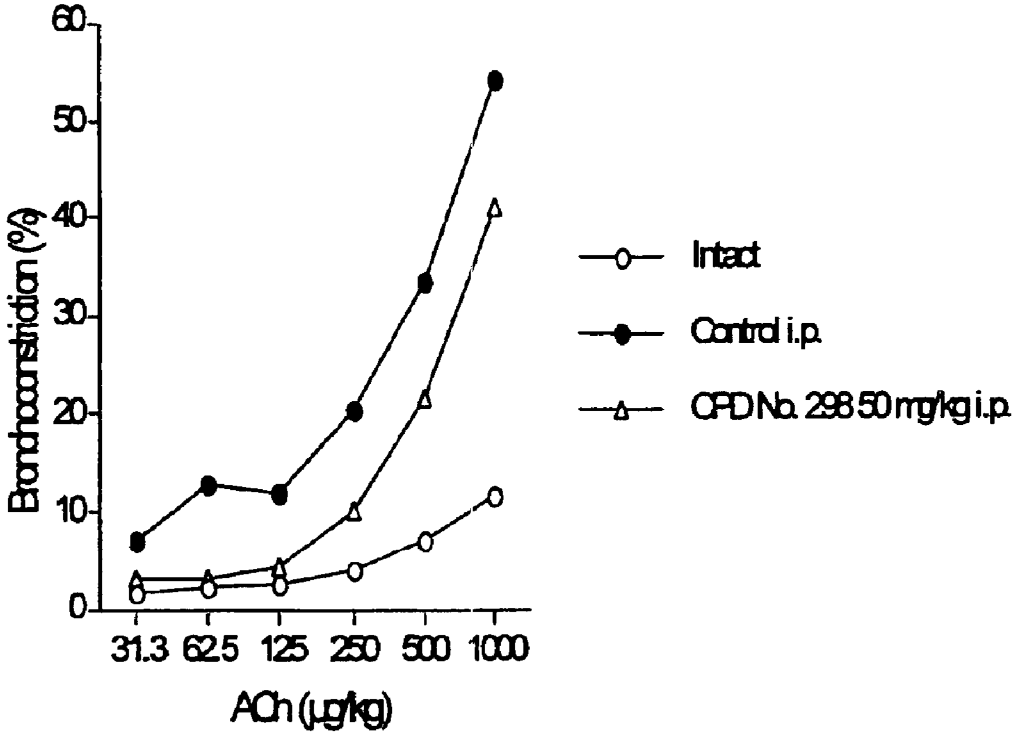

FIG. 2A shows the dose-response curves of bronchoconstriction against acetylcholine (murine asthma model) with and without treatment of compound No. 298.

Figure 2B:
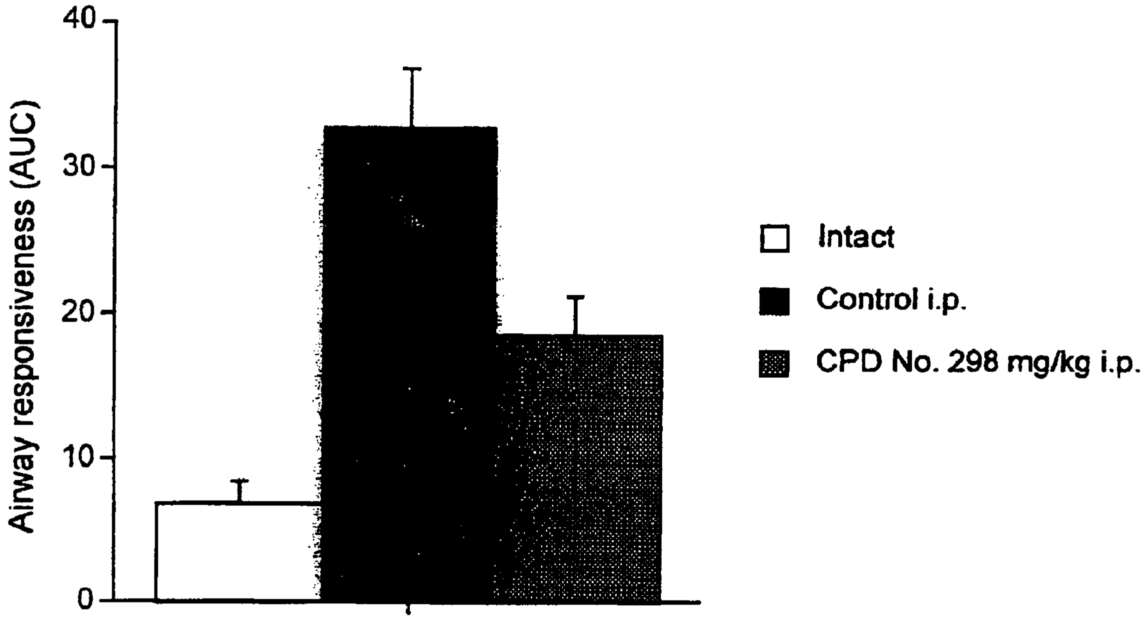

FIG. 2B shows the area under each of the dose-response curves of FIG. 2A.

Figure 2C:
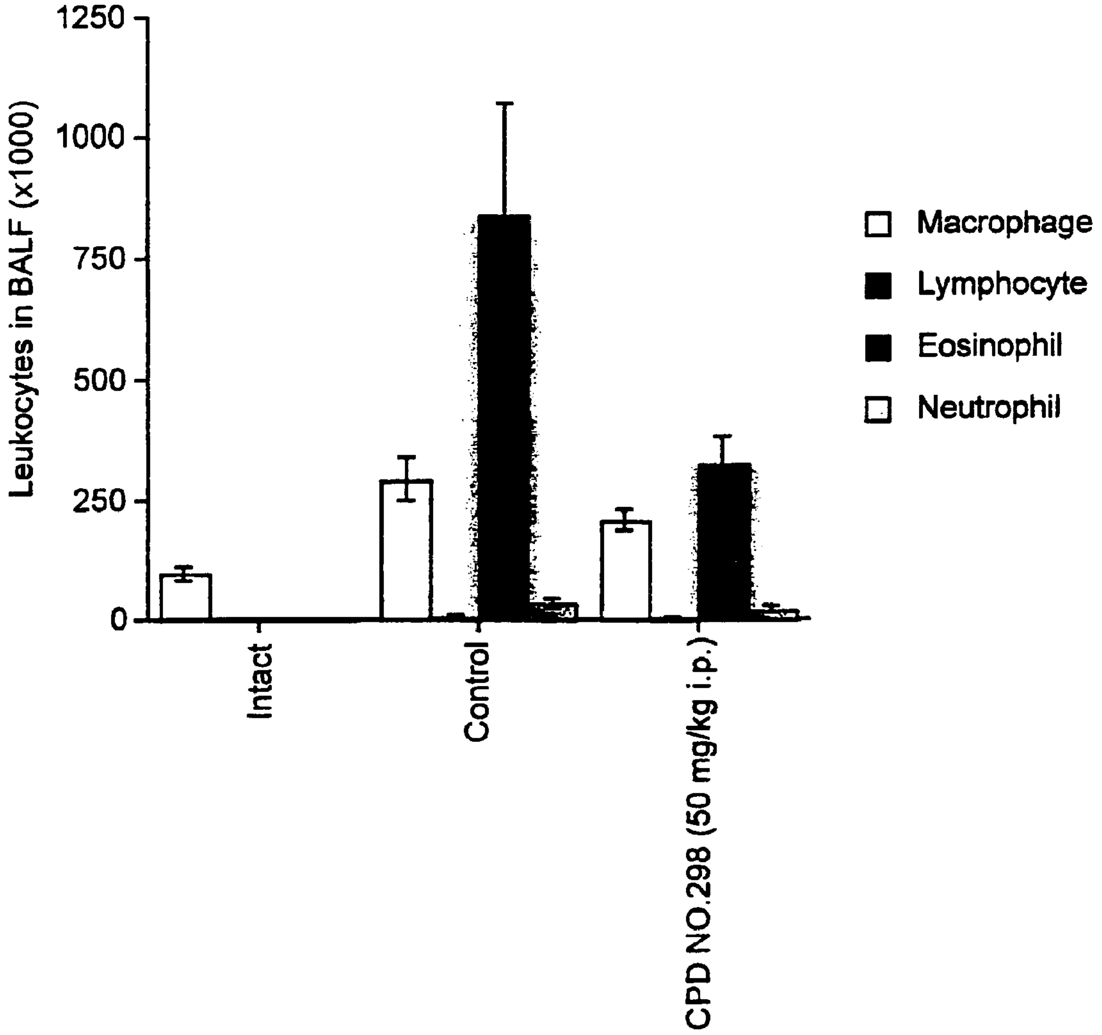

FIG. 2C shows the suppression of compound No. 298 (CPD No. 298) on eosinophil infiltration to bronchoalveolar lavage fluid (BALF). Two hundred cells were counted in each experiment.

DETAILED DESCRIPTION OF THE PREFERRED EMBODIMENTS

The present invention provides a new class of compounds which inhibit CCR-3 receptor activity. Because the CCR-3 receptor is understood to mediate a variety of diseases, the disclosed compounds, which are derived from urea, are useful for treating CCR-3-mediated diseases. Examples of such diseases include, without limitation, eosinophil-mediated diseases such as asthma, rhinitis, eczema, inflammatory bowel diseases, parasitic infections, and diseases that are mediated by T-cells, mast cells (Ochi H. et al., *J. Exp. Med.* (1999) 190:267–280, Romagnani P. et al., *Am. J. Pathol.* (1999) 155:1195–1204) and/or dendritic cells, such as autoimmune and inflammatory diseases and HIV infection.

In one embodiment of the present invention, there is provided a variety of compounds that inhibit cell function mediated by the chemokine receptor CCR-3. In general, these compounds are either urea derivatives (Formula I) or thiourea derivatives (Formula III). Their formulas are depicted below:

(I)

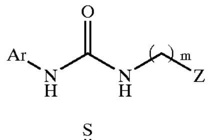

and (III)

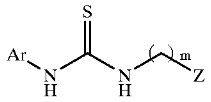

The compounds of Formula (I) and (III), as defined above, include variable groups such as an aryl group, a heteroaryl group and a heterocyclic group.

An aryl group is defined as a 6–15 membered aromatic carbocyclic moiety. This includes but is not limited to phenyl, naphthyl, anthryl, indenyl, phenanthrenyl and others.

A heteroaryl group is defined as a 5–15 membered aromatic ring system containing at least one hetero atom selected from the group consisting of N, O, and S. These include but are not limited to 2- or 3-thienyl, 2- or 3-furyl, 2- or 3-pyrrolyl, 2-, 3- or 4-pyridyl, 2-, 4- or 5-oxazolyl, 2-, 4- or 5-thiazolyl, 3-, 4- or 5-pyrazolyl, 2-, 4- or 5-imidazolyl, 3-, 4- or 5-isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxido-2-, 3- or 4-pyridyl, 2-, 4- or 5-pyrimidinyl, N-oxido-2-, 4- or 5 pyrimidinyl, 3- or 4-pyridazinyl, pyrazinyl, N-oxido-3- or 4-pyridazinyl, benzofuryl, indolyl, benzothizolyl, benzoxazolyl, triazinyl, oxotriazinyl, tetrazolo[1,5-b]pyridazinyl, triazolo[4,5-b] pyridazinyl, oxoimidazinyl, dioxotriazinyl, pyrrolidinyl, pyranyl, thiopyranyl, 1,4-oxazinyl, 1,4-thiazinyl, 1,3-thiazinyl, benzimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenothiazinyl and phenoxazinyl.

A heterocyclic group is defined as a 5–15 membered non-aromatic ring system containing at least one hetero atom selected from the group consisting of N, O, and S. These include but are not limited to hydrogenated derivatives of 2- or 3-thienyl, 2- or 3-furyl, 2- or 3-pyrrolyl, 2-, 3- or 4-pyridyl, 2-, 4 or 5-oxazolyl, 2-, 4- or 5 thiazolyl, 3-, 4- or 5-pyrazolyl, 2-, 4- or 5-imidazolyl, 3-, 4- or 5 -isoxazolyl, 3-, 4- or 5-isothiazolyl, 3- or 5-(1,2,4-oxadiazolyl), 1,3,4-oxadiazolyl, 3- or 5-(1,2,4-thiadiazolyl), 1,3,4-thiadiazolyl, 4- or 5-(1,2,3-thiadiazolyl), 1,2,5-thiadiazolyl, 1,2,3-triazolyl, 1,2,4-triazolyl, 1H- or 2H-tetrazolyl, N-oxide 2-, 3- or 4-pyridyl, 2-, 4- or 5-pyrimidinyl, N-oxido-2-, 4- or 5-pyrimidinyl, 3- or 4-pyridazinyl, pyrazinyl, N-oxido-3- or 4-pyridazinyl, benzofuryl, indolyl, benzothiazolyl, benzoxazolyl, triazinyl, oxotriazinyl, tetrazolo [1,5-b] pyridazinyl, triazolo[4,5-b]pyridazinyl, oxoimidazinyl, dioxotriazinyl, pyrrolidinyl, pyranyl, thiopyranyl, 1,4-oxazinyl, 1,4-thiazinyl, 1,3-thiazinyl, benzimidazolyl, quinolyl, isoquinolyl, cinnolinyl, phthalazinyl, quinazolinyl, quinoxalinyl, indolizinyl, quinolizinyl, 1,8-naphthyridinyl, purinyl, pteridinyl, dibenzofuranyl, carbazolyl, acridinyl, phenanthridinyl, phenazinyl, phenotiazinyl and phenoxazinyl. The heterocyclic moiety may also include dioxolanyl, morpholinyl, piperidinyl, and piperazinyl.

In another embodiment of the present invention, there is provided another family of compounds which inhibit cell function mediated by the chemokine receptor CCR-3. In general, these compounds have the Formula (11) depicted below:

(II)

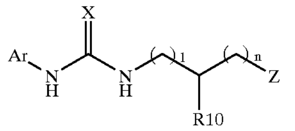

or a salt, hydrate, or complex thereof, wherein:

1 and n are independently 0, 1, 2, 3, 4 or 5;

(1+n) is 1,2,3, 4 or 5;

X is O or S;

R10 is selected from the group consisting of hydrogen, hydroxy, $C_{3-7}$cycloalkyloxy, acyloxy, carboxy, carbamoyl, acyl, amino, alkylamino, arylamino, acylamino, $C_{1-5}$alkyl, aryl, $C_{1-5}$alkoxy, aryloxy, alkylcarbamoyl, arylcarbamoyl, alkyloxycarbonyl, Wherein the $C_{1-5}$alkyl, aryl, $C_{1-5}$alkoxy, aryloxy, alkylcarbamoyl, arylcarbamoyl or alkyloxycarbonyl is optionally substituted with one or more groups independently selected from the group consisting of carboxy, carbamoyl, alkylcarbamoyl, arylcarbamoyl, alkylsulfonylcarbamoyl, arylsulfonylcarbamoyl, alkyloxycarbonyl, sulfonyl, alkylsulfonyl, arylsulfonyl, sulfamoyl, alkylsulfamoyl, arylsulfamoyl, alkylsulfonamide, arylsulfonamide, alkylthio, halogen, hydroxy, acyloxy, $C_{1-5}$alkoxy, aryloxy, heteroaryloxy, nitro, amino, acylamino, alkylamino, arylamino, cyano, aryl, heteroaryl Wherein the aryl or heteroaryl is optionally substituted with one or more groups independently selected from the group consisting of $C_{1-5}$alkyl or $C_{1-5}$alkoxy, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, sulfonyl, alklylsulfonyl, arylsulfonyl, sulfamoyl, alkylsulfamoyl, arylsulfamoyl, alkylsulfonamide, arylsulfonamide, alkylthio, acyl, acyloxy, hydroxy, and halogen;

Ar may be aryl or heteroaryl optionally substituted with one or more groups independently selected from the group consisting of hydroxy, halogen, trihalomethyl, trihalomethoxy, $C_{1-5}$alkyl, $C_{1-5}$alkoxy, cyano, nitro, amino, carboxy, alkyloxycarbonyl, arylmethyloxycarbonyl, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylarino, hydroxyamino, amidino, guanidino, and cyanoguanidino, and heteroaryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Z may be

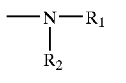

or

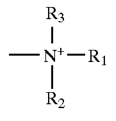

wherein $R_1$ is:

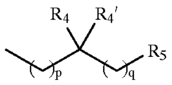 or 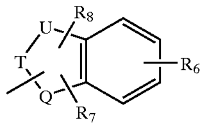 or

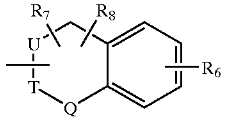 or 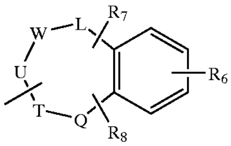

p is 0, 1 or 2;

q is 0, 1 or 2;

$R_4$ and R4' are independently selected from the group consisting of hydrogen, halogen, $C_{1-5}$ alkyl, aryl, heteroaryl wherein the aryl or heteroaryl is optionally substituted with one or more groups independently selected from the group of consisting of hydrogen, hydroxy, halogen, trihalomethyl, $C_{1-5}$ alkyl, $C_{1-5}$alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

and $COR_9$; wherein $R_9$ is hydroxy, $C_{1-5}$alkyl, $C_{1-5}$alkoxy, amino, alkylamino or arylamino;

$R_5$ is aryl or heteroaryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_6$ is selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_7$ and R8 are independently selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Q, T, U, W and L are independently selected from the group of atoms consisting of C, N, O and S; wherein adjacent atoms U-T, T-Q, U-W, W-L may form one or more double bonds;

$R_2$ and $R_3$ are independently selected from the group consisting of $C_{1-8}$ alkyl, $C_{1-8}$ alkenyl and $C_{1-8}$ alkynyl optionally substituted with one or more groups independently selected from the group consisting of carboxy, carbamoyl, alylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, halogen, acyloxy, hydroxy, nitro, amino, acylamino, alkylamino, cyano, aryl optionally substituted with one or more groups independently selected from the group consisting of $C_{1-5}$ alkyl or $C_{1-5}$ alkoxy, wherein the alkyl or alkoxy may be optionally substituted with carboxy or alkyloxycarbonyl, cyano, nitro, ammo, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, aryloxy, arylmethyloxy, hydrazino, hydroxyamino, amidino, guanidino, cyanoguanidino, hydroxy, and halogen, heteroaryl optionally substituted with one or more groups independently selected from the group consisting of $C_{1-5}$ alkyl or $C_{1-5}$ alkoxy which may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, $C_{1-5}$ alkoxy optionally substituted with one or more groups independently selected from the group consisting of $C_{1-5}$ alkyl or $C_{1-5}$ alkoxy which may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, arylmethyloxy optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, $C_{3-7}$ cycloalkyl optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, and heterocycle;

provided that none of $R_1$, $R_2$, and $R_3$ bond together;

further provided that Ar is not 2-hydroxy-5-methoxyphenyl, and further provided that when Ar is phenyl, Z is

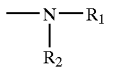

and $R_2$ is methyl, then $R_1$ is not

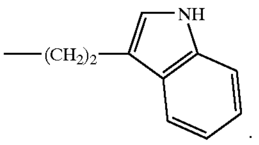

The compounds of the present invention can be prepared by various methods including, but not limited to, liquid phase or a solvent based synthesis and solid phase synthesis involving a polymeric resin.

The liquid phase synthesis generally involves addition of a substituted or unsubstituted alkyl amine containing compound to a protected amine containing starting material bearing a leaving group (e.g., Cl, Br, I, OTs, OMs, etc.). The resulting product bearing a protonated amine is reacted with an alkyl halide to yield a substituted amine. Then, the protected amine moiety is deprotected by addition of base or e.g., hydrazine. The resultant free amine is reacted with a compound containing an aromatic isocyanate to yield the aromatic urea derivative.

A second synthesis involves the reaction of aromatic isocyanate with a haloalkylamine. The resultant product is then further reacted with an optionally substituted amine containing compound, the amine of the optionally substituted amine containing compound is substituted by reaction with an alkyl halide to yield the aromatic urea derivative.

An additional method that can be used to prepare the present compounds involves reaction of a protected amine containing starting compound with an alkylamine. The resultant diamine is reacted with an ester containing a leaving group, after deprotection, the aromatic urea derivative is formed by reaction with a compound containing an aromatic isocyanate.

The aromatic urea derivatives can be further derivatized by conventional organic synthesis techniques, for example, an ester can be converted to an acid by addition of a metal hydroxide. Additionally, salts of the compounds can be formed by conventional synthetic techniques, such as addition to an amine moiety to form an ammonium salt.

Solid phase synthesis involves the use of polymeric resins. Reductive amination of the linker to the resin occurs by reacting a haloalkylamine with the polymeric resin. The protonated amine is then protected by reaction with a substituted or unsubstituted acid chloride. The halogen of the original haloalkylamine is displaced by reaction with an alkyl amine compound and reductive amination follows by reaction with an aldehyde. The protected amine is deprotected by reaction with, for example, tin chloride, an acid or an amine. The deprotected amine is subsequently reacted with an isocyanate to yield the urea moiety, the product is isolated by working up the reaction mixture, for example, in HCl gas.

In one embodiment of the present invention, an effective amount of a pharmaceutical composition comprising one or more of the disclosed compounds is administered to a patient suffering from CCR-3 mediated disease. The active compound of the pharmaceutical composition can be administered in a variety of forms, including, but not limited to a salt, a hydrate or a prodrug. In addition, the pharmaceutical composition can optionally contain suitable carriers or excipients.

A "pharmaceutical composition" refers to a mixture of one or more of the compounds described herein, or pharmaceutically acceptable salts, hydrates or prodrugs thereof, with other chemical components, such as physiologically acceptable carriers and excipients. The purpose of a pharmaceutical composition is to facilitate administration of a compound to an organism.

A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug.

As used herein, a "physiologically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples of excipients include, but are not limited to, calcium carbonate, calcium phosphate, sugars, starches, cellulose derivatives, gelatin, vegetable oils and polyethylene glycol.

The form of the administered compound depends, in part, upon the use or the route of entry. Such forms should allow the agent to reach a target cell whether the target cell is present in a multicellular host or in culture. For example, pharmacological agents or compositions injected into the blood stream should be soluble in the concentrations used. Other factors are known in the art, and include considerations such as toxicity and forms which prevent the compound or composition from exerting its effect.

A compound of the present invention also can be formulated as a pharmaceutically acceptable salt, e.g., acid addition salt, and complexes thereof. The preparation of such salts can facilitate the pharmacological use by altering the physical characteristics of the agent without preventing its physiological effect. Examples of useful alterations in physical properties include, but are not limited to, lowering the melting point to facilitate transmucosal administration and increasing the solubility to facilitate administering higher concentrations of the drug.

A compound of the present invention can be administered to a mammal, including a human patient, using a variety of techniques. For example, for systemic administration, oral administration or injection can be used. For oral administration, a compound of the present invention is formulated into conventional oral administration dosage forms such as capsules, tablets, and tonics. For injection, a compound is formulated in liquid solutions, preferably in physiologically compatible buffers such as Hank's solution or Ringer's solution. In addition, a compound can be formulated in a solid form and redissolved or suspended immediately prior to use. Lyophilized forms can also be produced. Examples of systemic administrations by injection include intramuscularly, intravenously, intraperitoneally and subcutaneously.

Administration also can be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration also can be achieved, for example, by using nasal sprays or suppositories.

Administration of a compound of the present invention can be achieved by any means which transports the compound to the airways and/or lungs of a mammal, including a human patient. In a preferred embodiment, a compound is administered by generating an aerosol comprised of respirable particles, comprising said compound. Delivery is achieved by animal or patient inhalation of the respirable particles. The respirable particles can be liquid or solid and, optionally, can contain other therapeutic ingredients.

For topical administration, the molecules of the invention are formulated into ointments, salves, gels, or creams, as is generally known in the art.

Generally, a therapeutically effective amount for a human patient is between about 10 mmole and 3 mmole of the compound, preferably 1 $\mu$mole to 1 mmole. A therapeutically effective amount for a non-human mammal is between about 0.01 and 50 mg/kg, preferably 0.01 and 20 mg/kg. Optimization of the timing and dosage of a disclosed compound is by convention adapted to, among other things, the particular characteristics of the patient or the non-human mammal and the nature and extent of the disease state, and the EC50 or IC50 of the compound. Such adaptations are routine and do not require abnormal experimentation or skill in the art.

In accordance with yet another aspect of the present invention, there is provided a kit suitable for treating CCR-3 mediated diseases in a patient, comprising a pharmaceutical composition comprising one or more compounds of the present invention, reagents to effect administration of the pharmaceutical composition to the patient and instruments to effect administration of the pharmaceutical composition to the patient. Examples of such instruments include, but are not limited to application devices, such as syringes or inhalers.

In yet another emobobyment, the claimed compounds are useful for treatment and/or prevention of rheumatoid arthritis. The treatment includes, but not limited to, administration of the claimed compounds through subcacutaneous, intradermal, intramuscular, intraperitoneal, intravascular, and intracranial injections to human or other mammalian animal bodies.

EXAMPLES

Synthesis of Active Compounds

Example 1

Synthesis of N-Phenylcarbamoyl-N'-[2-(4-chlorophenyl)ethyl]-N'-ethyl-1,3-diaminopropane (Compound 1)

The following synthesis is depicted in Scheme 1.

Step 1: To a mixture of 2-(4-chlorophenyl)ethylamine (1.56 g, 10 mmol) and potassium carbonate (2.8 g, 20 mmol) in $CH_3CN$ (50 ml) was added N-(3-bromopropyl) phthalimide (3.0 g, 11 mmol). The mixture was refluxed under stirring for 16 h, and then filtered. The filtrate was concentrated under vacuum to dryness, and the residue was chromatographed on silica gel (eluting with 2.5% methanol/chloroform) to afford N-[3-[2-(4-chlorophenyl)ethylamino] propyl]phthalimide (2.28 g, 67%): MS(FD) m/e 343 $[M+H]^+$; $^1H$ NMR (400 MHz, $CDCl_3$) δ 7.84 (m, 2H), 7.71 (m, 2H), 7.24 (d, J=8.3 Hz, 2H), 7.11 (d, J=8.3 Hz, 2H), 3.74 (d, J=6.8 Hz, 2H), 2.82 (t, J=6.8 Hz, 2H), 2.73 (t, J=6.8 Hz, 2H), 2.66 (t, J=6.8 Hz, 2H), 1.84 (m, 2H).

Step 2: To a mixture of N-[3-[2-(4-chlorophenyl) ethylamino]propyl]phthalimide (2.28 g, 6.65 mmol) and potassium carbonate (1.8 g, 13 mmol) in $CH_3CN$ (50 ml) was added ethyl iodide (1.6 ml, 20 mmol). The mixture was stirred at 70° C. for 16 h, and then filtered. The filtrate was concentrated under vacuum to dryness, and the residue was chromatographed on silica gel (eluting with 2% methanol/chloroform) to afford N-[3-[[2-(4-chlorophenyl)ethyl](ethyl)amino]propyl]phthalimide (1.41 g, 57%): MS(ES$^+$) m/e 371 [M+H]$^+$; $^1$H NMR (400 MHz, $CDCl_3$) δ 7.84 (m, 2H), 7.71 (m, 2H), 7.23 (d, J=8.5 Hz, 2H), 7.11 (d, J=8.5 Hz, 2H), 3.71 (t, J=7.3 Hz, 2H), 2.66 (m, 4H), 2.57 (m, 4H), 1.83 (m, 2H), 1.00 (t, J=7.1 Hz, 3H).

Step 3: To a solution of N-[3-[[2-(4-chlorophenyl)ethyl](ethyl)amino]propyl]-phthalimide (1.41 g, 3.8 mmol) in EtOH (20 ml) was added a solution of hydrazine monohydrate (1.5 g, 30 mmol) in EtOH (5 ml). The solution was stirred at RT for 4h, and then filtered. The filtrate was concentrated under vacuum to dryness. After adding water, the mixture was extracted with chloroform, washed with brine, dried over sodium sulfate, and filtered. Concentrating under vacuum gave N-[2-(4-chlorophenyl)ethyl]-N-ethyl-1,3-diaminopropane (903 mg, 99%) which was used in the next step without further purification.

Step 4: To a solution of N-[2-(4-chlorophenyl)ethyl]-N-ethyl-1,3-diaminopropane (30 mg, 0.125 mmol) in $CH_2Cl_2$ (1 ml) was added phenyl isocyanate (18 mg, 0.15 mmol). After stirring at RT for 1 h, the reaction mixture was chromatographed on silica gel (eluting with 2.5% methanol/chloroform) to afford N-phenylcarbamoyl-N'-[2-(4-chlorophenylethyl]-N'-ethyl-1,3-diaminopropane (38.7 mg, 86%): MS(ES$^+$) m/e 360 [M+H]$^+$; $^1$H NMR (400 MHz, $CDCl_3$) δ 7.34–7.23 (m, 6H), 7.08 (d, J=8.3 Hz, 2H), 7.03 (m, 1H), 6.93 (br, 2H), 3.34 (m, 2H), 2.76–2.70 (m, 8H), 1.76 (m, 2H), 1.08 (t, J=7.1 Hz, 33H).

Compound 2, N4-Nitrophenylcarbamoyl)-N'-[2-(4-chlorophenyl)ethyl]-N'-ethyl-1,3 diaminopropane, can be obtained in an analogous manner to that described for compound 1 and contains the following characteristics: MS(FD) m/e 405 [M+H]$^+$; $^1$H NMR (400 MHz, $CDCl_3$) δ 8.12 (d, J=9.3 Hz, 2H), 7.65 (br, 1H), 7.51 (d, J=9.2 Hz, 2H), 7.27 (d, J=8.3 Hz, 2H), 7.13 (d, J=8.3 Hz, 2H), 6.38 (br, 1H), 3.33 (m, 2H), 2.83 (m, 4H), 2.74 (m, 4H), 1.76 (m, 2H), 1.11 (t, J=7.1 Hz, 3H).

Compound 3, N4-Bromophenylcarbamoyl)-N'-[2-(4-chlorophenyl)ethyl]-N'-ethyl-1,3 diaminopropane, can be obtained in an analogous manner to that described for compound 1 and contains the following characteristics: MS(ES$^+$) m/e 438 [M+H]$^+$; $^1$H NMR (400 MHz, $CDCl_3$) δ 7.60 (br, 1H), 7.32 (d, J=8.8, Hz, 2H), 7.26 (m, 4H), 7.08 (d, J=8.3 Hz, 2H), 6.25 (br, 1H), 3.26 (t, J=6.1 Hz, 2H), 2.73 (m, 8H), 1.71 (m, 2H), 1.08 (t, J=7.3 Hz, 3H).

Compounds 4–9, 191, 192, 202, 204, 215, 230–234, 239–245, 274–276, 280, 291, 292 can be obtained in an analogous manner to that of Compound 1.

Example 2

Synthesis of N-Phenylcarbamoyl-N'-[2-(4-chlorophenyl)ethyl]-N'-propyl-1,3-diaminopropane (Compound 10)

The following synthesis is depicted in Scheme 2.

Step 1: Phenyl isocyanate (1.4 ml, 13 mmol) was added to a solution of 3-bromopropylamine hydrobromide (2.5 g, 11 mmol) and triethylamine (1.7 ml, 12 mmol) in DMF (50 ml) at 0° C., and the mixture was stirred at 0° C. for 1.5 h. After adding water, the mixture was extracted with ethyl acetate, washed with water and brine, dried over sodium sulfate, and filtered. The filtrate was concentrated under vacuum to dryness, and the residue was chromatographed on silica gel (eluting with 2.5% ethyl acetate/hexane to 50% ethyl acetate/hexane) to afford N-phenylcarbamoyl-3-bromopropylamine (2.7 g, 96%); MS(FD) m/e 256 M$^+$; $^1$H NMR (400 MHz, $CDCl_3$) δ 7.35–7.26 (m, 4H), 7.11 (m, 1H), 6.45 (br, 2H), 3.46 (t, J=6.3 Hz, 2H), 3.41 (t, J=6.6 Hz, 2H), 2.10 (m, 2H).

Step 2:2(4-Chlorophenyl)ethylamine (1.8 g, 12 mmol) was added to a mixture of N-phenylcarbamoyl-3-bromopropylamine (2.5 g, 9.7 mmol) and potassium carbonate (2.6 g, 19 mmol) in $CH_3CN$ (50 ml). The mixture was stirred at 70° C. for 4.5 h, and then filtered. The filtrate was concentrated under vacuum to dryness, and the residue was dissolved with chloroform, washed with water, 1N-HCl and brine. The organic layer was dried over sodium sulfate, filtered, and then concentrated under vacuum to dryness. The residue was chromatographed on silica gel (eluting with 2% methanol/chloroform) to afford N-phenylcarbamoyl-N'-[2-(4- chlorophenyl)ethyl]-1,3- diaminopropane (1.43 g, 45%): MS(ES$^+$) m/e 332 M$^+$; $^1$H NMR (400 MHz, $CD_3OD$) δ 7.35–7.15 (m, 8H), 6.99 (m, 1H), 3.31 (m, 2H), 3.23 (m, 2H), 3.06 (t, J=7.1 Hz, 2H), 3.00 (m, 2H), 1.89 (m, 2H).

Step 3: Propyl iodide (51 mg, 0.30 mmol) was added to a mixture of N-phenylcarbamoyl-N'-[2-(4-chlorophenyl)ethyl]-1,3-diaminopropane (33 mg, 0.10 mmol) and potassium carbonate (28 mg, 0.20 mmol) in $CH_3CN$ (2 ml). The mixture was stirred at 75° C. for 5 h, and then filtered. The filtrate was concentrated under vacuum to dryness, and the residue was purified by preparative normal phase HPLC using linear gradients of (A) chloroform and (B) methanol (0–5% B, in 0–10 min; 5–10% B, in 10–30 min; 10–15% B, in 30–40 min) at a flow rate of 10 ml/min. Fractions containing the major peak were pooled and concentrated to afford N-phenylcarbamoyl-N'-[2-(4-chlorophenyl)ethyl]-N'-propyl-1,3 diaminopropane (27 mg, 59%): MS(ES$^+$) m/e 374 [M+H]$^+$; $^1$H NMR (400 MHz, $CDCl_3$) δ 7.35 (d, J=8.3 Hz, 2H), 7.25 (m, 4H), 7.07 (m, 3H), 5.98 (br, 1H), 5.00 (br, 1H), 3.31 (m, 2H), 2.78 (m, 6H), 2.59 (m, 2H), 1.76 (m, 2H), 1.52 (m, 2H), 0.90 (t, J=7.3 Hz, 3H).

Compounds 11–28, 219–221 can be obtained in an analogous manner to that of Compound 10.

Example 3

Synthesis of Methyl 4-[[3-(4-bromophenylureido)propyl](1,2,3,4-tetrahydro-1-naphthyl)amino]butylate (Compound 29)

The following synthesis is depicted in Scheme 3.

Step 1: N3-Bromopropyl)phthalimide (13.0 g, 48.5 mmol) was added to a mixture of 1,2,3,4-tetrahydro-1-naphthylamine (6.96 ml, 48.5 mmol) and potassium carbonate (13.4 g, 97.0 mmol) in $CH_3CN$ (200 ml). The mixture was refluxed under stirring for 21 h, and then filtered. The filtrate was concentrated under vacuum to dryness, and the residue was chromatographed on silica gel (eluting with 1.5% methanol/chloroform) to afford N-[3-(1,2,3,4-tetrahydro-1-naphthylamino)propyl]phthalimide (23.9 g, 74%): MS(ES$^+$) m/e 335 [M+H]$^+$; $^1$H NMR (400 MHz, $CDCl_3$) δ 7.84 (m, 2H), 7.71 (m, 2H), 7.39 (m, 1H), 7.13 (m, 2H), 7.06 (m, 1H), 3.81 (m, 3H), 2.81 (m, 2H), 2.71 (m, 2H), 2.00–1.85 (m, 4H), 1.72 (m, 2H).

Step 2: Methyl 4-bromobutylate (16.3 g, 89.8 mmol) was added to a mixture of N-[3-(1,2,3,4-tetrahydro-1-naphthylamino)propyl]phthalimide (10.0 g, 29.9 mmol) and potassium carbonate (8.28 g, 59.9 mmol) in DMF (150 ml). The mixture was stirred at 130° C. for 22 h. After adding water, the mixture was extracted with chloroform, washed with brine, dried over sodium sulfate, and filtered. The filtrate was concentrated under vacuum to dryness, and the residue was chromatographed on silica gel (eluting with 5% methanol/chloroform) to afford methyl 4-[[(3-phthalimido) propyl](1,2,3,4-tetrahydro-1-naphthyl)amino]butylate (4.62 g, 36%): MS(ES$^+$) m/e 435 [M+H]$^+$; $^1$H NMR (400 MHz, $CDCl_3$) δ 7.75 (m, 2H), 7.63 (m, 2H), 7.60 (d, J=7.6 Hz, 1H), 7.03 (m, 1H), 6.94 (m, 2H), 3.90 (m, 1H), 3.51 (m, 2H), 2.63 (m, 2H), 2.45–2.20 (m, 6H), 1.91 (m, 2H), 1.74 (m, 4H), 1.52 (m, 2H).

Step 3: Hydrazine monohydrate (1.03 ml, 21.3 mmol) was added to a solution of methyl 4-[[(3-phthalimido)propyl](1,2,3,4-tetrahydro-1-naphthyl)amino]butylate (4.62 g, 10.6 mmol) in EtOH (80 ml) at 0° C. After stirring at RT for 2h, additional hydrazine monohydrate (1.03 ml, 21.3 mmol) was added. The solution was stirred at RT for 2h, and concentrated under vacuum to dryness. After adding water, the mixture was extracted with chloroform, dried over sodium sulfate, and filtered. The filtrate was dissolved with chloroform, and then extracted with 1N-HCl. The water layer was neutralized with 1N-NaOH at 0° C., washed with chloroform, and then basified with 1N-NaOH (pH=14), extracted with chloroform. The organic layer was washed with brine, dried over sodium sulfate, and filtered. Concentrating under vacuum gave methyl 4[(3-aminopropyl)(1,2,3,4 -tetrahydro-1-naphthyl)amino]butylate (1.05 g, 33%) which was used in the next step without further purification.

Step 4:4-Bromophenyl isocyanate (83 mg, 0.42 mmol) was added to a solution of methyl 4-[(3-aminopropyl)(1,2,3,4-tetrahydro-1-naphthyl)amino]butylate (106 mg, 0.35 mmol) in $CH_2Cl_2$ (3 ml). After stirring at RT for 1 h, the reaction mixture was concentrated under vacuum to dryness. The residue was adsorbed on a plate of silica gel and the plate was developed with 6% methanol/chloroform to afford methyl 4[[3-(4-bromophenylureido)propyl](1,2,3,4-tetrahydro-1-naphthyl)amino]butylate (89 mg, 51%): MS(FD) m/e 502 [M+H]$^+$; $^1$H NMR (400 MHz, DMSO-d6) δ 8.50 (br, 1H), 7.57 (d, J=7.6 Hz, 1H), 7.35 (m, 4H), 7.13–7.01 (m, 3H), 6.09 (t, J=5.5 Hz, 1H), 3.89 (dd, J=9.0, 5.1 Hz, 1H), 3.53 (s, 3H), 3.12 (m, 1H), 3.03 (m, 1H), 2.67 (m, 2H), 2.43–2.25 (m, 6H), 2.00–1.88 (m, 2H), 1.70–1.50 (m, 6H).

Compound 30, Methyl 4-[[3-(4-bromophenylureido) propyl][(1R)-1-phenylethyl]-amino]butylate, can be obtained in an analogous manner to that described for compound 29 and contains the following characteristics: MS(ES$^+$) m/e 476 [M+H]$^+$; $^1$H NMR (400 MHz, $CDCl_3$) δ 7.73 (m, 1H), 7.38–7.21 (m, 8H), 7.08 (br, 1H), 5.47 (br, 1H), 3.91 (m, 1H), 3.65 (s, 3H), 3.20 (m, 2H), 2.49 (m, 3H), 2.29(m, 3H), 1.77 (m, 2H), 1.61 (m, 2H), 1.31 (d, J=6.6 Hz, 3H).

Compound 31, Methyl 4-[[3-(4-bromophenylureido) propyl][2-(4-chlorophenyl)-ethyl]amino]butylate, can be obtained in an analogous manner to that described for compound 29 and contains the following characteristics: MS(ES$^+$) m/e 510 [M+H]$^+$; $^1$H NMR (400 MHz, $CDCl_3$) δ 8.61 (br, 1H), 7.34 (d, J=8.8 Hz, 2H), 7.25 (m, 4H), 7.08 (d, J=8.3 Hz, 2H), 5.99 (br, 1H), 3.70 (s, 3H), 3.28 (t, J=5.9 Hz, 2H), 2.68 (br, 4H), 2.59 (t, J=5.9 Hz, 2H), 2.53 (t, J=6.8 Hz, 2H), 2.35 (t, J=7.1 Hz, 2H), 1.79 (m, 2H), 1.68 (m, 2H).

Compound 32, Methyl 4-[[4-(4-bromophenylureido) butyl](1,2,3,4-tetrahydro-1-naphthyl)amino]butylate, can be obtained in an analogous manner to that described for compound 29 and contains the following characteristics: MS(ES$^+$) m/e 516 [M+H]$^+$; $^1$H NMR (400 MHz, $CDCl_3$) δ 8.09 (br, 1H), 7.62 (m, 1H), 7.31 (d, J=8.8 Hz, 2H), 7.20 (d, J=8.8 Hz, 2H), 7.10 (m, 2H), 7.03 (m, 1H), 5.37 (m, 1H), 3.89 (m, 1H), 3.66 (s, 3H), 3.17 (m, 2H), 2.70 (m, 2H), 2.51–2.29 (m, 6H), 1.96 (m, 2H), 1.76 (m, 2H), 1.68–1.40 (m, 6H).

Compound 33, Methyl 4-[[5-(4-bromophenylureido) pentyl](1,2,3,4-tetrahydro-1-naphthyl)amino]butylate, can be obtained in an analogous manner to that described for compound 29 and contains the following characteristics: MS(ES$^+$) m/e 530 [M+H]$^+$; $^1$H NMR (400 MHz, $CDCl_3$) δ 7.63 (m, 1H), 7.32 (d, J=8.8 Hz, 2H), 7.29 (br, 1H), 7.21 (d, J=9.0 Hz, 2H), 7.09 (m, 2H), 7.02 (m, 1H), 5.31 (m, 1H), 3.90 (m, 1H), 3.66 (s, 3H), 3.20 (m, 2H), 2.71 (m, 2H), 2.49–2.27 (m, 6H), 1.97 (m, 2H), 1.76 (m, 2H), 1.60 (m, 2H), 1.43 (m, 4H), 1.27 (m, 2H).

Compound 34, Methyl 4-[[3-(4-methylphenylureido) propyl](1,2,3,4-tetrahydro-1-naphthyl)amino]butylate, can be obtained in an analogous manner to that described for compound 29 and contains the following characteristics: MS(ES$^+$) m/e 438 [M+H]$^+$; $^1$H NMR (400 MHz, DMSO-d6) δ 8.21 (br, 1H), 7.59 (d, J=7.6 Hz, 1H), 7.24 (d, J=8.5 Hz, 2H), 7.13–6.99 (m, 5H), 5.98 (t, J=5.6 Hz, H1), 3.90 (dd, J=9.5, 4.9 Hz, 1H), 3.54 (s, 3H), 3.11 (m, 1H), 3.02 (m, 1H), 2.67 (m, 2H), 2.43–2.23 (m, 6H), 2.20 (s, 3H), 1.94 (m, 2H), 1.70–1.50 (m, 6H).

Compound 35, Methyl 4[[3-(3,4-dichlorophenylureido) propyl](1,2,3,4-tetrahydro-1-naphthyl)amino]butylate, can be obtained in an analogous manner to that described for compound 29 and contains the following characteristics: MS(ES$^+$) m/e 492 [M+H]$^+$; $^1$H NMR (400 MHz, DMSO-d6) δ 9.20 (br, 1H), 7.89 (d, J=2.4 Hz, 1H), 7.64 (d, J=7.3 Hz, 1H), 7.49 (d, 3=8.8 Hz, 1H), 7.28 (dd, J=8.8, 2.4 Hz, 1H), 7.19–7.07 (m, 3H), 6.27 (m, 1H), 3.95 (m, 1H), 3.60 (s, 3H), 3.18 (m, 1H), 3.10 (m, 1H), 2.73 (m, 2H), 2.57–2.29 (m, 6H), 2.00 (m, 2H), 1.74–1.54 (m, 6H).

Compound 172, Methyl 4-[[3-(4-bromophenylureido) propyl](1-indanyl)amino]butylate, can be obtained in an analogous manner to that described for compound 29 and contains the following characteristics: MS(ES$^+$) m/e 490 [M+H]$^+$; $^1$H NMR (400 MHz, $CDCl_3$) δ 8.32 (bs, 1H), 7.43 (m, 1H), 7.30 (m, 2H), 7.26 (m, 2H), 7.20 (m, 3H), 5.77 (br, 1H), 4.50 (m, 1H), 3.65 (s, 3H), 3.27 (m, 2H), 2.82 (m, 2H), 2.51 (m, 1H), 2.40 (m, 4H), 2.31 (m, 1H), 2.04 (m, 1H), 1.95 (m, 1H), 1.81 (m, 2H), 1.66 (m, 2H).

Compound 178, Methyl 4-[[3-(4-bromophenylureido) propyl][(1R)-1-indanyl]amino]butylate, can be obtained in an analogous manner to that described for compound 29 and contains the following characteristics: MS(ES$^+$) m/e 490 [M+H]$^+$; $^1$H NMR (400 MHz, $CDCl_3$) δ 8.24 (br, 1H), 7.31 (m, 3H), 7.26 (m, 3H), 7.20 (m, 2H), 5.69(br, 1H), 4.50 (t, J=6.8 Hz, 1H), 3.66 (s, 3H), 3.28 (m, 2H), 2.90–2.77 (m, 2H), 2.52–2.26 (m, 6H), 2.05 (m, 1H), 1.95 (m, 1H), 1.81 (m, 2H), 1.66 (m, 2H).

Compound 180, Methyl 4-[[3-(4-bromophenylureido) propyl][(1R)-1,2,3,4-tetrahydro-1-naphthyl]amino]butylate, can be obtained in an analogous manner to that described for compound 29 and contains the following characeristics: MS(ES$^+$) m/e 504 [M+H]$^+$; $^1$H NMR (400 MHz, $CDCl_3$) δ 8.19 (br, 1H), 7.58 (d, J=6.8 Hz, 1H), 7.31 (d, J=8.8 Hz, 2H), 7.20 (d, J=8.8 Hz, 2H), 7.12 (m, 2H), 7.05 (d, J=6.9 Hz, 1H), 5.43 (br, 1H), 3.95 (m, 1H), 3.66 (s, 3H), 3.24 (m, 2H), 2.70 (m, 2H), 2.55–2.36 (m, 5H), 2.27 (m, 1H), 1.94 (m, 2H), 1.79 (m, 2H), 1.62 (m, 4H).

Compound 184, Ethyl 4[[3-(4-bromophenylureido) propyl](1,2,3,4-tetrahydro-1-naphthyl)amino]butylate, can be obtained in an analogous manner to that described for compound 29 and contains the following characteristics:

MS($ES^+$) m/e 516 $[M+H]^+$; $^1H$ NMR (400 MHz, $CDCl_3$) δ 7.54 (d, J=7.3 Hz, 1H), 7.27 (d, J=8.8 Hz, 2H), 7.19 (d, J=8.8 Hz, 2H), 7.09 (m, 2H), 7.01 (d, J=6.8 Hz, 1H), 5.33 (br, 2H), 4.06 (q, J=7.1 Hz, 2H), 3.98 (m, 1H), 3.26 (m, 1H), 3.20 (m, 1H), 2.65 (m, 2H), 2.61–2.31 (m, 5H), 2.22 (m, 1H), 1.91 (m, 2H), 1.74 (m, 2H), 1.60 (m, 4H), 1.18 (t, J=7.1 Hz, 3H).

Compounds 36–59, 174, 176, 182, 185, 187, 189, 194, 198, 200, 206, 208, 212, 213, 224 can be obtained in an analogous manner to that of Compound 29.

Example 4

Synthesis of 4[[3-(4-Bromophenylureido)propyl](1,2,3,4-tetrahydro-1-naphthyl)amino]butanoic acid (Compound 60)

The following synthesis is depicted in Scheme 4.

Lithium hydroxide monohydrate (14 mg, 0.33 mmol) was added to a solution of methyl 4[[3-(4-bromophenylureido)propyl](1,2,3,4-tetrahydro-1-naphthyl)amino]butylate (Compound 29, 83 mg, 0.17 mmol) in 10% water/methanol (2 ml). After stirring at RT for 16 h, additional lithium hydroxide monohydrate (14 mg, 0.33 mmol) was added. The reaction mixture was stirred at RT for 6 h, and then concentrated under vacuum to dryness. The residue was dissolved with ether and water, and partitioned. The water layer was acidified with 1N—HCl (pH=1), extracted with ethyl acetate, washed with brine, dried over sodium sulfate, and filtered. The filtrate was concentrated under vacuum to dryness. The residue was adsorbed on a plate of silica gel and the plate was developed with 17% methanol/chloroform to afford 4[[3-(4-bromophenylureido)propyl](1,2,3,4-tetrahydro-1-naphthyl)amino]butanoic acid (44 mg, 53%): MS($ES^+$) m/e 488 $[M+H]^+$; $^1H$ NMR (400 MHz, $CDCl_3$) δ 9.40 (br, 1H), 8.76 (br, 1H), 7.72 (m, 1H), 7.38 (m, 4H), 7.23 (m, 3H), 0.35 (br, 1H), 4.92 (br, 1H), 2.97 (m, 2H), 2.85–2.65 (m, 8H), 2.18 (m, 2H), 2.00 (m, 2H), 1.67 (m, 4H).

Compound 61, 4-[[3-(4-Bromophenylureido)propyl][(1R)-1-phenylethyl]amino]-butanoic acid, can be obtained in an analogous manner to that described for compound 60 and contains the following characteristics: MS($ES^+$) m/e 462 $[M+H]^+$; $^1H$ NMR (400 MHz, $CDCl_3$) δ 8.80 (br, 1H), 7.50 (br, 1H), 7.40–7.25 (m, 9H), 6.90 (br, 1H), 4.31 (br, 1H), 3.23 (m, 2H), 2.50–2.21 (m, 6H), 1.74 (m, 4H), 1.27 (m, 3H).

Compound 62, 4-[[4-(4-Bromophenylureido)butyl](1,2,3,4-tetrahydro-1-naphthyl)-amino]butanoic acid, can be obtained in an analogous manner to that described for compound 60 and contains the following characteristics: MS($ES^+$) m/e 502 $[M+H]^+$; $^1H$ NMR (400 MHz, $CD_3OD$) δ 7.52 (d, J=7.3 Hz, 1H), 7.38–7.24 (m, 7H), 5.01 (t, J=7.5 Hz, 1H), 3.20 (br, 2H), 2.92–2.76 (m, 4H), 2.45–2.29 (m, 4H), 2.04 (m, 4H), 1.87 (m, 2H), 1.75 (m, 2H), 1.53 (br, 2H).

Compound 63, 4-[[5(4-Bromophenylureido)pentyl](1,2,3,4-tetrahydro-1-naphthyl)-amino]butanoic acid, can be obtained in an analogous manner to that described for compound 60 and contains the following characteristics: MS($ES^+$) m/e 516 $[M+H]^+$; $^1H$ NMR (400 MHz, $CD_3OD$) δ 7.53 (d, J=7.1 Hz, 1H), 7.36–7.24 (m, 7H), 5.01 (t, J=7.5 Hz, 1H), 3.17 (br, 2H), 2.91–2.76 (m, 4H), 2.45–2.28 (m, 4H), 2.04 (m, 4H), 1.84 (m, 2H), 1.75 (m, 2H), 1.51 (m, 2H), 1.35 (m, 2H).

Compound 64, 4-[[3-(4-Methylphenylureido)propyl](1,2,3,4-tetrahydro-1-naphthyl)-amino]butanoic acid, can be obtained in an analogous manner to that described for compound 60 and contains the following characteristics: MS($ES^{30}$ ) m/e 424 $[M+H]^+$; $^1H$ NMR (400 MHz, DMSO-d6) δ 9.29 (br, 1H), 8.31 (br, 1H), 7.67 (br, 1H), 7.25 (m, 4H), 7.02 (m, 3H), 6.15 (br, 1H), 4.90 (br, 1H), 2.99 (m, 2H), 2.71–2.48 (m, 8H), 2.21 (s,3H), 2.20 (m, 2H), 1.93 (m, 2H), 1.64 (m, 4H).

Compound 65, 4[[3-(3,4-Dichlorophenylureido)propyl](1,2,3,4-tetrahydro-1-naphthyl)amino]butanoic acid, can be obtained in an analogous manner to that described for compound 60 and contains the following characteristics: MS($ES^+$) m/e 478 $[M+H]^+$; $^1H$ NMR (400 MHz, DMSO-d6) δ 9.23 (br, 1H), 8.95 (br, 1H), 7.82 (br, 1H), 7.69 (br, 1H), 7.45 (d, J=8.8 Hz, 1H), 7.29–7.18 (m, 4H), 6.38 (br, 1H), 4.91 (br, 1H), 3.00 (m, 2H), 2.74–2.65 (m, 8H), 2.18 (m, 2H), 1.94 (m, 2H), 1.65 (m, 4H).

Compound 171, 4-[[3-(4-Chlorophenylureido)propyl](1,2,3,4-tetrahydro-1-naphthyl)amino]butanoic acid, can be obtained in an analogous manner to that described for compound 60 and contains the following characteristics: MS($ES^+$) m/e 444 $[M+H]^+$; $^1H$ NMR (400 MHz, DMSO-d6) δ 8.99 (s, 1H), 8.31 (s, 1H), 7.66 (m, 1H), 7.46 (m, 4H), 7.24 (m, 3H), 6.21 (br, 1H), 4.87 (m, 1H), 3.00 (m, 2H), 2.72–2.49 (m, 8H), 2.18 (m, 2H), 1.93 (m, 2H), 1.65 (m, 4H).

Compound 173, 4-[[3-(4-Bromophenylureido)propyl](1-indanyl)amino]butanoic acid, can be obtained in an analogous manner to that described for compound 60 and contains the following characteristics: MS($ES^+$) m/e 476 $[M+H]^+$; $^1H$ NMR (400 MHz, $CD_3OD$) δ 7.63 (m, 1H), 7.39 (m, 2H), 7.34 (m, 4H), 7.27 (m, 1H), 5.25 (dd, J=8.5, 3.4 Hz, 1H), 3.30 (m, 2H), 3.19 (m, 6H), 3.03 (m, 2H), 2.53 (m, 1H), 2.41 (m, 3H), 2.03 (m, 2H).

Compound 179, 4[[3-(4-Bromophenylureido)propyl][(1R)-1-indanyl]amino]butanoic acid, can be obtained in an analogous manner to that described for compound 60 and contains the following characteristics: MS($ES^+$) m/e 476 $[M+H]^+$; $^1H$ NMR (400 MHz, $CD_3OD$) δ 7.63 (d, J=7.8 Hz, 1H), 7.38 (m, 3H), 7.33 (m, 3H), 7.27 (m, 11), 5.24 (dd, J=8.6, 3.7 Hz, 1H), 3.29 (m, 4H), 3.18 (m, 4H), 3.02 (m, 2H), 2.53 (m, 1H), 2.41 (m, 3H), 2.02 (m, 2H).

Compound 181, 4-[[3-(4-Bromophenylureido)propyl][((1R)1,2,3,4-tetrahydro-1-naphthyl]amino]butanoic acid, can be obtained in an analogous manner to that described for compound 60 and contains the following characteristics: MS($ES^+$) m/e 490 $[M+H]^+$; $^1H$ NMR (400 MHz, $CD_3OD$) δ 7.64 (m, 1H), 7.39 (d, J=9.0 Hz, 2H), 7.33 (d, J=9.0 Hz, 2H), 7.29 (m, 2H), 7.20 (m, 1H), 5.06 (m, 1H), 3.24 (m, 6H), 2.91–2.76 (m, 4H), 2.33 (m, 4H), 2.02 (m, 4H).

Compound 227, 4[[3-(4-Bromophenylureido)propyl][(1R)-1-(4-methoxyphenyl)ethyl]amino]butanoic acid, can be obtained in an analogous manner to that described for compound 60 and contains the following characteristics: MS($ES^+$) m/e 494 $[M+H]^+$; $^1H$ NMR (400 MHz, $CDCl_3$) δ 9.57 (s, 1H), 7.88 (br, 1H), 7.44 (d, J=8.8 Hz, 2H), 7.30 (d, J=8.8 Hz, 2H), 7.27 (m, 1H), 6.90 (m, 4H), 4.24 (q, J=6.8 Hz, 1H), 3.75 (s, 3H), 3.26 (m, 2H), 3.13 (m, 1H), 2.98 (m, 1H), 2.91 (m, 2H), 2.43 (m, 2H), 1.90 (m, 3H), 1.81 (m, 1H), 1.63 (d, J=6.8 Hz, 3H).

Compounds 66–90, 175, 177, 183, 186, 188, 190, 195, 199, 201, 207, 209, 211, 214, 223, 226 can be obtained in an analogous manner to that of Compound 60.

Example 5

Synthesis of [3-(Phenylureido)propyl][2-(4-chlorophenyl)ethyl]-diethylammonium iodide (Compound 91).

The following synthesis is depicted in Scheme 5.

A solution of N-phenylcarbamoyl-N'-[2-(4-chlorophenyl)ethyl]-N'-ethyl-1,3-diaminopropane (Compound 1, 13.7 mg, 0.0381 mmol) in ethyl iodide (2 ml) was refluxed for 3 h, and concentrated under vacuum to dryness. The residue was adsorbed on a plate of silica gel and the plate was developed with 17% methanol/chloroform to afford [3-(phenylureido)propyl][2-(4-chlorophenyl)ethyl]diethylammonium iodide (15.4 mg, 78%): MS($ES^+$) m/e 388 $[M-I]^+$; $^1H$ NMR (400 MHz, $CDCl_3$) δ 8.15 (br, 1H), 7.35 (d, J=7.6 Hz, 2H), 7.16 (m, 6H), 6.90 (m, 1H), 6.54 (m, 1H), 3.50 (m, 2H), 3.33 (m, 6H), 3.25 (m, 2H), 2.96 (m, 2H), 1.91 (m, 2H), 1.28 (t, J=7.1 Hz, 6H).

Compound 92, [3-(4-Bromophenylureido)propyl][2-(4-chlorophenyl)ethyl]-diethylammonium iodide, can be obtained in an analogous manner to that described for compound 91 and contains the following characteristics: MS($ES^+$) m/e 466 $[M-I]^+$; $^1H$ NMR (400 MHz, $CDCl_3$) δ 8.25 (br, 1H), 7.30 (d, J=9.0 Hz, 2H), 7.22 (d, J=8.8 Hz, 2H), 7.18 (d, J=8.3 Hz, 2H), 7.12 (d, J=8.3 Hz, 2H), 6.67 (t, J=6.0 Hz, 1H), 3.60 (m, 2H), 3.32 (m, 6H), 3.24 (m, 2H), 2.98 (m, 2H), 1.91 (m, 2H), 1.30 (t, J=7.2 Hz, 6H).

Compound 298, [3-(Phenylureido)propyl][2(4-chlorophenyl)ethyl](4 chlorobenzyl)ethylammonium iodide, can be obtained in an analogous manner to that described for compound 91 and contains the following characteristics: MS($ES^+$) m/e 484 $[M-I]^+$; $^1H$ NMR (400 MHz, $CDCl_3$) δ 8.00 (s, 1H), 7.40 (m, 4H), 7.34 (d, J=8.5 Hz, 2H), 7.11 (m, 6H), 6.87 (t, J=7.3 Hz, 1H), 6.73 (t, J=6.1 Hz, 1H), 4.65 (d, J=13.4 Hz, 1H), 4.57 (d, J=13.4 Hz, 1H), 3.78 (m, 1H), 3.66 (m, 1H), 3.39 (m, 1H), 3.29 (m, 2H), 3.19 (m, 4H), 3.11 (m, 1H), 2.00 (m, 2H), 1.41 (t, J=7.1 Hz, 3H).

Compound 302, [3-(Phenylureido)propyl][2-(4-chlorophenyl)ethyl](benzyl)ethylammonium iodide, can be obtained in an analogous manner to that described for compound 91 and contains the following characteristics: MS($ES^+$) m/e 450 $[M-I]^+$; $^1H$ NMR (400 MHz, $CD_3OD$) δ 7.60 (m, 2H), 7.51 (m, 3H), 7.33 (m, 6H), 7.26 (m, 2H), 7.00 (m, 1H), 4.63 (s, 2H), 3.48–3.30 (m, 8H), 3.18 (m, 2H), 2.17 (m, 2H), 1.51 (t, 1=7.1 Hz, 3H).

Compound 309, [3-(Phenylureido)propyl][2-(3-chlorophenyl)ethyl]diethylammonium iodide, can be obtained in an analogous manner to that described for compound 91 and contains the following characteristics. MS($ES^+$) m/e 388 $[M-I]^+$; $^1H$ NMR (400 MHz, $CDCl_3$/$CD_3OD$) δ 8.09 (s, 1H), 7.39 (d, J=8.5 Hz, 2H), 7.13 (m, 5H), 7.08 (d, J=7.3 Hz, 1H), 6.88 (t, J=7.3 Hz, 1H), 6.69 (m, 1H), 3.65 (m, 2H), 3.35 (m, 6H), 3.24 (m, 2H), 3.00 (m, 2H), 1.93 (m, 2H), 1.32 (t, J=7.1 Hz, 6H).

Compound 320, [3-(Phenylureido)propyl][2(4-chlorophenyl)etyl][4-(methoxycarbonyl)butyl]ethylammonium iodide, can be obtained in an analogous manner to that described for compound 91 and contains the following characteristics: MS($ES^+$) m/e 474 $[M-I]^+$; $^1H$ NMR (400 MHz, $CD_3OD$) δ 7.36 (m, 2H), 7.32 (m, 4H), 7.24 (m, 2H), 6.98 (m, 1H), 3.66 (s, 3H), 3.44 (m, 6H), 3.31 (m, 4H), 3.05 (m, 2H), 2.44 (m, 2H), 1.98 (m, 2H), 1.78 (m, 2H), 1.67 (m, 2H), 1.36 (m, 3H).

Compound 323, [5-(Phenylureido)pentyl][2-(4 (chlorophenyl)ethyl]diethylammonium iodide, can be obtained in an analogous manner to that described for compound 91 and contains the following characteristics: MS($ES^+$) m/e 416 $[M-I]^+$; $^1H$ NMR (400 MHz, $CDCl_3$) δ 8.37 (bs, 1H), 7.53 (d, J=7.6 Hz, 2H), 7.24 (m, 4H), 7.16 (m, 2H), 6.89 (t, J=7.3 Hz, 1H), 6.40 (m, 1H), 3.43–3.28 (m, 10H), 3.01 (m, 2H), 1.78 (m, 2H), 1.58 (m, 4H), 1.29 (t, J=7.3 Hz, 6H).

Compound 343, [3-(Phenylureido)propyl][2-(4-chlorophenyl)ethyl](2-chlorobenzyl)ethylammonium iodide, can be obtained in an analogous manner to that described for compound 91 and contains the following characteristics: MS($ES_+$) m/e 484 $[M-I]^+$; $^1H$ NMR (400 MHz, $CDCl_3$) δ 8.23 (bs, 1H), 7.71 (dd, J=7.6, 1.5 Hz, 1H), 7.48 (m, 4H), 7.40 (m, 1H), 7.22 (m, 2H), 7.18 (m, 4H), 7.09 (m, 1H), 6.93 (m, 1H), 4.80 (d, J=2.2 Hz, 2H), 3.98 (m, 2H), 3.57–3.48 (m, 6H), 3.12 (m, 2H), 2.13 (m, 2H), 1.49 (t, J=7.1 Hz, 3H).

Compound 351, [3-(Phenylureido)propyl][2-(chlorophenyl)ethyl](2,5-difluorobenzyl)ethylammonium iodide, can be obtained in an analogous manner to that described for compound 91 and contains the following characteristics: MS($ES^+$) m/e 486 $[M-I]^+$; $^1H$ NMR (400 MHz, $CDCl_3$) δ 8.15 (bs, 1H), 7.43 (m, 3H), 7.18–7.10 (m, 7H), 6.92–6.84 (m, 3H), 4.75 (d, J=13.9 Hz, 1H), 4.69 (d, J=13.9 Hz, 1H), 3.85 (m, 2H), 3.47–3.26 (m, 6H), 3.18 (m, 2H), 2.11 (m, 2H), 1.47 (t, J=7.1 Hz, 3H).

Compound 352, [3-(Phenylureido)propyl][2-(4-chlorophenyl)ethyl](3-fluorobenzyl)ethylammonium iodide, can be obtained in an analogous manner to that described for compound 91 and contains the following characteristics: MS($ES^+$) m/e 470 $[M-I]^+$; $^1H$ NMR (400 MHz, $CDCl^3$) δ 8.14 (bs, 1H), 7.42 (m, 4H), 7.34 (d, J=7.8 Hz, 1H), 7.23 (m, 1H), 7.17 (m, 6H), 6.91 (m, 1H), 6.77 (m, 1H), 4.73 (d, J=13.7 Hz, 1H), 4.67 (d, J=13.7 Hz, 1H1), 3.74 (m, 2H), 3.45-3.11 (m, 8H), 2.08 (m, 2H), 1.45 (t, J=6.8 Hz, 3H).

Compound 394, [3(4-Cyanophenylureido)propyl][2-(3-chlorophenyl)ethyl][2-(2-methoxyehtoxy)ethyl] ethylammonium iodide, can be obtained in an analogous manner to that described for compound 91 and contains the following characteristics: MS($ES^+$) m/e 487 $[M-I]^+$; $^1H$ NMR (400 z, $CDCl_3$) δ 8.62 (bs, 1H), 7.59 (d, J=8.8 Hz, 2H), 7.40 (d, J=9.1 Hz, 2H), 7.13 (m, 3H), 7.06 (m, 1H), 6.96 (t, J=6.1 Hz, 1H), 3.91 (m, 2H), 3.77 (dd, J=11.2, 5.9 Hz, 2H), 3.66–3.35 (m, 12H), 3.23 (s, 3H), 3.07 (t, J=8.8 Hz, 2H), 1.92 (m, 2H), 1.37 (t, J=7.1 Hz, 3H).

Compound 438, [3(4-Methoxyphenylureido)propyl][2-(3-chlorophenyl)ethyl][2-(2-methoxyehtoxy)ethyl] ethylammonium iodide, can be obtained in an analogous manner to that described for compound 91 and contains the following characteristics: MS($ES^+$) m/e 492 $[M-I]^+$; $^1H$ NMR (400 MHz, $CDCl_3$) δ 7.81 (br, 1H), 7.30 (d, J=9.0 Hz, 2H), 7.14 (m, 3H), 7.09 (m, 1H), 6.68 (m, 3H), 3.89 (m, 2H), 3.76 (m, 2H), 3.66 (s, 3H), 3.59 (m, 4H), 3.46–3.37 (m, 8H), 3.23 (s, 3H), 3.03 (m, 2H), 1.91 (m, 2H), 1.34 (t, J=7.1 Hz, 3H).

Compounds 294, 295, 297, 299–301, 303–308, 310–314, 317–319, 321, 324–342, 344–350, 353–393, 395–437, 439–453 can be obtained in an analogous manner to that of Compound 91.

Example 6

Synthesis of Active Compounds by Solid Phase Synthesis

The following synthesis is depicted in Scheme 6.

Step 1: Reductive amination of the linker to the resin. Novabiochem 2-(4-formyl-3-methoxy)phenoxyethyl polystyrene resin (0.5 mmol/g, 100 g, 50 mmol) was added to a 500 ml erlenmyer flask. 3-Chloropropylamine hydrochloride (35.03 g, 0.3 mole), 100 ml of 1% HOAc in DMF, and DIEA (53 ml, 0.3 mole) were added to the flask. The reaction mixture was stirred for one hour, $NaBH(OAc)_3$ (0.3 mole) was added and the reaction was stirred for four hours.

The reaction mixture was poured into a 1000 ml sintered glass funnel and the solvent was removed by vacuum. DMF (500 ml) was added and the solution was mixed thoroughly for five minutes. A vacuum again removed the solvent. This wash process was repeated two times. The resin was then washed in this manner three times with MeOH, three times with DCM, and three times with MeOH. The final resin was dried under a vacuum until constant weight.

Step 2: Protection of linker. The resin prepared above (30 g, 15 mmole) was placed into a 250 ml roundbottom flask. To this flask, DCM was added until a thick slurry was obtained. DIEA (31.3 ml, 90 mmole) was added followed by the p-nitrabenzylchloroformate, which was added in 5 g batches as a solid (19.4 g, 45 mmole) while being stirred magnetically. The reaction was stirred for two hours. The reaction mixture was poured into a 1 L sintered glass funnel and a vacuum removed the solvent. The resin was resuspended in DCM and mixed thoroughly for five minutes before the solvent was again removed. This was repeated two more times with DCM, and three times with MeOH. The resin was dried under a vacuum until constant weight.

Step 3: Displacement of chlorine by amine. The protected resin prepared above was transferred to a 96 well polyfiltronics plate (80 mg, 0.04 mmole per well). The plate was placed onto a vacuum block and the resin was washed into their wells with DMSO. The solvent was removed by vacuum. The plate was transferred onto a clamp and the bottom was sealed. To each of the wells with resin, a solution of TBAI (300 $\mu$l, 0.16 M) in DMSO and amine (R1-NH2, 0.26 mmole) were added. The plate was sealed from the top and placed into an oven at 80° C. for 48 hours.

The plate was unclamped and placed onto the vacuum block where the solvent was removed by vacuum. The plate was placed over a catch tray and each well with resin received roughly 1.5 ml of DMSO each with a squirt bottle. The solvent was allowed to drain by gravity, then the remaining solvent was removed by vacuum. This was repeated two more times with DMSO, three times with MeOH, three times with DCM, and three more times with MeOH. The plate was dried under a vacuum.

Step 4: Reductive amination of secondary amine. The plate was placed onto the vacuum block and the resin was washed down with a solution of 30% EtOH in DMF. The solvent was removed with a vacuum. The plate bottom was sealed with the clamp and the 30% EtOH in DMF (300 $\mu$l) was added to each well with resin. Aldehydes (R2-CHO, 0.2 mmole) were added to their respective wells. The plate was sealed from the top and shaken for 2 hours. The plate was unclamped from the top and BAP (0.2 mmole) was added to each of the wells with resin. The plate was then reclamped and shaken for 48 hours. The plate was unclamped and a vacuum removed the solvent. Each well was washed three times with DMF, three times MeOH, and three times DCM.

Step 5: Deprotection of the p-nitrobenzyl carbamate. A solution of $SnCl_2$ dihydrate in DMF (2.0 M) was prepared. The plate was again clamped and to each of the wells with resin, this solution was added (0.5 ml). The top of the plate was sealed and was allowed to stand overnight. The plate was unclamped, and washed two times with DMF. This deprotection was repeated a second time. The final wash solvents were three times DMF, three times MeOH, three times DMF, two times MeOH, then three times DCM.

Step 6: Acylation of linker. To the deprotected plate, a solution of DIEA in THF (150 $\mu$l, 1.2 M) was added to all wells containing resin. These wells each received the respective isocyanates (R3-NCO, 0.09 mmole) in THF (150 $\mu$l). The plate was sealed and allowed to stand for three hours. The plate was unclamped and washed with the following solvents: three times DCM, three times MeOH, three times DMF, three times MeOH, then three times DCM. The plate was dried under a vacuum.

Step 7: Isolation of Final Products. The dried plate was placed into the HCl gas cleavage apparatus. The system was flushed with nitrogen for ten minutes followed by a 10 minute flush with HCl gas. The system was sealed and the plate was allowed to sit for one hour in HCl gas. The system was recharged after the hour and the plate was allowed to sit for an additional hour. The system was flushed with nitrogen for ten minutes and the plate was removed. The plate was placed on a tarred 2 ml deepwell plate and the resin treated with a DCM wash (300 $\mu$l). The solvent was allowed to drain by gravity and was followed by a MeOH wash (300 $\mu$l). The process was repeated with a DCM and two MEOH washes. The collected filtrate was left out to dry overnight. The final material was placed into a desicator and was dried under a vacuum. The dried plate was weighed and the yield calculated; each well had an average weight of 12 mg.

Example 7

Synthesis of N-phenylcarbamoyl-N'-[2-(4-chlorophenyl)ethyl]-N'-ethyl 2-hydroxy-1.3-diaminopropane (Compound 163)

The following synthesis is depicted in Scheme 7.

Step1: To a suspension of potassium phthalimide (5.0 g, 27 mmol) in DMF (75 ml) was added epibromohydrin (2.5 ml, 29 mmol), and the mixture was stirred at 120° C. for 3 h. After adding water, the mixture was extracted with (hexane/ethyl acetate=3/1), washed with brine, dried over magnesium sulfate, and then filtered. Concentrating under vacuum gave N-(2,3-epoxypropyl)phthalimide (2.81 g, 51%) which was used in the next step without further purification.

Step2: To a mixture of 2-(4-chlorophenyl)ethylamine (3.00 g, 19.3 mmol) and acetaldehyde (1.40 ml, 25.0 mmol) in MeOH (30 ml) were added $NaBH_3CN$ (1.33 g, 21.2 mmol) and HOAc (1.22 ml, 21.3 mmol), and the mixture was stirred at RT for 24 h. After adding saturated $NaHCO_3$ and water, the mixture was extracted with chloroform, washed with brine, dried over magnesium sulfate, and then filtered. The filtrate was concentrated under vacuum to dryness, and the residue was dissolved in o-dichlorobenzene (40 ml). To the solution was added N-(2,3-epoxypropyl) phthalimide (2.81 g), and the solution was stirred at 140° C. for 13 h. The reaction mixture was chromatographed on silica gel (eluting with 1% methanol/chloroform) to afford N-[3-[[2-(4-chlorophenyl)ethyl](ethyl)amino]-2-hydroxypropyl]phthalimide (2.30 g, 31%): MS($ES^+$) m/e 387 $[M+H]^+$; $^1H$ NMR (400 MHz, $CDCl_3$) δ 7.86 (dd, J=5.4, 3.2 Hz, 2H), 7.73 (dd, J=5.4, 2.9 Hz, 2H), 7.24 (d, J=8.3 Hz, 2H), 7.11 (d, J=8.3 Hz, 2H), 3.96 (m, 2H), 3.81 (dd, J=13.9, 6.8 Hz, 1H), 3.70 (dd, J=13.9, 4.6 Hz, 1H), 2.90–2.60 (m, 8H), 1.09 (br, 3H).

Step3: To a solution of N-[3-[[2-(4 chlorophenyl)ethyl](ethyl)amino]-2-hydroxypropyl]phthalimide (2.27 g, 5.88 mmol) in EtOH (50 ml) was added hydrazine monohydrate (1.15 ml, 23.7 mmol), and the mixture was stirred at RT for 5 h. After adding 1N-HCl, the mixture was washed with chloroform, neutralized with 1N-NaOH, and then washed with chloroform. After adding 1N-NaOH (pH=12), the mixture was extracted with chloroform, washed with brine, dried over magnesium sulfate, and filtered. The filtrate was concentrated under vacuum to dryness, and the residue was dissolved in $CH_2Cl_2$ (30 ml). To the solution was added phenyl isocyanate (0.35 ml, 3.2 mmol), and the solution was stirred at RT for 3 h. The reaction mixture was chromatographed on silica gel (eluting with 2% methanol/chloroform to 10% methanol/chloroform) to afford N-phenylcarbamoyl-N'phenylcarbamoyl-N'-[2-(4-chlorophenyl)ethyl]-N'-ethyl-2-hydroxy-1,3-diaminopropane (828 mg, 38%): MS($ES^+$) m/e 376 $[M+H]^+$; $^1H$ NMR (400 MHz, $CDCl_3$) δ 7.31 (m, 5H), 7.24 (d, J=8.3 Hz, 2H), 7.08 (d, J=8.5 Hz, 2H), 7.05 (m, 2H), 5.44 (br, 1H), 3.73 (m, 1H), 3.47 (m, 1H), 3.12 (dt, J=14.1, 5.9 Hz, 1H), 2.85–2.45 (m, 8H), 1.05 (t, J=7.1 Hz, 3H).

Example 8

Synthesis of 4-[[3-(4-chlorophenylthioureido)propyl](1,2,3,4-tetrahydro-1-naphthyl)amino]butanoic acid (Compound 164)

The following synthesis is depicted in Scheme 8.

Step 1: To a solution of methyl 4-[[(3-phthalimido)propyl](1,2,3,4-tetrahydro-1-naphthyl)amino]butylate (39 mg, 0.09 mmol) in EtOH (1 ml) was added hydrazine monohydrate (23 μl, 0.45 mmol), and the mixture was stirred at RT for 3.5 h. After adding water, the mixture was extracted with chloroform, washed with water and brine, dried over sodium sulfate, and filtered. To the filtrate was added 4-chlorophenyl isothiocyanate (17 mg, 0.1 mmol), and the mixture was stirred at RT for 30 min. The residue was adsorbed on a plate of silica gel and then developed with 3% methanol/chloroform to afford methyl 4-[[3-(4-chlorophenylthioureido)propyl](1,2,3,4-tetrahydro-1-naphthyl)amino]butylate (25 mg, 29%): MS($ES^+$) m/e 474 $[M+H]^+$; $^1H$ NMR (400 MHz, $CDCl_3$) δ 7.66 (br, 1H), 7.56 (d, J=7.3 Hz, 1H), 7.32 (m, 2H), 7.12–7.01 (m, 5H), 6.14 (br, 1H), 3.93 (m, 1H), 3.68 (m, 1H), 3.64 (s, 3H), 3.63 (m, 1H), 2.71 (m, 2H), 2.50–2.25 (m, 6H), 1.96 (m, 2H), 1.79–1.53 (m, 6H).

Step2: To a solution of methyl 4-[[3-(4-chlorophenylthioureido)propyl](1,2,3,4-tetrahydro-1-naphthyl)amino]butylate (25 mg, 0.052 mmol) in 10% water/methanol (4.4 ml) was added lithium hydroxide monohydrate (7.5 mg, 0.18 mmol), and the mixture was stirred at RT for 24 h. The reaction mixture was concentrated under vacuum to dryness, and the residue was adsorbed on a plate of silica gel and then developed with 3% methanol/chloroform to afford 4-[[3-(4-chlorophenylthioureido)propyl](1,2,3,4-tetrahydro-1-naphthyl)amino]butanoic acid (21 mg, 90%): MS($ES^+$) m/e 460 $[M+H]^+$; $^1H$ NMR (400 MHz, $CDCl_3$) δ 10.60 (br, 1H), 9.29 (br, 1H), 7.63 (d, J=8.8 Hz, 2H), 7.57 (d, J=7.6 Hz, 1H), 7.24 (m, 3H), 7.15 (m, 3H), 4.74 (t, J=7.6 Hz, 1H), 3.82 (m, 1H), 3.69 (m, 1H), 3.26 (m, 1H), 3.12 (m, 1H), 2.90 (m, 2H), 2.77 (m, 2H), 2.53 (dd, J=15.6, 7.3 Hz, 1H), 2.26 (m, 2H), 2.15 (m, 1H), 1.99 (m, 2H), 1.83 (m, 2H), 1.71 (m, 2H).

Compound 288, 4-[[3(4-Bromophenylthioureido)propyl][(1R)-1-indanyl]amino]butanoic acid, can be obtained in an analogous manner to that described for compound 164 and contains the following characteristics: MS($ES^+$) m/e 490 $[M+H]^+$; $^1H$ NMR (400 MHz, $CDCl_3$) δ 10.53 (bs, 1H), 9.25 (bs, 1H), 7.58 (d, J=8.8 Hz, 2H), 7.51 (d, J=7.8 Hz, 1H), 7.40 (d, J=8.8 Hz, 2H), 7.30 (m, 3H), 7.16 (m, 1H), 4.95 (m, 1H), 3.81 (m, 1H), 3.67 (m, 1H), 3.12–2.94 (m, 4H), 2.87 (m, 2H), 2.59 (dd, J=16.3, 7.3 Hz, 1H), 2.41 (m, 1H), 2.19 (m, 3H), 2.01 (m, 2H), 1.77 (m, 1H).

Compound 290, 4-[[3(4-Bromophenylthioureido)propyl][(1R)-1,2,3,4-tetrahydro-1-naphthyl]amino]butanoic acid, can be obtained in an analogous manner to that described for compound 164 and contains the following characteristics: MS($ES^+$) m/e 504 $[M+H]^+$; $^1H$ NMR (400 MHz, $CDCl_3$) δ 10.50 (br, 1H), 9.21 (br, 1H), 7.59 (m, 3H), 7.40 (m, 2H), 7.23 (m, 2H), 7.17 (m, 2H), 4.74 (m, 1H), 3.82 (m, 1H), 3.67 (m, 1H), 3.26 (m, 1H), 3.11 (m, 1H), 2.90 (m, 2H), 2.79 (m, 2H). 2.53 (m, 1H), 2.26 (m, 3H), 2.00 (m, 3H), 1.86–1.72 (m, 3H).

Compounds 246–257, 289 can be obtained in an analogous manner to that of Compound 164.

Example 9

Synthesis of 4[[(3S)3-(4-bromophenylureido)-3(tert-butoxycarbonyl)propyl](1,2,3,4-tetrahydro-1-naphthyl)amino]butanoic acid (Compound 165 and 166)

The following synthesis is depicted in Scheme 9.

Step 1: To a mixture of Fmoc-L-Asp(OtBu)-OH (100 mg, 0.243 mmol) and 1,2,3,4-tetrahydro-1-naphthylamine (39 mg, 0.27 mmol) in $CH_2Cl_2$ (1 ml) were added WSC.HCl (51 mg, 0.27 mmol), HOBt.$H_2O$ (36 mg, 0.27 mmol) and triethylamine (34 μl, 0.27 mmol), and the mixture was stirred at RT for 5 h. After adding water, the mixture was extracted with chloroform, washed with brine, dried over magnesium sulfate, and filtered. The filtrate was concentrated under vacuum to dryness, and the residue was adsorbed on a plate of silica gel and then developed with 2.5% methanol/chloroform to afford tert-butyl (2S)-2-[[(9H-9-fluorenylmethoxy)carbonyl]amino]4-oxo-4-1,2,3,4-tetrahydro-1-naphthylarino)butanoate (113 mg, 86%): MS($ES^+$) m/e 541 $[M+H]^+$; $^1H$ NMR (400 MHz, $CDCl_3$) δ 7.70 (d, J=7.6 Hz, 2H), 7.55 (d, J=7.3 Hz, 2H), 7.33 (m, 2H), 7.24 (m, 2H), 7.16–6.97 (m, 4H), 6.05 (dd, J=20.0, 7.8 Hz, 1H), 5.74 (m, 1H), 5.10 (br, 1H), 4.42 (m, 1H), 4.31 (m, 1H), 4.24 (m, 1H), 4.16 (m, 1H), 2.87–2.65 (m, 4H), 1.96 (m, 1H), 1.74 (m, 3H), 1.43 (s, 9H).

Step 2: To a solution of tert-butyl (2S)-2-[[(9H-9-fluorenylmethoxy)carbonyl]amino]-4-oxo-4-(1,2,3,4-tetrahydro-1-naphthylamio)butanoate (43 mg,0.080 mmol) in THF (2 ml) was added $BH_3$-$SMe_2$ (0.20 ml, 0.40 mmol), and the mixture was stirred at RT for 15 h. After adding 1N-HCl (1 ml), the mixture was stirred at RT for 1.5 h, and then 1N-NaOH (1 ml) was added. The mixture was extracted with chloroform, washed with brine, dried over magnesium sulfate, and filtered. The filtrate was concentrated under vacuum to dryness, and the residue was adsorbed on a plate of silica gel and then developed with 6% methanol/chloroform to afford tert-butyl (2S)-2-[[(9H-9-fluorenylmethxy)carbonyl]amino]-4-(1,2,3,4-tetrahydro-1-naphthylamino)butanoate (23 mg, 54%): MS($ES^+$) m/e 527 $[M+H]^+$; $^1H$ NMR (400 MHz, $CDCl_3$) δ 7.69 (dd, J=7.6, 3.9 Hz, 2H), 7.52 (d, J=7.3 Hz, 2H), 7.32 (m, 3H), 7.22 (m, 2H), 7.04 (m, 3H), 6.69 (br, 1H), 6.52 (br, 1H), 4.35–4.10 (m, 4H), 3.70 (m, 1H), 2.86–2.61 (m, 4H), 1.90–1.60 (m, 6H), 1.38 (s, 9H).

Step 3: To a solution of tert-butyl (2S)-2-[[(9H-9-fluorenylmethoxy)carbonyl]amino]-4-(1,2,3,4-tetrahydro-1-naphthylamino)butanoate (16 mg,0.030 mmol) in MeOH (0.5 ml) were added succinic semialdehyde (15 wt. % solution in water, 48 μl, 0.077 mmol), HOAc (2 μl, 0.035 mmol) and $NaBH_3CN$ (2.3 mg, 0.074 mmol), and the mixture was stirred at RT for 6 h. After adding water, the mixture was extracted with chloroform, washed with brine, dried over magnesium sulfate, and filtered. The filtrate was concentrated under vacuum to dryness, and the residue was adsorbed on a plate of silica gel and then developed with 10% methanol/chloroform to afford 4-[[(3S)-3-(tert-butoxycarbonyl)-3-[[(9H-9-fluorenylmethoxy)carbonyl]amino]propyl](1,2,3,4-tetrahydro-1-naphthyl)amino]butanoic acid (18 mg, 98%): MS($ES^+$) m/e 613 $[M+H]^+$; $^1H$ NMR (400 MHz, $CDCl_3$) δ 7.98 (br, 1H), 7.76 (d, J=7.3 Hz, 2H), 7.61 (m, 3H), 7.40 (t, J=7.3 Hz, 2H), 7.31 (m, 2H), 7.15 (m, 2H), 7.06 (d, J7.6 =Hz, 1H), 5.64 (br, 1H), 4.36 (m, 2H), 4.22 (m, 3H), 2.75–2.17 (m, 8H), 2.10–1.65 (m, 8H), 1.42 (s, 9H).

Step 4: To a solution of 4-[[(3S)-3-(tert-butoxycarbonyl)-3-[[(9H-9-fluorenylmethoxy)carbonyl]amino]propyl](1,2,3,4-tetrahydro-1-naphthyl)amino]butanoic acid (18 mg, 0.029 mmol) in DMF (0.4 ml) was added piperidine (0.1 ml), and the mixture was stirred at RT for 1.5 h. The reaction mixture was concentrated under vacuum to dryness, and the residue was dissolved in $CH_2Cl_2$ (0.5 ml). To the solution was added 4-bromophenyl isocyanate (8.7 mg, 0.044 mmol), and the mixture was stirred at RT for 2h. The reaction mixture was adsorbed on a plate of silica gel and then developed with 10% methanol/chloroform to afford 2 diastereoisomers of 4-[[(3S)-3-(4-bromophenylureido)-3-(tert-butoxycarbonyl)propyl](1,2,3,4-tetrahydro-1-naphthyl)amino]butanoic acid (6.8 mg, 39%, less polar isomer, Compound 165): MS($ES^+$) m/e 588 $[M+H]^+$; $^1H$ NMR (400 MHz, $CDCl_3$) δ 9.86 (br, 1H), 8.38 (br, 1H), 7.99 (br, 1H), 7.70 (d, J=7.8 Hz, 1H), 7.42 (d, 1=8.3 Hz, 2H), 7.25 (d, J=8.8 Hz, 2H), 7.08 (m, 3H), 4.81 (t, J=7.3 Hz, 1H), 4.41 (m, 1H), 3.42 (m, 1H), 2.97 (m, 1H), 2.71 (m, 1H), 2.59 (m, 1H), 2.46 (dd, J=16.3, 7.1 Hz, 1H), 2.18 (m, 2H), 1.95–1.74 (m, 4H), 1.62 (m, 1H), 1.48 (m, 1H), 1.32 (s, 9H). (7.4 mg, 43%, more polar isomer, Compound 166): MS($ES^+$) m/e 588 $[M+H]^+$; $^1H$ NMR (400 MHz, $CDCl_3$) δ 9.16 (br, 1H), 8.57 (br, 1H), 7.58 (d, J=8.8 Hz, 1H), 7.42 (br, 1H), 7.33 (d, 1=8.8 Hz, 2H), 7.23 (d, J=8.8 Hz, 2H), 7.15 (m, 2H), 7.07 (m, 1H), 4.57 (t, J=7.3 Hz, 1H), 4.26 (m, 1H), 3.25 (m, 1H), 2.92 (m, 1H), 2.69 (m, 5H), 2.40 (m, 1H), 2.11 (m, 4H), 1.90 (m, 2H), 1.65 (m, 2H), 1.33 (s, 9H).

The absolute configuration at the chiral carbon of 1,2,3,4-tetrahydro-1-naphthyl is not determined.

Example 10

Synthesis of 4-[[3-(4-bromophenylureido)-2-hydroxypropyl](1,2,3,4-tetrahdro-1-naphthyl)amino]butanoic acid (Compound 167)

The following synthesis is depicted in Scheme 10.

Step 1: To a solution of 1,2,3,4-tetrahydro-1-naphthylamine (99 mg, 0.68 mmol) in o-dichlorobenzene (1 ml) was added N-(2,3-epoxypropyl)phthalimide (137 mg, 0.68 mmol), and the mixture was stirred at 150° C. for 4 h. The reaction mixture was chromatographed on silica gel (eluting with 0.5% methanol/chloroform) to afford N-[2-hydroxy-3-(1,2,3,4-tetrahydro-1-naphthylamino)propyl]phthalimide (108 mg, 47%): MS($ES^+$) m/e 351 $[M+H]^+$; $^1H$ NMR (400 MHz, $CDCl_3$) δ 7.78 (m, 2H), 7.66 (m, 2H), 7.36 (m, 1H), 7.10 (m, 2H), 7.02 (m, 1H), 6.77 (br, 1H), 5.09 (m, 1H), 3.98 (m, 1H), 3.86–3.63 (m, 3H), 2.95–2.60 (m, 4H), 1.91–1.66 (m, 4H).

Step 2: To a solution of N-[2-hydroxy-3-(1,2,3,4-tetrahydro-1-naphthylamino)propyl]phthalimide (93 mg, 0.27 mmol) in MeOH (1 ml) were added succinic semialdehyde (15 wt. % solution in water, 220 μl, 0.35 mmol), HOAc (17 μl, 0.30 mmol) and $NaBH_3CN$ (18 mg, 0.29 mmol), and the mixture was stirred at RT for 2.5 h. After adding water, the mixture was extracted with chloroform, washed with brine, dried over magnesium sulfate, and filtered. The filtrate was concentrated under vacuum to dryness, and the residue was adsorbed on a plate of silica gel and then developed with 10% methanol/chloroform to afford 4-[[2-hydroxy-(3-phthalimido)propyl](1,2,3,4-tetrahydro-1-naphthyl)amino]butanoic acid (101 mg, 87%): MS($ES^+$) m/e 437 $[M+H]^+$; $^1H$ NMR (400 MHz, $CDCl^3$) δ 8.01 (br, 1H), 7.80 (m, 2H), 7.73–7.52 (m, 3H), 7.11 (t, J=7.3 Hz, 1H), 7.02 (m, 1H), 6.92–6.78 (m, 1H), 4.63 (br, 1H), 4.44–3.96 (m, 2H), 3.77–3.54 (m, 2H), 2.99–2.81 (m, 1H), 2.77–2.51 (m, 5H), 2.43 (m, 1H), 2.32 (m, 1H), 2.19–2.04 (m, 1H), 1.97 (m, 1H), 1.83 (m, 2H), 1.66 (m, 2H).

Step 3: To a solution of 4[[2-hydroxy-(3-phthalimido)propyl](1,2,3,4-tetrahydro-1-naphthyl)amino]butanoic acid (68 mg, 0.16 mmol) in EtOH (1 ml) was added hydrazine monohydrate (38 μl, 0.78 mmol), and the mixture was stirred at RT for 3 h. The reaction mixture was concentrated under vacuum to dryness, and the residue was suspended in $CH_2Cl_2$ (2 ml). To the suspension was added 4-bromophenyl isocyanate (47 mg, 0.24 mmol), and the mixture was stirred at RT for 40 h. The reaction mixture was adsorbed on a plate of silica gel and then developed with 10% methanol/chloroform to afford 4-[[3-(4-bromophenylureido)2-hydroxypropyl](1,2,3,4-tetrahydro-1-naphthyl)amino]butanoic acid (13 mg, 16%): MS($ES^+$) m/e 504 $[M+H]^+$; $^1H$ NMR (400 MHz, DMSO-d6) δ 8.74 (s, 1H), 8.07 (br, 2H), 7.62 (d, J=7.6 Hz, 1H), 7.36 (m, 4H), 7.13–7.00 (m, 3H), 6.15 (m, 1H), 3.92 (m, 1H), 3.66–3.45 (m, 3H), 2.70 (m, 1H), 2.67 (m, 2H), 2.51 (m, 2H), 2.36 (m, 2H), 2.25 (m, 1H), 2.14 (m, 1H), 2.02 (m, 1H), 1.19 (m, 1H), 1.67–1.49 (m, 3H).

Example 11

Synthesis of 4-[[3-(4-Bromophenylureido)propyl](1,2,3,4-tetrahydro-1-naphthyl)amino]butanamide (Compound 193)

The following synthesis is depicted in Scheme 11.

To a solution of methyl 4-[[3-(4-bromophenylureido)propyl](1,2,3,4-tetrahydro-1-naphthyl)amino]butylate (40 mg, 0.080 mmol) and formamide (11 mg, 0.24 mmol) in DMF (2 ml) was added sodium methoxide (0.5 M solution in MeOH, 112 μl, 0.056 mmol), and the mixture was stirred at 100° C. for 2.5 h. After adding water, the mixture was extracted with chloroform, washed with brine, dried over sodium sulfate, and filtered. The filtrate was concentrated under vacuum to dryness, and the residue was adsorbed on a plate of silica gel and then developed with 10% methanol/chloroform to afford 4-[[3-(4-bromophenylureido)propyl](1,2,3,4-tetrahydro-1-naphthyl)amino]butanamide (17 mg, 43%): MS($ES^+$) m/e 487 $[M+H]^+$; $^1H$ NMR (400 MHz, $CDCl_3$) δ 8.00 (br, 1H), 7.82 (br, 1H), 7.59 (d, J=7.1 Hz, 1H1), 7.31 (s, 4H), 7.12 (m, 2H), 7.05 (m, 1H), 6.08 (br, 1H), 5.64 (br, 1H), 3.99 (m, 1H), 3.41 (m, 1H), 3.22 (m, 1H), 2.70 (m, 1H), 2.61 (m, 1H), 2.55 (m, 1H), 2.39 (m, 3H), 2.12 (m, 2H), 1.96 (m, 3H), 1.87 (m, 1H), 1.64 (m, 4H).

Example 12

Synthesis of 3-[[3-(4-Bromophenylureido)propyl](1,2,3,4-tetrahydro-1-naphthyl)amino]-1-[(phenylsulfonyl)carbamoyl]propane (Compound 196)

The following synthesis is depicted in Scheme 12.

To a mixture of 4-[[3-(4-bromophenylureido)propyl](1,2,3,4-tetrahydro-1-naphthyl)amino]butanoic acid (20 mg, 0.041 mmol) and benzenesulfonamide (7.0 mg, 0.045 mmol) in $CH_2Cl_2$ (1 ml) were added WSC.HCl (8.6 mg, 0.045 mmol) and DMAP (5.5 mg, 0.045 mmol), and the mixture was stirred at RT for 18 h. The reaction mixture was purified by preparative normal phase HPLC using linear gradients of (A) chloroform and (B) methanol (2–4% B, in 0–2 min; 4–5% B, in 2–6 min; 5% B, in 6–12 min) at a flow rate of 12 ml/min. Fractions containing the major peak were pooled and concentrated to afford 3-[[3-(4-bromophenylureido)propyl](1,2,3,4-tetrahydro-1-naphthyl)amino]-1-[(phenylsulfonyl)carbamoyl]propane (5.4 mg, 21%): MS($ES^+$) m/e 627 $[M+H]^+$; $^1H$ NMR (400 MHz, $CDCl_3$) δ 8.27 (s, 1H), 8.05 (m, 2H), 7.50 (m, 3H), 7.44 (d, J=8.8 Hz, 2H), 7.31 (d, J=9.0 Hz, 2H), 7.23 (m, 3H), 7.15 (d, J=7.0 Hz, 1H), 7.02 (m, 1H), 6.92 (m, 1H), 4.72 (m, 1H), 3.73 (m, 1H), 3.58 (m, 1H), 3.21 (m, 1H), 2.96 (m, 1H), 2.79–2.65 (m, 5H), 2.57 (m, 1H), 2.17 (m, 1H), 2.03 (m, 1H), 1.94–1.66 (m, 4H).

Compounds 197, 210 can be obtained in an analogous manner to that of Compound 196.

Example 13

Synthesis of 4-[[3-(4-Bromophenylureido)propyl](1,2,3,4-tetrahydro-1-naphthyl)amino]-1-butanol (Compound 203)

The following synthesis is depicted in Scheme 13.

Lithium hydroxide monohydrate (11 mg, 0.26 mmol) was added to a solution of 4-[[3-(4-bromophenylureido)propyl](1,2,3,4-tetrahydro-1-naphthyl)amino]butyl acetate (67 mg, 0.13 mmol) in 10% water/methanol (1.1 ml). After stirring at RT for 16 h, additional lithium hydroxide monohydrete (22 mg, 0.52 mmol) was added. The reaction mixture was stirred at RT for 17 h, and then concentrated under vacuum to dryness. The residue was adsorbed on a plate of silica get and then developed with 10% methanol/chloroform to afford 4-[[3-(4-bromophenylureido)propyl](1,2,3,4-tetrahydro-1-naphthyl)amino]-1-butanol (48 mg, 77%): MS($ES^+$) m/e 476 $[M+H]^+$; $^1H$ NMR (400 MHz, DMSO-d6) δ 8.52 (br, 1H), 7.63 (d, J=7.6 Hz, 1H), 7.36 (m, 4H), 7.11–7.03 (m, 3H), 6.10 (br, 1H), 4.33 (br, 1H), 3.90 (m, 1H), 3.37 (m, 2H), 3.13 (m, 1H), 3.02 (m, 1H), 2.67 (m, 2H), 2.54–2.47 (m, 4H), 1.93 (m, 2H), 1.58 (m, 4H), 1.44 (m, 4H).

Compounds 205, 216 can be obtained in an analogous manner to that of Compound 203.

Example 14

Synthesis of 3-[[3-(4-Bromophenylureido)propyl](1,2,3,4-tetrahydro-1-naphthyl)amino]-1-(1H-tetrazol-5-yl)propane (Compound 218)

The following synthesis is depicted in Scheme 14.

Step 1: To a mixture of N-[3-(1,2,3,4-tetrahydro-1-naphthylamino)propyl]phthalimide (569 mg, 1.7 mmol), potassium carbonate (709 mg, 5.1 mmol) and potassium iodide (280 mg, 1.7 mmol) in $CH_3CN$ (20 ml) was added 4-bromobutyronitrile (754 mg, 5.1 mmol). The mixture was refluxed under stirring for 18 h, and then filtered. The filtrate was concentrated under vacuum to dryness, and the residue was chromatographed on silica gel (eluting with 20% ethyl acetate/chloroform) to afford 4-[[(3-phthalimido)propyl](1,2,3,4-tetrahydro-1-naphthyl)amino]butyronitrile (336 mg, 50%): MS($ES^+$) m/e 402 $[M+H]^+$; $^1H$ NMR (400 MHz, $CDCl_3$) δ 7.82 (dd, J=5.4, 2.9 Hz, 2H), 7.70 (m, 2H), 7.60 (d, J=7.6 Hz, 1H), 7.11 (m, 1H), 7.02 (m, 2H), 3.95 (m, 1H), 3.78 (m, 1H), 3.59 (m, 1H), 2.73 (m, 2H), 2.64 (m, 1H), 2.51 (m, 4H), 2.35 (m, 1H), 1.98 (m, 2H), 1.83 (m, 4H), 1.63 (m, 2H).

Step 2: To a solution of 4-[[(3-phthalimido)propyl](1,2,3,4-tetrahydro-1-naphthyl)amino]butyronitrile (336 mg, 0.84 mmol) in xylene (5 ml) was added trimethyltin azide (378 mg, 1.84 mmol). The mixture was stirrred at 115° C. for 18 h, and then filtered. The filtrate was concentrated under vacuum to dryness, and the residue was dissolved with 17% THF/$CH_2Cl_2$ (2.4 ml). To the solution was added 10 N NAOH solution (107 μl, 1.07 mmol). After srirring at RT for 30 min, triphenylmethyl chloride (297 mg, 1.07 mmol) was added, and the mixture was stirred at RT for 7 h, After adding water, the mixture was extracted with chloroform, washed with brine, dried over sodium sulfate, and filtered. Concentrating under vacuum gave 3-[[(3-phthalimido)propyl](1,2,3,4-tetrahydro 1-naphthyl)amino]-1-[1-(triphenylmethyl)tetrazol-5-yl]propane (125 mg, 22%) which was used in the next step without further purification.

Step 3: To a solution of 3-[[(3-phthalimido)propyl](1,2,3,4-tetrahydro-1-naphthyl)amino]-1-[1-(triphenylmethyl)tetrazol-5-yl]propane (50 mg, 0.073 mmol) in EtOH (1 ml) was added hydrazine monohydrate (17 μl, 0.36 mmol), and the mixture was stirred at RT for 3 h. The reaction mixture was concentrated under vacuum, and then water was added. The mixture was extracted with chloroform, washed with brine, dried over sodium sulfate, and filtered. To the filtrate was added 4-bromophenyl isocyanate (17 mg, 0.088 mmol), and the mixture was stirred at RT for 1 h. The reaction mixture was concentrated under vacuum to dryness, and the residue was adsorbed on a plate of silica gel and then developed with 3% methanol/chloroform to afford 3-[[3-(4-bromophenylureido)propyl](1,2,3,4-tetrahydro-1-naphthyl)amino]-1-[1-(triphenylmethyl)tetrazol-5-yl]propane (Compound 217, 33 mg, 60%): MS($ES^+$) m/e 756 $[M+H]^+$; $^1H$ NMR (400 MHz, $CDCl_3$) δ 7.62 (m, 1H), 7.53 (br, 1H), 7.34 (m, 10H), 7.09 (m, 12H), 5.79 (br, 1H), 4.05 (m, 1H), 3.48 (m, 1H), 3.31 (m, 1H), 3.17 (m, 1H), 2.74 (m, 4H), 2.55 (m, 1H), 2.44 (m, 2H), 1.96 (m, 3H), 1.86 (m, 1H), 1.72 (m, 2H), 1.61 (m, 2H).

Step 4: To a solution of 3-[[3-(4-bromophenylureido)propyl](1,2,3,4-tetraydro-1-naphthyl)amino]-1-[1-(triphenylmethyl)tetrazol-5-yl]propane (30 mg, 0.04 mmol) in THF (2 ml) was added 10 wt % HCl solution (1 ml), and the mixture was stirred at RT for 4 h. After adding water, the mixture was extracted with chloroform, washed with brine, dried over sodium sulfate, and filtered. The filtrate was adsorbed on a plate of silica gel and then developed with 20% methanol/chloroform to afford 3-[[3-(4-bromophenylureido)propyl](1,2,3,4-tetrahydro-1-naphthyl)amino]-1-(1H-tetrazol-5-yl)propane (12 mg, 57%): MS($ES^+$) m/e 514 $[M+H]^+$; $^1H$ NMR (400 MHz, $CD_3OD$) δ 7.89 (s, 1H), 7.64 (m, 1H), 7.36 (d, J=9.0 Hz, 2H), 7.27 (d, J=9.0 Hz, 2H), 7.21 (m, 2H), 7.11 (m, 1H), 3.31 (m, 1H), 3.21 (t, J=6.3 Hz, 2H), 3.14 (m, 1H), 3.08 (m, 3H), 2.94–2.72 (m, 4H), 2.24 (m, 1H), 2.17–2.01 (m, 3H), 1.98–1.80 (m, 3H), 1.71 (m, 1H).

Compounds 222 can be obtained in an analogous manner to that of Compound 218.

Example 15

Synthesis of Methyl 4-[[3-[4-(carboxy) phenylureido]propyl](1,2,3,4-tetrahydro-1-naphthyl) amino]butylate (Compound 225)

The following synthesis is depicted in Scheme 15.

Lithium hydroxide monohydrate (2.5 mg, 0.060 mmol) was added to a solution of methyl 4-[[3-[4-(ethoxycarbonyl) phenylureido]propyl)(1,2,3,4-tetrahydro-1-naphthyl)amino] butylate (28 mg, 0.057 mmol) in 7% water/methanol (4.3 ml). After stirring at RT for 24 h, additional lithium hydroxide monohydrete (5 mg, 0.12 mmol) was added. The reaction mixture was stirred at RT for 24 h, and then concentrated under vacuum to dryness. The residue was adsorbed on a plate of silica gel and then developed with 10% methanol/chloroform to afford methyl 4-[[3-[4-(carboxy) phenylureido]propyl](1,2,3,4-tetrahydro-1-naphthyl)amino] butylate (12 mg, 51%): MS($ES^+$) m/e 468 $[M+H]^+$; $^1H$ NMR (400 MHz, $CDCl_3$)δ 9.85 (bs, 1H), 7.91 (m, 3H), 7.61 (m, 3H), 7.21 (m, 1H), 7.13 (m, 3H), 4.72 (m, 1H), 3.86 (s, 3H), 3.33 (m, 3H), 3.25 (m, 1H), 3.02 (m, 1H), 2.88 (m, 2H), 2.75 (m, 2H), 2.56 (m, 1H), 2.22 (m, 2H), 2.00 (m, 3H), 1.85 (m, 1H), 1.71 (m, 2H).

Compounds 235 can be obtained in an analogous manner to that of Compound 225 except for the use of compound 228 as starting material instead of methyl 4-[[3-[4-(ethoxycarbonyl)phenylureido]propyl](1,2,3,4-tetrahydro-1-naphthyl)amino]butylate.

Example 16

Synthesis of 4-[[3-[4-(Ethoxycarbonyl) phenylureido]propyl](1,2,3,4 tetrahydro-1-naphthyl] amino]butanoic acid (Compound 228)

The following synthesis is depicted in Scheme 16.

Step 1: To a solution of N-[3-(1,2,3,4-tetrahydro-1-naphthylamino)propyl]phthalimide (200 mg, 0.60 mmol) in MeOH (10 ml) were added succinic semialdehyde (15 wt. % solution in water, 0.45 ml, 0.72 mmol), HOAc (41 μl, 0.72 mmol) and $NaBH_3CN$ (45 mg, 0.72 mmol), and the mixture was stirred at RT for 2.5 h. After adding water, the mixture was extracted with chloroform, washed with water and brine, dried over sodium sulfate, and filtered. The filtrate was concentrated under vacuum to dryness, and the residue was chromatographed on silica gel (eluting with 5% methanol/chloroform) to afford 4-[[(3-phthalimido)propyl] (1,2,3,4-tetrahydro-1-naphthyl)amino]butanoic acid (207 mg, 82%): MS($ES^+$) m/e 421 $[M+H]^+$; $^1H$ NMR (400 MHz, $CDCl_3$) δ 7.83 (dd, J=5.6, 2.9 Hz, 2H), 7.72 (m, 2H), 7.65 (d, J=7.6 Hz, 1H), 7.15 (m, 1H), 7.08 (m, 1H), 7.00 (d, J=7.3 Hz, 1H), 4.28 (m, 1H) 3.75 (m, 1H), 3.65 (m, 1H), 2.80–2.55 (m, 6H), 2.47 (m, 1H), 2.30 (m, 1H), 2.06–1.86 (m, 5H), 1.74–1.66 (m, 3H).

Step 2: To a solution of 4-[[(3-phthalimido)propyl](1,2,3,4-tetrahydro-1-naphthyl)amino]butanoic acid (137 mg, 0.32 mmol) in EtOH (5 ml) was added hydrazine monohydrate (63 μl, 1.3 mmol), and the mixture was stirred at RT for 4 h. The reaction mixture was concentrated under vacuum, and then water was added. The mixture was extracted with chloroform, washed with water and brine, dried over sodium sulfate, and filtered. To the filtrate was added 4-(ethoxycarbonyl)phenyl isocyanate (62 mg, 0.32 mmol), and the mixture was stirred at RT for 30 min. The reaction mixture was concentrated under vacuum to dryness, and the residue was adsorbed on a plate of silica gel and then developed with 17% methanol/chloroform to afford 4-[[3-[4-(ethoxycarbonyl)phenylureido]propyl](1,2,3,4-tetrahydro-1-naphthyl)amino]butanoic acid (25 mg, 16%): MS($ES^+$) m/e 482 $[M+H]^+$; $^1H$ NMR (400 MHz, $CDCl_3$) δ 9.86 (s, 1H), 8.80 (br, 1H), 7.91 (m, 3H), 7.61 (m, 3H), 7.21 (m, 1H), 7.12 (m, 2H), 4.70 (t, J=7.6 Hz, 1H), 4.33 (q, J=7.1 Hz, 2H), 3.32 (m, 2H), 3.23 (m, 1H), 3.03–2.84 (m, 3H), 2.74 (m, 2H), 2.55 (m, 1H), 2.21 (m, 2H), 2.02–1.78 (m, 5H), 1.70 (m, 2H), 1.37 (t, J=7.1 Hz, 3H).

Compound 229, 4-[[3-(4-Iodophenylureido)propyl](1,2,3,4-tetrahydro-1-naphthyl)amino]butanoic acid, can be obtained in an analogous manner to that described for compound 228 and contains the following characteristics: MS($ES^+$) m/e 536 $[M+H]^+$; $^1H$ NMR (400 MHz, $CDCl_3$) δ 9.50 (bs, 1H), 7.70 (br, 1H), 7.61 (d, J=7.8 Hz, 1H), 7.50 (d, J=7.8 Hz, 2H), 7.35 (d, J=7.8 Hz, 2H), 7.22 (m, 1H), 7.14 (m, 3H), 4.69 (m, 1H), 3.30 (m, 2H), 3.22 (m, 1H), 2.99 (m, 1H), 2.87 (m, 2H), 2.75 (m, 2H), 2.53 (dd, J=16.6, 7.3 Hz, 1H), 2.20 (m, 2H), 2.00–1.77 (m, 5H), 1.70 (m, 2H).

Compound 237, 4-[[3-[4-(Butoxycarbonyl)phenylureido] propyl(1,2,3,4-tetrahydro-1-naphthyl)amino]butanoic acid, can be obtained in an analogous manner to that described for compound 228 and contains the following characteristics: MS($ES^+$) m/e 510 $[M+H]^+$; $^1H$ NMR (400 MHz, $CDCl_3$) δ 9.70 (br, 1H), 7.91 (d, J=8.5 Hz, 2H), 7.72 (br, 1H), 7.62 (m, 3H), 7.20 (m, 3H), 7.13 (m, 1H), 4.71 (m, 1H), 4.27 (t, J 6.6 Hz, 2H), 3.33 (m, 2H), 3.26 (m, 1H), 3.01 (m, 1H), 2.88 (m, 2H), 2.75 (m, 2H), 2.54 (m, 1H), 2.20 (m, 2H), 2.01 (m, 4H), 1.84 (m, 1H), 1.73 (m, 4H), 1.47 (m, 2H), 0.97 (t, J=7.3 Hz, 3H).

Compound 258, 4[[3-(4-Bromophenylureido)propyl] [(1R)-1-(4-bromophenyl)ethyl]amino]butanoic acid, can be obtained in an analogous manner to that described for compound 228 and contain the following characteristics: MS($ES^+$) m/e 542 $[M+H]^+$; $^1H$ NMR (400 MHz, $CDCl_3$) δ 9.29 (bs, 1H), 7.82 (br, 1H), 7.69 (br, 1H), 7.47 (d, J=8.1 Hz, 2H), 7.40 (d, J=8.5 Hz, 2H), 7.31 (d, J=8.5 Hz, 2H), 7.22 (d, J=8.1 Hz, 2H), 4.24 (m, 1H), 3.20 (m, 2H), 2.99 (m, 1H), 2.84 (m, 3H), 2.40 (m, 2H), 1.82 (m, 4H), 1.56 (d, J=6.8 Hz, 3H).

Compound 269, 4-[[3(4-Bromophenylureido)propyl][1-(4-fluorophenyl)ethyl]amino]butanoic acid, can be obtained in an analogous manner to that described for compound 228 and contains the following characteristics: MS($ES^+$) m/e 482 $M+H]^+$; $^1H$ NMR (400 MHz, $CDCl_3$) δ 9.47 (s, 1H), 7.68 (br, 1H), 7.43 (d, J=9.0 Hz, 2H), 7.35 (m, 2H), 7.31 (d, J=8.8 Hz, 2H), 7.05 (m, 2H), 6.92 (m, 1H), 4.30 (q, J=6.8 Hz, 1H), 3.22 (m, 2H), 3.04 (m, 1H), 2.89 (m, 3H), 2.42 (m, 2H), 1.84 (m, 4H), 1.60 (d, J=7.1 Hz, 3H).

Compound 272, 4-[[3-(4-Bromophenylureido)propyl] [1-(4 chlorophenyl)ethyl]amino]butanoic acid, can be obtained in an analogous manner to that described for compound 228 and contains the following characteristics: MS($ES^+$) m/e 498 $[M+H]^+$; $^1H$ NMR (400 MHz, $CDCl_3$) δ 9.38 (bs, 1H), 7.60 (br, 1H), 7.43 (d, J=8.8 Hz, 2H), 7.31 (m, 6H), 7.20 (m, 1H), 4.26 (q, J=7.1 Hz, 1H), 3.21 (m, 2H), 3.02 (m, 1H), 2.87 (m, 3H), 2.43 (m, 2H), 1.83 (m, 4H), 1.59 (d, J=7.1 Hz, 3H).

Compound 293, 4[[3-(4-Bromophenylureido)propyl] [(1S)-1-(4-bromophenyl)ethyl]amino]butanoic acid, can be obtained in an analogous manner to that described for compound 228 and contains the following characteristics: MS($ES^+$) m/e 542 $[M+H]^+$; $^1H$ NMR (400 MHz, $CDCl_3$) δ 9.37 (bs, 1H), 9.14 (br, 1H), 7.56 (br, 1H), 7.48 (d, J=8.5 Hz, 2H), 7.43 (d, J=8.8 Hz, 2H), 7.32 (d, J=8.8 Hz, 2H), 7.23 (d, J=8.5 Hz, 2H), 4.24 (m, 1H), 3.21 (m, 2H), 3.01 (m, 1H), 2.87 (m, 3H), 2.44 (m, 2H), 1.84 (m, 4H), 1.58 (d, J=6.8 Hz, 3H).

Compounds 236, 259–268, 270, 271, 273, 277–279 can be obtained in an analogous manner to that of Compound 228.

Example 17

Synthesis of [3-Phenylureido)propyl]bis[2-(4-chlorophenyl)ethyl]amine (Compound 238)

The following synthesis is depicted in Scheme 17.

Step 1: To a mixture of 4-chlorophenylacetic acid (500 mg, 3.0 mmol) and 2-(4-chlorophenyl)ethylamine (456 mg, 3.0 mmol) in DMF (50 ml) were added WSC.HCl (592 mg, 3.1 mmol), HOBt.$H_2O$ (474 mg, 3.1 mmol) and triethylamine (0.43 ml, 3.1 mmol), and the mixture was stirred at RT for 18 h. After adding water, the mixture was extracted with ethyl acetate, washed with brine, dried over magnesium sulfate, and filtered. Concentrating under vacuum gave N-[2-(4-chlorophenyl)ethyl]-(4-chlorophenyl)acetamide (819 mg, 89%) which was used in the next step without further purification.

Step 2: To a solution of N-[2-(4-chlorophenyl)ethyl]-(4-chlorophenyl)acetamide (100 mg, 0.33 mmol) in THF (2 ml) was added borane-methyl sulfide complex (2.0 M solution in THF, 1.6 ml, 3.2 mmol), and the mixture was stirred at 70° C. for 1.5 h. After adding 1 N HCl solution (4 ml), the mixture was stirred at RT for 1 h. After adding 5 wt % NaOH solution (4 ml), the mixture was extracted with chloroform, dried over magnesium sulfate, and filtered. The filtrate was concentrated under vacuum to dryness, and the residue was chromatographed on silica gel (eluting with 10% methanol/chloroform) to afford bis[24-chlorophenyl)ethyl]amine (48 mg, 50%): MS($ES^+$) m/e 294 $[M+H]^+$.

Step 3: To a mixture of bis[2-(4-chlorophenyl)ethyl]amine (48 mg, 0.16 mmol), potassium carbonate (44 mg, 0.32 mmol) and potassium iodide (26 mg, 0.16 mmol) in $CH_3CN$ (2 ml) was added N-phenylcarbamoyl-3-bromopropylamine (215 mg, 0.64 mmol) in DMF (2 ml). The mixture was stirred at 80° C. for 18 h, and then concentrated under vacuum to dryness. The residue was adsorbed on a plate of silica gel and then developed with 10% methanol/chloroform to afford [3-(phenylureido)propyl]bis[2-(4-chlorophenyl)ethyl]amine (10 mg, 13%): MS($ES^+$) m/e 470 $[M+H]^+$; $^1H$ NMR (400 MHz, $CDCl_3$) δ 7.24 (m, 9H), 7.03 (m, 5H), 6.59 (br, 1H), 3.24 (t, J=6.3 Hz, 2H), 2.87 (m, 1H), 2.76 (m, 1H), 2.73–2.61 (m, 8H), 1.64 (m, 2H).

Example 18

Synthesis of 4-[[(3S)-3-(4-Bromophenylureido)-3-isopropylcarbamoyl)propyl](1,2,3,4-tetrahydro-1-naphthyl)amino]butanoic acid (Compound 286)

The following synthesis is depicted in Scheme 18.

Step 1: To a mixture of 50% KOH (10 ml) and ether (10 ml) was added 1-methyl-3-nitro-1-nitrosoguanidine (1.0 g, 6.8 mmol) at 0° C. After standing at 0° C. for 5 min, the organic layer was transferred to another erlenmeyer flask at 0° C., and KOH pellets (1.0 g) were added. After standing at 0° C. for 5 min, the supernatant was added to a solution of 4 [[(3S)-3-(4-bromophenylureido)-3-(tert-butoxycarbonyl)propyl](1,2,3,4-tetrahydro-1-naphthyl)amino]butanoic acid (Compound 166, 154 mg, 0.262 mmol) in $CH_2Cl_2$ (5 ml) at 0° C. After stirring at 0° C. for 30 min, the reaction mixture was concentrated under vacuum to dryness, and the residue was adsorbed on a plate of silica gel and then developed with 10% methanol/chloroform to afford methyl 4[[(3S-3-(4-bromophenylureido)-3-(tert-butoxycarbonyl)propyl](1,2,3,4-tetrahydro-1-naphthyl)amino]butylate (Compound 281, 128 mg, 81%): MS($ES^+$) m/e 602 $[M+H]^+$; $^1H$ NMR (400 MHz, $CDCl_3$) δ 7.56 (m, 1H), 7.35 (d, J=8.8 Hz, 2H), 7.20–7.04 (m, 5H), 6.62 (br, 1H), 5.61 (br, 1H), 4.41 (m, 1H), 4.03 (m, 1H), 3.63 (s, 3H), 2.73–2.25 (m, 8H), 2.10–1.81 (m, 6H), 1.64 (m, 2H), 1.43 (s, 9H).

Step 2: To a solution of methyl 4-[[(3S)-3-(4-bromophenylureido)-3-(tert-butoxycarbonyl)propyl](1,2,3,4-tetrahydro-1-naphthyl)amino]butylate (121 mg, 0.202 mmol) in $CH_2Cl_2$ (5 ml) was added TFA (2 ml). After stirring at RT for 3 h, the reaction mixture was concentrated under vacuum to dryness, and the residue was adsorbed on a plate of silica gel and then developed with 10% methanol/chloroform to afford (25)-2-(4-bromophenylureido)-4-[[3-(methoxycarbonyl)propyl](1,2,3,4-tetrahydro-1-naphthyl)amino]butanoic acid (53 mg, 48%): MS($ES^+$) m/e 546 $[M+H]^+$; $^1H$ NMR (400 MHz, $CDCl_3$) δ 8.77 (br, 1H), 7.82 (m, 1H), 7.44 (d, J=8.8 Hz, 2H), 7.30 (d, J=8.8 Hz, 2H), 7.21 (m, 2H), 7.17 (d, J=7.3 Hz, 1H), 7.13 (br, 2H), 4.86 (m, 1H), 3.67 (s, 3H), 3.66 (m, 1H), 3.23–2.96 (m, 2H), 2.79 (m, 2H), 2.55 (m, 1H), 2.34 (m, 3H), 2.17 (m, 2H), 2.06 (m, 2H), 1.87 (m, 2H), 1.72 (m, 2H).

Step 3: To a mixture of (2S)-2-(4-bromophenylureido)+[[3-(methoxycarbonyl)propyl](1,2,3,4-tetrahydro-1-naphthyl)amino]butanoic acid (25 mg, 0.046 mmol) and isopropylamine (6 μl, 0.055 mmol) in $CH_2Cl_2$ (1 ml) were added WSC.HCl (10 mg, 0.052 mmol), HOBt.$H_2O$ (7 mg, 0.052 mmol) and triethylamine (15 μl, 0.12 mmol), and the mixture was stirred at RT for 95 h. After adding water, the mixture was extracted with chloroform, washed with brine, dried over magnesium sulfate, and filtered. The filtrate was concentrated under vacuum to dryness, and the residue was adsorbed on a plate of silica gel and then developed with 5% methanol/chloroform to afford methyl 4-[[(3S)-3-(4-bromophenylureido)-3-(isopropylcarbamoyl)propyl](1,2,3,4-tetrahydro-1-naphthyl)amino]butylate (Compound 282, 17 mg, 64%): MS($ES^+$) m/e 587 $[M+H]^+$; $^1H$ NMR (400 MHz, $CDCl_3$) δ 7.60 (m, 1H), 7.31 (d, J=8.8 Hz, 2H), 7.23–7.06 (m, 5H), 6.47 (br, 1H), 6.20 (br, 1H), 4.35 (m, 1H), 4.00 (m, 2H), 3.65 (s, 3H), 2.72–2.36 (m, 8H), 2.09–1.83 (m, 6H), 1.63 (m, 2H), 1.14 (t, J=6.6 Hz, 6H).

Step 4: Lithium hydroxide monohydrate (10 mg, 0.24 mmol) was added to a solution of methyl 4-[[(3S)-3-(4-bromophenylureido)-3-(isopropylcarbamoyl)propyl](1,2,3,4-tetrahydro-1-naphthyl)amino]butylate (15 mg, 0.025 mmol) in 17% water/methanol (1.2 ml). After stirring at RT for 38 h, the reaction mixture was concentrated under vacuum to dryness. The residue was adsorbed on a plate of silica gel and then developed with 10% methanol/chloroform to afford 4[[(3S)-34-bromopbenylureido)-3-(isopropylcarbamoyl)propyl](1,2,3,4-tetrahydro-1-naphthyl)amino]butanoic acid (17 mg, quant.): MS($ES^+$) m/e 573 $[+H]^+$; $^1H$ NMR (400 MHz, $CDCl_3$) δ 9.80 (bs, 1H), 8.16 (br, 1H), 7.68 (m, 1H), 7.38 (d, J=8.8 Hz, 2H), 7.23 (d, J=8.8 Hz, 2H), 7.20 (m, 2H), 7.11 (m, 1H), 7.00 (d, J=7.8 Hz, 1H), 4.62 (t, J=7.8 Hz, 1H), 4.38 (m, 1H), 3.89 (m, 1H), 3.46 (m, 1H), 3.15 (m, 1H), 2.70 (m, 4H), 2.38 (m, 1H), 2.27 (m, 2H), 2.09 (m, 2H), 1.93 (m, 2H), 1.71 (m, 1H), 1.59 (m, 2H), 1.06 (m, 6H).

Compound 283, Methyl 4-[[(3S)-3-(4-bromophenylureido)-3-(benzylcarbamoyl)propyl](1,2,3,4-tetrahydro-1-naphthyl)amino]butylate, can be obtained in an analogous manner to that described for compound 282 except for the use of benzylamine instead of isopropylamine in step 3 and contains the following characteristics: MS($ES^+$) m/e 635 $[M+H]^+$; $^1H$ NMR (400 MHz, $CDCl_3$) δ 7.56 (d, J=6.1 Hz, 1H), 7.26 (m, 7H), 7.05 (m, 5H), 6.40 (br, 2H), 4.45 (m, 1H), 4.38 (m, 2H), 3.96 (m, 1H), 3.57 (s, 3H), 2.72–2.45 (m, 6H), 2.33 (m, 2H), 1.98–1.78 (m, 6H), 1.59 (m, 2H).

Compound 287, 4-[[(3S)-3-(4-Bromophenylureido)-3-(benzylcarbamoyl)propyl](1,2,3,4-tetrahydro-1-naphthyl)amino]butanoic acid, can be obtained in an analogous manner to that described for compound 286 except for the use of benzylamine instead of isopropylamine in step 3 and contains the following characteristics: MS($ES^+$) m/e 621

[M+H]$^+$; $^1$H NMR (400 MHz, $CDCl_3$) δ 9.90 (bs, 1H), 8.34 (br, 1H), 7.65 (m, 2H), 7.33 (d, J=8.8 Hz, 2H), 7.21–7.06 (m, 10H), 4.54 (m, 1H), 4.47 (m, 1H), 4.39 (dd, J=15.1, 6.3 Hz, 1H), 4.21 (dd, J=15.1, 5.4 Hz, 1H), 3.44 (m, 1H), 3.04 (m, 1H), 2.62 (m, 4H), 2.34 (m, 21H), 2.10 (m, 1H), 1.99 (m, 3H), 1.82 (m, 1H), 1.61–1.43 (m, 3H).

Compound 284, 4-[[(3S)-3-(4-Bromophenylureido)-3-(isopropylcarbamoyl)propyl](1,2,3,4-tetrahydro-1-naphthyl)amino]butanoic acid, can be obtained in an analogous manner to that described for compound 286 except for the use of compound 165 as starting material instead of compound 166 and contains the following characteristics: MS(ES$^+$) m/e 573 [M+H]$^+$; $^1$H NMR (400 MHz, $CDCl_3$) δ 9.77 (bs, 1H), 8.17 (br, 1H), 7.61 (d, J=7.1 Hz, 1H), 7.40 (m, 2H), 7.26 (m, 2H), 7.12 (m, 2H), 7.06 (m, 1H), 6.83 (d, J=7.8 Hz, 1H), 4.79 (t, J=7.8 Hz, 1H), 4.29 (m, 1H), 3.84 (m, 1H), 3.35 (m, 1H), 2.99 (m, 1H), 2.64 (m, 4H), 2.51–2.41 (m, 2H), 2.30 (m, 1H), 2.13 (m, 1H), 1.89 (m, 3H), 1.68 (m, 1H), 1.52 (m, 1H), 1.37 (m, 1H), 1.05 (d, J=6.3 Hz, 3H), 0.95 (d, J=6.6 Hz, 3H).

Compound 285, 4-[[(3S)-3-(4-Bromophenylureido)-3-(benzylcarbamoyl)propyl](1,2,3,4-tetrahydro-1-naphthyl)amino]butanoic acid, can be obtained in an analogous manner to that described for compound 287 except for the use of compound 165 as staring material instead of compound 166 and contains the following characteristics: MS(ES$^+$) m/e 621 [M+H]$^+$; $^1$H NMR (400 MHz, $CDCl_3$) δ 9.87 (bs, 1H), 8.36 (br, 1H), 7.51 (d, J=7.6 Hz, 1H), 7.39 (m, 1H), 7.35 (d, J=9.0 Hz, 2H), 7.23 (d, J=9.0 Hz, 2H), 7.15–6.98 (m, 8H), 4.63 (t, J=7.8 Hz, 1H), 4.42 (m, 1H), 4.30 (dd, J=14.9, 5.9 Hz, 1H), 4.20 (dd, J=14.9, 5.6 Hz, 1H), 3.39 (m, 1H), 2.95 (m, 1H), 2.61 (m, 4H), 2.43 (m, 2H), 2.35 (m, 1H), 2.05 (m, 1H), 1.93–1.80 (m, 3H), 1.62 (m, 1H), 1.50 (m, 1H), 1.35 (m, 1H).

Example 19

Synthesis of [3-(Phenylureido)propyl][2-(4-chlorophenyl)ethyl]bis(4-methylbenzyl)ammonium iodide (Compound 296)

The following synthesis is depicted in Scheme 19.

To a mixture of N-phenylcarbamoyl-N'-[2-(4-chlorophenyl)ethyl]-1,3-diaminopropane (80 mg, 0.24 mmol) and potassium carbonate (100 mg, 0.72 mmol) in $CH_3CN$ (2 ml) was added 4-methylbenzyl bromide (134 mg, 0.72 mmol). The mixture was refluxed under stirring for 1.5 h, and then filtered. The filtrate was concentrated under vacuum to dryness, and the residue was adsorbed on a plate of silica gel and then developed with 33% methanol/chloroform to afford [3-(phenylureido)propyl][2-(4-chlorophenyl)ethyl]bis(4-methylbenzyl)ammonium iodide (101 mg, 68%): MS(ES$^+$) m/e 540 [M-Br]$^+$; $^1$H NMR (400 MHz, $CDCl_3$) δ 8.13 (s, 1H), 7.50 (d, J=7.6 Hz, 2H), 7.40 (d, J=8.1 Hz, 4H), 7.19 (m, 8H), 7.07 (d, J=8.5 Hz, 2H), 6.94 (t, J=7.3 Hz, 1H), 6.86 (m, 1H), 4.81 (d, J=13.2 Hz, 2H), 4.57 (d, J=13.2 Hz, 2H), 3.75 (m, 2H), 3.35 (m, 2H), 3.25 (m, 2H), 3.19 (m, 2H), 2.11 (m, 2H), 1.60 (s, 6H).

Example 20

Synthesis of [3-(4-Bromophenylureido)propyl][(1S)-1-phenylethyl][3-(carboxy)propyl]ethylammonium trifluoroacetate (Compound 315)

The following synthesis is depicted in Scheme 20.

Lithium hydroxide monohydrate (10 mg, 0.24 mmol) was added to a solution of [3-(4-bromophenylureido)propyl][(1S)-1-phenylethyl][3-(methoxycarbonyl)propyl]ethylammonium iodide (24 mg, 0.05 mmol) in 10% water/methanol (3.3 ml). After, stirring at RT for 4.5 h, the reaction mixture was concentrated under vacuum to dryness. The residue was purified by preparative reverse phase HPLC using linear gradients of (A) 0.05% TFA/$H_2O$ and (B) 0.05% TFA/$CH_3CN$ (20–80% B, in 0–15 min; 80% B, in 15–18 min) at a flow rate of 3 ml/min. Fractions containing the major peak were pooled and concentrated to afford [3-(4-bromophenylureido)propyl][(1S)-1-phenylethyl][3-(carboxy)propyl]ethylammonium trifluoroacetate (6 mg, 20%): MS(ES$^+$) m/e 492 [M-$CF_3COO$]$^+$; $^1$H NMR (400 MHz, $CD_3OD$) δ 7.63 (m, 2H), 7.45 (m, 3H), 7.39 (d, J=9.0 Hz, 2H), 7.31 (d, J=9.0 Hz, 2H), 3.47 (m, 3H), 3.38 (m, 4H), 3.26 (m, 2H), 2.41 (m, 2H), 1.96 (m, 4H), 1.83 (d, J=6.8 Hz, 3H), 1.30 (m, 3H).

Compound 316, [3-(4-Bromophenylureido)propyl][(1R)-1-phenylethyl][3-(carboxy)propyl]ethylammonium trifluoroacetate, can be obtained in an analogous manner to that described for compound 315 and contains the following characteristics: MS(ES$^+$) m/e 492 [M-$CF_3COO$)$^+$; $^1$H NMR (400 MHz, $CD_3OD$) δ 7.63 (m, 2H), 7.45 (m, 3H), 7.39(d, J=9.0 Hz, 2H), 7.31 (d, J=8.8 Hz, 2H), 3.47 (m, 3H), 3.37 (m, 4H), 3.26 (m, 2H), 2.41 (m, 2H), 1.96 (m, 4H), 1.83 (d, J=6.8 Hz, 3H), 1.31 (m, 3H).

Example 21

Synthesis of [3-(Phenylureido)propyl][2-(4-chlorophenyl)ethyl][4-(carboxy)benzyl]ethylammonium iodide (Compound 322)

The following synthesis is depicted in Scheme 21.

Lithium hydroxide monohydrate (4 mg, 0.095 mmol) was added to a solution of [3-(phenylureido)propyl][2-(4 chlorophenyl)ethyl][4-(methoxycarbonyl)benzyl]ethylammonium iodide (28 mg, 0.044 mmol) in 10% water/methanol (1.3 ml). After stirring at RT for 26 h, the reaction mixture was concentrated under vacuum to dryness. The residue was adsorbed on a plate of silica gel and then developed with 33% methanol/chloroform to afford [3-(phenylureido)propyl][2-(4-chlorophenyl)ethyl][4-(carboxy)benzyl]ethylammonium iodide (19 mg, 70%): MS(ES$^+$) m/e 496 [M-I]$^+$; $^1$H NMR (400 MHz, $CD_3OD$) δ 8.01 (d, J=8.3 Hz, 2H), 7.53 (d, J=8.3 Hz, 2H), 7.38 (m, 2H), 7.30 (m, 4H), 7.24 (m, 2H), 6.97 (m, 1H), 4.59 (s, 2H), 3.31 (m, 8H), 3.15 (m, 2H), 2.15 (m, 2H), 1.48 (t, J=7.1 Hz, 3H).

Abbrevations:

| | |
|---|---|
| EtOH | ethanol |
| $CH_2Cl_2$ | dichloromethane |
| DMSO | dimethylsulfoxide |
| MeOH | methanol |
| HOAc | acetic acid |
| DIEA | diisopropylethylamine |
| DCM | dichloromethane |
| DMF | N,N-dimethylformamide |
| BAP | borane and pyridine |
| TBAI | tetrabutylammonium iodide |
| $SnCl_2$ | tin chloride |
| Fmoc | 9H-9-fluorenylmethoxycarbonyl |
| Asp | aspartic acid residue |
| tBu | tert-butyl |
| WSC | 1-[3-(diethylamino)propyl]-3-ethylcarbodiimide |
| HOBt | 1-hydroxybenzotriazole |
| THF | tetrahydrofuran |
| TFA | trifluoroacetic acid |
| DMAP | 4-(dimethylamino)pyridine |

Table 1a and 1b list a variety of compounds that can be synthesized by using one of the methods described above.

TABLE 1a
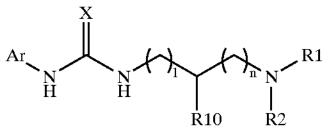
| CPD No. | Ar | X | l | n | R1 | R2 | R10 | Mass Spec. m/e |
|---|---|---|---|---|---|---|---|---|
| 1 | phenyl | O | 1 | 1 | 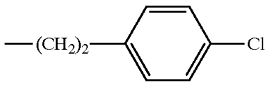 | ethyl | H | ES$^+$ 360 $[M + H]^+$ |
| 2 | 4-nitrophenyl | O | 1 | 1 | 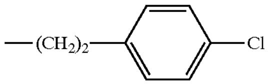 | ethyl | H | FD 405 $[M + H]^+$ |
| 3 | 4-bromophenyl | O | 1 | 1 | 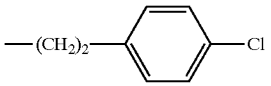 | ethyl | H | ES$^+$ 438 $[M + H]^+$ |
| 4 | 4-nitrophenyl | O | 1 | 0 | 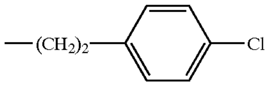 | ethyl | H | ES$^+$ 391 $[M + H]^+$ |
| 5 | 4-nitrophenyl | O | 1 | 2 | 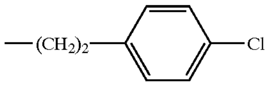 | ethyl | H | ES$^-$ 417 $[M - H]^-$ |
| 6 | 4-chlorophenyl | O | 1 | 1 | 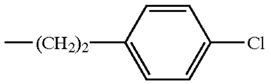 | ethyl | H | ES$^-$ 392 $[M - H]^-$ |
| 7 | phenyl | O | 1 | 2 | 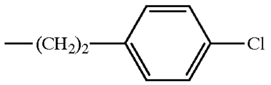 | ethyl | H | ES$^+$ 374 $[M + H]^+$ |
| 8 | phenyl | O | 1 | 3 | 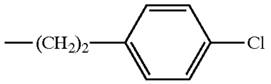 | ethyl | H | ES$^+$ 388 $[M + H]^+$ |

TABLE 1a-continued
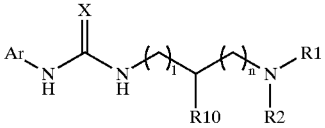
| CPD No. | Ar | X | l | n | R1 | R2 | R10 | Mass Spec. m/e | | |
|---|---|---|---|---|---|---|---|---|---|---|
| 9 | 2-methoxyphenyl | O | 1 | 1 | 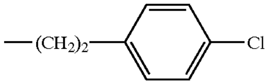 | ethyl | H | $ES^+$ | 390 | $[M + H]^+$ |
| 10 | phenyl | O | 1 | 1 | 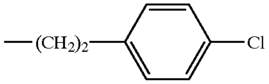 | n-propyl | H | $ES^+$ | 374 | $[M + H]^+$ |
| 11 | phenyl | O | 1 | 1 | 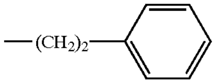 | ethyl | H | $ES^+$ | 326 | $[M + H]^+$ |
| 12 | phenyl | O | 1 | 1 | 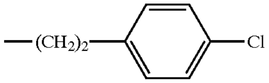 | 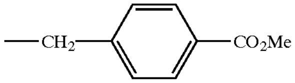 | H | $ES^+$ | 480 | $[M + H]^+$ |
| 13 | phenyl | O | 1 | 1 | 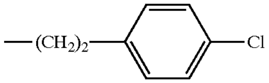 | 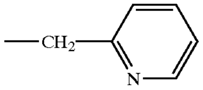 | H | FD | 422 | $M^+$ |
| 14 | phenyl | O | 1 | 1 | 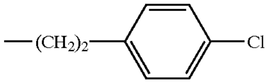 | n-butyl | H | $ES^+$ | 388 | $[M + H]^+$ |
| 15 | phenyl | O | 1 | 1 | 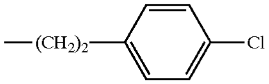 | 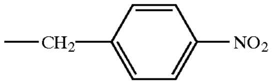 | H | $ES^+$ | 467 | $[M + H]^+$ |
| 16 | phenyl | O | 1 | 1 | 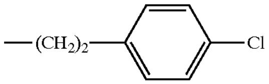 | 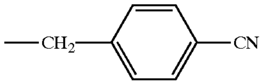 | H | $ES^+$ | 447 | $[M + H]^+$ |
| 17 | phenyl | O | 1 | 1 | 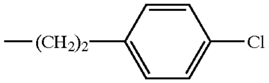 | 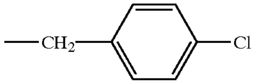 | H | $ES^+$ | 456 | $[M + H]^+$ |

TABLE 1a-continued
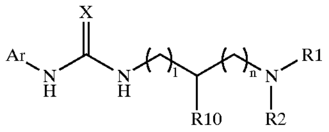
| CPD No. | Ar | X | l | n | R1 | R2 | R10 | Mass Spec. m/e |
|---|---|---|---|---|---|---|---|---|
| 18 | phenyl | O | 1 | 1 | 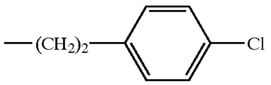 | 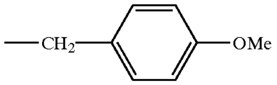 | H | ES$^+$ 452 $[M + H]^+$ |
| 19 | phenyl | O | 1 | 1 | 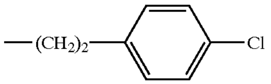 | 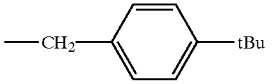 | H | ES$^+$ 478 $[M + H]^+$ |
| 20 | phenyl | O | 1 | 1 | 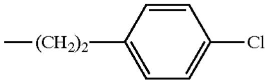 | 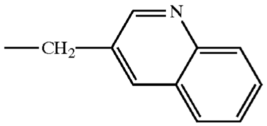 | H | ES$^+$ 473 $[M + H]^+$ |
| 21 | phenyl | O | 1 | 1 | 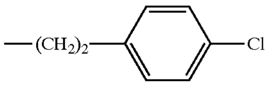 | 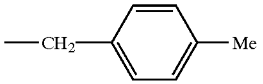 | H | ES$^+$ 436 $[M + H]^+$ |
| 22 | phenyl | O | 1 | 1 | 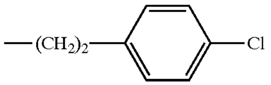 | 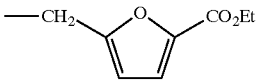 | H | ES$^+$ 484 $[M + H]^+$ |
| 23 | phenyl | O | 1 | 1 | 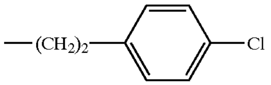 | 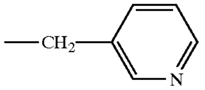 | H | ES$^+$ 423 $[M + H]^+$ |
| 24 | phenyl | O | 1 | 1 | 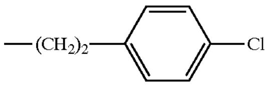 | 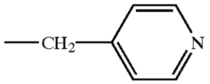 | H | ES$^+$ 423 $[M + H]^+$ |
| 25 | phenyl | O | 1 | 1 | 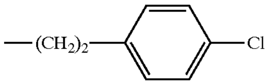 | 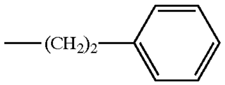 | H | ES$^+$ 436 $[M + H]^+$ |

TABLE 1a-continued
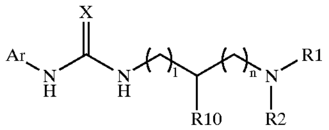
| CPD No. | Ar | X | l | n | R1 | R2 | R10 | Mass Spec. m/e |
|---|---|---|---|---|---|---|---|---|
| 26 | phenyl | O | 1 | 1 | 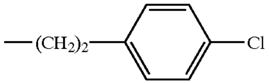 | 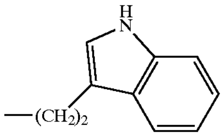 | H | $ES^+$ 475 $[M + H]^+$ |
| 27 | phenyl | O | 1 | 1 | 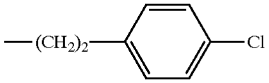 | methyl | H | $ES^+$ 346 $[M + H]^+$ |
| 28 | phenyl | O | 1 | 1 | 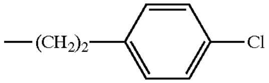 | 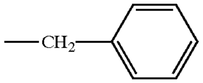 | H | $ES^+$ 422 $[M + H]^+$ |
| 29 | 4-bromophenyl | O | 1 | 1 | 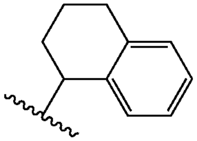 | $-(CH_2)_3CO_2Me$ | H | FD 502 $[M + H]^+$ |
| 30 | 4-bromophenyl | O | 1 | 1 | 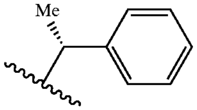 | $-(CH_2)_3CO_2Me$ | H | $ES^+$ 476 $[M + H]^+$ |
| 31 | 4-bromophenyl | O | 1 | 1 | 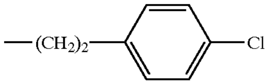 | $-(CH_2)_3CO_2Me$ | H | $ES^+$ 510 $[M + H]^+$ |
| 32 | 4-bromophenyl | O | 1 | 2 | 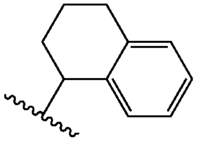 | $-(CH_2)_3CO_2Me$ | H | $ES^+$ 516 $[M + H]^+$ |

TABLE 1a-continued
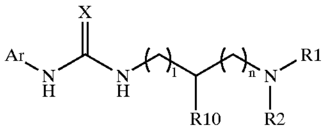
| CPD No. | Ar | X | l | n | R1 | R2 | R10 | Mass Spec. m/e |
|---|---|---|---|---|---|---|---|---|
| 33 | 4-bromophenyl | O | 1 | 3 | 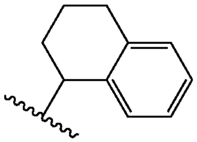 | —$(CH_2)_3CO_2Me$ | H | $ES^+$ 530 $[M + H]^+$ |
| 34 | 4-methylphenyl | O | 1 | 1 | 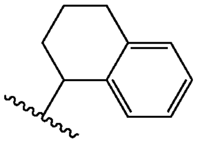 | —$(CH_2)_3CO_2Me$ | H | $ES^+$ 438 $[M + H]^+$ |
| 35 | 3,4-dichlorophenyl | O | 1 | 1 | 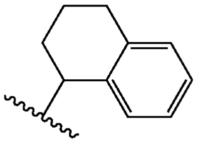 | —$(CH_2)_3CO_2Me$ | H | $ES^+$ 492 $[M + H]^+$ |
| 36 | 4-bromophenyl | O | 1 | 1 | 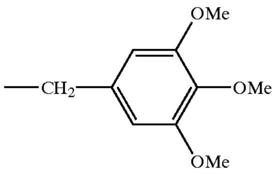 | —$(CH_2)_3CO_2Me$ | H | $ES^+$ 522 $[M + H]^+$ |
| 37 | 4-bromophenyl | O | 1 | 1 | 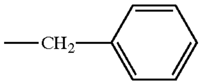 | —$(CH_2)_3CO_2Me$ | H | $ES^+$ 462 $[M + H]^+$ |
| 38 | 4-bromophenyl | O | 1 | 1 | 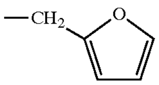 | —$(CH_2)_3CO_2Me$ | H | $ES^+$ 452 $[M + H]^+$ |

TABLE 1a-continued
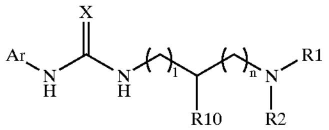
| CPD No. | Ar | X | l | n | R1 | R2 | R10 | Mass Spec. m/e |
|---|---|---|---|---|---|---|---|---|
| 39 | 4-bromophenyl | O | 1 | 1 | 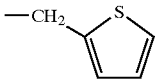 | $—(CH_2)_3CO_2Me$ | H | $ES^+$ 468 $[M + H]^+$ |
| 40 | 4-bromophenyl | O | 1 | 1 | 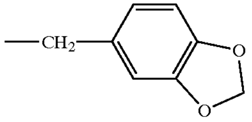 | $—(CH_2)_3CO_2Me$ | H | $ES^+$ 506 $[M + H]^+$ |
| 41 | 4-bromophenyl | O | 1 | 1 | 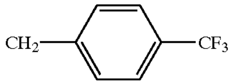 | $—(CH_2)_3CO_2Me$ | H | $ES^+$ 528 $[M + H]^+$ |
| 42 | 4-bromophenyl | O | 1 | 1 | 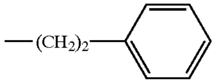 | $—(CH_2)_3CO_2Me$ | H | $ES^+$ 475 $[M + H]^+$ |
| 43 | 4-bromophenyl | O | 1 | 1 | 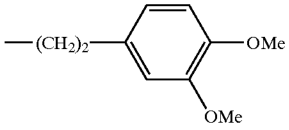 | $—(CH_2)_3CO_2Me$ | H | $ES^+$ 536 $[M + H]^+$ |
| 44 | 4-bromophenyl | O | 1 | 1 | 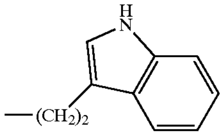 | $—(CH_2)_3CO_2Me$ | H | $ES^+$ 515 $[M + H]^+$ |

TABLE 1a-continued
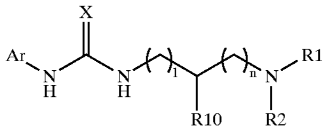
| CPD No. | Ar | X | l | n | R1 | R2 | R10 | Mass Spec. m/e |
|---|---|---|---|---|---|---|---|---|
| 45 | 4-bromophenyl | O | 1 | 1 | 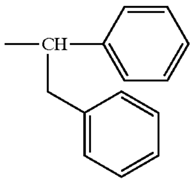 | —$(CH_2)_3CO_2Me$ | H | $ES^+$ 552 $[M + H]^+$ |
| 46 | 4-bromophenyl | O | 1 | 1 | 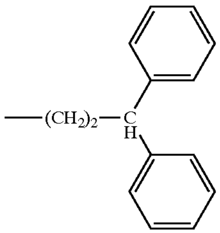 | —$(CH_2)_3CO_2Me$ | H | $ES^+$ 566 $[M + H]^+$ |
| 47 | 4-bromophenyl | O | 1 | 1 | 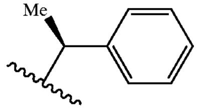 | —$(CH_2)_3CO_2Me$ | H | $ES^+$ 476 $[M + H]^+$ |
| 48 | 4-bromophenyl | O | 1 | 1 | 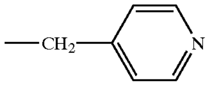 | —$(CH_2)_3CO_2Me$ | H | $ES^+$ 463 $[M + H]^+$ |
| 49 | phenyl | O | 1 | 1 | 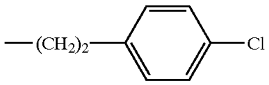 | —$(CH_2)_3CO_2Me$ | H | $ES^+$ 432 $[M + H]^+$ |

TABLE 1a-continued
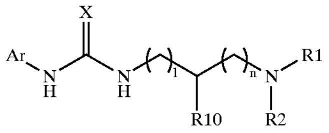
| CPD No. | Ar | X | l | n | R1 | R2 | R10 | Mass Spec. m/e |
|---|---|---|---|---|---|---|---|---|
| 50 | 4-bromophenyl | O | 1 | 0 | 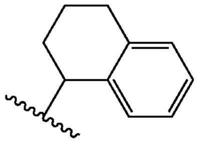 | $—(CH_2)_3CO_2Me$ | H | $ES^+$ 488 $[M + H]^+$ |
| 51 | 3-chlorophenyl | O | 1 | 1 | 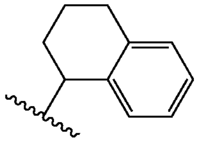 | $—(CH_2)_3CO_2Me$ | H | $ES^+$ 458 $[M + H]^+$ |
| 52 | 3-methylphenyl | O | 1 | 1 | 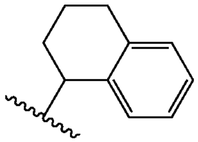 | $—(CH_2)_3CO_2Me$ | H | $ES^+$ 438 $[M + H]^+$ |
| 53 | 4-chloro-3-(trifluoromethyl)phenyl | O | 1 | 1 | 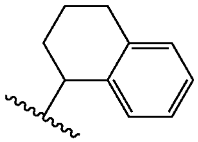 | $—(CH_2)_3CO_2Me$ | H | $ES^+$ 526 $[M + H]^+$ |
| 54 | 2-biphenyl | O | 1 | 1 | 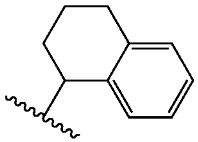 | $—(CH_2)_3CO_2Me$ | H | $ES^+$ 500 $[M + H]^+$ |

TABLE 1a-continued
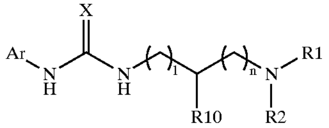
| CPD No. | Ar | X | l | n | R1 | R2 | R10 | Mass Spec. m/e |
|---|---|---|---|---|---|---|---|---|
| 55 | 2,4-dimethoxyphenyl | O | 1 | 1 | 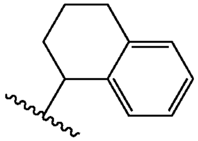 | $-(CH_2)_3CO_2Me$ | H | $ES^+$ 484 $[M + H]^+$ |
| 56 | phenyl | O | 1 | 1 | 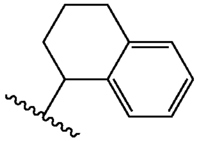 | $-(CH_2)_3CO_2Me$ | H | $ES^+$ 424 $[M + H]^+$ |
| 57 | 4-methoxyphenyl | O | 1 | 1 | 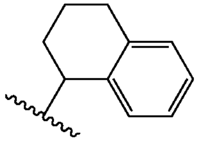 | $-(CH_2)_3CO_2Me$ | H | $ES^+$ 454 $[M + H]^+$ |
| 58 | 4-phenoxyphenyl | O | 1 | 1 | 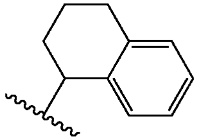 | $-(CH_2)_3CO_2Me$ | H | $ES^+$ 516 $[M + H]^+$ |
| 59 | 1-naphthyl | O | 1 | 1 | 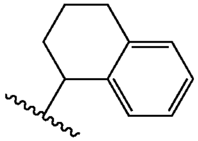 | $-(CH_2)_3CO_2Me$ | H | $ES^+$ 474 $[M + H]^+$ |

TABLE 1a-continued
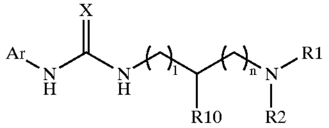
| CPD No. | Ar | X | l | n | R1 | R2 | R10 | Mass Spec. m/e |
|---|---|---|---|---|---|---|---|---|
| 60 | 4-bromophenyl | O | 1 | 1 | 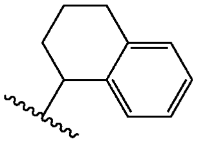 | —$(CH_2)_3CO_2H$ | H | $ES^+$ 488 $[M + H]^+$ |
| 61 | 4-bromophenyl | O | 1 | 1 | 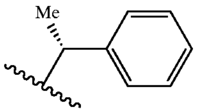 | —$(CH_2)_3CO_2H$ | H | $ES^+$ 462 $[M + H]^+$ |
| 62 | 4-bromophenyl | O | 1 | 2 | 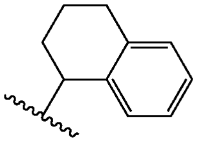 | —$(CH_2)_3CO_2H$ | H | $ES^+$ 502 $[M + H]^+$ |
| 63 | 4-bromophenyl | O | 1 | 3 | 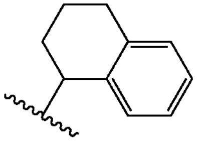 | —$(CH_2)_3CO_2H$ | H | $ES^+$ 516 $[M + H]^+$ |
| 64 | 4-methylphenyl | O | 1 | 1 | 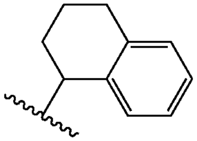 | —$(CH_2)_3CO_2H$ | H | $ES^+$ 424 $[M + H]^+$ |
| 65 | 3,4-dichlorophenyl | O | 1 | 1 | 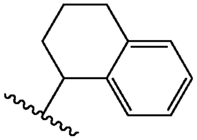 | —$(CH_2)_3CO_2H$ | H | $ES^+$ 478 $[M + H]^+$ |

TABLE 1a-continued
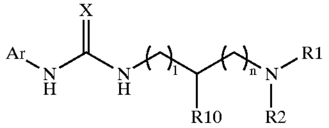
| CPD No. | Ar | X | l | n | R1 | R2 | R10 | Mass Spec. m/e |
|---|---|---|---|---|---|---|---|---|
| 66 | 4-bromophenyl | O | 1 | 1 | 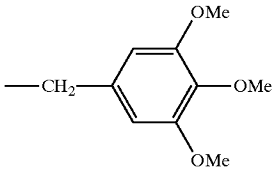 | $—(CH_2)_3CO_2H$ | H | $ES^+$ 538 $[M + H]^+$ |
| 67 | 4-bromophenyl | O | 1 | 1 | 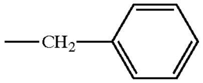 | $—(CH_2)_3CO_2H$ | H | $ES^+$ 448 $[M + H]^+$ |
| 68 | 4-bromophenyl | O | 1 | 1 | 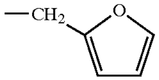 | $—(CH_2)_3CO_2H$ | H | $ES^+$ 438 $[M + H]^+$ |
| 69 | 4-bromophenyl | O | 1 | 1 | 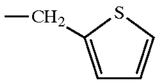 | $—(CH_2)_3CO_2H$ | H | $ES^+$ 454 $[M + H]^+$ |
| 70 | 4-bromophenyl | O | 1 | 1 | 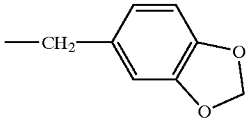 | $—(CH_2)_3CO_2H$ | H | $ES^+$ 492 $[M + H]^+$ |
| 71 | 4-bromophenyl | O | 1 | 1 | 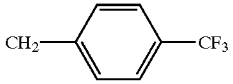 | $—(CH_2)_3CO_2H$ | H | $ES^+$ 516 $[M + H]^+$ |
| 72 | 4-bromophenyl | O | 1 | 1 | 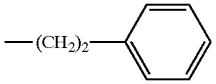 | $—(CH_2)_3CO_2H$ | H | $ES^+$ 462 $[M + H]^+$ |

TABLE 1a-continued
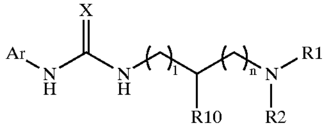
| CPD No. | Ar | X | l | n | R1 | R2 | R10 | Mass Spec. m/e |
|---|---|---|---|---|---|---|---|---|
| 73 | 4-bromophenyl | O | 1 | 1 | 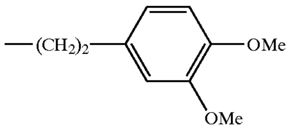 | $—(CH_2)_3CO_2H$ | H | $ES^+$ 522 $[M + H]^+$ |
| 74 | 4-bromophenyl | O | 1 | 1 | 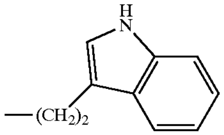 | $—(CH_2)_3CO_2H$ | H | $ES^+$ 501 $[M + H]^+$ |
| 75 | 4-bromophenyl | O | 1 | 1 | 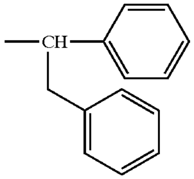 | $—(CH_2)_3CO_2H$ | H | $ES^+$ 538 $[M + H]^+$ |
| 76 | 4-bromophenyl | O | 1 | 1 | 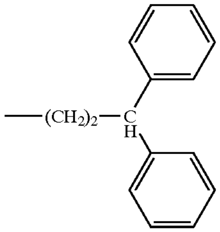 | $—(CH_2)_3CO_2H$ | H | $ES^+$ 552 $[M + H]^+$ |
| 77 | 4-bromophenyl | O | 1 | 1 | 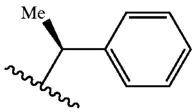 | $—(CH_2)_3CO_2H$ | H | $ES^-$ 462 $[M + H]^+$ |

TABLE 1a-continued
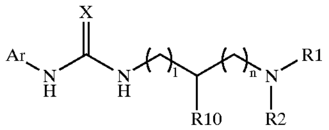
| CPD No. | Ar | X | l | n | R1 | R2 | R10 | Mass Spec. m/e |
|---|---|---|---|---|---|---|---|---|
| 78 | 4-bromophenyl | O | 1 | 1 | 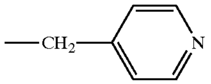 | $—(CH_2)_3CO_2H$ | H | $ES^+$ 447 $[M-H]^-$ |
| 79 | 4-bromophenyl | O | 1 | 1 | 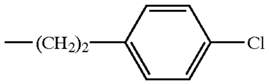 | $—(CH_3)_3CO_2H$ | H | $ES^+$ 496 $[M+H]^+$ |
| 80 | phenyl | O | 1 | 1 | 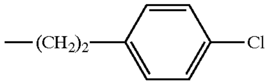 | $—(CH_2)_3CO_2H$ | H | $ES^+$ 418 $[M+H]^+$ |
| 81 | 4-bromophenyl | O | 1 | 0 | 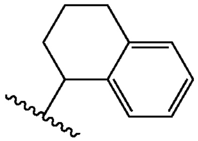 | $—(CH_2)_3CO_2H$ | H | $ES^+$ 474 $[M+H]^+$ |
| 82 | 3-chlorophenyl | O | 1 | 1 | 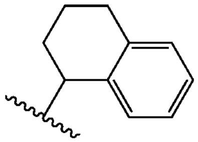 | $—(CH_2)_3CO_2H$ | H | $ES^+$ 444 $[M+H]^+$ |
| 83 | 3-methylphenyl | O | 1 | 1 | 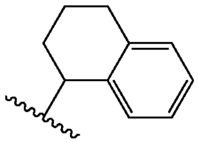 | $—(CH_2)_3CO_2H$ | H | $ES^+$ 424 $[M+H]^+$ |

TABLE 1a-continued
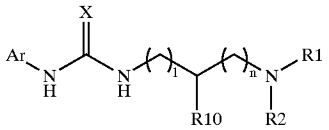
| CPD No. | Ar | X | l | n | R1 | R2 | R10 | Mass Spec. m/e |
|---|---|---|---|---|---|---|---|---|
| 84 | 4-chloro-3-(trifluoromethyl)phenyl | O | 1 | 1 | 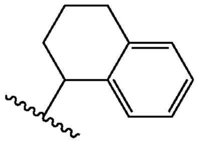 | $—(CH_2)_3CO_2H$ | H | $ES^+$ 512 $[M + H]^+$ |
| 85 | 2-biphenyl | O | 1 | 1 | 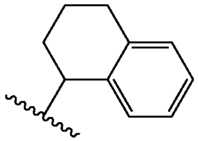 | $—(CH_2)_3CO_2H$ | H | $ES^+$ 486 $[M + H]^+$ |
| 86 | 2,4-dimethoxyphenyl | O | 1 | 1 | 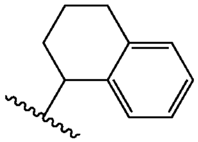 | $—(CH_2)_3CO_2H$ | H | $ES^+$ 470 $[M + H]^+$ |
| 87 | phenyl | O | 1 | 1 | 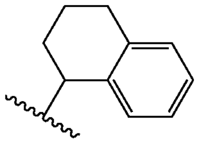 | $—(CH_2)_3CO_2H$ | H | $ES^+$ 410 $[M + H]^+$ |
| 88 | 4-methoxyphenyl | O | 1 | 1 | 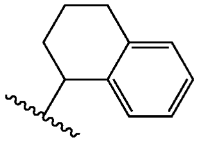 | $—(CH_2)_3CO_2H$ | H | $ES^+$ 440 $[M + H]^+$ |

TABLE 1a-continued

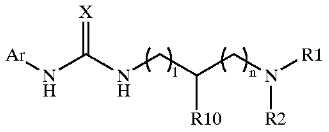

| CPD No. | Ar | X | l | n | R1 | R2 | R10 | Mass Spec. m/e |
|---|---|---|---|---|---|---|---|---|
| 89 | 4-phenoxyphenyl | O | 1 | 1 | 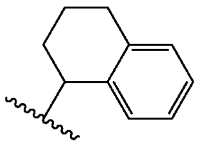 | $—(CH_2)_3CO_2H$ | H | $ES^+$ 502 $[M + H]^+$ |
| 90 | 1-naphthyl | O | 1 | 1 | 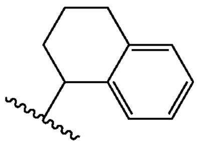 | $—(CH_2)_3CO_2H$ | H | $ES^+$ 460 $[M + H]^+$ |
| 93 | 4-chloro-3-(trifluoromethyl)phenyl | O | 1 | 1 | 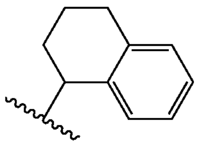 | ethyl | H | $ES^+$ 454 $[M + H]^+$ |
| 94 | 4-chloro-3-(trifluoromethyl)phenyl | O | 1 | 1 | 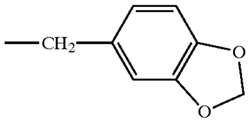 | $—(CH_2)_3SMe$ | H | $ES^+$ 518 $[M + H]^+$ |
| 95 | 4-chloro-3-(trifluoromethyl)phenyl | O | 1 | 1 | 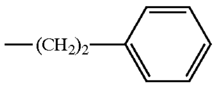 | $—CH_2CH(CH_3)_2$ | H | $ES^+$ 456 $[M + H]^+$ |
| 96 | 4-chloro-3-(trifluoromethyl)phenyl | O | 1 | 1 | 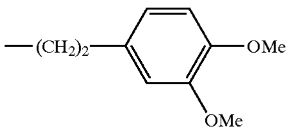 | $—CH_2CH(CH_3)_2$ | H | $ES^+$ 516 $[M + H]^+$ |

TABLE 1a-continued
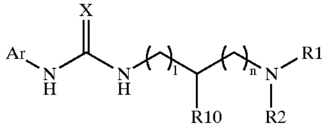
| CPD No. | Ar | X | l | n | R1 | R2 | R10 | Mass Spec. m/e | |
|---|---|---|---|---|---|---|---|---|---|
| 97 | 4-chloro-3-(trifluoromethyl)phenyl | O | 1 | 1 | 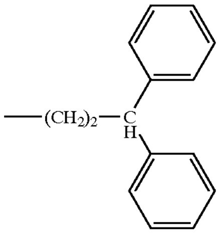 | $—(CH_2)_3CO_2H$ | H | $ES^+$ | 576 $[M + H]^+$ |
| 98 | 2-biphenyl | O | 1 | 1 | 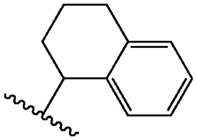 | 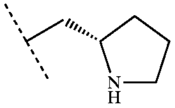 | H | $ES^+$ | 483 $[M + H]^+$ |
| 99 | 2-biphenyl | O | 1 | 1 | 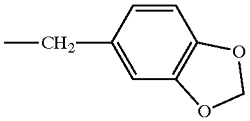 | $—(CH_2)_2CH(CH_3)_2$ | H | $ES^+$ | 474 $[M + H]^+$ |
| 100 | 2-biphenyl | O | 1 | 1 | 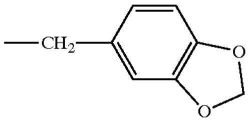 | $—(CH_2)_3SMe$ | H | $ES^+$ | 492 $[M + H]^+$ |
| 101 | 2-biphenyl | O | 1 | 1 | 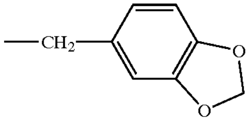 | $—(CH_2)_3CO_2H$ | H | $ES^+$ | 490 $[M + H]^+$ |

TABLE 1a-continued
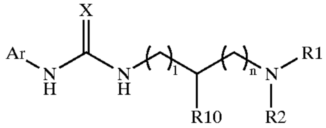
| CPD No. | Ar | X | l | n | R1 | R2 | R10 | Mass Spec. m/e |
|---|---|---|---|---|---|---|---|---|
| 102 | 2-biphenyl | O | 1 | 1 | 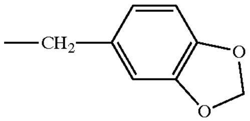 | 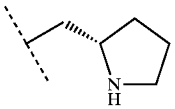 | H | $ES^+$ 487 $[M + H]^+$ |
| 103 | 2-biphenyl | O | 1 | 1 | 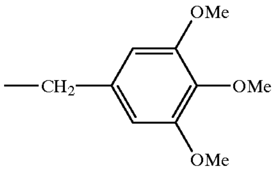 | $—(CH_2)_3SMe$ | H | $ES^+$ 538 $[M + H]^+$ |
| 104 | 2-biphenyl | O | 1 | 1 | 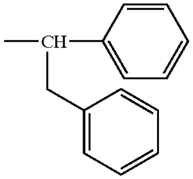 | $—(CH_2)_2CH(CH_3)_2$ | H | $ES^+$ 506 $[M + H]^+$ |
| 105 | 2-biphenyl | O | 1 | 1 | 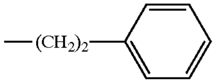 | $—(CH_2)_3SMe$ | H | $ES^+$ 462 $[M + H]^+$ |
| 106 | 2-biphenyl | O | 1 | 1 | 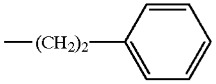 | $—(CH_2)_3CO_2Me$ | H | $ES^+$ 474 $[M + H]^+$ |
| 107 | 2-biphenyl | O | 1 | 1 | 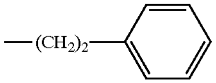 | 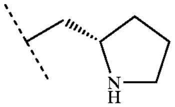 | H | $ES^+$ 457 $[M + H]^+$ |

TABLE 1a-continued
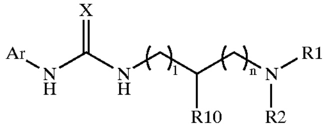
| CPD No. | Ar | X | l | n | R1 | R2 | R10 | Mass Spec. m/e |
|---|---|---|---|---|---|---|---|---|
| 108 | 2-biphenyl | O | 1 | 1 | 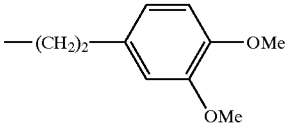 | $—CH_2CH(CH_3)_2$ | H | $ES^+$ 490 $[M + H]^+$ |
| 109 | 2-biphenyl | O | 1 | 1 | 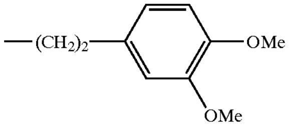 | 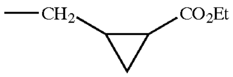 | H | $ES^+$ 560 $[M + H]^+$ |
| 110 | 2-biphenyl | O | 1 | 1 | 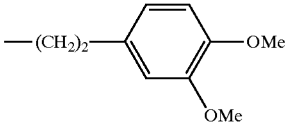 | 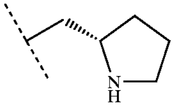 | H | $ES^+$ 517 $[M + H]^+$ |
| 111 | 2-biphenyl | O | 1 | 1 | 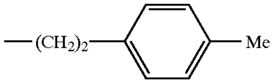 | $—CH_2CH(CH_3)_2$ | H | $ES^+$ 444 $[M + H]^+$ |
| 112 | 2-biphenyl | O | 1 | 1 | 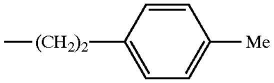 | 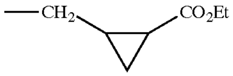 | H | $ES^+$ 514 $[M + H]^+$ |
| 113 | 2-biphenyl | O | 1 | 1 | 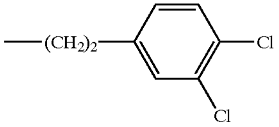 | $—CH_2CH(CH_3)_2$ | H | $ES^+$ 498 $[M + H]^+$ |

TABLE 1a-continued
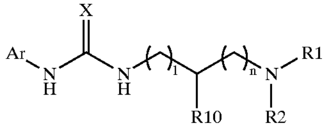
| CPD No. | Ar | X | l | n | R1 | R2 | R10 | Mass Spec. m/e |
|---|---|---|---|---|---|---|---|---|
| 114 | 2-biphenyl | O | 1 | 1 | 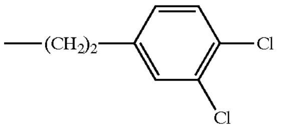 | 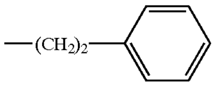 | H | $ES^+$ 546 $[M + H]^+$ |
| 115 | 2-biphenyl | O | 1 | 1 | 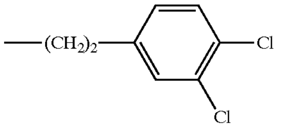 | 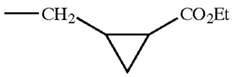 | H | $ES^+$ 568 $[M + H]^+$ |
| 116 | 2-biphenyl | O | 1 | 1 | 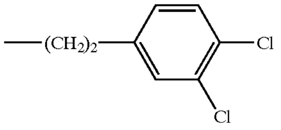 | 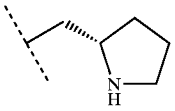 | H | $ES^+$ 525 $[M + H]^+$ |
| 117 | 2-biphenyl | O | 1 | 1 | 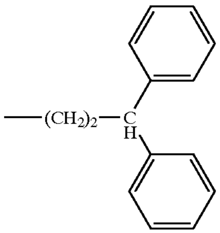 | $—CH_2CH(CH_3)_2$ | H | $ES^+$ 520 $[M + H]^+$ |
| 118 | 4-bromophenyl | O | 1 | 1 | 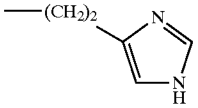 | $—CH_2CH(CH_3)_2$ | H | $ES^+$ 422 $[M + H]^+$ |

TABLE 1a-continued
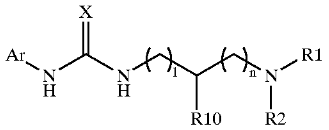
| CPD No. | Ar | X | l | n | R1 | R2 | R10 | Mass Spec. m/e |
|---|---|---|---|---|---|---|---|---|
| 119 | 4-bromophenyl | O | 1 | 1 | 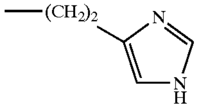 | $—(CH_2)_2CH(CH_3)_2$ | H | ES+ 436 [M + H]+ |
| 120 | 4-bromophenyl | O | 1 | 1 | 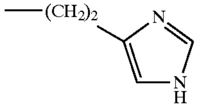 | 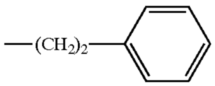 | H | ES+ 470 [M + H]+ |
| 121 | 4-bromophenyl | O | 1 | 1 | 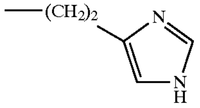 | 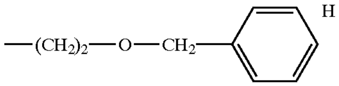 | H | ES+ 500 [M + H]+ |
| 122 | 4-bromophenyl | O | 1 | 1 | 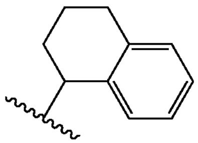 | $—CH_2CH(CH_3)_2$ | H | ES+ 458 [M + H]+ |
| 123 | 4-bromophenyl | O | 1 | 1 | 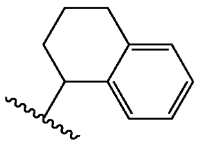 | 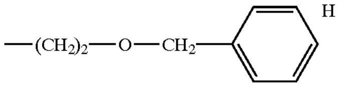 | H | ES+ 536 [M + H]+ |
| 124 | 4-bromophenyl | O | 1 | 1 | 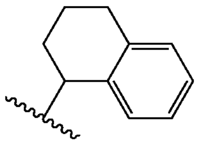 | $—(CH_2)_3SMe$ | H | ES+ 490 [M + H]+ |

TABLE 1a-continued
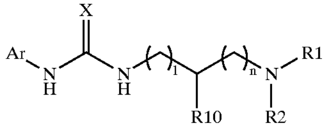
| CPD No. | Ar | X | l | n | R1 | R2 | R10 | Mass Spec. m/e |
|---|---|---|---|---|---|---|---|---|
| 125 | 4-bromophenyl | O | 1 | 1 | 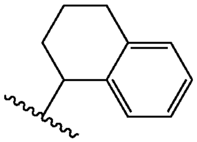 | 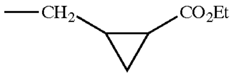 | H | ES+ 528 [M + H]+ |
| 126 | 4-bromophenyl | O | 1 | 1 | 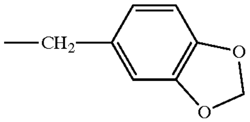 | $—CH_2CH(CH_3)_2$ | H | ES+ 462 [M + H]+ |
| 127 | 4-bromophenyl | O | 1 | 1 | 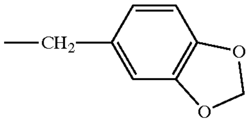 | 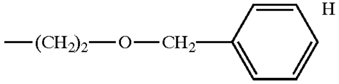 | H | ES+ 540 [M + H]+ |
| 128 | 4-bromophenyl | O | 1 | 1 | 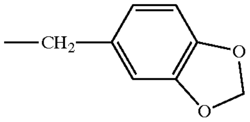 | 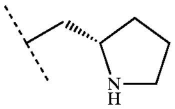 | H | ES+ 489 [M + H]+ |
| 129 | 4-bromophenyl | O | 1 | 1 | 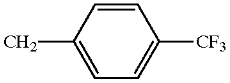 | $—CH_2H(CH_3)_2$ | H | ES+ 486 [M + H]+ |
| 130 | 4-bromophenyl | O | 1 | 1 | 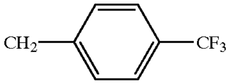 | $—(CH_2)_3SMe$ | H | ES+ 518 [M + H]+ |

TABLE 1a-continued
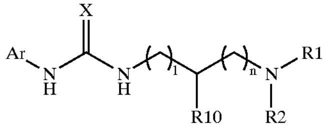
| CPD No. | Ar | X | l | n | R1 | R2 | R10 | Mass Spec. m/e |
|---|---|---|---|---|---|---|---|---|
| 131 | 4-bromophenyl | O | 1 | 1 | 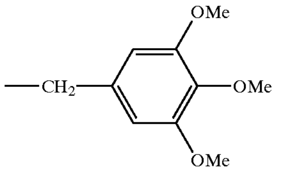 | $—(CH_2)_2CH(CH_3)_2$ | H | $ES^+$ 522 $[M + H]^+$ |
| 132 | 4-bromophenyl | O | 1 | 1 | 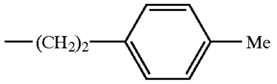 | $—(CH_2)_3CO_2H$ | H | $ES^+$ 476 $[M + H]^+$ |
| 133 | 4-bromophenyl | O | 1 | 1 | 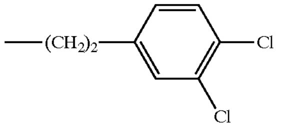 | $—(CH_2)_3CO_2H$ | H | $ES^+$ 530 $[M + H]^+$ |
| 134 | 4-bromophenyl | O | 1 | 1 | 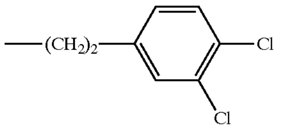 | 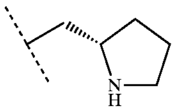 | H | $ES^+$ 527 $[M + H]^+$ |
| 135 | 3-methylphenyl | O | 1 | 1 | 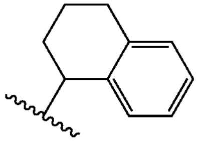 | 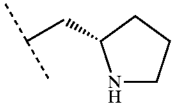 | H | $ES^+$ 421 $[M + H]^+$ |
| 136 | 3-methylphenyl | O | 1 | 1 | 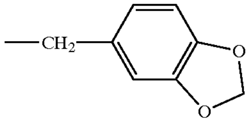 | $—CH_2CH(CH_3)_2$ | H | $ES^+$ 398 $[M + H]^+$ |

TABLE 1a-continued
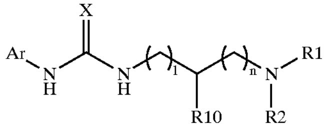
| CPD No. | Ar | X | l | n | R1 | R2 | R10 | Mass Spec. m/e |
|---|---|---|---|---|---|---|---|---|
| 137 | 3-methylphenyl | O | 1 | 1 | 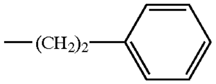 | ethyl | H | $ES^+$ 340 $[M + H]^+$ |
| 138 | 3-methylphenyl | O | 1 | 1 | 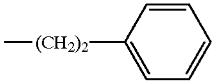 | 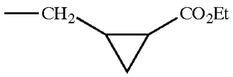 | H | $ES^+$ 438 $[M + H]^+$ |
| 139 | 3-methylphenyl | O | 1 | 1 | 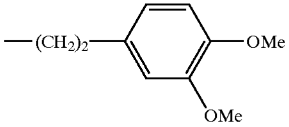 | $—(CH_2)_3SMe$ | H | $ES^+$ 460 $[M + H]^+$ |
| 140 | 3-methylphenyl | O | 1 | 1 | 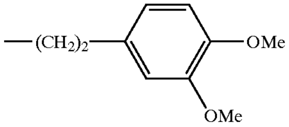 | $—(CH_2)_3CO_2H$ | H | $ES^+$ 458 $[M + H]^+$ |
| 141 | 3-methylphenyl | O | 1 | 1 | 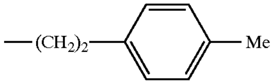 | $—(CH_2)_3SMe$ | H | $ES^+$ 414 $[M + H]^+$ |
| 142 | 3-methylphenyl | O | 1 | 1 | 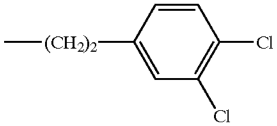 | $—(CH_2)_3SMe$ | H | $ES^+$ 468 $[M + H]^+$ |
| 143 | 3-methylphenyl | O | 1 | 1 | 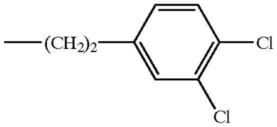 | 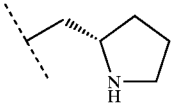 | H | $ES^+$ 463 $[M + H]^+$ |

TABLE 1a-continued
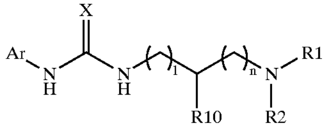
| CPD No. | Ar | X | l | n | R1 | R2 | R10 | Mass Spec. m/e |
|---|---|---|---|---|---|---|---|---|
| 144 | 3-chlorophenyl | O | 1 | 1 | 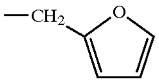 | 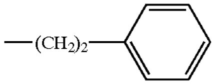 | H | ES+ 412 $[M + H]^+$ |
| 145 | 3-chlorophenyl | O | 1 | 1 | 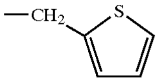 | $—(CH_2)_2CH(CH_3)_2$ | H | ES+ 394 $[M + H]^+$ |
| 146 | 3-chlorophenyl | O | 1 | 1 | 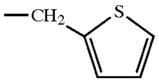 | 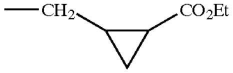 | H | ES+ 450 $[M + H]^+$ |
| 147 | 3-chlorophenyl | O | 1 | 1 | 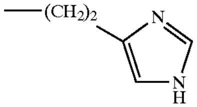 | 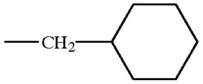 | H | ES+ 418 $[M + H]^+$ |
| 148 | 3-chlorophenyl | O | 1 | 1 | 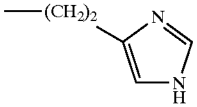 | 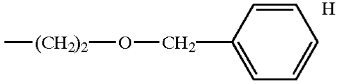 | H | ES+ 456 $[M + H]^+$ |
| 149 | 3-chlorophenyl | O | 1 | 1 | 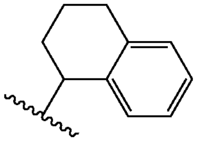 | 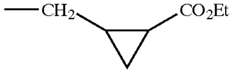 | H | ES+ 484 $[M + H]^+$ |
| 150 | 3-chlorophenyl | O | 1 | 1 | 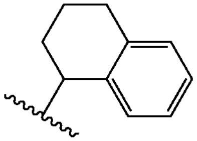 | 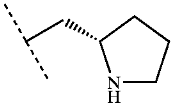 | H | ES+ 441 $[M + H]^+$ |

TABLE 1a-continued
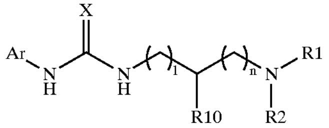
| CPD No. | Ar | X | l | n | R1 | R2 | R10 | Mass Spec. m/e |
|---|---|---|---|---|---|---|---|---|
| 151 | 3-chlorophenyl | O | 1 | 1 | 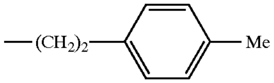 | $—CH_2CH(CH_3)_2$ | H | $ES^+$ 402 $[M + H]^+$ |
| 152 | 3-chlorophenyl | O | 1 | 1 | 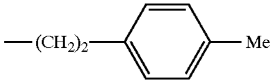 | 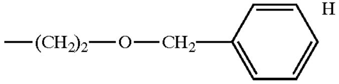 | H | $ES^+$ 480 $[M + H]^+$ |
| 153 | 3-chlorophenyl | O | 1 | 1 | 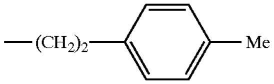 | 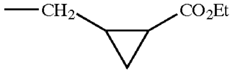 | H | $ES^+$ 472 $[M + H]^+$ |
| 154 | 3-chlorophenyl | O | 1 | 1 | 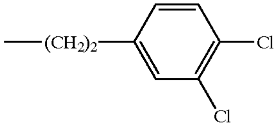 | 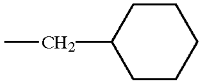 | H | $ES^+$ 496 $[M + H]^+$ |
| 155 | 3-chlorophenyl | O | 1 | 1 | 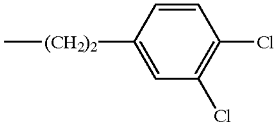 | 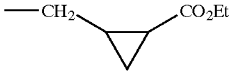 | H | $ES^+$ 526 $[M + H]^+$ |
| 156 | 3-chlorophenyl | O | 1 | 1 | 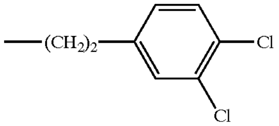 | $—(CH_2)_3CO_2Me$ | H | $ES^+$ 500 $[M + H]^+$ |
| 157 | 2,4-dimethoxyphenyl | O | 1 | 1 | 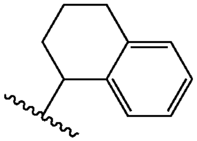 | $—(CH_2)_3SMe$ | H | $ES^+$ 472 $[M + H]^+$ |

TABLE 1a-continued
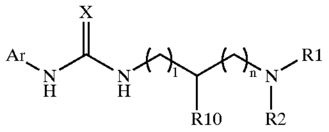
| CPD No. | Ar | X | l | n | R1 | R2 | R10 | Mass Spec. m/e |
|---|---|---|---|---|---|---|---|---|
| 158 | 2,4-dimethoxyphenyl | O | 1 | 1 | 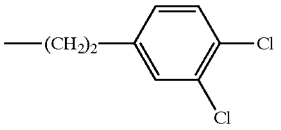 | —$(CH_2)_3SMe$ | H | ES+ 514 [M + H]+ |
| 159 | 4-methoxyphenyl | O | 1 | 1 | 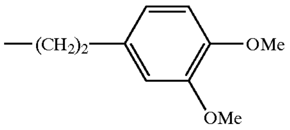 | 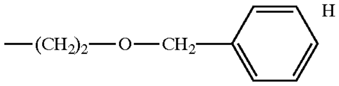 | H | ES+ 522 [M + H]+ |
| 160 | 3,4-dichlorophenyl | O | 1 | 1 | 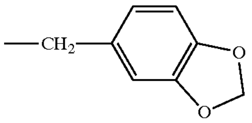 | —$(CH_2)_3CO_2Me$ | H | ES+ 496 [M + H]+ |
| 161 | 1-naphthyl | O | 1 | 1 | 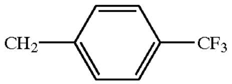 | —$(CH_2)_3CO_2H$ | H | ES+ 488 [M + H]+ |
| 162 | 1-naphthyl | O | 1 | 1 | 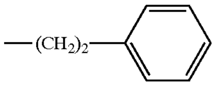 | 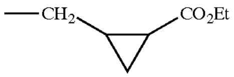 | H | ES+ 474 [M + H]+ |
| 163 | phenyl | O | 1 | 1 | 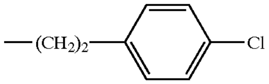 | ethyl | OH | ES+ 376 [M + H]+ |
| 164 | 4-chlorophenyl | S | 1 | 1 | 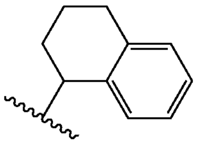 | —$(CH_2)_3CO_2H$ | H | ES+ 460 [M + H]+ |

TABLE 1a-continued
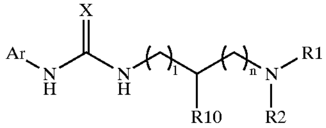
| CPD No. | Ar | X | l | n | R1 | R2 | R10 | Mass Spec. m/e |
|---|---|---|---|---|---|---|---|---|
| 165 | 4-bromophenyl | O | 0 | 2 | 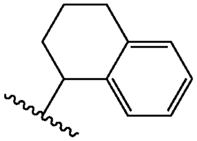 | $-(CH_2)_3CO_2H$ | 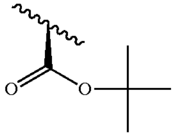 | $ES^+$ 588 $[M + H]^+$ |
| 166 | 4-bromophenyl | O | 0 | 2 | 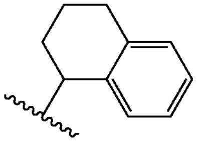 | $-(CH_2)_3CO_2H$ | 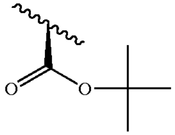 | $ES^+$ 588 $[M + H]^+$ |
| 167 | 4-bromophenyl | O | 1 | 1 | 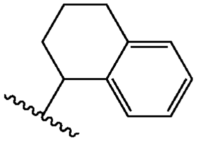 | $-(CH_2)_3CO_2H$ | OH | $ES^+$ 504 $[M + H]^+$ |
| 168 | 4-methoxyphenyl | S | 1 | 1 | 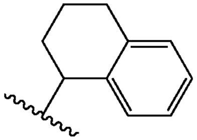 | $-(CH_2)_3CO_2H$ | H | $ES^+$ 456 $[M + H]^+$ |
| 169 | 4-benzyloxyphenyl | S | 1 | 1 | 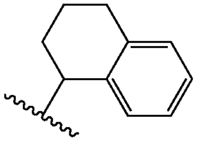 | $-(CH_2)_3CO_2H$ | H | $ES^+$ 532 $[M + H]^+$ |

TABLE 1a-continued
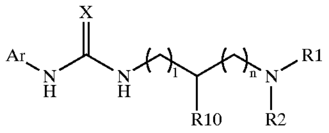
| CPD No. | Ar | X | l | n | R1 | R2 | R10 | Mass Spec. m/e |
|---|---|---|---|---|---|---|---|---|
| 170 | 4-(trifluoromethoxy)phenyl | S | 1 | 1 | 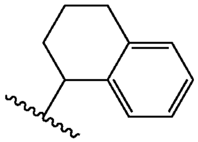 | —$(CH_2)_3CO_2H$ | H | $ES^+$ 510 $[M + H]^+$ |
| 171 | 4-chlorophenyl | O | 1 | 1 | 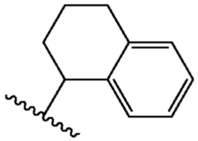 | —$(CH_2)_3CO_2H$ | H | $ES^+$ 444 $[M + H]^+$ |
| 172 | 4-bromophenyl | O | 1 | 1 | 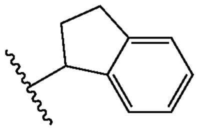 | —$(CH_2)_3CO_2Me$ | H | $ES^+$ 490 $[M + H]^+$ |
| 173 | 4-bromophenyl | O | 1 | 1 | 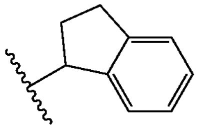 | —$(CH_2)_3CO_2H$ | H | $ES^+$ 476 $[M + H]^+$ |
| 174 | 4-bromophenyl | O | 1 | 1 | 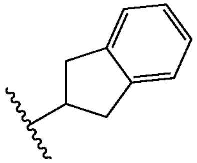 | —$(CH_2)_3CO_2Me$ | H | $ES^+$ 490 $[M + H]^+$ |

TABLE 1a-continued
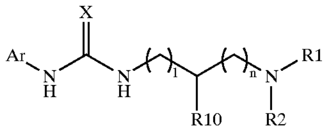
| CPD No. | Ar | X | l | n | R1 | R2 | R10 | Mass Spec. m/e |
|---|---|---|---|---|---|---|---|---|
| 175 | 4-bromophenyl | O | 1 | 1 | 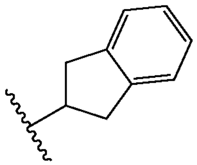 | —$(CH_2)_3CO_2H$ | H | $ES^+$ 476 $[M + H]^+$ |
| 176 | 4-bromophenyl | O | 1 | 1 | 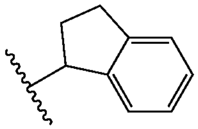 | —$(CH_2)_3CO_2Me$ | H | $ES^+$ 488 $[M + H]^+$ |
| 177 | 4-bromophenyl | O | 1 | 1 | 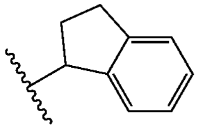 | —$(CH_2)_3CO_2H$ | H | $ES^+$ 476 $[M + H]^+$ |
| 178 | 4-bromophenyl | O | 1 | 1 | 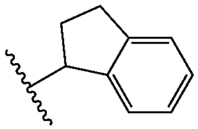 | —$(CH_2)_3CO_2Me$ | H | $ES^+$ 490 $[M + H]^+$ |
| 179 | 4-bromophenyl | O | 1 | 1 | 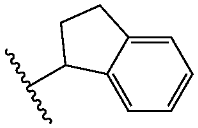 | —$(CH_2)_3CO_2H$ | H | $ES^+$ 476 $[M + H]^+$ |

TABLE 1a-continued
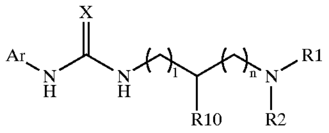
| CPD No. | Ar | X | l | n | R1 | R2 | R10 | Mass Spec. m/e |
|---|---|---|---|---|---|---|---|---|
| 180 | 4-bromophenyl | O | 1 | 1 | 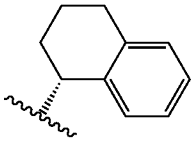 | $—(CH_2)_3CO_2Me$ | H | $ES^+$ 504 $[M + H]^+$ |
| 181 | 4-bromophenyl | O | 1 | 1 | 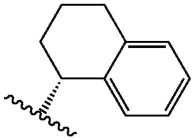 | $—(CH_2)_3CO_2H$ | H | $ES^+$ 490 $[M + H]^+$ |
| 182 | 4-bromophenyl | O | 1 | 1 | 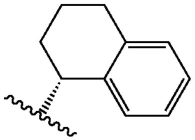 | $—(CH_2)_3CO_2Me$ | H | $ES^+$ 504 $[M + H]^+$ |
| 183 | 4-bromophenyl | O | 1 | 1 | 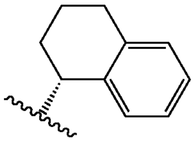 | $—(CH_2)_3CO_2H$ | H | $ES^+$ 490 $[M + H]^+$ |
| 184 | 4-bromophenyl | O | 1 | 1 | 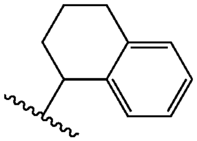 | $—(CH_2)_3CO_2Et$ | H | $ES^+$ 516 $[M + H]^+$ |

TABLE 1a-continued
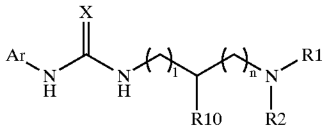
| CPD No. | Ar | X | l | n | R1 | R2 | R10 | Mass Spec. m/e |
|---|---|---|---|---|---|---|---|---|
| 185 | 4-chlorophenyl | O | 1 | 1 | 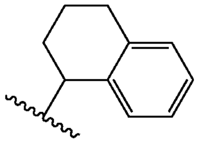 | $—(CH_2)_3CO_2Me$ | H | $ES^+$ 458 $[M + H]^+$ |
| 186 | 4-bromophenyl | O | 1 | 1 | 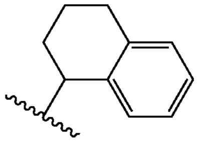 | $—CH_2CO_2H$ | H | $ES^+$ 460 $[M + H]^+$ |
| 187 | 4-fluorophenyl | O | 1 | 1 | 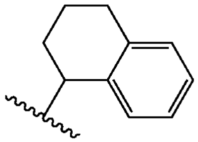 | $—(CH_2)_3CO_2Me$ | H | $ES^+$ 442 $[M + H]^+$ |
| 188 | 4-fluorophenyl | O | 1 | 1 | 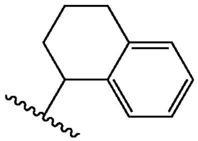 | $—(CH_2)_3CO_2H$ | H | $ES^+$ 428 $[M + H]^+$ |
| 189 | 2-bromophenyl | O | 1 | 1 | 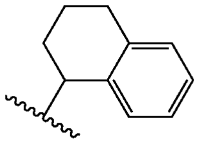 | $—(CH_2)_3CO_2Me$ | H | $ES^+$ 504 $[M + H]^+$ |

TABLE 1a-continued
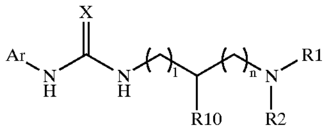
| CPD No. | Ar | X | l | n | R1 | R2 | R10 | Mass Spec. m/e |
|---|---|---|---|---|---|---|---|---|
| 190 | 2-bromophenyl | O | 1 | 1 | 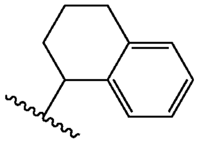 | $-(CH_2)_3CO_2H$ | H | $ES^+$ 490 $[M + H]^+$ |
| 191 | 2-bromophenyl | O | 1 | 1 | 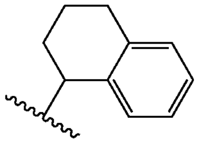 | ethyl | H | $ES^+$ 430 $[M + H]^+$ |
| 192 | phenyl | O | 1 | 1 | 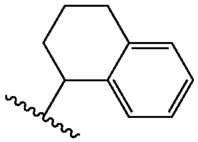 | ethyl | H | $ES^+$ 352 $[M + H]^+$ |
| 193 | 2-bromophenyl | O | 1 | 1 | 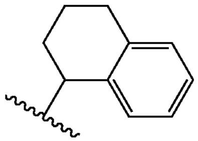 | $-(CH_2)_3CONH_2$ | H | $ES^+$ 487 $[M + H]^+$ |
| 194 | 2-bromophenyl | O | 1 | 1 | 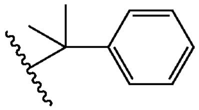 | $-(CH_2)_3CO_2Me$ | H | $ES^+$ 492 $[M + H]^+$ |
| 195 | 2-bromophenyl | O | 1 | 1 | 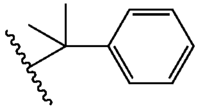 | $-(CH_2)_3CO_2H$ | H | $ES^+$ 478 $[M + H]^+$ |

TABLE 1a-continued
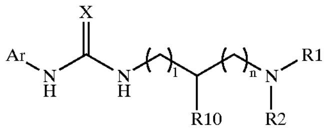
| CPD No. | Ar | X | l | n | R1 | R2 | R10 | Mass Spec. m/e |
|---|---|---|---|---|---|---|---|---|
| 196 | 4-bromophenyl | O | 1 | 1 | 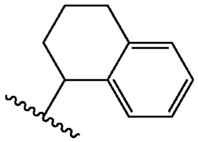 | 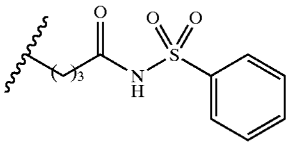 | H | ES+ 627 [M + H]+ |
| 197 | 4-bromophenyl | O | 1 | 1 | 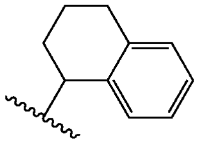 | 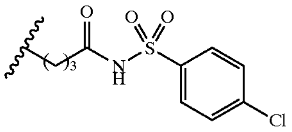 | H | ES+ 663 [M + H]+ |
| 198 | 3-bromophenyl | O | 1 | 1 | 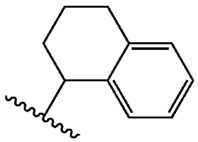 | —$(CH_2)_3CO_2Me$ | H | ES+ 502 [M + H]+ |
| 199 | 3-bromophenyl | O | 1 | 1 | 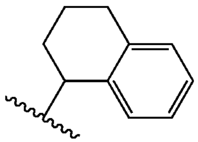 | —$(CH_2)_3CO_2H$ | H | ES+ 488 [M + H]+ |
| 200 | 4-bromo-2-methylphenyl | O | 1 | 1 | 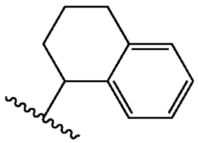 | —$(CH_2)_3CO_2Me$ | H | ES+ 518 [M + H]+ |

TABLE 1a-continued
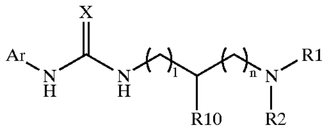
| CPD No. | Ar | X | l | n | R1 | R2 | R10 | Mass Spec. m/e |
|---|---|---|---|---|---|---|---|---|
| 201 | 4-bromo-2-methylphenyl | O | 1 | 1 | 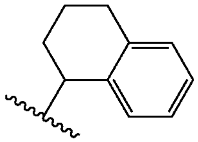 | $—(CH_2)_3CO_2H$ | H | $ES^+$ 502 $[M + H]^+$ |
| 202 | 4-bromophenyl | O | 1 | 1 | 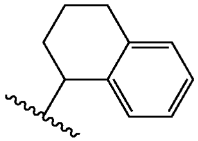 | $—(CH_2)_4OCOCH_3$ | H | $ES^+$ 516 $[M + H]^+$ |
| 203 | 4-bromophenyl | O | 1 | 1 | 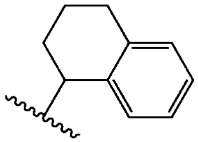 | $—(CH_2)_4OH$ | H | $ES^+$ 476 $[M + H]^+$ |
| 204 | 4-bromophenyl | O | 1 | 1 | 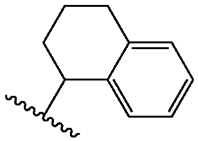 | $—(CH_2)_3OCOCH_3$ | H | $ES^+$ 532 $[M + H]^+$ |
| 205 | 4-bromophenyl | O | 1 | 1 | 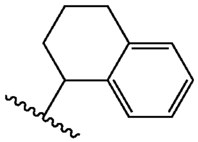 | $—(CH_2)_5OH$ | H | $ES^+$ 488 $[M + H]^+$ |

TABLE 1a-continued
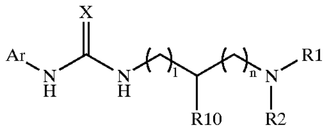
| CPD No. | Ar | X | l | n | R1 | R2 | R10 | Mass Spec. m/e |
|---|---|---|---|---|---|---|---|---|
| 206 | 4-bromophenyl | O | 1 | 1 | 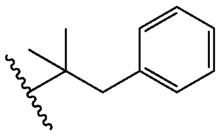 | —$(CH_2)_3CO_2Me$ | H | $ES^+$ 506 $[M + H]^+$ |
| 207 | 4-bromophenyl | O | 1 | 1 | 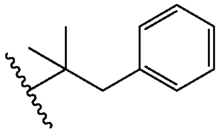 | —$(CH_2)_3CO_2H$ | H | $ES^+$ 492 $[M + H]^+$ |
| 208 | 4-bromophenyl | O | 1 | 1 | 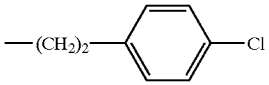 | —$(CH_2)_3CO_2Me$ | H | $ES^+$ 546 $[M + H]^+$ |
| 209 | 4-bromophenyl | O | 1 | 1 | 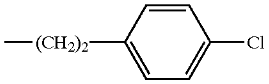 | —$(CH_2)_3CO_2H$ | H | $ES^+$ 532 $[M + H]^+$ |
| 210 | 4-bromophenyl | O | 1 | 1 | 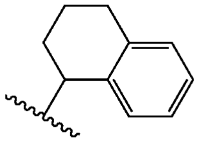 | 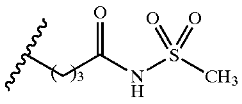 | H | $ES^+$ 567 $[M + H]^+$ |
| 211 | 4-bromophenyl | O | 1 | 1 | 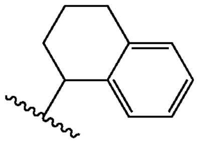 | —$(CH_2)_3CO_2H$ | H | $ES^+$ 518 $[M + H]^+$ |

TABLE 1a-continued
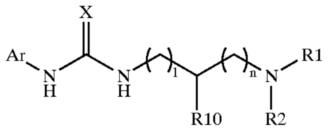
| CPD No. | Ar | X | l | n | R1 | R2 | R10 | Mass Spec. m/e |
|---|---|---|---|---|---|---|---|---|
| 212 | 4-bromophenyl | O | 1 | 1 | 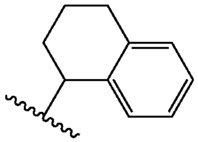 | 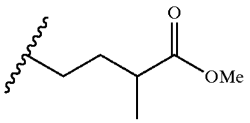 | H | $ES^+$ 518 $[M + H]^+$ |
| 213 | 4-bromophenyl | O | 1 | 1 | 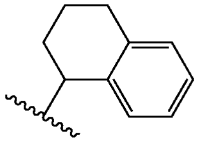 | $-(CH_2)_4CO_2Me$ | H | $ES^+$ 516 $[M + H]^+$ |
| 214 | 4-bromophenyl | O | 1 | 1 | 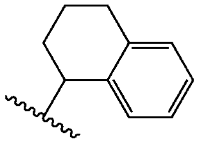 | $-(CH_2)_4CO_2H$ | H | $ES^+$ 504 $[M + H]^+$ |
| 215 | 4-bromophenyl | O | 1 | 1 | 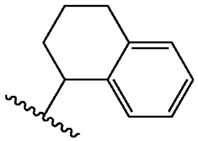 | $-(CH_2)_3OCOCH_3$ | H | $ES^+$ 502 $[M + H]^+$ |
| 216 | 4-bromophenyl | O | 1 | 1 | 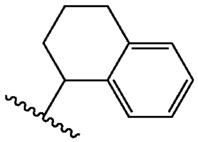 | $-(CH_2)_3OH$ | H | $ES^+$ 460 $[M + H]^+$ |

TABLE 1a-continued
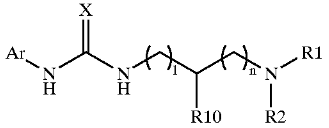
| CPD No. | Ar | X | l | n | R1 | R2 | R10 | Mass Spec. m/e |
|---|---|---|---|---|---|---|---|---|
| 217 | 4-bromophenyl | O | 1 | 1 | 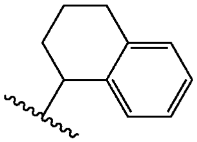 | 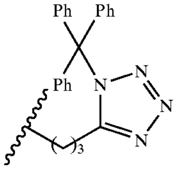 | H | ES⁺ 756 [M + H]⁺ |
| 218 | 4-bromophenyl | O | 1 | 1 | 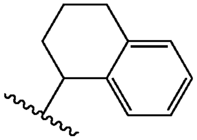 | 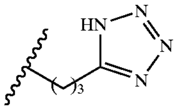 | H | ES⁺ 514 [M + H]⁺ |
| 219 | phenyl | O | 1 | 1 | 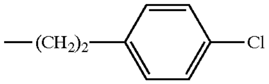 | $—(CH_2)_3OH$ | H | ES⁺ 390 [M + H]⁺ |
| 220 | phenyl | O | 1 | 1 | 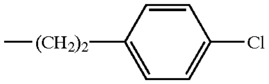 | $—CH_2CONH_2$ | H | ES⁺ 389 [M + H]⁺ |
| 221 | phenyl | O | 1 | 1 | 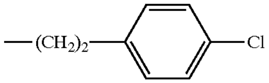 | $—CH_2CH{=}CH_2$ | H | ES⁺ 372 [M + H]⁺ |
| 222 | 4-bromophenyl | O | 1 | 1 | 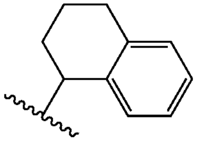 | 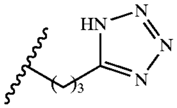 | H | ES⁺ 528 [M + H]⁺ |

TABLE 1a-continued
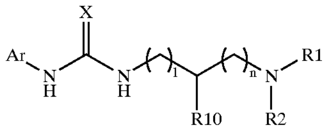
| CPD No. | Ar | X | l | n | R1 | R2 | R10 | Mass Spec. m/e |
|---|---|---|---|---|---|---|---|---|
| 223 | 4-bromophenyl | O | 1 | 1 | 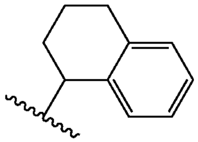 | 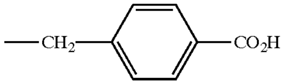 | H | $ES^+$ 538 $[M + H]^+$ |
| 224 | 4-bromophenyl | O | 1 | 1 | 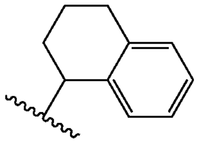 | 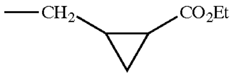 | H | $ES^+$ 530 $[M + H]^+$ |
| 225 | 4-carboxyphenyl | O | 1 | 1 | 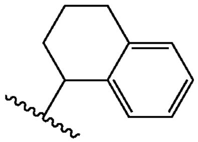 | $—(CH_2)_3CO_2Me$ | H | $ES^+$ 468 $[M + H]^+$ |
| 226 | 4-bromophenyl | O | 1 | 1 | 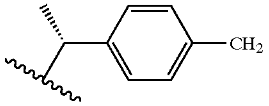 | $—(CH_2)_3CO_2H$ | H | $ES^+$ 478 $[M + H]^+$ |
| 227 | 4-bromophenyl | O | 1 | 1 | 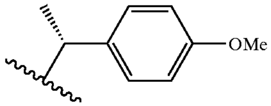 | $—(CH_2)_3CO_2H$ | H | $ES^+$ 494 $[M + H]^+$ |
| 228 | 4-(ethoxycarbonyl)phenyl | O | 1 | 1 | 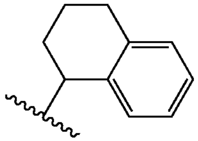 | $—(CH_2)_3CO_2H$ | H | $ES^+$ 482 $[M + H]^+$ |

TABLE 1a-continued
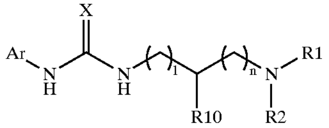
| CPD No. | Ar | X | l | n | R1 | R2 | R10 | Mass Spec. m/e |
|---|---|---|---|---|---|---|---|---|
| 229 | 4-iodophenyl | O | 1 | 1 | 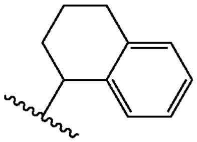 | —$(CH_2)_3CO_2H$ | H | $ES^+$ 536 $[M + H]^+$ |
| 230 | phenyl | O | 1 | 1 | 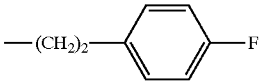 | ethyl | H | $ES^+$ 344 $[M + H]^+$ |
| 231 | phenyl | O | 1 | 1 | 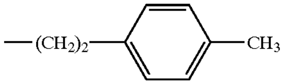 | ethyl | H | $ES^+$ 340 $[M + H]^+$ |
| 232 | phenyl | O | 1 | 1 | 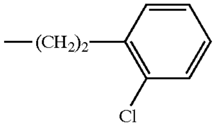 | ethyl | H | $ES^+$ 360 $[M + H]^+$ |
| 233 | phenyl | O | 1 | 1 | 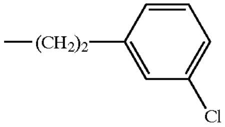 | ethyl | H | $ES^+$ 360 $[M + H]^+$ |
| 234 | phenyl | O | 1 | 1 | 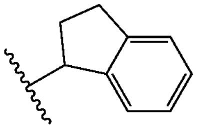 | ethyl | H | $ES^+$ 338 $[M + H]^+$ |

TABLE 1a-continued
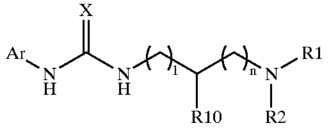
| CPD No. | Ar | X | l | n | R1 | R2 | R10 | Mass Spec. m/e |
|---|---|---|---|---|---|---|---|---|
| 235 | 4-carboxyphenyl | O | 1 | 1 | 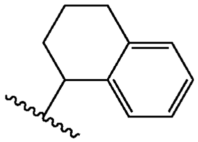 | $—(CH_2)_3CO_2H$ | H | $ES^+$ 454 $[M + H]^+$ |
| 236 | 3-(ethoxycarbonyl)phenyl | O | 1 | 1 | 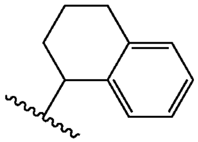 | $—(CH_2)_3CO_2H$ | H | $ES^+$ 482 $[M + H]^+$ |
| 237 | 4-(n-butyloxycarbonyl)phenyl | O | 1 | 1 | 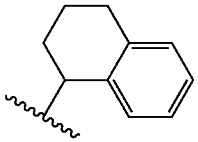 | $—(CH_2)_3CO_2H$ | H | $ES^+$ 510 $[M + H]^+$ |
| 238 | phenyl | O | 1 | 1 | 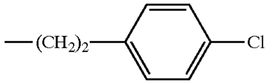 | 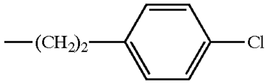 | H | $ES^+$ 470 $[M + H]^+$ |
| 239 | phenyl | O | 1 | 1 | 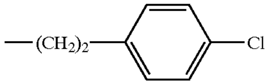 | $—CH_2CH(CH_3)_2$ | H | $ES^+$ 388 $[M + H]^+$ |
| 240 | phenyl | O | 1 | 1 | 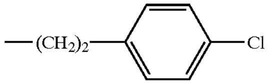 | 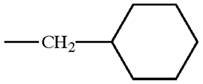 | H | $ES^+$ 429 $[M + H]^+$ |
| 241 | phenyl | O | 1 | 1 | 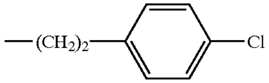 | $—(CH_2)_4CO_2Me$ | H | $ES^+$ 446 $[M + H]^+$ |

TABLE 1a-continued
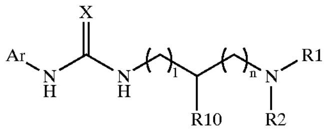
| CPD No. | Ar | X | l | n | R1 | R2 | R10 | Mass Spec. m/e |
|---|---|---|---|---|---|---|---|---|
| 242 | phenyl | O | 1 | 1 | 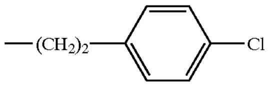 | $—(CH_2)_5CO_2Et$ | H | $ES^+$ 474 $[M + H]^+$ |
| 243 | phenyl | O | 1 | 1 | 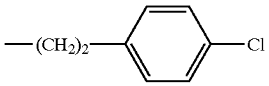 | $—(CH_2)_2CONH_2$ | H | $ES^+$ 403 $[M + H]^+$ |
| 244 | phenyl | O | 1 | 1 | 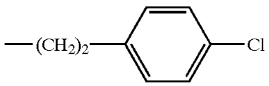 | $—(CH_2)_2OCOCH_3$ | H | $ES^+$ 418 $[M + H]^+$ |
| 245 | phenyl | O | 1 | 1 | 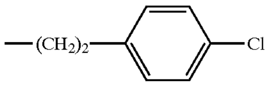 | $—CH_2CO_2Me$ | H | $ES^+$ 404 $[M + H]^+$ |
| 246 | 4-bromophenyl | S | 1 | 1 | 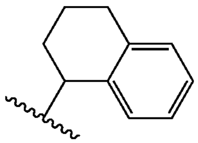 | $—(CH_2)_3CO_2H$ | H | $ES^+$ 506 $[M + H]^+$ |
| 247 | 3-bromophenyl | S | 1 | 1 | 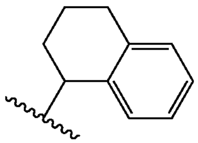 | $—(CH_2)_3CO_2H$ | H | $ES^+$ 506 $[M + H]^+$ |
| 248 | 3-chlorophenyl | S | 1 | 1 | 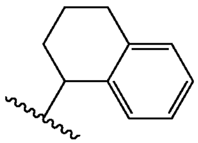 | $—(CH_2)_3CO_2H$ | H | $ES^+$ 460 $[M + H]^+$ |

TABLE 1a-continued
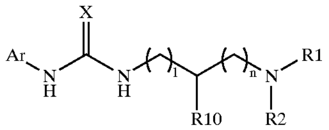
| CPD No. | Ar | X | l | n | R1 | R2 | R10 | Mass Spec. m/e |
|---|---|---|---|---|---|---|---|---|
| 249 | 4-iodophenyl | S | 1 | 1 | 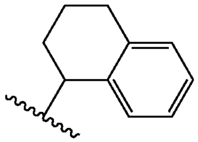 | $—(CH_2)_3CO_2H$ | H | $ES^+$ 552 $[M + H]^+$ |
| 250 | 4-methylphenyl | S | 1 | 1 | 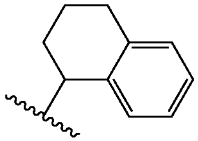 | $—(CH_2)_3CO_2H$ | H | $ES^+$ 440 $[M + H]^+$ |
| 251 | 3,4-dichlorophenyl | S | 1 | 1 | 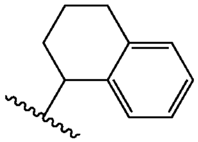 | $—(CH_2)_3CO_2H$ | H | $ES^+$ 494 $[M + H]^+$ |
| 252 | 4-bromophenyl | S | 1 | 1 | 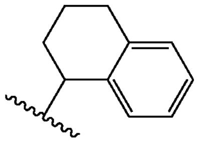 | $—(CH_2)_3CO_2Me$ | H | $ES^+$ 520 $[M + H]^+$ |
| 253 | 3-bromophenyl | S | 1 | 1 | 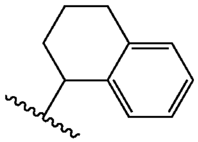 | $—(CH_2)_3CO_2Me$ | H | $ES^+$ 520 $[M + H]^+$ |

TABLE 1a-continued
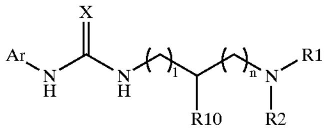
| CPD No. | Ar | X | l | n | R1 | R2 | R10 | Mass Spec. m/e |
|---|---|---|---|---|---|---|---|---|
| 254 | 3-chlorophenyl | S | 1 | 1 | 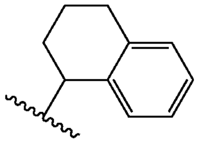 | $—(CH_2)_3CO_2Me$ | H | $ES^+$ 474 $[M + H]^+$ |
| 255 | 4-iodophenyl | S | 1 | 1 | 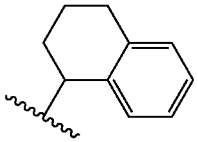 | $—(CH_2)_3CO_2Me$ | H | $ES^+$ 566 $[M + H]^+$ |
| 256 | 3,4-dichlorophenyl | S | 1 | 1 | 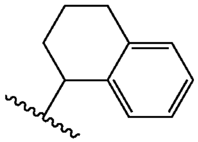 | $—(CH_2)_3CO_2Me$ | H | $ES^+$ 508 $[M + H]^+$ |
| 257 | 4-fluorophenyl | S | 1 | 1 | 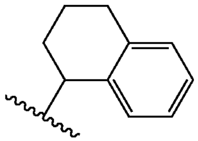 | $—(CH_2)_3CO_2H$ | H | $ES^+$ 444 $[M + H]^+$ |
| 258 | 4-bromophenyl | O | 1 | 1 | 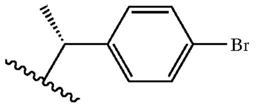 | $—(CH_2)_3CO_2H$ | H | $ES^+$ 542 $[M + H]^+$ |
| 259 | 4-bromophenyl | O | 1 | 1 | 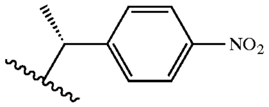 | $—(CH_2)_3CO_2H$ | H | $ES^+$ 509 $[M + H]^+$ |

TABLE 1a-continued
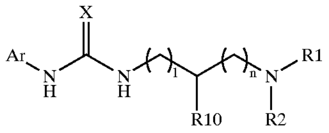
| CPD No. | Ar | X | l | n | R1 | R2 | R10 | Mass Spec. m/e |
|---|---|---|---|---|---|---|---|---|
| 260 | 3-cyanophenyl | O | 1 | 1 | 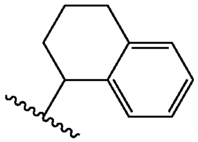 | $—(CH_2)_3CO_2H$ | H | $ES^+$ 435 $[M + H]^+$ |
| 261 | 3-methoxyphenyl | O | 1 | 1 | 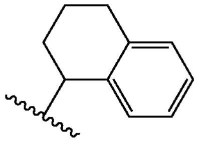 | $—(CH_2)_3CO_2H$ | H | $ES^+$ 440 $[M + H]^+$ |
| 262 | 3-acetylphenyl | O | 1 | 1 | 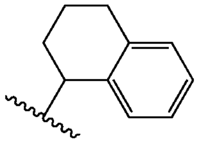 | $—(CH_2)_3CO_2H$ | H | $ES^+$ 452 $[M + H]^+$ |
| 263 | 3-(methylthio)phenyl | O | 1 | 1 | 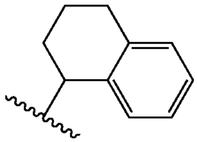 | $—(CH_2)_3CO_2H$ | H | $ES^+$ 456 $[M + H]^+$ |
| 264 | 4-methylthiophenyl | O | 1 | 1 | 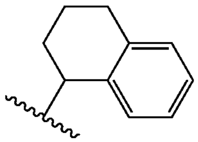 | $—(CH_2)_3CO_2H$ | H | $ES^+$ 456 $[M + H]^+$ |

TABLE 1a-continued
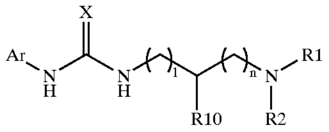
| CPD No. | Ar | X | l | n | R1 | R2 | R10 | Mass Spec. m/e |
|---|---|---|---|---|---|---|---|---|
| 265 | 2-naphthyl | O | 1 | 1 | 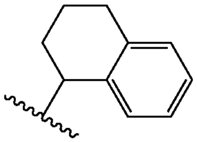 | —$(CH_2)_3CO_2H$ | H | $ES^+$ 460 $[M + H]^+$ |
| 266 | 4-(trifluoromethoxy)phenyl | O | 1 | 1 | 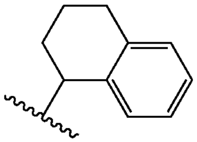 | —$(CH_2)_3CO_2H$ | H | $ES^+$ 494 $[M + H]^+$ |
| 267 | 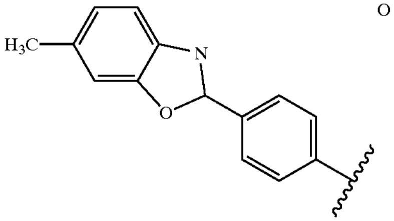 | O | 1 | 1 | 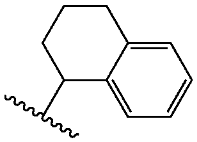 | —$(CH_2)_3CO_2H$ | H | $ES^+$ 557 $[M + H]^+$ |
| 268 | 4-bromophenyl | O | 1 | 1 | 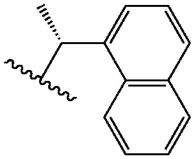 | —$(CH_2)_3CO_2H$ | H | $ES^+$ 512 $[M + H]^+$ |
| 269 | 4-bromophenyl | O | 1 | 1 | 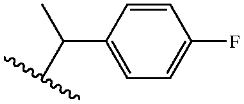 | —$(CH_2)_3CO_2H$ | H | $ES^+$ 482 $[M + H]^+$ |

TABLE 1a-continued
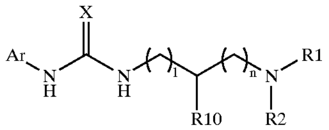
| CPD No. | Ar | X | l | n | R1 | R2 | R10 | Mass Spec. m/e |
|---|---|---|---|---|---|---|---|---|
| 270 | 4-bromophenyl | O | 1 | 1 | 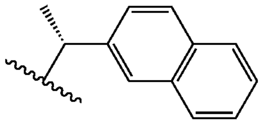 | $—(CH_2)_3CO_2H$ | H | $ES^+$ 512 $[M + H]^+$ |
| 271 | 4-bromophenyl | O | 1 | 1 | 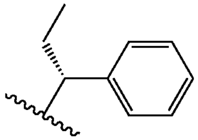 | $—(CH_2)_3CO_2H$ | H | $ES^+$ 478 $[M + H]^+$ |
| 272 | 4-bromophenyl | O | 1 | 1 | 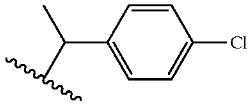 | $—(CH_2)_3CO_2H$ | H | $ES^+$ 498 $[M + H]^+$ |
| 273 | 4-bromophenyl | O | 1 | 1 | 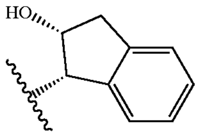 | $—(CH_2)_3CO_2H$ | H | $ES^+$ 492 $[M + H]^+$ |
| 274 | phenyl | O | 1 | 1 | 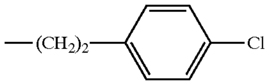 | $—(CH_2)_3CO_2Me$ | H | $ES^+$ 432 $[M + H]^+$ |
| 275 | phenyl | O | 1 | 1 | 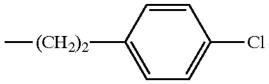 | $—(CH_2)_2OCH_3$ | H | $ES^+$ 390 $[M + H]^+$ |
| 276 | phenyl | O | 1 | 1 | 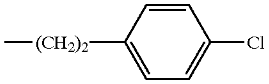 | $—CH(CH_3)_2$ | H | $ES^+$ 374 $[M + H]^+$ |

TABLE 1a-continued
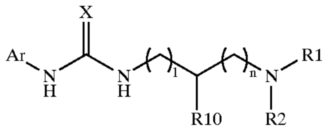
| CPD No. | Ar | X | l | n | R1 | R2 | R10 | Mass Spec. m/e |
|---|---|---|---|---|---|---|---|---|
| 277 | 4-biphenyl | O | 1 | 1 | 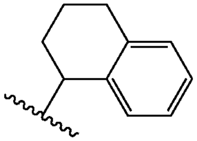 | $—(CH_2)_3CO_2H$ | H | ES$^+$ 486 [M + H]$^+$ |
| 278 | 4-acetylphenyl | O | 1 | 1 | 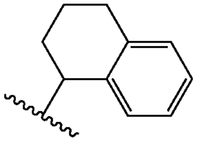 | $—(CH_2)_3CO_2H$ | H | ES$^+$ 474 [M + Na]$^+$ |
| 279 | 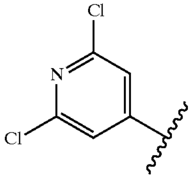 | O | 1 | 1 | 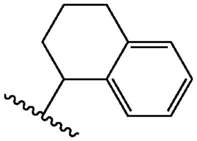 | $—(CH_2)_3CO_2H$ | H | ES$^+$ 479 [M + H]$^+$ |
| 280 | phenyl | O | 1 | 1 | 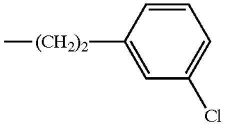 | 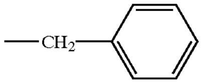 | H | ES$^+$ 422 [M + H]$^+$ |
| 281 | 4-bromophenyl | O | 0 | 2 | 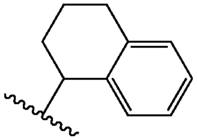 | $—(CH_2)_3CO_2Me$ | 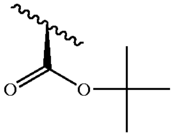 | ES$^+$ 602 [M + H]$^+$ |

TABLE 1a-continued
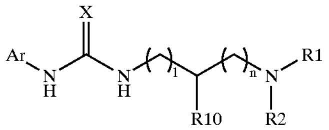
| CPD No. | Ar | X | l | n | R1 | R2 | R10 | Mass Spec. m/e |
|---|---|---|---|---|---|---|---|---|
| 282 | 4-bromophenyl | O | 0 | 2 | 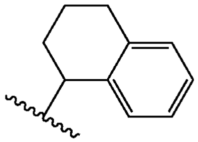 | $—(CH_2)_3CO_2Me$ | 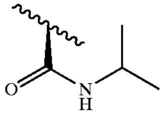 | $ES^+$ 587 $[M + H]^+$ |
| 283 | 4-bromophenyl | O | 0 | 2 | 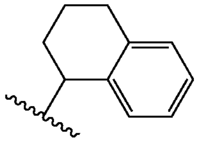 | $—(CH_2)_3CO_2Me$ | 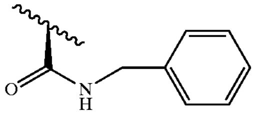 | $ES^+$ 635 $[M + H]^+$ |
| 284 | 4-bromophenyl | O | 0 | 2 | 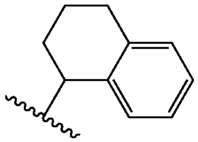 | $—(CH_2)_3CO_2H$ | 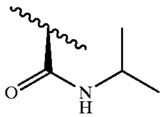 | $ES^+$ 573 $[M + H]^+$ |
| 285 | 4-bromophenyl | O | 0 | 2 | 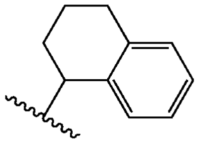 | $—(CH_2)_3CO_2H$ | 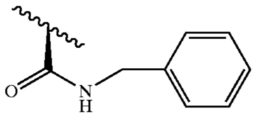 | $ES^+$ 621 $[M + H]^+$ |
| 286 | 4-bromophenyl | O | 0 | 2 | 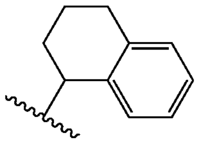 | $—(CH_2)_3CO_2H$ | 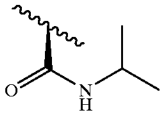 | $ES^+$ 573 $[M + H]^+$ |

TABLE 1a-continued
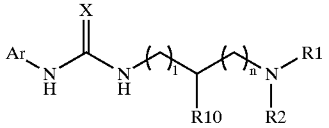
| CPD No. | Ar | X | l | n | R1 | R2 | R10 | Mass Spec. m/e |
|---|---|---|---|---|---|---|---|---|
| 287 | 4-bromophenyl | O | 0 | 2 | 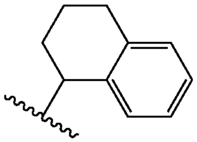 | $-(CH_2)_3CO_2H$ | 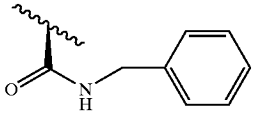 | $ES^+$ 621 $[M + H]^+$ |
| 288 | 4-bromophenyl | S | 1 | 1 | 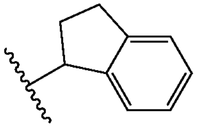 | $-(CH_2)_3CO_2H$ | H | $ES^+$ 490 $[M + H]^+$ |
| 289 | 4-bromophenyl | S | 1 | 1 | 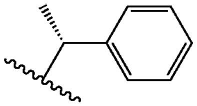 | $-(CH_2)_3CO_2H$ | H | $ES^+$ 478 $[M + H]^+$ |
| 290 | 4-bromophenyl | S | 1 | 1 | 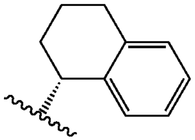 | $-(CH_2)_3CO_2H$ | H | $ES^+$ 504 $[M + H]^+$ |
| 291 | phenyl | O | 1 | 1 | 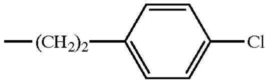 | 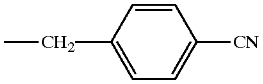 | H | $ES^+$ 447 $[M + H]^+$ |
| 292 | phenyl | O | 1 | 1 | 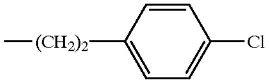 | 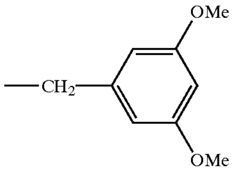 | H | $ES^+$ 482 $[M + H]^+$ |
| 293 | 4-bromophenyl | O | 1 | 1 | 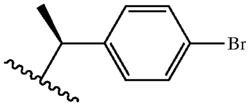 | $-(CH_2)_3CO_2H$ | H | $ES^+$ 542 $[M + H]^+$ |

TABLE 1b
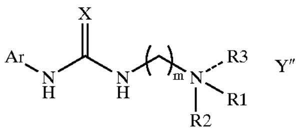
| CPD No. | Ar | X | m | R1 | R2 | R3 | Y | Mass ($ES^+$) | Spec. m/e |
|---|---|---|---|---|---|---|---|---|---|
| 91 | phenyl | O | 3 | 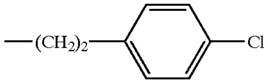 | ethyl | ethyl | I | 388 | $[M - I]^+$ |
| 92 | 4-bromo-phenyl | O | 3 | 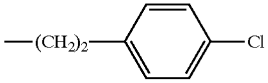 | ethyl | ethyl | I | 466 | $[M—I]^+$ |
| 294 | 4-bromo-phenyl | O | 3 | 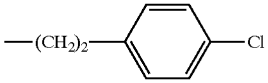 | n-butyl | ethyl | I | 494 | $[M—I]^+$ |
| 295 | 4-bromo-phenyl | O | 3 | 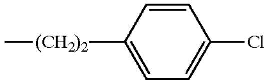 | n-propyl | ethyl | I | 480 | $[M—I]^+$ |
| 296 | phenyl | O | 3 | 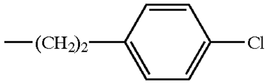 | 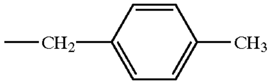 | 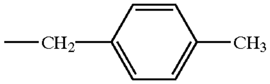 | Br | 540 | $[M—Br]^+$ |
| 297 | phenyl | O | 3 | 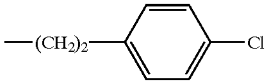 | 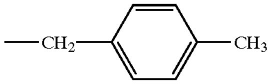 | ethyl | I | 464 | $[M—I]^+$ |
| 298 | phenyl | O | 3 | 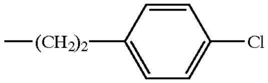 | 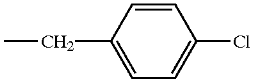 | ethyl | I | 484 | $[M—I]^+$ |
| 299 | phenyl | O | 3 | 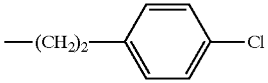 | $—(CH_2)_3OH$ | ethyl | I | 418 | $[M—I]^+$ |

TABLE 1b-continued
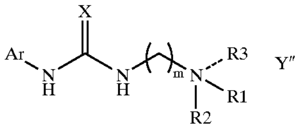
| CPD No. | Ar | X | m | R1 | R2 | R3 | Y | Mass (ES⁺) | Spec. m/e |
|---|---|---|---|---|---|---|---|---|---|
| 300 | phenyl | O | 3 | 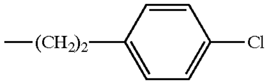 | $-CH_2CONH_2$ | ethyl | I | 417 | $[M-I]^+$ |
| 301 | phenyl | O | 3 | 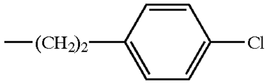 | $-CH_2CH=CH_2$ | ethyl | I | 400 | $[M-I]^+$ |
| 302 | phenyl | O | 3 | 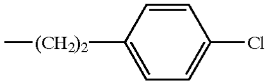 | 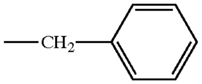 | ethyl | I | 450 | $[M-I]^+$ |
| 303 | phenyl | O | 3 | 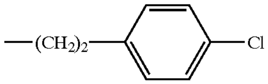 | 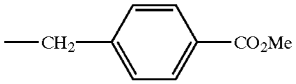 | ethyl | I | 508 | $[M-I]^+$ |
| 304 | phenyl | O | 3 | 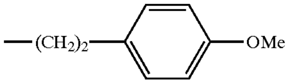 | ethyl | ethyl | I | 384 | $[M-I]^+$ |
| 305 | phenyl | O | 3 | 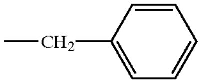 | ethyl | ethyl | I | 340 | $[M-I]^+$ |
| 306 | phenyl | O | 3 | 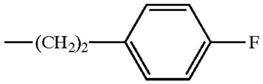 | ethyl | ethyl | I | 372 | $[M-I]^+$ |
| 307 | phenyl | O | 3 | 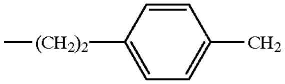 | ethyl | ethyl | I | 368 | $[M-I]^+$ |

TABLE 1b-continued
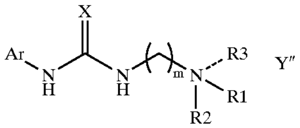
| CPD No. | Ar | X | m | R1 | R2 | R3 | Y | Mass (ES⁺) | Spec. m/e |
|---|---|---|---|---|---|---|---|---|---|
| 308 | phenyl | O | 3 | 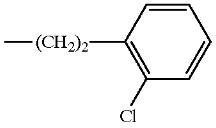 | ethyl | ethyl | I | 388 | $[M-I]^+$ |
| 309 | phenyl | O | 3 | 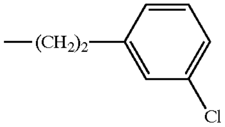 | ethyl | ethyl | I | 388 | $[M-I]^+$ |
| 310 | phenyl | O | 3 | 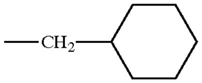 | ethyl | ethyl | I | 374 | $[M-I]^+$ |
| 311 | phenyl | O | 3 | 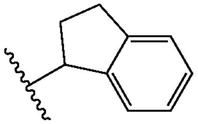 | ethyl | ethyl | I | 366 | $[M-I]^+$ |
| 312 | 4-bromo-phenyl | O | 3 | 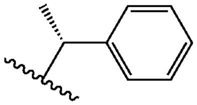 | $-(CH_2)_3CO_2Me$ | ethyl | I | 506 | $[M-I]^+$ |
| 313 | 4-bromo-phenyl | O | 3 | 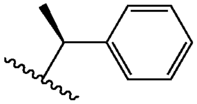 | $-(CH_2)_3CO_2Me$ | ethyl | I | 504 | $[M-I]^+$ |

TABLE 1b-continued
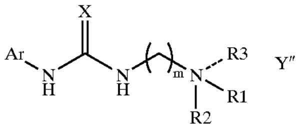
| CPD No. | Ar | X | m | R1 | R2 | R3 | Y | Mass ($ES^+$) | Spec. m/e |
|---|---|---|---|---|---|---|---|---|---|
| 314 | 4-bromo-phenyl | O | 3 | 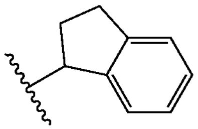 | $—(CH_2)_3CO_2Me$ | ethyl | I | 518 | $[M—I]^+$ |
| 315 | 4-bromo-phenyl | O | 3 | 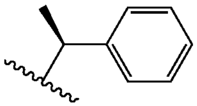 | $—(CH_2)_3CO_2H$ | ethyl | $CF_3COO$ | 492 | $[H—CF_3COO]^+$ |
| 316 | 4-bromo-phenyl | O | 3 | 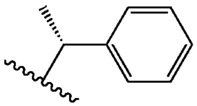 | $—(CH_2)_3CO_2H$ | ethyl | $CF_3COO$ | 492 | $[H—CF_3COO]^+$ |
| 317 | phenyl | O | 3 | 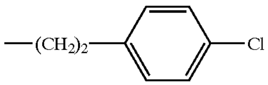 | 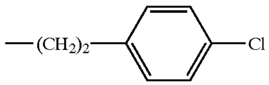 | ethyl | I | 498 | $[M—I]^+$ |
| 318 | phenyl | O | 3 | 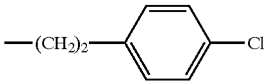 | $—CH_2CH(CH_3)_2$ | ethyl | I | 416 | $[M—I]^+$ |
| 319 | phenyl | O | 3 | 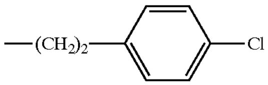 | 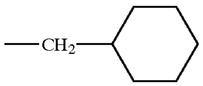 | ethyl | I | 456 | $[M—I]^+$ |
| 320 | phenyl | O | 3 | 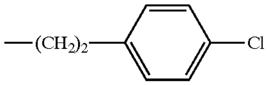 | $—(CH_2)_4CO_2Me$ | ethyl | I | 474 | $[M—I]^+$ |
| 321 | phenyl | O | 3 | 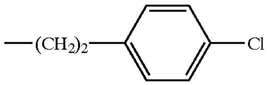 | $—(CH_2)_5CO_2Et$ | ethyl | I | 502 | $[M—I]^+$ |

TABLE 1b-continued
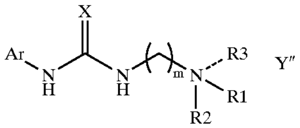
| CPD No. | Ar | X | m | R1 | R2 | R3 | Y | Mass (ES⁺) | Spec. m/e |
|---|---|---|---|---|---|---|---|---|---|
| 322 | phenyl | O | 3 | 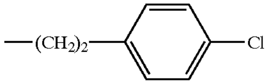 | 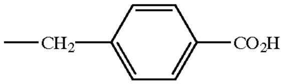 | ethyl | I | 496 | $[M-I]^+$ |
| 323 | phenyl | O | 5 | 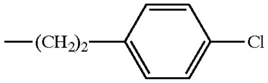 | ethyl | ethyl | I | 416 | $[M-I]^+$ |
| 324 | 4-methoxy-phenyl | O | 3 | 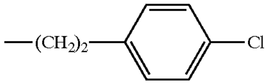 | 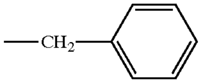 | ethyl | I | 480 | $[M-I]^+$ |
| 325 | 3,4-dichloro-phenyl | O | 3 | 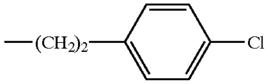 | 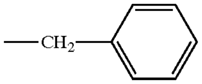 | ethyl | I | 520 | $[M-I]^+$ |
| 326 | 4-cyano-phenyl | O | 3 | 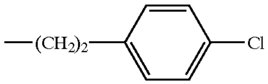 | 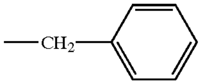 | ethyl | I | 475 | $[M-I]^+$ |
| 327 | phenyl | O | 3 | 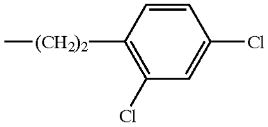 | 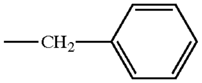 | ethyl | I | 484 | $[M-I]^+$ |
| 328 | phenyl | O | 3 | 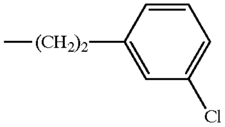 | 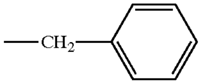 | ethyl | I | 450 | $[M-I]^+$ |

TABLE 1b-continued
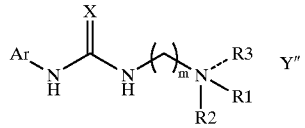
| CPD No. | Ar | X | m | R1 | R2 | R3 | Y | Mass (ES+) | Spec. m/e |
|---|---|---|---|---|---|---|---|---|---|
| 329 | phenyl | O | 3 | 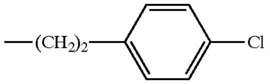 | 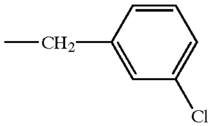 | ethyl | I | 484 | [M—I]+ |
| 330 | phenyl | O | 3 | 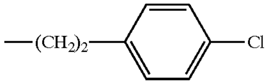 | 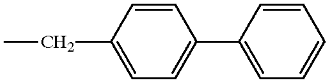 | ethyl | I | 526 | [M—I]+ |
| 331 | phenyl | O | 3 | 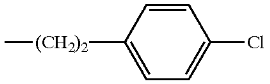 | 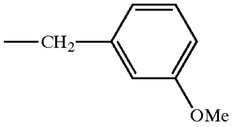 | ethyl | I | 480 | [M—I]+ |
| 332 | phenyl | O | 3 | 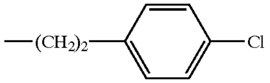 | 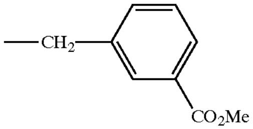 | ethyl | I | 508 | [M—I]+ |
| 333 | phenyl | O | 3 | 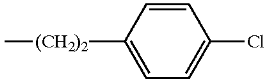 | 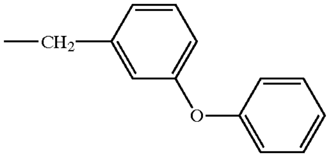 | ethyl | I | 542 | [M—I]+ |
| 334 | phenyl | O | 3 | 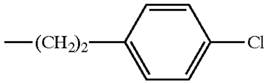 | 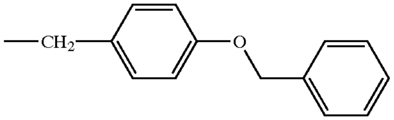 | ethyl | I | 556 | [M—I]+ |

TABLE 1b-continued
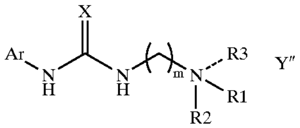
| CPD No. | Ar | X | m | R1 | R2 | R3 | Y | Mass ($ES^+$) | Spec. m/e |
|---|---|---|---|---|---|---|---|---|---|
| 335 | 4-bromo-phenyl | S | 3 | 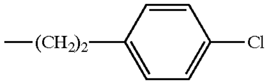 | ethyl | ethyl | I | 482 | $[M—I]^+$ |
| 336 | phenyl | S | 3 | 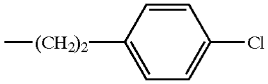 | ethyl | ethyl | I | 404 | $[M—I]^+$ |
| 337 | phenyl | O | 3 | 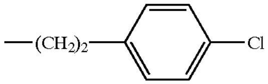 | 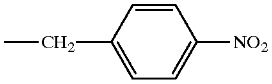 | ethyl | I | 495 | $[M—I]^+$ |
| 338 | phenyl | O | 3 | 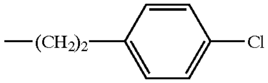 | 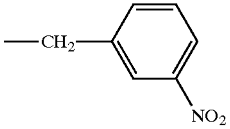 | ethyl | I | 495 | $[M—I]^+$ |
| 339 | phenyl | O | 3 | 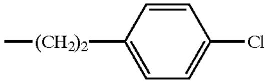 | 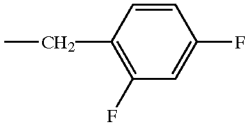 | ethyl | I | 486 | $[M—I]^+$ |
| 340 | phenyl | O | 3 | 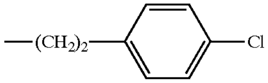 | 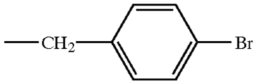 | ethyl | I | 530 | $[M—I]^+$ |
| 341 | phenyl | O | 3 | 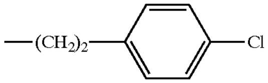 | 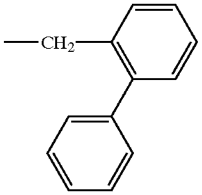 | ethyl | I | 526 | $[M—I]^+$ |

TABLE 1b-continued
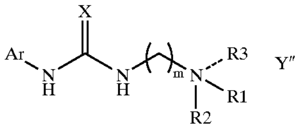
| CPD No. | Ar | X | m | R1 | R2 | R3 | Y | Mass ($ES^+$) | Spec. m/e |
|---|---|---|---|---|---|---|---|---|---|
| 342 | phenyl | O | 3 | 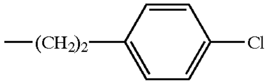 | 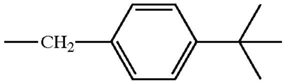 | ethyl | I | 506 | $[M-I]^+$ |
| 343 | phenyl | O | 3 | 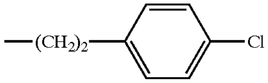 | 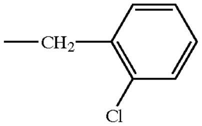 | ethyl | I | 484 | $[M-I]^+$ |
| 344 | phenyl | O | 3 | 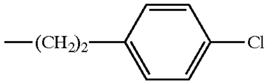 | 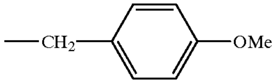 | ethyl | I | 480 | $[M-I]^+$ |
| 345 | phenyl | O | 3 | 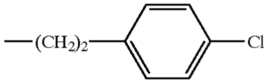 | 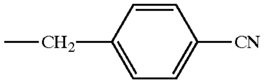 | ethyl | I | 475 | $[M-I]^+$ |
| 346 | phenyl | O | 3 | 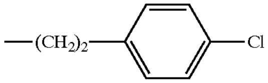 | 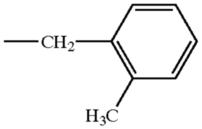 | ethyl | I | 464 | $[M-I]^+$ |
| 347 | phenyl | O | 3 | 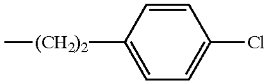 | 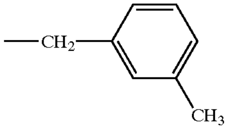 | ethyl | I | 464 | $[M-I]^+$ |

TABLE 1b-continued
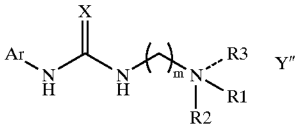
| CPD No. | Ar | X | m | R1 | R2 | R3 | Y | Mass (ES+) | Spec. m/e |
|---|---|---|---|---|---|---|---|---|---|
| 348 | phenyl | O | 3 | 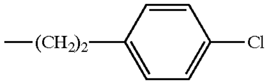 | 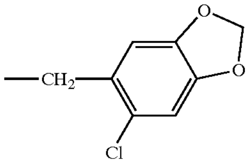 | ethyl | I | 528 | [M—I]+ |
| 349 | phenyl | O | 3 | 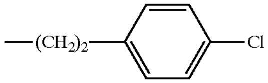 | 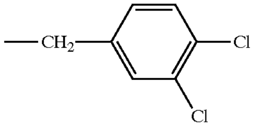 | ethyl | I | 520 | [M—I]+ |
| 350 | phenyl | O | 3 | 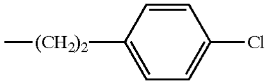 | 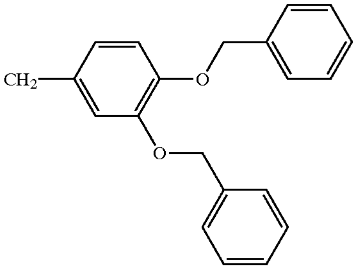 | ethyl | I | 662 | [M—I]+ |
| 351 | phenyl | O | 3 | 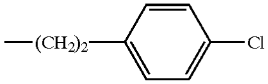 | 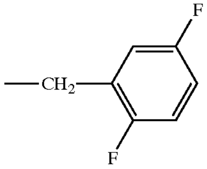 | ethyl | I | 486 | [M—I]+ |

TABLE 1b-continued
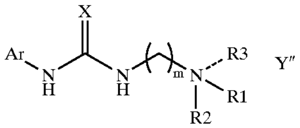
| CPD No. | Ar | X | m | R1 | R2 | R3 | Y | Mass ($ES^+$) | Spec. m/e |
|---|---|---|---|---|---|---|---|---|---|
| 352 | phenyl | O | 3 | 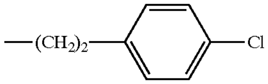 | 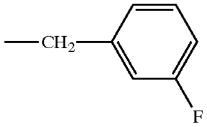 | ethyl | I | 470 | $[M—I]^+$ |
| 353 | phenyl | O | 3 | 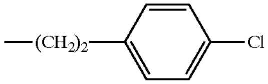 | 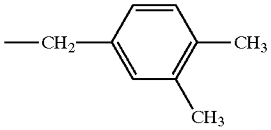 | ethyl | I | 480 | $[M—I]^+$ |
| 354 | phenyl | O | 3 | 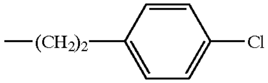 | 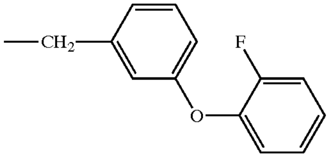 | ethyl | I | 562 | $[M—I]^+$ |
| 355 | 3,4-dichloro-phenyl | O | 3 | 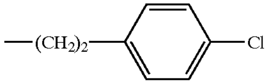 | $—(CH_2)_2O(CH_2)_2OMe$ | ethyl | I | 530 | $[M—I]^+$ |
| 356 | 3,4-dichloro-phenyl | O | 3 | 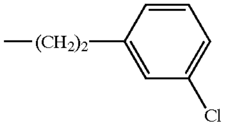 | $—(CH_2)_2O(CH_2)_2OMe$ | ethyl | I | 530 | $[M—I]^+$ |
| 357 | 3,4-dichloro-phenyl | O | 3 | 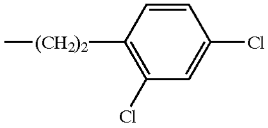 | $—(CH_2)_2O(CH_2)_2OMe$ | ethyl | I | 564 | $[M—I]^+$ |

TABLE 1b-continued
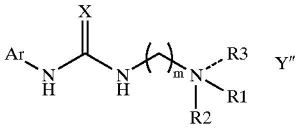
| CPD No. | Ar | X | m | R1 | R2 | R3 | Y | Mass ($ES^+$) | Spec. m/e |
|---|---|---|---|---|---|---|---|---|---|
| 358 | 3,4-dichloro-phenyl | O | 3 | 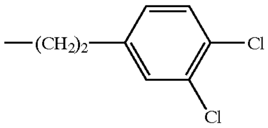 | $-(CH_2)_2O(CH_2)_2OMe$ | ethyl | I | 564 | $[M-I]^+$ |
| 359 | 3,4-dichloro-phenyl | O | 3 | 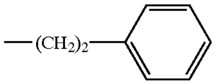 | $-(CH_2)_2O(CH_2)_2OMe$ | ethyl | I | 496 | $[M-I]^+$ |
| 360 | 3,4-dichloro-phenyl | O | 3 | 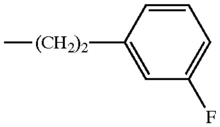 | $-(CH_2)_2O(CH_2)_2OMe$ | ethyl | I | 514 | $[M-I]^+$ |
| 361 | 3,4-dichloro-phenyl | O | 3 | 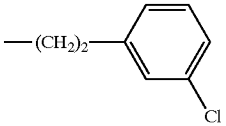 | 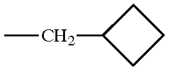 | ethyl | I | 496 | $[M-I]^+$ |
| 362 | 3,4-dichloro-phenyl | O | 3 | 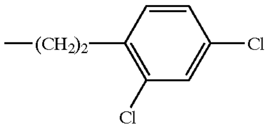 | 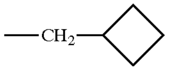 | ethyl | I | 530 | $[M-I]^+$ |
| 363 | 3,4-dichloro-phenyl | O | 3 | 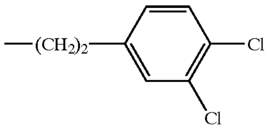 | 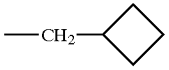 | ethyl | I | 530 | $[M-I]^+$ |

TABLE 1b-continued
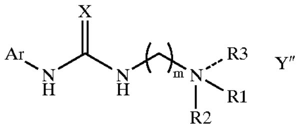
| CPD No. | Ar | X | m | R1 | R2 | R3 | Y | Mass (ES⁺) | Spec. m/e |
|---|---|---|---|---|---|---|---|---|---|
| 364 | 3,4-dichloro-phenyl | O | 3 | 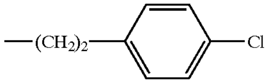 | 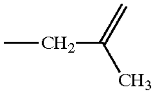 | ethyl | I | 482 | [M—I]⁺ |
| 365 | 3,4-dichloro-phenyl | O | 3 | 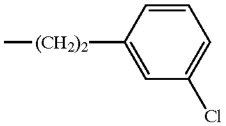 | 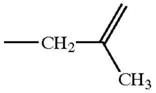 | ethyl | I | 482 | [M—I]⁺ |
| 366 | 3,4-dichloro-phenyl | O | 3 | 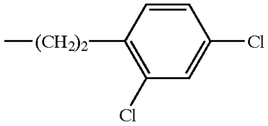 | 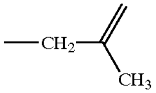 | ethyl | I | 516 | [M—I]⁺ |
| 367 | 3,4-dichloro-phenyl | O | 3 | 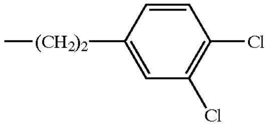 | 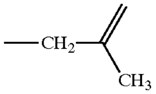 | ethyl | I | 516 | [M—I]⁺ |
| 368 | 3,4-dichloro-phenyl | O | 3 | 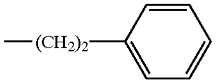 | 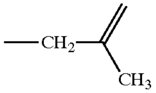 | ethyl | I | 448 | [M—I]⁺ |
| 369 | 3,4-dichloro-phenyl | O | 3 | 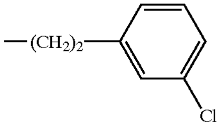 | $-(CH_2)_2F$ | ethyl | I | 474 | [M—I]⁺ |
| 370 | 3,4-dichloro-phenyl | O | 3 | 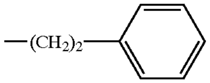 | $-(CH_2)_2F$ | ethyl | I | 440 | [M—I]⁺ |

TABLE 1b-continued
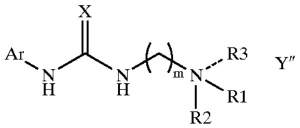
| CPD No. | Ar | X | m | R1 | R2 | R3 | Y | Mass (ES+) | Spec. m/e |
|---|---|---|---|---|---|---|---|---|---|
| 371 | 3,4-dichloro-phenyl | O | 3 | 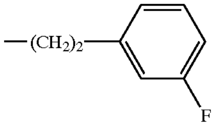 | $-(CH_2)_2F$ | ethyl | I | 458 | $[M-I]^+$ |
| 372 | 4-bromo-phenyl | O | 3 | 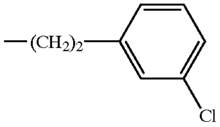 | $-CH_2CN$ | ethyl | I | 477 | $[M-I]^+$ |
| 373 | 4-bromo-phenyl | O | 3 | 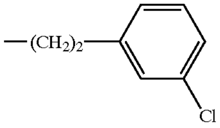 | $-(CH_2)_2O(CH_2)_2OMe$ | ethyl | I | 540 | $[M-I]^+$ |
| 374 | 4-bromo-phenyl | O | 3 | 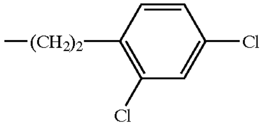 | $-(CH_2)_2O(CH_2)_2OMe$ | ethyl | I | 574 | $[M-I]^+$ |
| 375 | 4-bromo-phenyl | O | 3 | 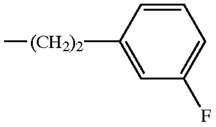 | $-(CH_2)_2O(CH_2)_2OMe$ | ethyl | I | 524 | $[M-I]^+$ |
| 376 | 4-bromo-phenyl | O | 3 | 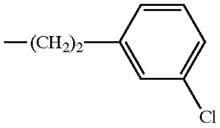 | 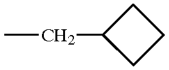 | ethyl | I | 506 | $[M-I]^+$ |

TABLE 1b-continued
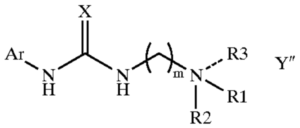
| CPD No. | Ar | X | m | R1 | R2 | R3 | Y | Mass ($ES^+$) | Spec. m/e |
|---|---|---|---|---|---|---|---|---|---|
| 377 | 4-bromo-phenyl | O | 3 | 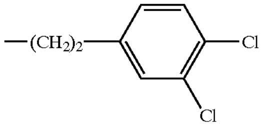 | 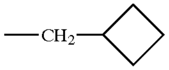 | ethyl | I | 541 | $[M-I]^+$ |
| 378 | 4-bromo-phenyl | O | 3 | 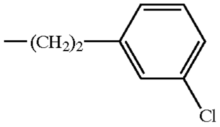 | 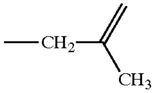 | ethyl | I | 492 | $[M-I]^+$ |
| 379 | 4-bromo-phenyl | O | 3 | 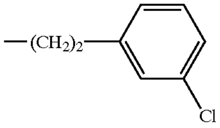 | $-CH_2CH(CH_2CH_3)_2$ | ethyl | I | 522 | $[M-I]^+$ |
| 380 | 4-bromo-phenyl | O | 3 | 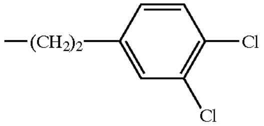 | $-CH_2CH(CH_2CH_3)_2$ | ethyl | I | 557 | $[M-I]^+$ |
| 381 | 4-bromo-phenyl | O | 3 | 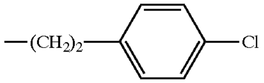 | $-(CH_2)_2F$ | ethyl | I | 484 | $[M-I]^+$ |
| 382 | 4-bromo-phenyl | O | 3 | 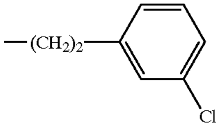 | $-(CH_2)_2F$ | ethyl | I | 484 | $[M-I]^+$ |

TABLE 1b-continued
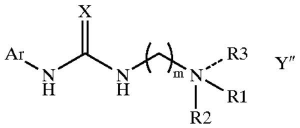
| CPD No. | Ar | X | m | R1 | R2 | R3 | Y | Mass ($ES^+$) | Spec. m/e |
|---|---|---|---|---|---|---|---|---|---|
| 383 | 4-bromo-phenyl | O | 3 | 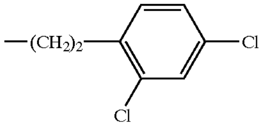 | $—(CH_2)_2F$ | ethyl | I | 518 | $[M—I]^+$ |
| 384 | 4-bromo-phenyl | O | 3 | 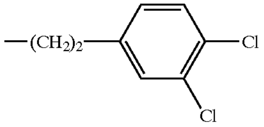 | $—(CH_2)_2F$ | ethyl | I | 518 | $[M—I]^+$ |
| 385 | 4-bromo-phenyl | O | 3 | 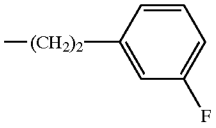 | $—(CH_2)_2F$ | ethyl | I | 468 | $[M—I]^+$ |
| 386 | 4-(trifluoro-methyl)phenyl | O | 3 | 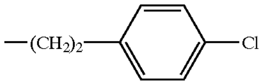 | $—(CH_2)_2O(CH_2)_2OMe$ | ethyl | I | 530 | $[M—I]^+$ |
| 387 | 4-(trifluoro-methyl)phenyl | O | 3 | 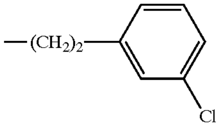 | $—(CH_2)_2O(CH_2)_2OMe$ | ethyl | I | 530 | $[M—I]^+$ |
| 388 | 4-(trifluoro-methyl)phenyl | O | 3 | 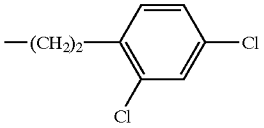 | $—(CH_2)_2O(CH_2)_2OMe$ | ethyl | I | 564 | $[M—I]^+$ |

TABLE 1b-continued
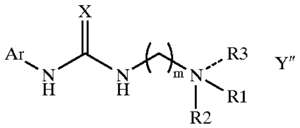
| CPD No. | Ar | X | m | R1 | R2 | R3 | Y | Mass (ES+) | Spec. m/e |
|---|---|---|---|---|---|---|---|---|---|
| 389 | 4-(trifluoro-methyl)phenyl | O | 3 | 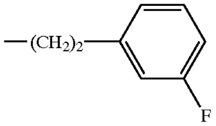 | $-(CH_2)_2O(CH_2)_2OMe$ | ethyl | I | 514 | $[M-I]^+$ |
| 390 | 4-(trifluoro-methyl)phenyl | O | 3 | 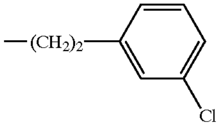 | 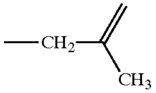 | ethyl | I | 482 | $[M-I]^+$ |
| 391 | 4-(trifluoro-methyl)phenyl | O | 3 | 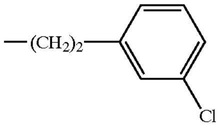 | $-(CH_2)_2F$ | ethyl | I | 474 | $[M-I]^+$ |
| 392 | 4-cyano-phenyl | O | 3 | 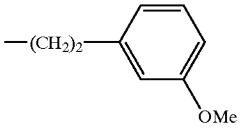 | $-(CH_2)_2O(CH_2)_2OMe$ | ethyl | I | 483 | $[M-I]^+$ |
| 393 | 4-cyano-phenyl | O | 3 | 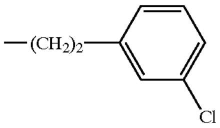 | $-(CH_2)_2CH(CH_3)_2$ | ethyl | I | 455 | $[M-I]^+$ |
| 394 | 4-cyano-phenyl | O | 3 | 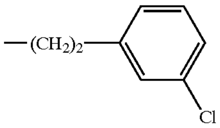 | $-(CH_2)_2O(CH_2)_2OMe$ | ethyl | I | 487 | $[M-I]^+$ |

TABLE 1b-continued
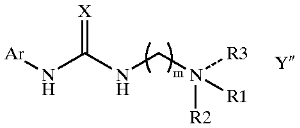
| CPD No. | Ar | X | m | R1 | R2 | R3 | Y | Mass (ES+) | Spec. m/e |
|---|---|---|---|---|---|---|---|---|---|
| 395 | 4-cyano-phenyl | O | 3 | 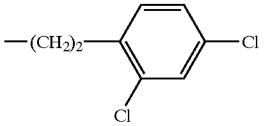 | $-(CH_2)_2O(CH_2)_2OMe$ | ethyl | I | 521 | [M—I]+ |
| 396 | 4-cyano-phenyl | O | 3 | 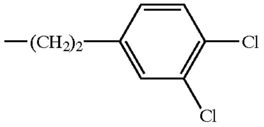 | $-(CH_2)_2O(CH_2)_2OMe$ | ethyl | I | 521 | [M—I]+ |
| 397 | 4-cyano-phenyl | O | 3 | 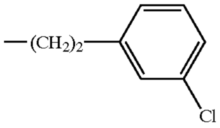 | 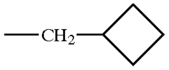 | ethyl | I | 453 | [M—I]+ |
| 398 | 4-cyano-phenyl | O | 3 | 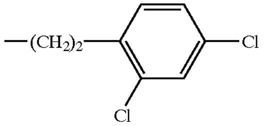 | 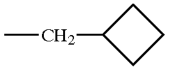 | ethyl | I | 487 | [M—I]+ |
| 399 | 4-cyano-phenyl | O | 3 | 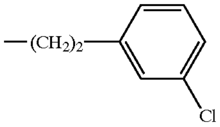 | 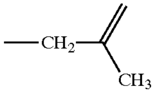 | ethyl | I | 439 | [M—I]+ |
| 400 | 4-cyano-phenyl | O | 3 | 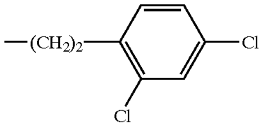 | 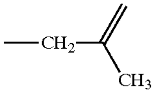 | ethyl | I | 473 | [M—I]+ |

TABLE 1b-continued
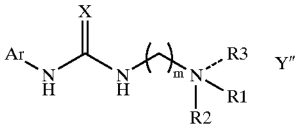
| CPD No. | Ar | X | m | R1 | R2 | R3 | Y | Mass ($ES^+$) | Spec. m/e |
|---|---|---|---|---|---|---|---|---|---|
| 401 | 4-cyano-phenyl | O | 3 | 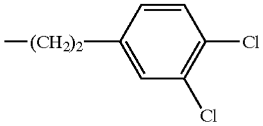 | 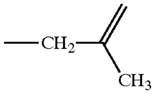 | ethyl | I | 473 | $[M—I]^+$ |
| 402 | 4-cyano-phenyl | O | 3 | 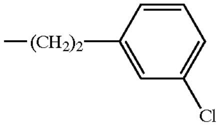 | $—CH_2CH(CH_2CH_3)_2$ | ethyl | I | 469 | $[M—I]^+$ |
| 403 | 4-cyano-phenyl | O | 3 | 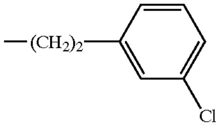 | $—(CH_2)_2F$ | ethyl | I | 431 | $[M—I]^+$ |
| 404 | 4-cyano-phenyl | O | 3 | 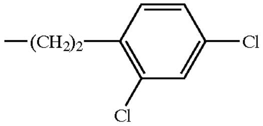 | $—(CH_2)_2F$ | ethyl | I | 465 | $[M—I]^+$ |
| 405 | 4-cyano-phenyl | O | 3 | 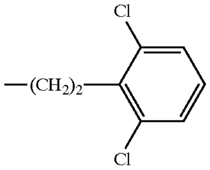 | $—(CH_2)_2F$ | ethyl | I | 465 | $[M—I]^+$ |
| 406 | phenyl | O | 3 | 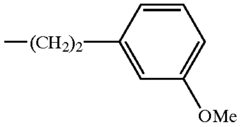 | $—(CH_2)_2O(CH_2)_2OMe$ | ethyl | I | 458 | $[M—I]^+$ |

TABLE 1b-continued
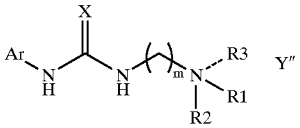
| CPD No. | Ar | X | m | R1 | R2 | R3 | Y | Mass (ES⁺) | Spec. m/e |
|---|---|---|---|---|---|---|---|---|---|
| 407 | phenyl | O | 3 | 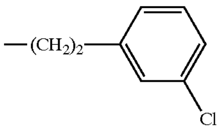 | $—(CH_2)_2CH(CH_3)_2$ | ethyl | I | 430 | $[M—I]^+$ |
| 408 | phenyl | O | 3 | 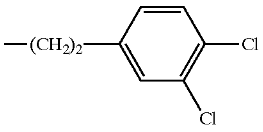 | $—(CH_2)_2CH(CH_3)_2$ | ethyl | I | 464 | $[M—I]^+$ |
| 409 | phenyl | O | 3 | 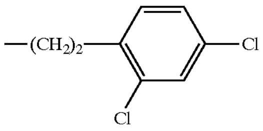 | $—CH_2CONH_2$ | ethyl | I | 451 | $[M—I]^+$ |
| 410 | phenyl | O | 3 | 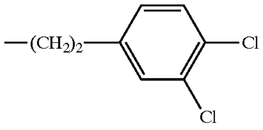 | $—CH_2CONH_2$ | ethyl | I | 451 | $[M—I]^+$ |
| 411 | phenyl | O | 3 | 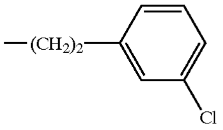 | $—CH_2CN$ | ethyl | I | 399 | $[M—I]^+$ |
| 412 | phenyl | O | 3 | 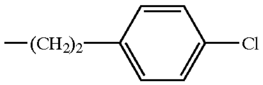 | $—(CH_2)_2O(CH_2)_2OMe$ | ethyl | I | 462 | $[M—I]^+$ |

TABLE 1b-continued
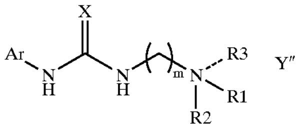
| CPD No. | Ar | X | m | R1 | R2 | R3 | Y | Mass (ES⁺) | Spec. m/e |
|---|---|---|---|---|---|---|---|---|---|
| 413 | phenyl | O | 3 | 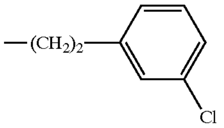 | —$(CH_2)_2O(CH_2)_2OMe$ | ethyl | I | 462 | $[M—I]^+$ |
| 414 | phenyl | O | 3 | 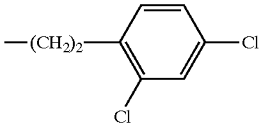 | —$(CH_2)_2O(CH_2)_2OMe$ | ethyl | I | 496 | $[M—I]^+$ |
| 415 | phenyl | O | 3 | 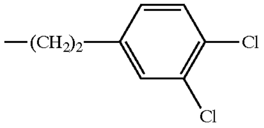 | —$(CH_2)_2O(CH_2)_2OMe$ | ethyl | I | 496 | $[M—I]^+$ |
| 416 | phenyl | O | 3 | 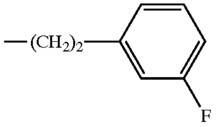 | —$(CH_2)_2O(CH_2)_2OMe$ | ethyl | I | 446 | $[M—I]^+$ |
| 417 | phenyl | O | 3 | 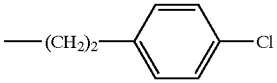 | 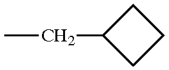 | ethyl | I | 428 | $[M—I]^+$ |
| 418 | phenyl | O | 3 | 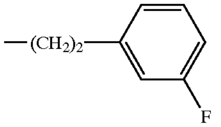 | 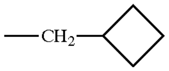 | ethyl | I | 428 | $[M—I]^+$ |

TABLE 1b-continued
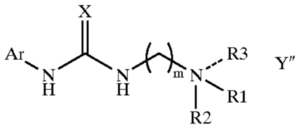
| CPD No. | Ar | X | m | R1 | R2 | R3 | Y | Mass (ES⁺) | Spec. m/e |
|---|---|---|---|---|---|---|---|---|---|
| 419 | phenyl | O | 3 | 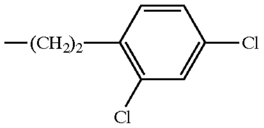 | 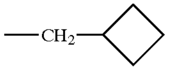 | ethyl | I | 462 | [M—I]⁺ |
| 420 | phenyl | O | 3 | 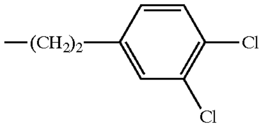 | 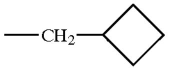 | ethyl | I | 462 | [M—I]⁺ |
| 421 | phenyl | O | 3 | 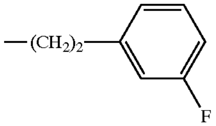 | 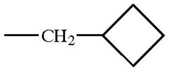 | ethyl | I | 412 | [M—I]⁺ |
| 422 | phenyl | O | 3 | 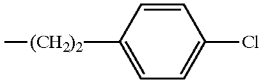 | 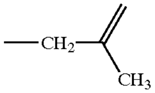 | ethyl | I | 414 | [M—I]⁺ |
| 423 | phenyl | O | 3 | 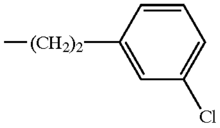 | 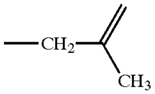 | ethyl | I | 414 | [M—I]⁺ |
| 424 | phenyl | O | 3 | 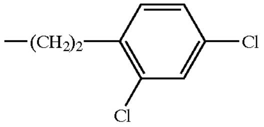 | 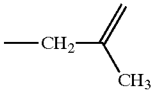 | ethyl | I | 448 | [M—I]⁺ |

TABLE 1b-continued
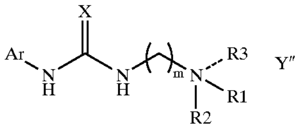
| CPD No. | Ar | X | m | R1 | R2 | R3 | Y | Mass (ES⁺) | Spec. m/e |
|---|---|---|---|---|---|---|---|---|---|
| 425 | phenyl | O | 3 | 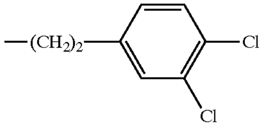 | 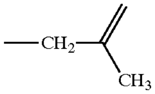 | ethyl | I | 448 | $[M-I]^+$ |
| 426 | phenyl | O | 3 | 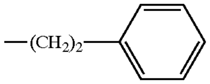 | 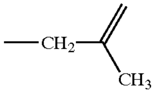 | ethyl | I | 380 | $[M-I]^+$ |
| 427 | phenyl | O | 3 | 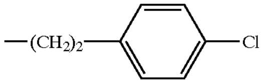 | $-CH_2CH(CH_2CH_3)_2$ | ethyl | I | 444 | $[M-I]^+$ |
| 428 | phenyl | O | 3 | 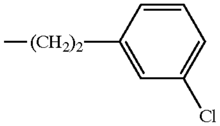 | $-CH_2CH(CH_2CH_3)_2$ | ethyl | I | 444 | $[M-I]^+$ |
| 429 | phenyl | O | 3 | 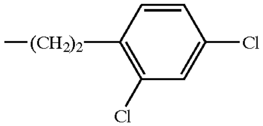 | $-CH_2CH(CH_2CH_3)_2$ | ethyl | I | 478 | $[M-I]^+$ |
| 430 | phenyl | O | 3 | 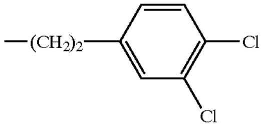 | $-CH_2CH(CH_2CH_3)_2$ | ethyl | I | 478 | $[M-I]^+$ |

TABLE 1b-continued
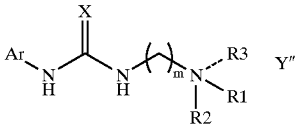
| CPD No. | Ar | X | m | R1 | R2 | R3 | Y | Mass ($ES^+$) | Spec. m/e |
|---|---|---|---|---|---|---|---|---|---|
| 431 | phenyl | O | 3 | 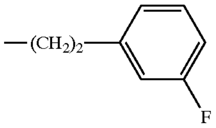 | $—CH_2CH(CH_2CH_3)_2$ | ethyl | I | 428 | $[M—I]^+$ |
| 432 | phenyl | O | 3 | 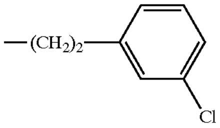 | $—(CH_2)_2F$ | ethyl | I | 406 | $[M—I]^+$ |
| 433 | phenyl | O | 3 | 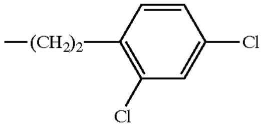 | $—(CH_2)_2F$ | ethyl | I | 440 | $[M—I]^+$ |
| 434 | phenyl | O | 3 | 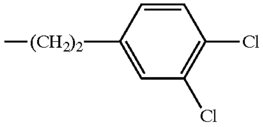 | $—(CH_2)_2F$ | ethyl | I | 440 | $[M—I]^+$ |
| 435 | 4-methoxy-phenyl | O | 3 | 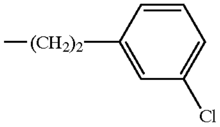 | $—(CH_2)_2CH(CH_3)_2$ | ethyl | I | 460 | $[M—I]^+$ |
| 436 | 4-methoxy-phenyl | O | 3 | 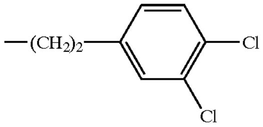 | $—(CH_2)_2CH(CH_3)_2$ | ethyl | I | 494 | $[M—I]^+$ |

TABLE 1b-continued
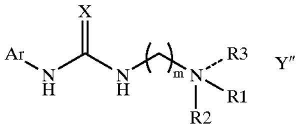
| CPD No. | Ar | X | m | R1 | R2 | R3 | Y | Mass (ES+) | Spec. m/e |
|---|---|---|---|---|---|---|---|---|---|
| 437 | 4-methoxy-phenyl | O | 3 | 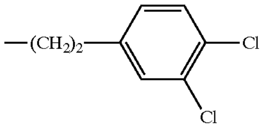 | $-CH_2CONH_2$ | ethyl | I | 481 | [M—I]+ |
| 438 | 4-methoxy-phenyl | O | 3 | 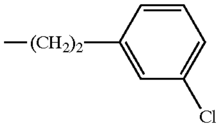 | $-(CH_2)_2O(CH_2)_2OMe$ | ethyl | I | 492 | [M—I]+ |
| 439 | 4-methoxy-phenyl | O | 3 | 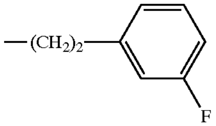 | $-(CH_2)_2O(CH_2)_2OMe$ | ethyl | I | 476 | [M—I]+ |
| 440 | 4-methoxy-phenyl | O | 3 | 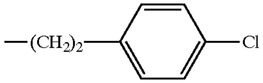 | 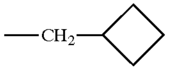 | ethyl | I | 458 | [M—I]+ |
| 441 | 4-methoxy-phenyl | O | 3 | 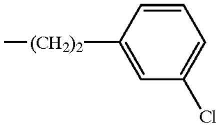 | 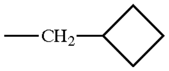 | ethyl | I | 458 | [M—I]+ |
| 442 | 4-methoxy-phenyl | O | 3 | 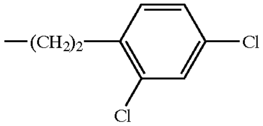 | 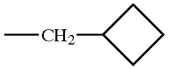 | ethyl | I | 492 | [M—I]+ |

TABLE 1b-continued
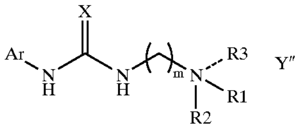
| CPD No. | Ar | X | m | R1 | R2 | R3 | Y | Mass ($ES^+$) | Spec. m/e |
|---|---|---|---|---|---|---|---|---|---|
| 443 | 4-methoxy-phenyl | O | 3 | 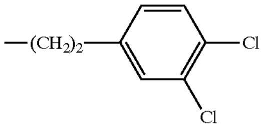 | 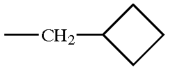 | ethyl | I | 492 | $[M-I]^+$ |
| 444 | 4-methoxy-phenyl | O | 3 | 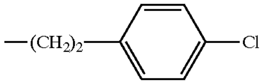 | 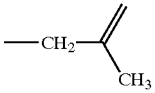 | ethyl | I | 444 | $[M-I]^+$ |
| 445 | 4-methoxy-phenyl | O | 3 | 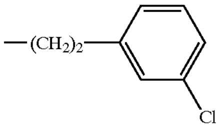 | 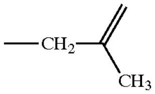 | ethyl | I | 444 | $[M-I]^+$ |
| 446 | 4-methoxy-phenyl | O | 3 | 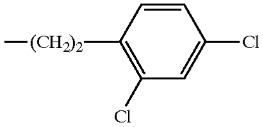 | 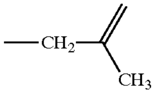 | ethyl | I | 478 | $[M-I]^+$ |
| 447 | 4-methoxy-phenyl | O | 3 | 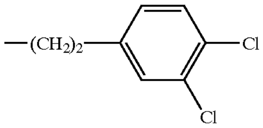 | 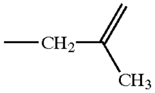 | ethyl | I | 478 | $[M-I]^+$ |
| 448 | 4-methoxy-phenyl | O | 3 | 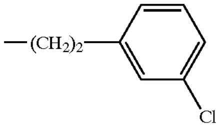 | $-CH_2CH(CH_2CH_3)_2$ | ethyl | I | 474 | $[M-I]^+$ |

TABLE 1b-continued
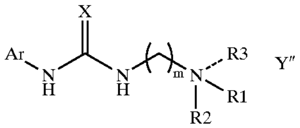
| CPD No. | Ar | X | m | R1 | R2 | R3 | Y | Mass (ES⁺) | Spec. m/e |
|---|---|---|---|---|---|---|---|---|---|
| 449 | 4-methoxy-phenyl | O | 3 | 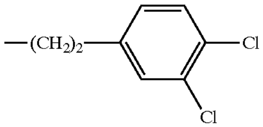 | $—CH_2CH(CH_2CH_3)_2$ | ethyl | I | 508 | $[M—I]^+$ |
| 450 | 4-methoxy-phenyl | O | 3 | 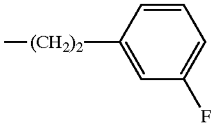 | $—CH_2CH(CH_2CH_3)_2$ | ethyl | I | 458 | $[M—I]^+$ |
| 451 | 4-methoxy-phenyl | O | 3 | 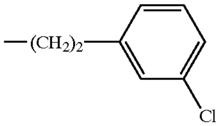 | $—(CH_2)_2F$ | ethyl | I | 436 | $[M—I]^+$ |
| 452 | 4-methoxy-phenyl | O | 3 | 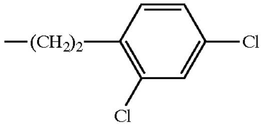 | $—(CH_2)_2F$ | ethyl | I | 470 | $[M—I]^+$ |
| 453 | 4-methoxy-phenyl | O | 3 | 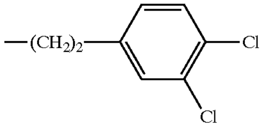 | $—(CH_2)_2F$ | ethyl | I | 470 | $[M—I]^+$ |

Example 22

Evaluation of CCR-3 Inhibition Using a Calcium Mobilization Assay

The CCR-3 inhibitory activity of the disclosed compounds was determined by measuring the inhibition of eotaxin-induced calcium mobilization using the assay described below. Compounds 93–162 used in this assay were synthesized by using the method described in Example 6, and Compounds 168–170 were synthesized by using the method described in Example 6 except for the use of isothiocyanates instead of isocyanates in step 6.

CCR-3 transfectant cells (CCR3/HEK293) were isolated and resuspended with assay buffer (20 mM HEPES, 125 mM NaCl, 5 mM KCl, 0.5 mM glucose, 1 mM $CaCl_2$, 1 mM $MgCl_2$, 0.1% BSA). After washing CCR3/HEK293 cells with assay buffer, cells were loaded with Fura-2/AM in assay buffer for 1 hour at room temperature. Cells were washed and resuspended with assay buffer at $5\times10^6$ cells/ml in assay buffer, and placed in a tissue culture plate (Falcon, no. 3296). Test compounds dissolved in DMSO were added to the wells, followed by eotaxin (10 nM at final concentration). Cells were excited at 340 nm and 380 nm in a fluorimeter (ARGUS50,FDSS2000, Hamamatsu Photonics) and the relative ratio of the fluorescence emitted at 510 nm was recorded. For a control, DMSO without a test compound was added. Intracellular calcium mobilization was calculated as described in Krogel C. et al., FEBS Let. (1989) 243, 41–46.

The results shown in Table 2a and Table 2b indicate that the disclosed compounds inhibit calcium mobilization.

TABLE 2

Inhibitory effects of compounds on eotaxin-induced intracellular calcium mobilization

| CPD No. | $Ca^{2+}$ mobilization 6.25 μg/ml (inhibition %) |
|---|---|
| 93 | 50 |
| 94 | 50 |
| 95 | 55 |
| 96 | 53 |
| 97 | 57 |
| 98 | 51 |
| 99 | 53 |
| 100 | 53 |
| 101 | 63 |
| 102 | 63 |
| 103 | 53 |
| 104 | 51 |
| 105 | 53 |
| 106 | 57 |
| 107 | 53 |
| 108 | 61 |
| 109 | 51 |
| 110 | 57 |
| 111 | 51 |
| 112 | 52 |
| 113 | 51 |
| 114 | 51 |
| 115 | 57 |
| 116 | 68 |
| 117 | 55 |
| 118 | 58 |
| 119 | 62 |
| 120 | 57 |
| 121 | 52 |
| 122 | 66 |
| 123 | 53 |
| 124 | 55 |

TABLE 2-continued

Inhibitory effects of compounds on eotaxin-induced intracellular calcium mobilization

| CPD No. | $Ca^{2+}$ mobilization 6.25 μg/ml (inhibition %) |
|---|---|
| 125 | 65 |
| 126 | 54 |
| 127 | 59 |
| 128 | 55 |
| 129 | 50 |
| 130 | 51 |
| 131 | 52 |
| 132 | 55 |
| 133 | 63 |
| 134 | 59 |
| 135 | 57 |
| 136 | 63 |
| 137 | 50 |
| 138 | 56 |
| 139 | 65 |
| 140 | 54 |
| 141 | 53 |
| 142 | 58 |
| 143 | 64 |
| 144 | 51 |
| 145 | 53 |
| 146 | 52 |
| 147 | 51 |
| 148 | 57 |
| 149 | 56 |
| 150 | 70 |
| 151 | 54 |
| 152 | 54 |
| 153 | 59 |
| 154 | 55 |
| 155 | 69 |
| 156 | 63 |
| 157 | 53 |
| 158 | 50 |
| 159 | 51 |
| 160 | 58 |
| 161 | 51 |
| 162 | 50 |
| 168 | 23 |
| 169 | 48 |
| 170 | 45 |

TABLE 2b

Inhibitory effects of compounds on eotaxin-induced intracellular calcium mobilization

| CPD No. | $Ca^{2+}$ mobilization 1.25 μg/ml (inhibition %) |
|---|---|
| 355 | 63 |
| 356 | 57 |
| 357 | 57 |
| 358 | 63 |
| 361 | 70 |
| 362 | 49 |
| 363 | 56 |
| 364 | 66 |
| 365 | 65 |
| 366 | 46 |
| 367 | 50 |
| 393 | 56 |
| 394 | 76 |
| 395 | 69 |
| 396 | 67 |
| 397 | 69 |
| 398 | 70 |
| 399 | 58 |
| 400 | 68 |

TABLE 2b-continued

| Inhibitory effects of compounds on eotaxin-induced intracellular calcium mobilization | |
|---|---|
| CPD No. | $Ca^{2+}$ mobilization 1.25 μg/ml (inhibition %) |
| 401 | 57 |
| 435 | 62 |
| 436 | 57 |
| 437 | 64 |
| 438 | 70 |
| 440 | 62 |
| 441 | 71 |
| 442 | 63 |
| 443 | 69 |
| 444 | 72 |
| 445 | 63 |
| 446 | 76 |
| 447 | 65 |

Example 23

Evaluation of Eotaxin-induced Chemotaxis of CCR-3 Transfectant Cell

The inhibitory activity of the compounds against eotaxin-induced chemotaxis was determined by measuring the inhibition of migration of CCR-3 transfectant cells (CCR3/U937), using a minor modification of the method described by Ohashi, H. et al., *Int Arch Allergy Immunol.* (1999) 118, 44–50. CCR-3 transfectant cells were grown in PRMI1640 medium containing 10% fetal calf serum (FCS) and Geneticin 418 (0.8 mg/ml). For the assay, CCR-3 transfectant cells were isolated and resuspended at $1\times10^7$ cells/ml in assay medium (RPMI 1640 medium containing 0.1% bovine serum albumin (BSA)). The chemotaxis assay was performed in a 24-well culture plate. Human eotaxin suspended in assay medium was added to the wells at $1\times10^{-9}$ M along with test compounds at various concentrations. For a positive control, eotaxin was added to the wells without a test compound, and for a negative control, neither eotaxin nor a test compound was added to the walls. Chemotaxicell (Kurabo Co., Ltd.) having 5 micrometers pore size were inserted into each well and 100 micro liters of CCR-3 transfectant cells suspension were added to the top chamber. The plates were incubated at 37° C. for 1 hour. After incubation, migrated cells in lower wells were diluted and counted by particle size distribution analyzer (CDP-500, Sysmex Co., Ltd.)

The results shown in Table 3a, 3b, 3c and 3d indicate that the disclosed compounds inhibit eotaxin-induced chemotaxis.

TABLE 3a

| Inhibitory effects of compounds on eotaxin-induced chemotaxis of CCR3 transfectants | |
|---|---|
| CPD No. | Chemotaxis Assay 10 μM (inhibition %) |
| 1 | 100 |
| 2 | 100 |
| 3 | 100 |
| 4 | 59 |
| 5 | 99 |
| 6 | 100 |
| 7 | 99 |
| 8 | 94 |

TABLE 3a-continued

| Inhibitory effects of compounds on eotaxin-induced chemotaxis of CCR3 transfectants | |
|---|---|
| CPD No. | Chemotaxis Assay 10 μM (inhibition %) |
| 9 | 100 |
| 10 | 99 |
| 11 | 86 |
| 14 | 97 |
| 16 | 63 |
| 17 | 51 |
| 18 | 58 |
| 19 | 47 |
| 20 | 26 |
| 21 | 40 |
| 22 | 25 |
| 23 | 82 |
| 24 | 100 |
| 25 | 88 |
| 27 | 97 |
| 28 | 76 |
| 29 | 100 |
| 30 | 100 |
| 31 | 97 |
| 32 | 99 |
| 33 | 95 |
| 34 | 96 |
| 35 | 100 |
| 36 | 34 |
| 37 | 100 |
| 38 | 46 |
| 39 | 78 |
| 40 | 88 |
| 41 | 20 |
| 42 | 96 |
| 43 | 50 |
| 45 | 62 |
| 47 | 58 |
| 48 | 34 |
| 49 | 100 |
| 50 | 54 |
| 51 | 100 |
| 52 | 100 |
| 53 | 93 |
| 54 | 19 |
| 55 | 38 |
| 56 | 100 |
| 57 | 100 |
| 58 | 100 |
| 59 | 87 |
| 60 | 98 |
| 61 | 100 |
| 62 | 98 |
| 63 | 100 |
| 64 | 100 |
| 65 | 100 |
| 66 | 32 |
| 67 | 100 |
| 68 | 31 |
| 69 | 81 |
| 70 | 89 |
| 71 | 64 |
| 72 | 68 |
| 73 | 44 |
| 74 | 50 |
| 75 | 68 |
| 76 | 44 |
| 77 | 76 |
| 79 | 78 |
| 80 | 65 |
| 81 | 58 |
| 82 | 100 |
| 83 | 100 |
| 84 | 100 |
| 85 | 19 |
| 86 | 37 |
| 87 | 97 |
| 88 | 100 |

TABLE 3a-continued

Inhibitory effects of compounds on eotaxin-induced chemotaxis of CCR3 transfectants

| CPD No. | Chemotaxis Assay 10 $\mu$M (inhibition %) |
|---|---|
| 89 | 89 |
| 90 | 100 |
| 163 | 96 |
| 164 | 100 |
| 165 | 100 |
| 166 | 100 |
| 167 | 100 |
| 171 | 100 |
| 172 | 100 |
| 173 | 100 |
| 174 | 100 |
| 175 | 100 |
| 176 | 75 |
| 177 | 89 |
| 178 | 100 |
| 179 | 100 |
| 180 | 100 |
| 181 | 100 |
| 182 | 97 |
| 183 | 94 |
| 184 | 100 |
| 185 | 100 |
| 186 | 69 |
| 187 | 100 |
| 188 | 100 |
| 189 | 94 |
| 190 | 90 |
| 191 | 100 |
| 192 | 100 |
| 193 | 100 |
| 194 | 100 |
| 195 | 100 |
| 196 | 100 |
| 197 | 100 |
| 198 | 100 |
| 199 | 100 |
| 200 | 100 |
| 201 | 100 |
| 202 | 100 |
| 203 | 100 |
| 204 | 78 |
| 205 | 97 |
| 206 | 64 |
| 207 | 50 |
| 208 | 63 |
| 209 | 94 |
| 210 | 100 |
| 211 | 67 |
| 212 | 100 |
| 213 | 92 |
| 214 | 99 |
| 215 | 89 |
| 216 | 100 |
| 217 | 87 |
| 218 | 99 |
| 219 | 86 |
| 220 | 77 |
| 221 | 100 |
| 222 | 79 |
| 223 | 86 |
| 224 | 75 |
| 225 | 100 |
| 226 | 100 |
| 227 | 100 |
| 228 | 100 |
| 229 | 100 |
| 230 | 100 |
| 231 | 90 |
| 232 | 100 |
| 233 | 100 |
| 234 | 89 |
| 235 | 91 |
| 236 | 97 |

TABLE 3a-continued

Inhibitory effects of compounds on eotaxin-induced chemotaxis of CCR3 transfectants

| CPD No. | Chemotaxis Assay 10 $\mu$M (inhibition %) |
|---|---|
| 237 | 100 |
| 238 | 69 |
| 239 | 100 |
| 240 | 86 |
| 241 | 100 |
| 242 | 73 |
| 243 | 84 |
| 244 | 81 |
| 245 | 100 |
| 246 | 100 |
| 247 | 99 |
| 248 | 100 |
| 249 | 100 |
| 250 | 99 |
| 251 | 100 |
| 252 | 100 |
| 253 | 74 |
| 254 | 82 |
| 255 | 100 |
| 256 | 100 |
| 257 | 100 |
| 258 | 100 |
| 259 | 100 |
| 260 | 100 |
| 261 | 100 |
| 262 | 62 |
| 263 | 100 |
| 264 | 100 |
| 265 | 95 |
| 266 | 100 |
| 267 | 99 |
| 268 | 100 |
| 269 | 100 |
| 270 | 100 |
| 271 | 100 |
| 272 | 89 |
| 273 | 88 |
| 274 | 60 |
| 275 | 100 |
| 276 | 100 |
| 277 | 76 |
| 278 | 100 |
| 279 | 96 |
| 280 | 60 |
| 281 | 100 |
| 282 | 100 |
| 283 | 100 |
| 284 | 95 |
| 285 | 58 |
| 286 | 100 |
| 287 | 100 |
| 288 | 100 |
| 289 | 100 |
| 290 | 100 |
| 291 | 53 |
| 292 | 56 |
| 293 | 95 |

TABLE 3b

Inhibitory effects of compounds on eotaxin-induced chemotaxis of CCR3 transfectants

| CPD No. | CCR-3 Transfectant Chemotaxis Assay 6.25 $\mu$g/ml (inhibition %) |
|---|---|
| 97 | 21 |
| 99 | 47 |

TABLE 3b-continued

Inhibitory effects of compounds on eotaxin-induced chemotaxis of CCR3 transfectants

| CPD No. | CCR-3 Transfectant Chemotaxis Assay 6.25 $\mu$g/ml (inhibition %) |
|---|---|
| 100 | 54 |
| 102 | 19 |
| 106 | 47 |
| 107 | 55 |
| 108 | 23 |
| 109 | 12 |
| 110 | 32 |
| 111 | 44 |
| 112 | 26 |
| 113 | 66 |
| 114 | 22 |
| 115 | 62 |
| 116 | 82 |
| 118 | 62 |
| 119 | 65 |
| 120 | 34 |
| 121 | 64 |
| 122 | 92 |
| 125 | 90 |
| 126 | 54 |
| 128 | 33 |
| 132 | 11 |
| 133 | 21 |
| 135 | 12 |
| 136 | 32 |
| 137 | 40 |
| 138 | 31 |
| 149 | 31 |
| 155 | 56 |

TABLE 3c

Inhibitory effects of compounds on eotaxin-induced chemotaxis of CCR3 transfectants

| CPD No. | Chemotaxis Assay 10 $\mu$M (inhibition %) |
|---|---|
| 91 | 100 |
| 92 | 100 |
| 294 | 100 |
| 295 | 100 |
| 296 | 67 |
| 297 | 100 |
| 298 | 100 |
| 299 | 100 |
| 300 | 100 |
| 301 | 100 |
| 302 | 100 |
| 303 | 100 |
| 304 | 66 |
| 305 | 100 |
| 306 | 100 |
| 307 | 92 |
| 308 | 100 |
| 309 | 100 |
| 310 | 100 |
| 311 | 93 |
| 312 | 97 |
| 313 | 86 |
| 314 | 100 |
| 315 | 63 |
| 316 | 82 |
| 317 | 100 |
| 318 | 100 |
| 319 | 100 |
| 320 | 100 |
| 321 | 100 |

TABLE 3c-continued

Inhibitory effects of compounds on eotaxin-induced chemotaxis of CCR3 transfectants

| CPD No. | Chemotaxis Assay 10 $\mu$M (inhibition %) |
|---|---|
| 322 | 93 |
| 323 | 100 |
| 324 | 100 |
| 325 | 100 |
| 326 | 100 |
| 327 | 100 |
| 328 | 100 |
| 329 | 100 |
| 330 | 100 |
| 331 | 100 |
| 332 | 100 |
| 333 | 100 |
| 334 | 100 |
| 335 | 100 |
| 336 | 100 |
| 337 | 99 |
| 338 | 100 |
| 339 | 100 |
| 340 | 100 |
| 341 | 100 |
| 342 | 97 |
| 343 | 100 |
| 344 | 100 |
| 345 | 100 |
| 346 | 100 |
| 347 | 100 |
| 348 | 100 |
| 349 | 100 |
| 350 | 59 |
| 351 | 100 |
| 352 | 100 |
| 353 | 100 |
| 354 | 100 |

TABLE 3d

Inhibitory effects of compounds on eotaxin-induced chemotaxis of CCR3 transfectants

| CPD No. | Chemotaxis Assay 0.1 $\mu$g/ml (inhibition %) |
|---|---|
| 359 | 49 |
| 360 | 70 |
| 368 | 88 |
| 369 | 82 |
| 370 | 64 |
| 371 | 86 |
| 372 | 76 |
| 373 | 100 |
| 374 | 100 |
| 375 | 91 |
| 376 | 87 |
| 377 | 46 |
| 378 | 81 |
| 379 | 80 |
| 380 | 46 |
| 381 | 68 |
| 382 | 98 |
| 383 | 43 |
| 384 | 76 |
| 385 | 68 |
| 386 | 43 |
| 387 | 94 |
| 388 | 56 |
| 389 | 65 |
| 390 | 51 |
| 391 | 47 |
| 392 | 45 |
| 402 | 71 |

TABLE 3d-continued

| Inhibitory effects of compounds on eotaxin-induced chemotaxis of CCR3 transfectants | |
|---|---|
| CPD No. | Chemotaxis Assay 0.1 μg/ml (inhibition %) |
| 403 | 77 |
| 404 | 47 |
| 405 | 57 |
| 406 | 43 |
| 407 | 52 |
| 408 | 74 |
| 409 | 53 |
| 410 | 50 |
| 411 | 42 |
| 412 | 84 |
| 413 | 95 |
| 414 | 98 |
| 415 | 99 |
| 416 | 69 |
| 417 | 59 |
| 418 | 89 |
| 419 | 76 |
| 420 | 99 |
| 421 | 66 |
| 422 | 42 |
| 423 | 92 |
| 424 | 95 |
| 425 | 93 |
| 426 | 44 |
| 427 | 67 |
| 428 | 93 |
| 429 | 64 |
| 430 | 76 |
| 431 | 96 |
| 432 | 96 |
| 433 | 76 |
| 434 | 100 |
| 439 | 51 |
| 448 | 82 |
| 449 | 96 |
| 450 | 35 |
| 451 | 92 |
| 452 | 59 |
| 453 | 87 |

Example 24

Evaluation of Eotaxin-induced Chemotaxis of Eosinophils

The inhibitory activity of the compounds against eotaxin-mediated chemotaxis of human-derived eosinophils was determined assay described below.

Eosinophils were prepared from culture of human cord blood mononuclear cells as described by Ohashi, H. et al., *Int Arch Allergy Immunol.* (1999) 118, 44–50. For the assay, esosinophils were resuspended at $1\times10^7$ cells/ml in assay medium (RPMI 1640 medium containing 0.1% bovine serum albumin (BSA)). The chemotaxis assay was preformed in a 24-well culture plate. Human eotaxin suspended in assay medium was added into wells at $1\times10^{-9}$ M with test compounds at various concentrations. For a positive control, eotaxin was added without a test compound, and for a negative control, neither eotaxin nor a test compound was added to the wells. Chemotaxicell (Kurabo Co., Ltd.) having 5 micrometers pore size were inserted into each well and 100 microliters of eosinophil suspension were added to the top chamber. The plates were incubated at 37° C. for 1 hour. After incubation, migrated cells in lower wells were diluted and counted by particle size distribution analyzer (CDP-500, Sysmex Co., Ltd.).

Table results shown in Table 4 indicate that the disclosed compounds inhibit eotaxin-induced chemotaxis in cultured eosinophils.

TABLE 4

| Inhibitory effects of compounds on Eotaxin-induced chemotaxis of cultured eosinophils. | |
|---|---|
| CPD No. | Cultured Eosinophil Chemotaxis assay 10.00 μM (inhibition %) |
| 1 | 100 |
| 3 | 100 |
| 36 | 31 |
| 38 | 11 |
| 60 | 100 |
| 61 | 100 |
| 65 | 100 |
| 66 | 44 |
| 67 | 71 |
| 91 | 100 |
| 92 | 100 |

Example 25

Use of an Urea Derivative to teat a CCR-3 Mediated Disease

A patient suffering from asthma is administered N-Phenylcarbamoyl-N'-[2-(4-chlorophenyl)ethyl]-N'-ethyl-1,3-diaminopropane (Compound 1). Approximately 1 mmole of the compound is administered to the patient via inhalation of an aerosol comprising compound 1. The amount of compound administered should be between 0.01 and 20 mg/kg of the patient's weight.

Example 26

Suppression of Type II Collagen-induced Arthritis in Mice by Compound No. 60 and Compound No. 298

The inhibitory effects of Compound No. 60 (CPD No.60) and Compound No. 298 (CPD No. 298) on collagen-induced arthritis were evaluated in mice.

Male DBA/1 mice were purchased from Japan Charles River Inc. (Kanagawa, Japan) and used at 3 week of age. Mice were immunized intradermally at the base of the tail with mixture of 100 μg of bovine type II collagen (Collagen Gijyutsu-Kenshukai, Japan) and 100 μg of *Mycobacterium tuberculosis* H37Ra (Difco, Detroit, Mich.) in incomplete Freaund's adjuvant at the base of the tail, and then boosted 21 days later with same emulsion. The compound to be studied (20 mg/kg per day) was administered subcutaneously starting at 2nd immunization. In the control experiment, control vehicle (10% DMSO and 10% Cremophor EL in saline) was administered instead of the compound to be studied. Clinical scoring for each paw was assessed by reference to the following scale: 0=normal, 1=swelling and/or erythema of one toe, 2=swelling and/or erythema of two or more toes, 3=swelling and erythema of the entire paw, 4=complete sewlling and erythema of the entire paw and incapacity to bend the ankle. Clinical score for the whole animal was expressed as the cumulative value for all paws, with a maximum of 16. Each group consists of 10 animals.

The inhibitory effects of Compound No. 60 and Compound No. 298 on collagen-induced arthritis were shown in FIGS. 1A and 1B, respectively. A marked prevention in clinical score was observed by administration of Compound No. 60 or Compound No. 298, as opposed to administration of control vehicle.

Example 27

Suppression of Airway Hyperreactivity and Eosinophil Infiltration in Bronchoalveolar Lavage Fluid (BALF) by Compound No. 298

Male BALB/c mice were immunized by an intraperitoneal injection of 10 μg OVA adsorbed to 1 mg aluminum hydroxide gel (alum). A booster injection of the same dose of alum-adsorbed OVA was given 5 days later. Unimmunized control mice received saline.

Twelve days after primary immunization, both the immunized and unimmunized mice were exposed to aerosolized antigen. Aerosolization of OVA was performed using a nose-only aerosol chamber adapted for mice. Animals were exposed for 10 minutes to 5 mg/ml OVA aerosolized by an ultrasonic nebulizer (NE-U12, Omron, Tokyo, Japan) driven by a vacuum pump. The antigen bronchoprovocation was repeated on day 16 and day 20 under the same conditions. Compound No. 298 (CPD No. 298) was dissolved in saline containing 2% DMSO and 2% Cremophore and administered intraperitoneally for 9 days, starting on the first day of antigen inhalation.

Twenty-four hours after the final aerosol exposure, bronchoconstriction was measured by the overflow method of Konzett and Rössler. Mice were anesthetized by an intrapritoneal injection of sodium pentobarbitone (50 mg/kg), and the tracheas were surgically exposed, cannulated, and connected to a rodent ventilator (Model 683, Harvard Apparatus, South Natick, Mass.) and a bronchospasm transducer (Model 7020, Ugo Basile, Comerio-Varese, Italy). Animals were mechanically ventilated with air at 60 strokes/min with a stroke volume of 0.6 ml. A paralytic agent, pancuronium bromide, 0.1 mg/kg, was administered to eliminate spontaneous respiration. After a stable baseline airway pressure was established, acetylcholine chloride was injected intravenously in a volume of 1 μl/g of mouse per dose, starting with 31.3 μg/kg, and increasing the concentration two-fold for each subsequent dose. Bronchoconstriction was recorded on a flatbed recorder (Model FBR-252A, TOA Electronics Ltd., Tokyo, Japan). Bronchoconstriction (%) represent the respiratory overflow volume provoked by acetylcholine as a percentage of the maximal overflow volume (100%) obtained by totally occluding the tracheal cannula. See FIG. 2A. Inhibition of bronchoconstriction provoked by acetylcholine (Murine Asthma Model) by Compound No. 298 was shown in FIG. 2A. In some experiments, airway reactivity was expressed by the area under the dose-response curve (the curves in FIG. 2A) of bronchoconstriction against the acetylcholine concentration. See FIG. 2B.

Immediately after the measurement of airway reactivity to acethycholine, BALF was collected by lavaging whole-lung three times with 0.7-ml aliquots of physiological saline containing 0.1% BSA via the tracheal cannula while gently massaging the thorax. The BALF recovered from one mouse was pooled, centrifuged, and the cells were resuspended in 100 μl saline containing 0.1% BSA. Cell numbers were determined using a hemocytometer and $2 \times 10^4$ cells were cytecetrifuged onto a glass slide. Cells were stained with Diff-Quik (International reagent, Kobe, Japan), and cell types were identified by morphological criteria. Two hundred cells were examined per slide for differential count. See FIG. 2C. As shown in FIG. 2C, Compound No. 298 (CPD No. 298) significantly suppressed eosinophil infiltration to bronchoalveolar lavage fluid (BALF).

The invention has been disclosed broadly and illustrated in reference to representative embodiments described above. Those skilled in the art will recognize that various modifications can be made to the present invention without departing from the spirit and scope thereof.

All references cited herein are hereby incorporated herein by reference in their entireties.

Scheme 1

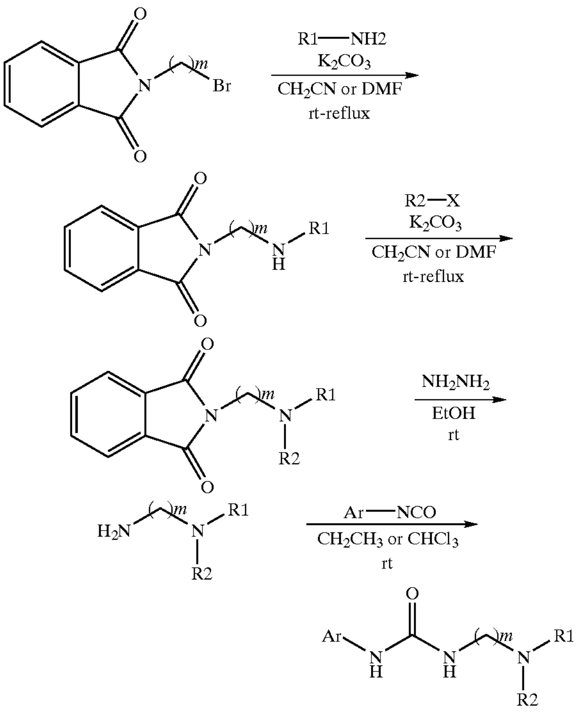

Scheme 2

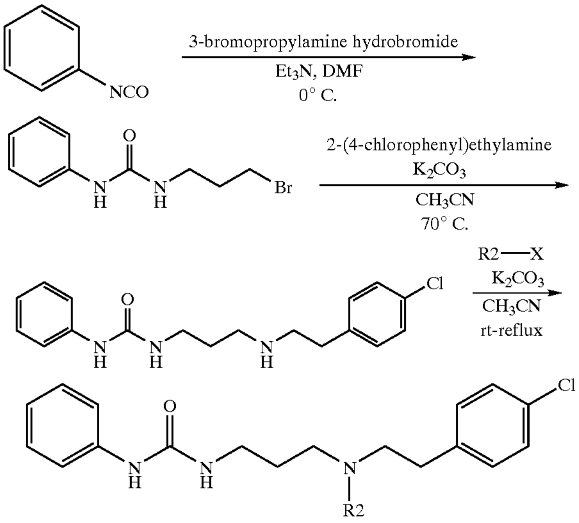

Scheme 3
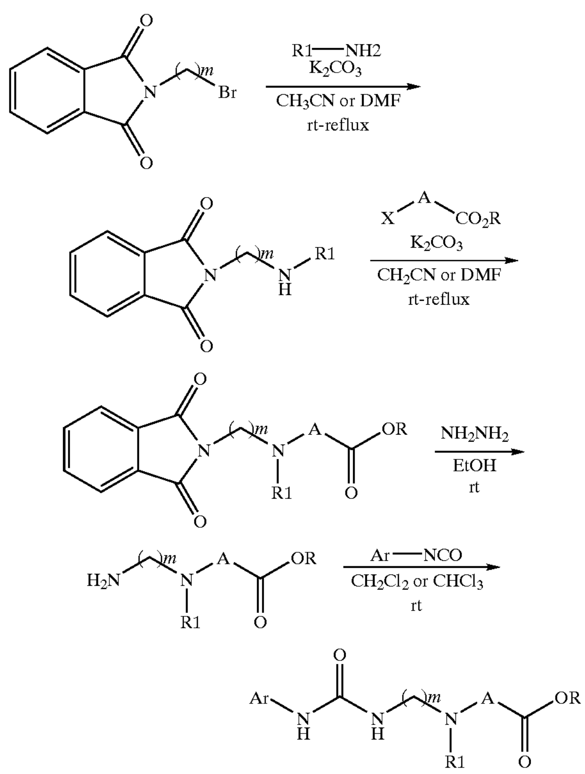
Scheme 4
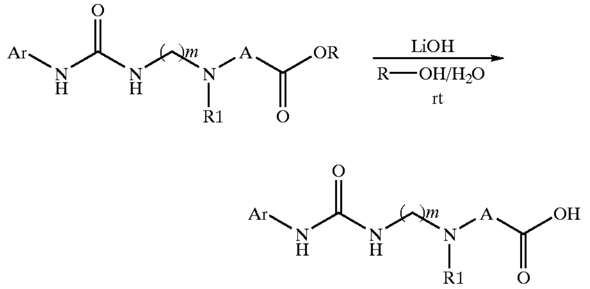
Scheme 5
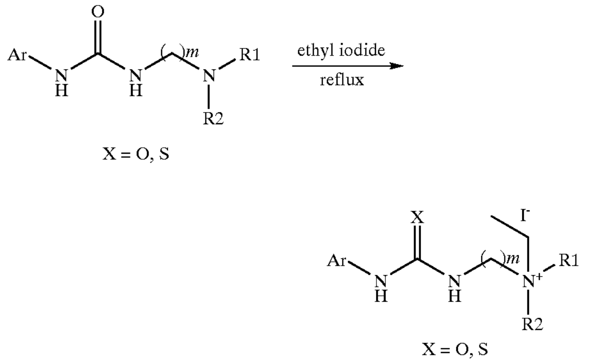
Scheme 6
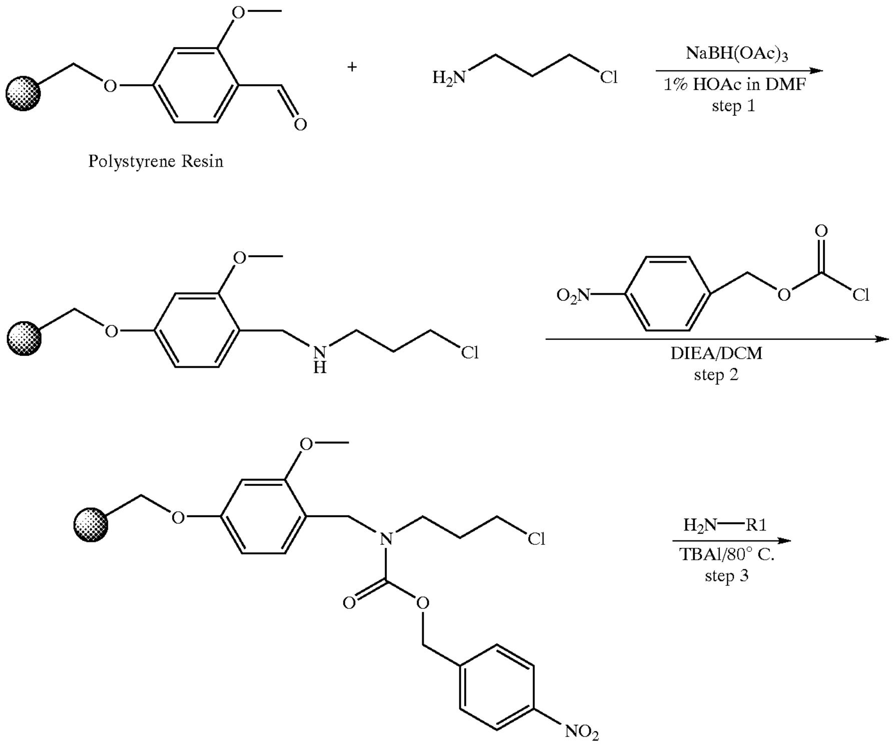

-continued
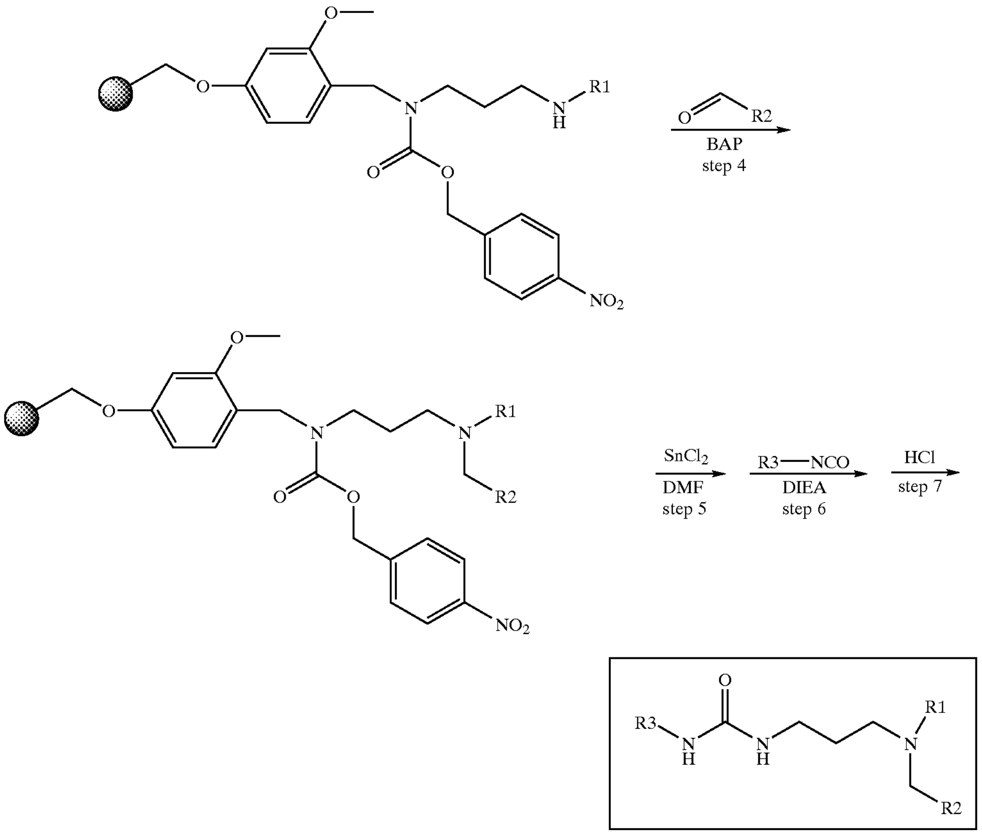
Scheme 7
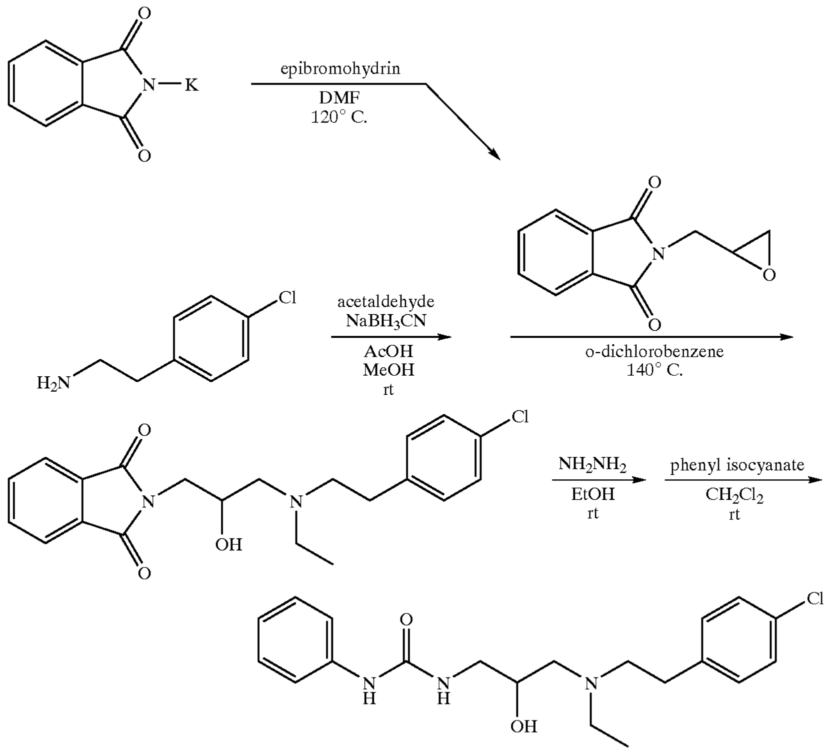

Scheme 8
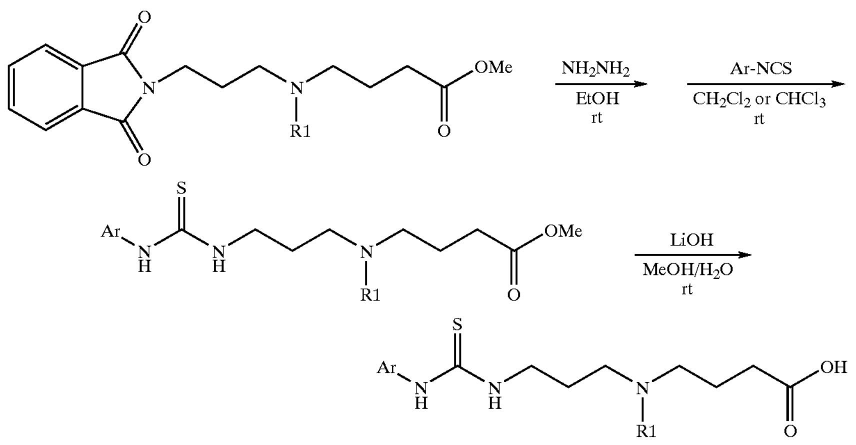
Scheme 9
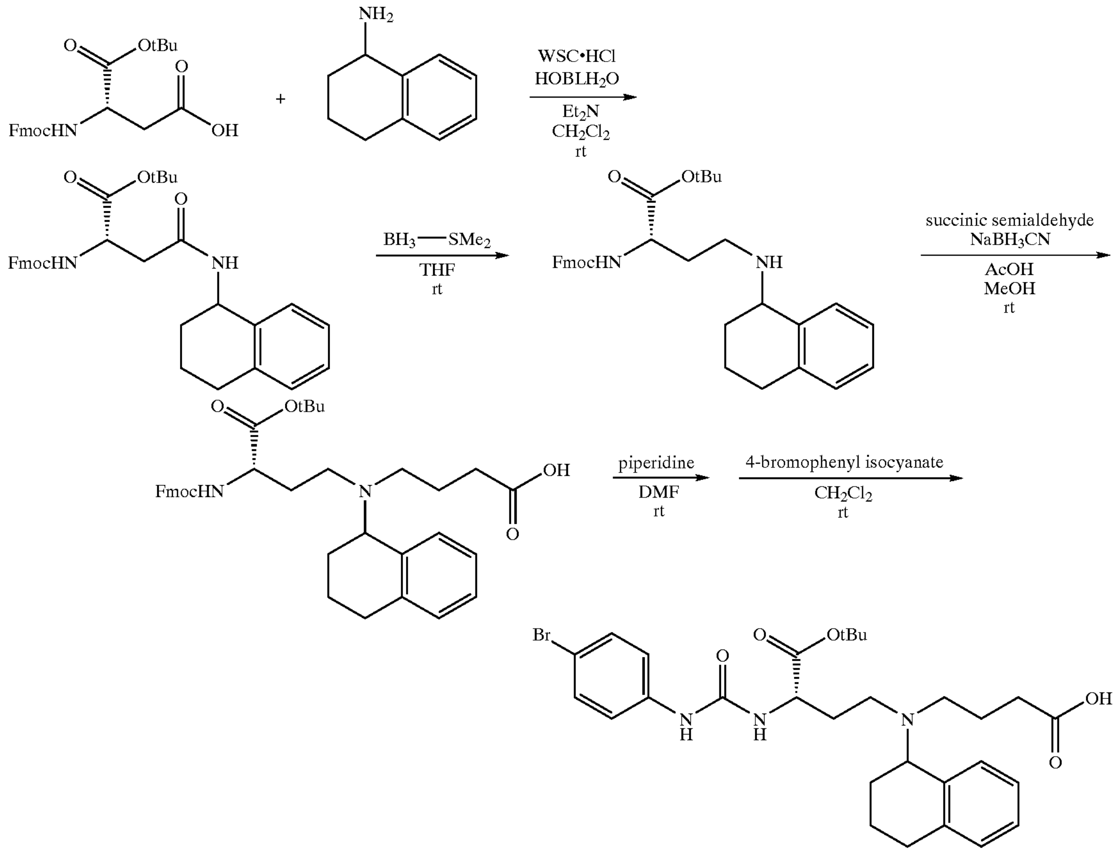
Scheme 10
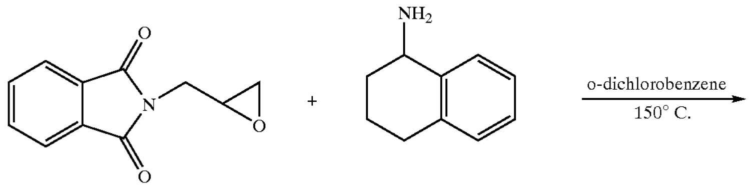

-continued
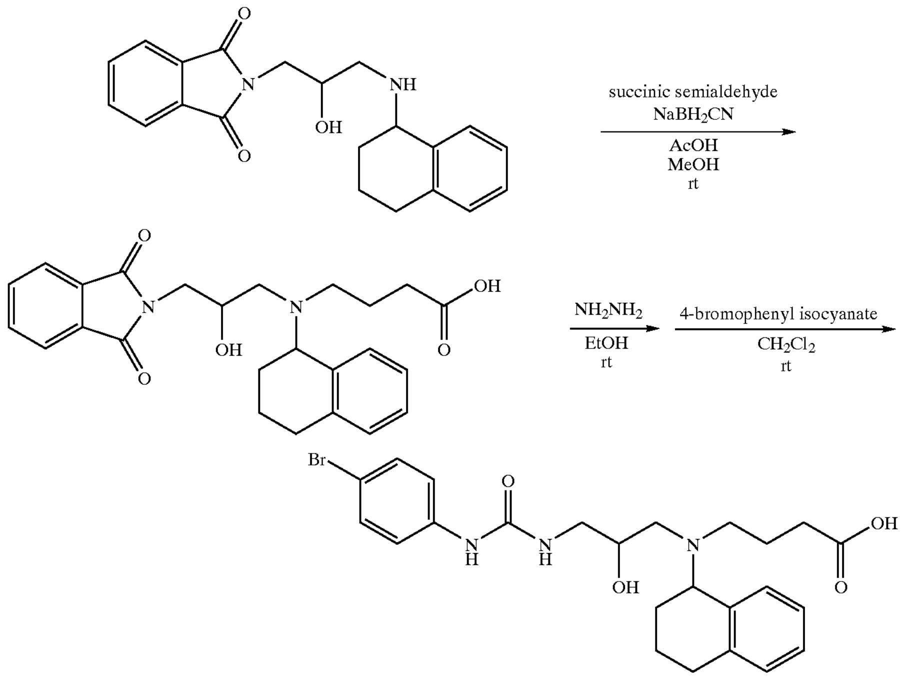
Scheme 11
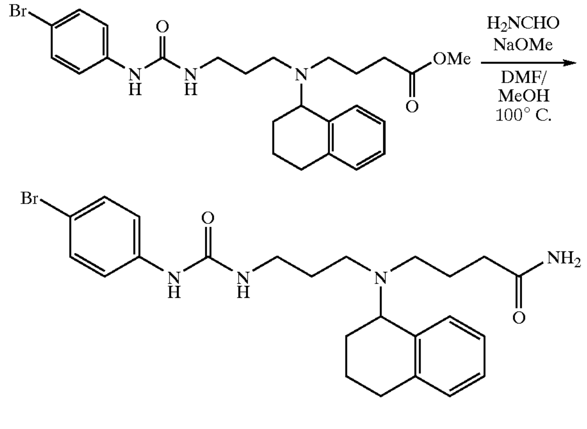
Scheme 12
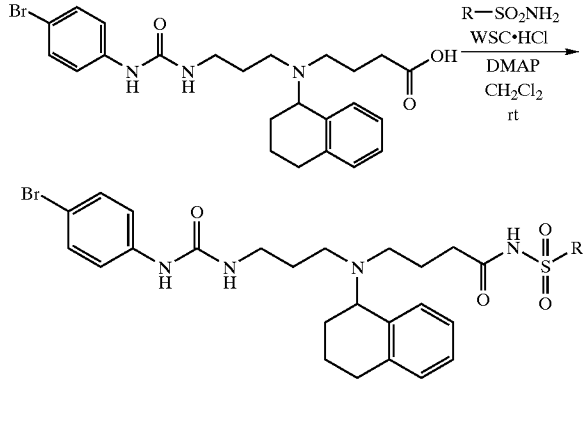
Scheme 13
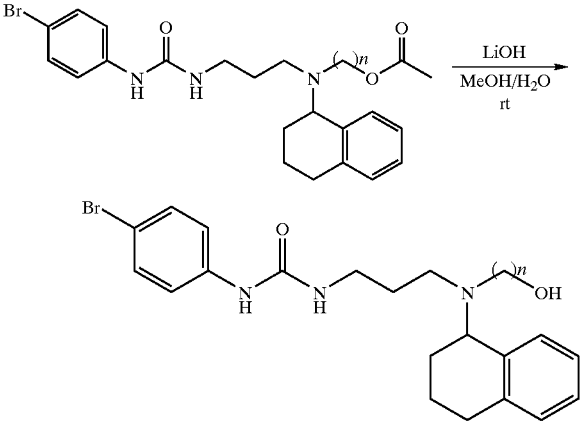
Scheme 14
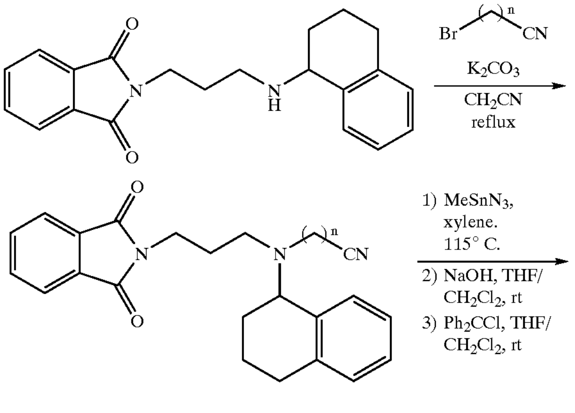

-continued
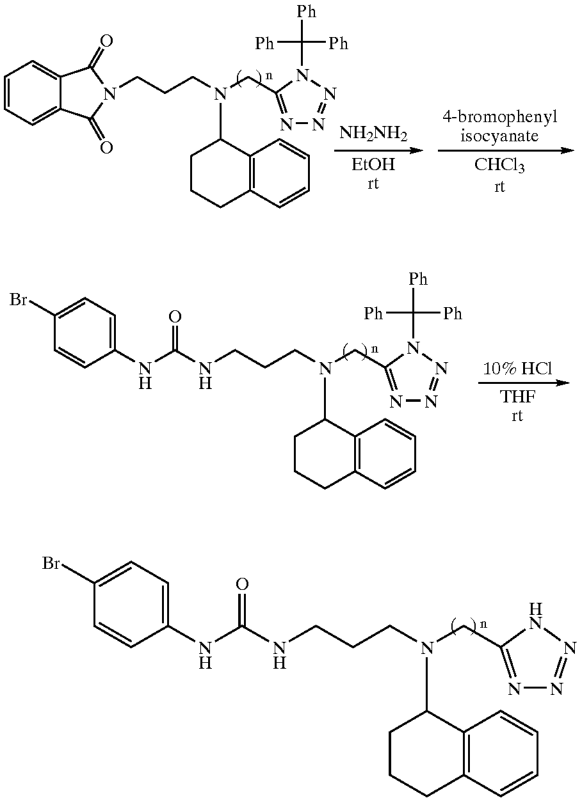
Scheme 15
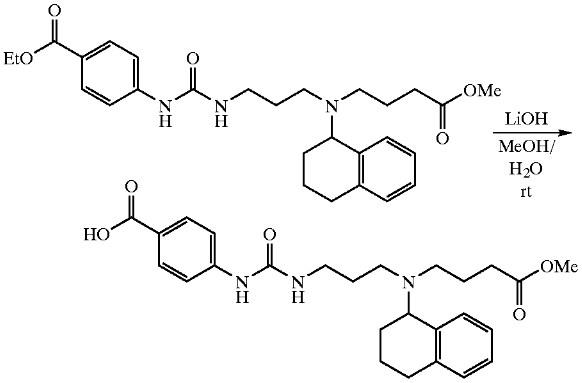
Scheme 16
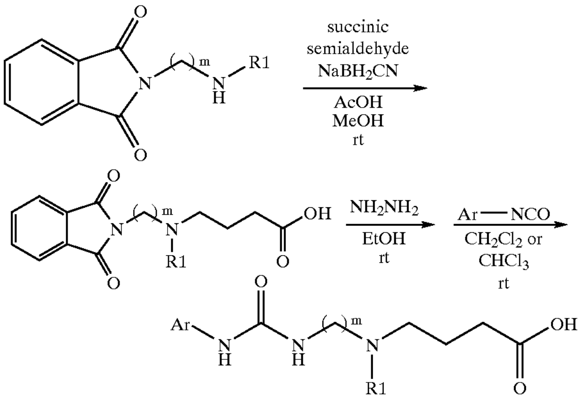
Scheme 17
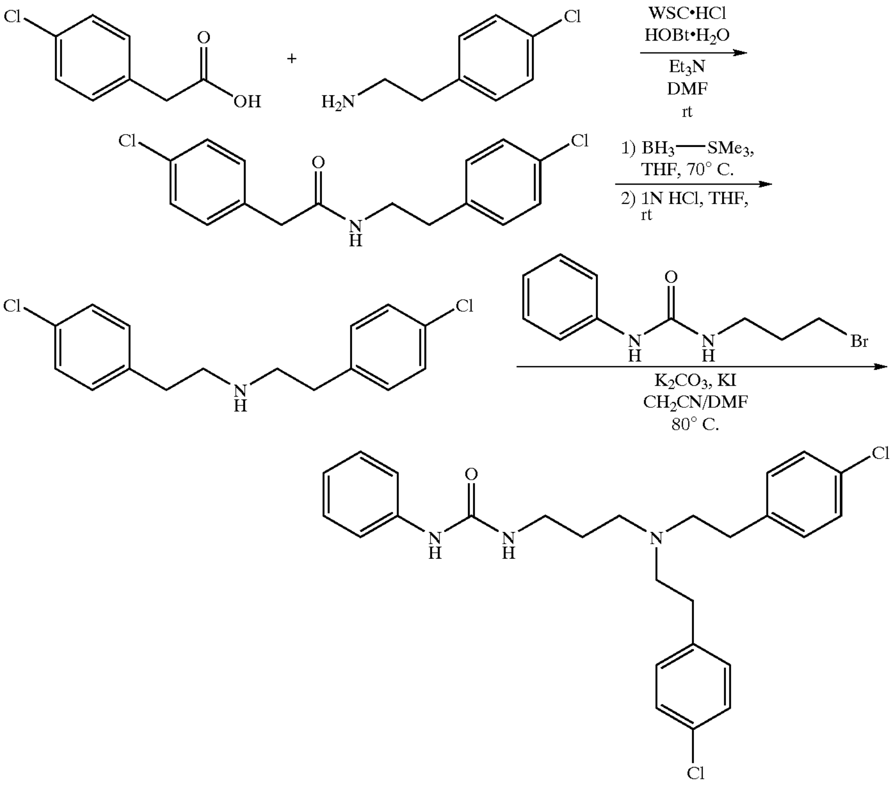

Scheme 18
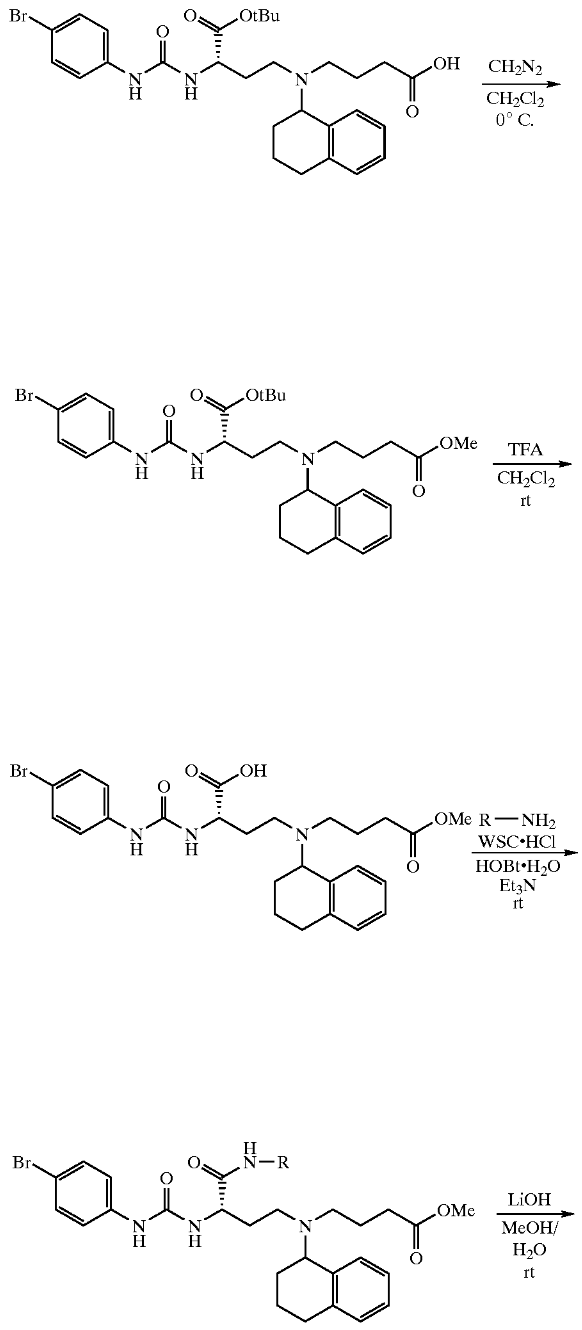
-continued
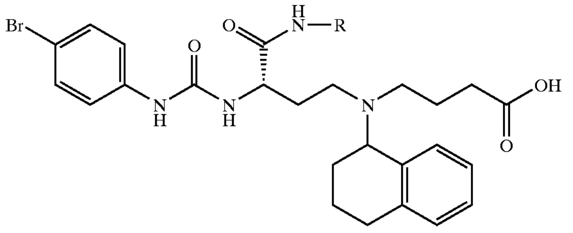
Scheme 19
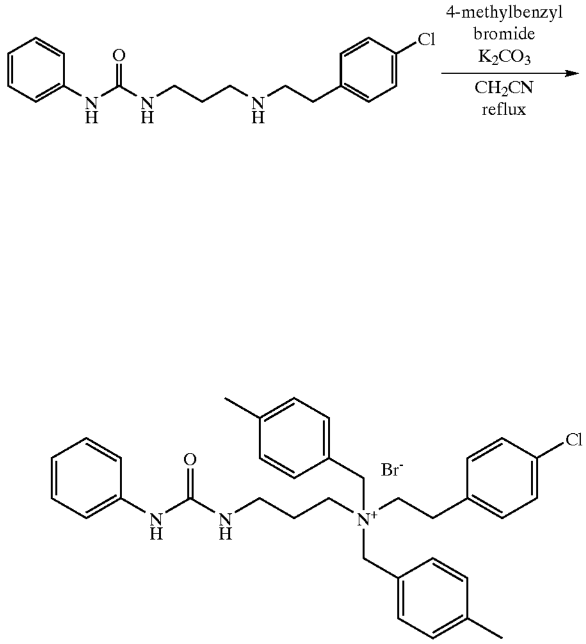
Scheme 20
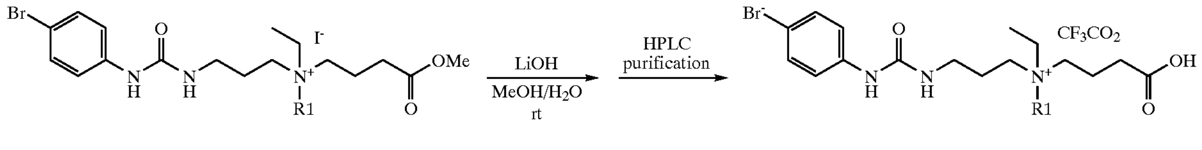

Scheme 21

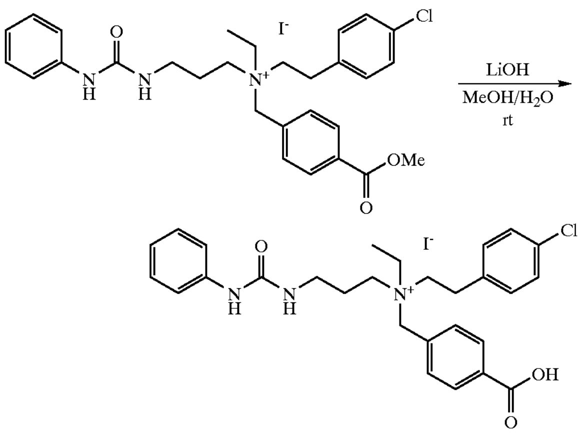

We claim:

1. A compound having the following Formula:

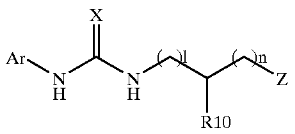

or a salt, hydrate, or complex thereof, wherein;

1 and n are independently 0, 1, 2, 3, 4 or 5;

(1+n) is 2, 3, 4 or 5;

X is O or S;

R10 is selected from the group consisting of hydrogen, hydroxy, $C_{3-7}$cycloalkyloxy, acyloxy, carboxy, carbamoyl, acyl, amino, alkylamino, arylamino, acylamino, $C_{1-5}$alkyl, $C_{1-5}$alkoxy, aryloxy, alkylcarbamoyl, arylcarbamoyl, alkyloxycarbonyl, wherein the $C_{1-5}$alkyl, aryl, $C_{1-5}$alkoxy, aryloxy, alkylcarbamoyl, arylcarbamoyl or alkyloxycarbonyl is optionally substituted with one or more groups independently selected from the group consisting of carboxy, carbamoyl, alkylcarbamoyl, arylcarbamoyl, alkylsulfonylcarbamoyl, arylsulfonylcarbamoyl, akyloxycarbonyl, sulfonyl, alkylsulfonyl, arylsulfonyl, sulfamoyl, alkylsulfamoyl, arylsulfamoyl, alkylsulfonamide, arylsulfonamide, alkylthio, halogen, hydroxy, acyloxy, $C_{1-5}$alkoxy, aryloxy, heteroaryloxy, nitro, amino, acylamino, alkylamino, arylamino, cyano, aryl, heteroaryl Wherein the aryl or heteroaryl is optionally substituted with one or more groups independently selected from the group consisting of $C_{1-5}$alkyl or $C_{1-5}$alkoxy, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, sulfonyl, alklylsulfonyl, arylsulfonyl, sulfamoyl, alkylsulfamoyl, arylsulfamoyl, alkylsulfonamide, arylsulfonamide, alkylthio, acyl, acyloxy, hydroxy, and halogen;

Ar is phenyl or naphthyl, optionally substituted with one or more groups independently selected from the group consisting of hydroxy, halogen, trihalomethyl, trihalomethoxy, $C_{1-5}$alkyl, $C_{1-5}$alkoxy, cyano, nitro, amino, carboxy, alkyloxycarbonyl, arylmethyloxycarbonyl, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$alkyl, $C_{1-5}$ alkoxy, cyano, nitro, amino, carboxy, carbamoyl, alkylcarbamoyl, arylcarbamoyl,acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino, and heteroaryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Z is:

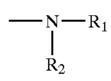

or

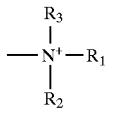

wherein $R_1$ is:

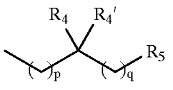

or

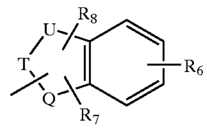

or

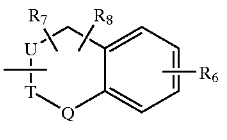

or

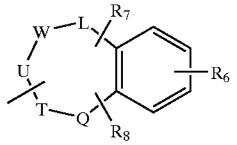

p is 0, 1 or 2;

q is 0, 1 or 2;

R4 and R4' are independently selected from the group consisting of hydrogen, halogen, $C_{1-5}$ alkyl, aryl, heteroaryl wherein the aryl or heteroaryl is optionally substituted with one or more groups independently selected from the group of consisting of hydrogen, hydroxy, halogen, trihalomethyl, $C_{1-5}$ alkyl, $C_{1-5}$alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

and $COR_9$; wherein $R_9$ is hydroxy, $C_{1-5}$alkyl, $C_{1-5}$alkoxy, amino, alkylamino or arylamino;

$R_5$ is aryl or heteroaryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkythio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_6$ is selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_7$ and $R_8$ are independently selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Q, T, U, W and L are independently C; wherein adjacent atoms U-T, T-Q, U-W, W-L may form one or more double bonds;

$R_2$ and $R_3$ are independently selected from the group consisting of $C_{1-8}$ alkyl, $C_{1-8}$ alkenyl and $C_{1-8}$ alkynyl optionally substituted with one or more groups independently selected from the group consisting of carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, halogen, acyloxy, hydroxy, nitro, amino, acylamino, alkylamino, cyano, aryl optionally substituted with one or more groups independently selected from the group consisting of $C_{1-5}$ alkyl or $C_{1-5}$ alkoxy, wherein the alkyl or alkoxy may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, aryloxy, arylmethyloxy, hydrazino, hydroxyamino, amidino, guanidino, cyanoguanidino, hydroxy, and halogen, heteroaryl optionally substituted with one or more groups independently selected from the group consisting of $C_{1-5}$ alkyl or $C_{1-5}$ alkoxy which may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, akyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, $C_{1-5}$ alkoxy optionally substituted with one or more groups independently selected from the group consisting of $C_{1-5}$ alkyl or $C_{1-5}$ alkoxy which may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, arylmethyloxy optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, $C_{3-7}$ cycloalkyl optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, and heterocycle;

provided that none of $R_1$, $R_2$, and $R_3$ bond together;

further provided that Ar is not 2-hydroxy-5-methoxyphenyl, 2-hydroxy-5-(lower) alkoxyphenyl, pyrene, chrysene, or phenanthrene.

2. The compound according to claim 1, wherein Z is

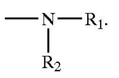

3. The compound according to claim 2, wherein (1+n) is 2, 3, or 4.

4. The compound according to claim 3, wherein (1+n) is 2, or 3.

5. The compound according to claim 3, wherein X is O.

6. The compound according to claim 5, wherein R10 is hydrogen.

7. The compound according to claim 6, wherein Ar is optionally substituted with one or more groups independently selected from the group consisting of hydroxy, halogen, trihalomethyl, trihalomethoxy, $C_{1-5}$ alkyl, $C_{1-5}$ alkoxy, cyano, nitro, amino, carboxy, alkyloxycarbonyl, arylmethyloxycarbonyl, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, and carboxy, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, and carboxy;

$R_5$ is aryl or heteroaryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, and carboxy, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, and carboxy;

$R_6$ is selected from the group consisting of hydrogen, hydroxy, halogen, trihalomethyl, $C_{1-5}$ alkyl, $C_{1-5}$ alkoxy, cyano, nitro, amino, and carboxy;

$R_7$ and $R_8$ are independently selected from the group consisting of hydrogen, hydroxy, halogen, trihalomethyl, $C_{1-5}$ alkyl, $C_{1-5}$ alkoxy, cyano, nitro, amino, and carboxy.

8. The compound of claim 7, wherein $R_2$ is independently selected from the group consisting of $C_{1-8}$ alkyl, $C_{1-4}$ alkenyl and $C_{1-8}$ alkynyl, substituted with one or more groups independently selected from the group consisting of carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, acyloxy, acylamino, aryl substituted with one or more groups independently selected from the group consisting of $C_{1-5}$ alkyl or $C_{1-5}$ alkoxy which are substituted with carboxy or alkyloxycarbonyl, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alklylsulfonyl, arylsulfonyl, sulfamoyl, alkylsulfamoyl, arylsulfamoyl, alkylsulfonamide, arylsulfonamide, aryloxy, arylmethyloxy, acylamino, hydroxy, and halogen, heteroaryl substituted with one or more groups independently selected from the group consisting of $C_{1-5}$ alkyl or $C_{1-5}$ alkoxy which are substituted with carboxy or alkyloxycarbonyl, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alklylsulfonyl, arylsulfonyl, sulfamoyl, alkylsulfamoyl, arylsulfamoyl, alkylsulfonamide, arylsulfonamide, acylamino, hydroxy, and halogen, $C_{1-5}$ alkoxy optionally substituted with one or more groups independently selected from the group consisting of $C_{1-5}$ alkyl or $C_{1-5}$ alkoxy which may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, arylmethyloxy substituted with one or more groups independently selected from the group consisting of $C_{1-5}$ alkyl or $C_{1-5}$ alkoxy which are substituted with carboxy or alkyloxycarbonyl, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alklylsulfonyl, arylsulfonyl, sulfamoyl, alkylsulfamoyl, arylsulfamoyl, alkylsulfonamide, arylsulfonamide, acylamino, hydroxy, and halogen, and $C_{3-7}$ cycloalkyl substituted with one or more groups independently selected from the group consisting of $C_{1-5}$ alkyl or $C_{1-5}$ alkoxy which is substituted with carboxy or alkyloxycarbonyl, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alklylsulfonyl, arylsulfonyl, sulfamoyl, alkylsulfamoyl, arylsulfamoyl, alkylsulfonamide, arylsulfonamide, and acylamino.

9. The compound of claim 8, wherein $R_2$ is independently selected from the group consisting of $C_{1-8}$ alkyl, $C_{1-8}$ alkenyl and $C_{1-8}$ alkynyl, substituted with one or more groups independently selected from the group consisting of carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, and acylamino.

10. The compound of claim 9, wherein $R_2$ is independently selected from the group consisting of $C_{1-8}$ alkyl, $C_{1-8}$ alkenyl and $C_{1-8}$ alkynyl, substituted with one or more groups independently selected from the group consisting of carboxy and alkyloxycarbonyl.

11. The compound according to claim 1, wherein Z is

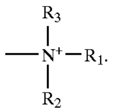

12. The compound according to claim 11, wherein (1+n) is 2, 3, or 4.

13. The compound according to claim 12, wherein (1+n) is 2, or 3.

14. The compound according to claim 13, wherein X is O.

15. The compound according to claim 14, wherein R10 is hydrogen.

16. The compound according to claim 15, wherein $R_3$ is $C_{1-8}$ alkyl optionally substituted with one or more groups independently selected from the group consisting of hydroxy, halogen, trihalomethyl, $C_{1-5}$ alkyl, $C_{1-5}$ alkoxy, cyano, nitro, amino, and carboxy.

17. A compound according to claim 6, wherein Ar is optionally substituted with one or more groups independently selected from the group consisting of hydroxy, halogen, trihalomethyl, $C_{1-5}$alkyl, $C_{1-5}$alkoxy, cyano, nitro, amino, carboxy, alkyloxycarbonyl, arylmethyloxycarbonyl, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Z is:

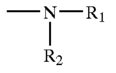

or

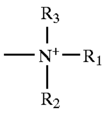

wherein $R_1$ is:

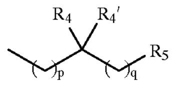

or

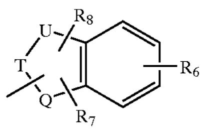

or

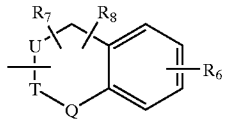

or

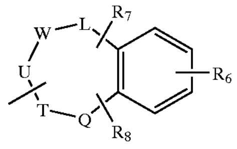

p is 0, 1 or 2;

q is 0, 1 or 2;

$R_4$ is selected from the group consisting of hydrogen, halogen, $C_{1-5}$ alkyl, aryl, heteroaryl wherein the aryl or heteroaryl is optionally substituted with one or more groups independently selected from the group of consisting of hydrogen, hydroxy, halogen, trihalomethyl, $C_{1-5}$ alkyl, $C_{1-5}$alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino; and $COR_9$; wherein $R_9$ is hydroxy, $C_{1-5}$alkyl, $C_{1-5}$alkoxy, amino, alkylamino or arylamino;

$R_5$ is aryl or heteroaryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_6$ is selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_7$ and $R_8$ are independently selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Q, T, U, W and L are independently C; wherein adjacent atoms U-T, T-Q, U-W, W-L may form one or more double bonds;

$R_2$ and $R_3$ are independently selected from the group consisting of $C_{1-8}$ alkyl, $C_{1-8}$ alkenyl and $C_{1-8}$ alkynyl optionally substituted with one or more groups independently selected from the group consisting of carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, halogen, hydroxy, nitro, amino, acylamino, alkylamino, cyano, aryl optionally substituted with one or more groups independently selected from the group consisting of $C_{1-5}$ alkyl or $C_{1-5}$ alkoxy, wherein the alkyl or alkoxy may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, heteroaryl optionally substituted with one or more groups independently selected from the group consisting of $C_{1-5}$ alkyl or $C_{1-5}$ alkoxy which may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, arylmethyloxy optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulforamide, alkylthio, acyl, acyloxy, hydrazino, hydroxyamino, amidino, guanidino, cyanoguanidino, hydroxy, and halogen, $C_{3-7}$ cycloalkyl optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isohiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, and heterocycle;

provided that none of $R_1$, $R_2$, and $R_3$ bond together;

further provided that Ar is not 2-hydroxy-5-methoxyphenyl.

18. A compound according to claim 17, wherein Ar is optionally substituted with one or more groups independently selected from the group consisting of hydroxy, halogen, trihalomethyl, $C_{1-5}$alkyl, $C_{1-5}$alkoxy; cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino.

19. The compound according to claim 1, wherein X is S.

20. The compound according to claim 19, wherein R10 is hydrogen.

21. A compound according to claim 20, wherein Ar is optionally substituted with one or more groups independently selected from the group consisting of hydroxy, halogen, trihalomethyl, $C_{1-5}$alkyl, $C_{1-5}$alkoxy, cyano, nitro, amino, carboxy, alkyloxycarbonyl, arylmethyloxycarbonyl, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, ar)sulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Z is:

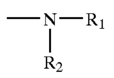

or

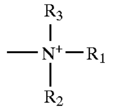

wherein $R_1$ is:

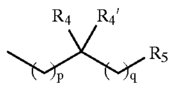

or

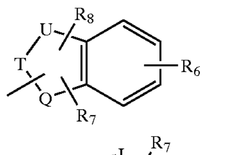

or

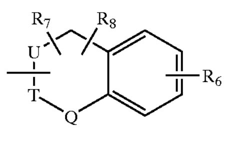

or

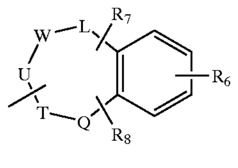

p is 0, 1 or 2;

q is 0, 1 or 2;

$R_4$ is selected from the group consisting of hydrogen, halogen, $C_{1-5}$ alkyl, aryl, heteroaryl wherein the aryl or heteroaryl is optionally substituted with one or more groups independently selected from the group of consisting of hydrogen, hydroxy, halogen, trihalomethyl, $C_{1-5}$ alkyl, $C_{1-5}$alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

and $COR_9$; wherein $R_9$ is hydroxy, $C_{1-5}$alkyl, $C_{1-5}$alkoxy, amino, alkylamino or arylamino;

$R_5$ is aryl or heteroaryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, auylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulforamide, hydrazino, acylamino, alkylamino, hydroxyamino, amidino, guanidino, and cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_6$ is selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_7$ and $R_8$ are independently selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Q, T, U, W and L are independently C; wherein adjacent atoms U-T, T-Q, U-W, W-L may form one or more double bonds;

$R_2$ and $R_3$ are independently selected from the group consisting of $C_{1-8}$ alkyl, $C_{1-8}$ alkenyl and $C_{1-8}$ alkynyl optionally substituted with one or more groups independently selected from the group consisting of carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, halogen, hydroxy, nitro, amino, acylamino, alkylamino, cyano, aryl optionally substituted with one or more groups independently selected from the group consisting of $C_{1-5}$ alkyl or $C_{1-5}$ alkoxy, wherein the alkyl or alkoxy may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, heteroaryl optionally substituted with one or more groups independently selected from the group consisting of $C_{1-5}$ alkyl or $C_{1-5}$ alkoxy which may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl,tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, arylmethyloxy optionally substituted with one or more groups independently selected from the group consisting of $C_{1-5}$ alkyl or $C_{1-5}$ alkoxy which is optionally substituted with carboxy or alkyloxycarbonyl, cyano,nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, $C_{3-7}$ cycloalkyl optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, and heterocycle;

provided that none of $R_1$, $R_2$, and $R_3$ bond together;

further provided that Ar is not 2-hydroxy-5-methoxyphenyl.

22. A compound according to claim 1, wherein R10 is selected from the group consisting of hydroxy, $C_{3-7}$cycloalkyloxy, acyloxy, carboxy, carbamoyl, acyl, amino, alkylamino, arylamino, acylamino, $C_{1-5}$alkyl, aryl, $C_{1-5}$alkoxy, aryloxy, alkylcarbamoyl, arylcarbamoyl, alkyloxycarbonyl, wherein the $C_{1-5}$alkyl, aryl, $C_{1-5}$alkoxy, aryloxy, alkylcarbamoyl, arylcarbamoyl or alkyloxycarbonyl is optionally substituted with one or more groups independently selected from the group consisting of carboxy, carbamoyl, alkylcarbamoyl, arylcarbamoyl, alkylsulfonylcarbamoyl, arylsulfonylcarbamoyl, alkyloxycarbonyl, sulfonyl, alkylsulfonyl, arylsulfonyl, sulfamoyl, alkylsulfamoyl, arylsulfamoyl, alkylsulfonamide, arylsulfonamide, alkylthio, halogen, hydroxy, acyloxy, $C_{1-5}$alkoxy, aryloxy, heteroaryloxy, nitro, amino, acylamino, alkylamino, arylamino, cyano, aryl, heteroaryl Wherein the aryl or heteroaryl is optionally substituted with one or more groups independently selected from the group consisting of $C_{1-5}$alkyl or $C_{1-5}$alkoxy, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, sulfonyl, alklylsulfonyl, arylsulfonyl, sulfamoyl, alkylsulfamoyl, arylsulfamoyl, alkylsulfonamide, arylsulfonamide, alkylthio, acyl, acyloxy, hydroxy, and halogen;

Ar is phenyl or naphthyl optionally substituted with one or more groups independently selected from the group consisting of hydroxy, halogen, trihalomethyl, $C_{1-5}$alkyl, $C_{1-5}$alkoxy, cyano, nitro, amino, carboxy, alkyloxycarbonyl, arylmethyloxycarbonyl, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Z is:

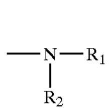

or

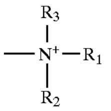

wherein $R_1$ is:

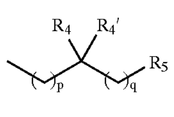

or

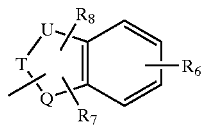

or

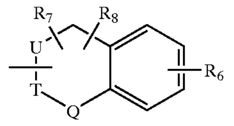

or

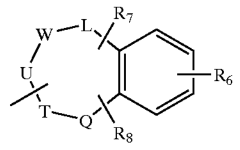

p is 0, 1 or 2;

q is 0, 1 or 2;

$R_4$ is selected from the group consisting of hydrogen, halogen, $C_{1-5}$ alkyl, aryl, heteroaryl wherein the aryl or heteroaryl is optionally substituted with one or more groups independently selected from the group of consisting of hydrogen, hydroxy, halogen, trihalomethyl, $C_{1-5}$ alkyl, $C_{1-5}$alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio,alkylsulfonamide, arylsulfonamide, hydrazino, acylamino, alkylamino, hydroxyamino, amidino, guanidino, and cyanoguanidino;

and $COR_9$; wherein $R_9$ is hydroxy, $C_{1-5}$alkyl, $C_{1-5}$alkoxy, amino, alkylamino or arylamino;

$R_5$ is aryl or heteroaryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_6$ is selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, aryl optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, cyanoguanidino, and aryloxy optionally substituted with one or more groups independently selected from the group consisting of hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

$R_7$ and $R_8$ are independently selected from the group consisting of hydrogen, hydroxy, halogen, trihalomethyl, $C_{1-5}$ alkyl, $C_{1-5}$ alkoxy, cyano, nitro, amino, carboxy, carbamoyl, alkylcarbamoyl, arylcarbamoyl, acyl, acyloxy, sulfonyl, alkylsulfonyl, arylsulfonyl, sulfamoyl, alkylsulfamoyl, arylsulfamoyl, alkylthio, alkylsulfonamide, arylsulfonamide, hydrazino, acylamino, alkylamino, hydroxyamino, amidino, guanidino, and cyanoguanidino;

Q, T, U, W and L are independently C; wherein adjacent atoms U-T, T-Q, U-W, W-L may form one or more double bonds;

$R_2$ and $R_3$ are independently selected from the group consisting of $C_{1-8}$ alkyl, $C_{1-8}$ alkenyl and $C_{1-8}$ alkynyl optionally substituted with one or more groups independently selected from the group consisting of carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, halogen, hydroxy, nitro, amino, acylamino, alkylamino, cyano, aryl optionally substituted with one or more groups independently selected from the group consisting of $C_{1-5}$ alkyl or $C_{1-5}$ alkoxy, wherein the alkyl or alkoxy may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, heteroaryl optionally substituted with one or more groups independently selected from the group consisting of $C_{1-5}$ alkyl or $C_{1-5}$ alkoxy which may be optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, arylmethyloxy optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, $C_{3-7}$ cycloalkyl optionally substituted with one or more groups independently selected from the group consisting of $C_{1-5}$ alkyl or $C_{1-5}$ alkoxy which is optionally substituted with carboxy or alkyloxycarbonyl, cyano, nitro, amino, acylamino, alkylamino, carboxy, carbamoyl, alkylcarbamoyl, arylcarbamoyl, alkylsulfonylcarbamoyl, arylsulfonylcarbamoyl, alkyloxycarbonyl, tetrazolyl, isoxazolyl, isothiazolyl, alkylsulfonamido, arylsulfonamido, sulfonyl, alkylsulfonyl, arylsulfonyl, sulfamoyl, alkylsulfamoyl, arylsulfamoyl, alkylsulfonamide, arylsulfonamide, alkylthio, acyl, acyloxy, hydrazino, hydroxyamino, amidino, guanidino, cyanoguanidino, hydroxy, and halogen, and heterocycle;

provided that none of $R_1$, $R_2$, and $R_3$ bond together;

further provided that Ar is not 2-hydroxy-5-methoxyphenyl.

23. The compound according to claim 1 selected from the group consisting of:

N-Phenylcarbamoyl-N'-[2-(4-chlorophenyl)ethyl]-N'-ethyl-1,3-diaminopropane;

N-(4-Nitrophenylcarbamoyl-N'-[2-(4-chlorophenyl)ethyl]-N'-ethyl-1,3-diaminopropane;

N-(4-Bromophenylcarbamoyl-N'-[2-(4-chlorophenyl)ethyl]-N'-ethyl-1,3-diaminopropane;

N-Phenylcarbamoyl-N'-[2-(4-chlorophenyl)ethyl]-N'-propyl-1,3-diaminopropane;

Methyl 4-[[3-(4-bromophenylureido)propyl](1,2,3,4-tetrahydro-1-naphthyl)amino]butylate;

Methyl 4[[3-(4-bromophenylureido)propyl][(1R)-1-phenylethyl]amino]butylate;

Methyl 4-[[3-(4-bromophenylureido)propyl][2-(4-chlorophenyl)ethyl]amino]butylate;

Methyl 4[[4-(4-bromophenylureido)butyl](1,2,3,4-tetrahydro-1-naphthyl)amino]butylate;

Methyl 4[[5-(4-bromophenylureido)pentyl](1,2,3,4-tetrahydro-1-naphthyl)amino]butylate;

Methyl 4-[[3-(4-methylphenylureido)propyl](1,2,3,4-tetrahydro-1-naphthyl)amino]butylate;

Methyl 4[[3-(3,4-dichlorophenylureido)propyl](1,2,3,4-tetrahydro-1-naphthyl)amino]butylate;

4-[[3-(4-Bromophenylureido)propyl](1,2,3,4-tetrahydro-1-naphthyl)amino]butanoic acid;

4-[[3-(4-Bromophenylureido)propyl][(1R)-1-phenylethyl]amino] butanoic acid;

4-[[4-(4-Bromophenylureido)butyl](1,2,3,4-tetrahydro-1-naphthyl)amino]butanoic acid;

4-[[5-(4-Bromophenylureido)pentyl](1,2,3,4-tetrahydro-1-naphthyl)amino]butanoic acid;

4-[[3-(4-Methylphenylureido)propyl](1,2,3,4-tetrahydro-1-naphthyl)amino]butanoic acid;

4-[(3-(3,4-Dichlorophenylureido)propyl](1,2,3,4-tetrahydro-1-naphthyl)amino]butanoic acid;

[3-(Phenylureido)propyl][2-(4-chlorophenyl)ethyl] diethylammonium iodide;

[3-(4-Bromophenylureido)propyl][2-(4-chlorophenyl) ethyl]diethylammonium iodide;

N-Phenylcarbamoyl-N'-[2-(4-chlorophenyl)ethyl-N'-ethyl-2-hydroxy-1,3-diaminopropane;

4-[[3-(4-Chlorophenylthioureido)propyl](1,2,3,4-tetrahydro-1-naphthyl)amino]butanoic acid;

4-[[(3S)-3-(4-Bromophenylureido)-3-(tert-butoxycarbonyl)propyl](1,2,3,4-tetrahydro-1-naphthyl)amino]butanoic acid;

4-[[3-(4-Bromophenylureido)-2-hydroxypropyl](1,2,3,4-tetrahydro-1-naphthyl)amino]butanoic acid;

4-[[3-(4-Chlorophenylureido)propyl](1,2,3,4-tetrahydro-1-naphthyl)amino]butanoic;

Methyl 4-[[3-(4-bromophenylureido)propyl](1-indanyl) amino]butylate;

4-[[3-(4-Bromophenylureido)propyl](1-indanyl)amino] butanoic acid;

Methyl 4-[[3-(4-bromophenylureido)propyl][(1R)-1-indanyl]amino]butylate;

4-[[3-(4-Bromophenylureido)propyl][(1R)-1-indanyl] amino]butanoic acid;

Methyl 4-[[3-(4-bromophenylureido)propyl][(1R)-1,2,3,4-tetrahydro-1-naphthyl]amino]butylate;

4-[[34-Bromophenylureido)propyl][(1R)-1,2,3,4-tetrahydro-1-naphthyl]amino]butanoic acid;

Ethyl 4-[[3-(4-bromnophenylureido)propyl](1,2,3,4-tetrahydro-1-naphthyl]amino]butylate;

4-[[3-(4-Bromophenylureido)propyl](1,2,3,4-tetrahydro-1-naphthyl)amino]butanamide;

3-[[3-(4-Bromophenylureido)propyl](1,2,3,4-tetrahydro-1-naphthyl)amino]-1-[(phenylsulfonyl)carbamoyl] propane;

4-[[3-(4-Bromophenylureido)propyl](1,2,3,4-tetrahydro-1-naphthyl)amino]-1-butanol;

3-[[3-(4-Bromophenylureido)propyl](1,2,3,4-tetrahydro-1-naphthyl)amino]-1-[1-(triphenylmethyl)tetrazol-5-yl]propane;

3-[[3-(4-Bromophenylureido)propyl](1,2,3,4-tetrahydro-1-naphthyl)amino]-1-(1H-tetazol-5-yl)propane;

Methyl 4-[[3-[4-(carboxy)phenylureido]propyl](1,2,3,4-tetrahydro-1-naphthyl)amino]butylate;

4-[[3-(4-Bromophenylureido)propyl][(1R)-1-(4-methoxyphenyl)ethyl]amino]butanoic acid;

4-[[3-[4-(Ethoxycarbonyl)phenylureido]propyl](1,2,3,4-tetrahydro-1-naphthyl)amino]butanoic acid;

4-[[3-(4-Iodophenylureido)propyl](1,2,3,4-tetrahydro-1-naphthyl)amino]butanoic acid;

4-[[3-[4-(Butoxycarbonyl)phenylureido]propyl](1,2,3,4-tetrahydro-1-naphthyl)amino]butanoic acid;

[3-(Phenylureido)propyl]bis[2(4-chlorophenyl)ethyl] amine;

4-[[3-(4-Bromophenylureido)propyl][(1R)-1-(4-bromophenyl)ethyl]amino]butanoic acid;

4-[[3-(4-Bromophenylureido)propyl][1-(4-fluorophenyl) ethyl]amino]butanoic acid;

4-[[3-(4-Bromophenylureido)propyl][1-(4-chlorophenyl) ethyl]amino]butanoic acid;

Methyl 4-[[(3S)-3-(4-bromophenylureido)-3-(tert-butoxycarbonyl)propyl](1,2,3,4-tetrahydro-1-naphthyl)amino]butylate;

Methyl 4-[[(3S)-3-(4-bromophenylureido)-3-(isopropylcarbamoyl)propyl](1,2,3,4-tetrahydro-1-naphthyl)amino]butylate;

Methyl 4-[[(3S)-3-(4-bromophenylureido)-3-(benzylcarbamoyl)propyl](1,2,3,4-tetrahydro-1-naphthyl)amino]butylate;

4-[[(3S)-3-(4-Bromophenylureido)-3-(isopropylcarbamoyl)propyl](1,2,3,4-tetrahydro-1-naphthyl)amino] butanoic acid;

4-[[(3S)-3-(4-Bromophenylureido)-3-(benzylcarbamoyl) propyl](1,2,3,4-tetrahydro-1-naphthyl)amino]butanoic acid;

4-[[3-(4-Bromophenylthioureido)propyl][(1R)-1-indanyl]amino]butanoic acid;

4-[[3-(4-Bromophenylthioureido)propyl][(1R)-1,2,3,4-tetrahydro-1-naphthyl]amino]butanoic acid;

4-[[3-(4-Bromophenylureido)propyl][(1S)-1-(4-bromophenyl)ethyl]amino]butanoic acid;

[3-(Phenylureido)propyl][2-(4-chlorophenyl)ethyl]bis(4-methylbenzyl)ammonium iodide;

[3-(Phenylureido)propyl][2-(4-chlorophenyl)ethyl](4-chlorobenzyl)ethylammonium iodide;

[3-(Phenylureido)propyl][2-(4-chlorophenyl)ethyl] (benzyl)ethylammonium iodide;

[3-(Phenylureido)propyl][2-(3-chlorophenyl)ethyl] diethylammonium iodide;

[3-(4-Bromophenylureido)propyl][(1S)-1-phenylethyl] [3-(carboxy)propyl]ethylammonium trifluoroacetate;

[3-(4-Bromophenylureido)propyl][(1R)-1-phenylethyl) [3-(carboxy)propyl]ethylammonium trifluoroacetate;

[3-(Phenylureido)propyl][2-(4-chlorophenyl)ethyl][4-(methoxycarbonyl)butyl]ethylammonium iodide;

[3-(Phenylureido)propyl][2-(4-chlorophenyl)ethyl](4-(carboxy)benzyl]ethylammonium iodide;

[5-(Phenylureido)pentyl][2-(4-chlorophenyl)ethyl] diethylammonium iodide;

[3-(Phenylureido)propyl][2-(4-chlorophenyl)ethyl](2-chlorobenzyl)ethylammonium iodide;

[3-(Phenylureido)propyl][2-(4-chlorophenyl)ethyl](2,5-difluorobenzyl)ethylammonium iodide;

[3-(Phenylureido)propyl][2-(4-chlorophenyl)ethyl](3-fluorobenzyl)ethylammonium iodide;

[3-(4-Cyanophenylureido)propyl][2-(3-chlorophenyl) ethyl][2-(2-methoxyehtoxy)ethyl] ethylammonium iodide; and

[3-(4-Methoxyphenylureido)propyl][2-(3-chlorophenyl) ethyl][2-(2-methoxyehtoxy)ethyl] ethylammonium iodide.

24. The compound according to claim 1, wherein the compound is defined below:

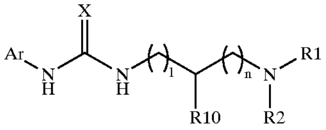
| CPD No. | Ar | X | l | n | R1 | R2 | R10 |
|---|---|---|---|---|---|---|---|
| 1 | phenyl | O | 1 | 1 | 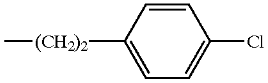 | ethyl | H |
| 2 | 4-nitrophenyl | O | 1 | 1 | 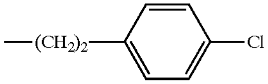 | ethyl | H |
| 3 | 4-bromophenyl | O | 1 | 1 | 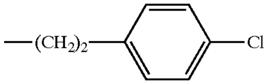 | ethyl | H |
| 5 | 4-nitrophenyl | O | 1 | 2 | 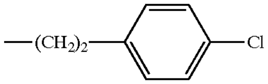 | ethyl | H |
| 6 | 4-chlorophenyl | O | 1 | 1 | 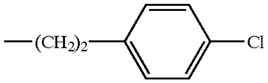 | ethyl | H |
| 7 | phenyl | O | 1 | 2 | 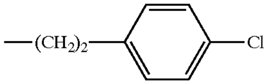 | ethyl | H |
| 8 | phenyl | O | 1 | 3 | 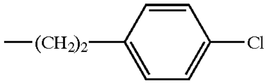 | ethyl | H |
| 9 | 2-methoxyphenyl | O | 1 | 1 | 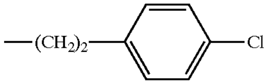 | ethyl | H |

-continued
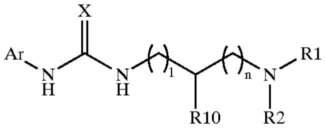
| CPD No. | Ar | X | l | n | R1 | R2 | R10 |
|---|---|---|---|---|---|---|---|
| 10 | phenyl | O | 1 | 1 | 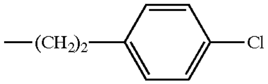 | n-propyl | H |
| 11 | phenyl | O | 1 | 1 | 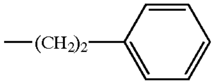 | ethyl | H |
| 12 | phenyl | O | 1 | 1 | 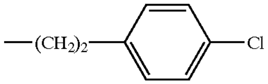 | 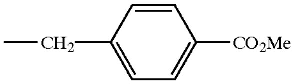 | H |
| 13 | phenyl | O | 1 | 1 | 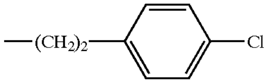 | 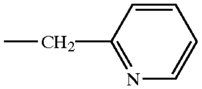 | H |
| 14 | phenyl | O | 1 | 1 | 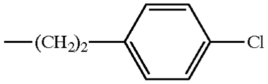 | n-butyl | H |
| 15 | phenyl | O | 1 | 1 | 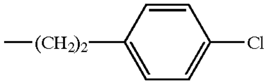 | 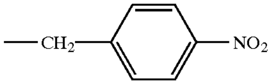 | H |
| 16 | phenyl | O | 1 | 1 | 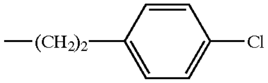 | 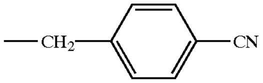 | H |
| 17 | phenyl | O | 1 | 1 | 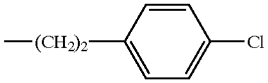 | 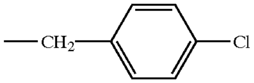 | |
| 18 | phenyl | O | 1 | 1 | 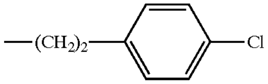 | 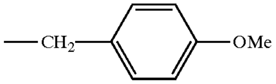 | H |

-continued
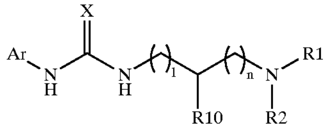
| CPD No. | Ar | X | l | n | R1 | R2 | R10 |
|---|---|---|---|---|---|---|---|
| 19 | phenyl | O | 1 | 1 | 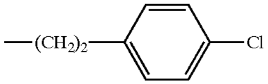 | 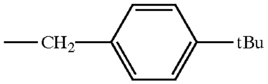 | H |
| 20 | phenyl | O | 1 | 1 | 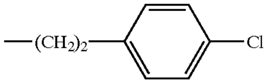 | 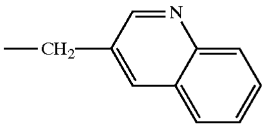 | H |
| 21 | phenyl | O | 1 | 1 | 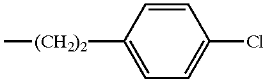 | 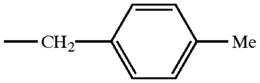 | H |
| 22 | phenyl | O | 1 | 1 | 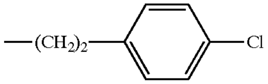 | 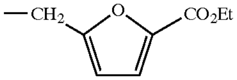 | H |
| 23 | phenyl | O | 1 | 1 | 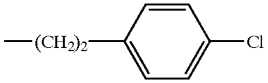 | 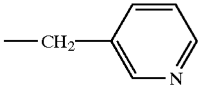 | H |
| 24 | phenyl | O | 1 | 1 | 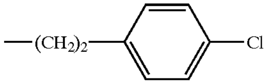 | 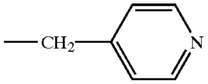 | H |
| 25 | phenyl | O | 1 | 1 | 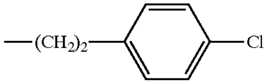 | 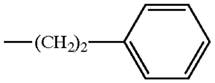 | H |

-continued
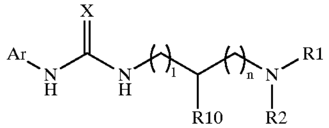
| CPD No. | Ar | X | l | n | R1 | R2 | R10 |
|---|---|---|---|---|---|---|---|
| 26 | phenyl | O | 1 | 1 | 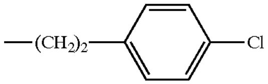 | 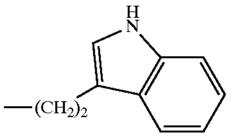 | H |
| 27 | phenyl | O | 1 | 1 | 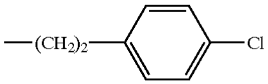 | methyl | H |
| 28 | phenyl | O | 1 | 1 | 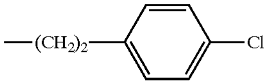 | 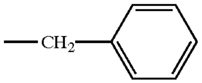 | H |
| 29 | 4-bromophenyl | O | 1 | 1 | 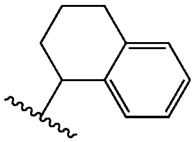 | $-(CH_2)_3CO_2Me$ | H |
| 30 | 4-bromophenyl | O | 1 | 1 | 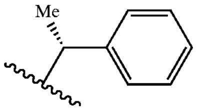 | $-(CH_2)_3CO_2Me$ | H |
| 31 | 4-bromophenyl | O | 1 | 1 | 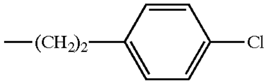 | $-(CH_2)_3CO_2Me$ | H |
| 32 | 4-bromophenyl | O | 1 | 2 | 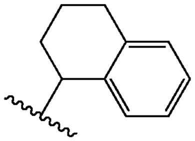 | $-(CH_2)_3CO_2Me$ | H |

-continued
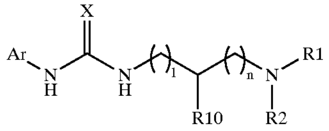
| CPD No. | Ar | X | l | n | R1 | R2 | R10 |
|---|---|---|---|---|---|---|---|
| 33 | 4-bromophenyl | O | 1 | 3 | 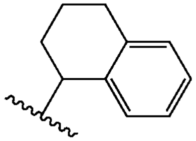 | $—(CH_2)_3CO_2Me$ | H |
| 34 | 4-methylphenyl | O | 1 | 1 | 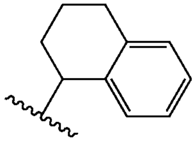 | $—(CH_2)_3CO_2Me$ | H |
| 35 | 3,4-dichlorophenyl | O | 1 | 1 | 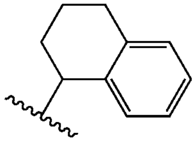 | $—(CH_2)_3CO_2Me$ | H |
| 36 | 4-bromophenyl | O | 1 | 1 | 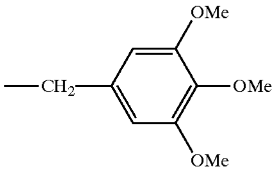 | $—(CH_2)_3CO_2Me$ | H |
| 37 | 4-bromophenyl | O | 1 | 1 | 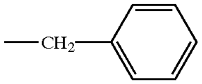 | $—(CH_2)_3CO_2Me$ | H |
| 38 | 4-bromophenyl | O | 1 | 1 | 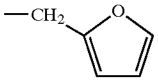 | $—(CH_2)_3CO_2Me$ | H |

-continued
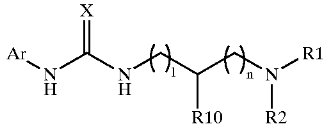
| CPD No. | Ar | X | l | n | R1 | R2 | R10 |
|---|---|---|---|---|---|---|---|
| 39 | 4-bromophenyl | O | 1 | 1 | 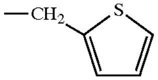 | $-(CH_2)_3CO_2Me$ | H |
| 40 | 4-bromophenyl | O | 1 | 1 | 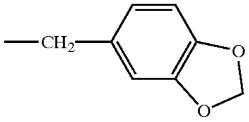 | $-(CH_2)_3CO_2Me$ | H |
| 41 | 4-bromophenyl | O | 1 | 1 | 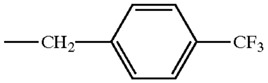 | $-(CH_2)_3CO_2Me$ | H |
| 42 | 4-bromophenyl | O | 1 | 1 | 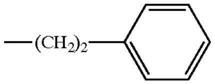 | $-(CH_2)_3CO_2Me$ | H |
| 43 | 4-bromophenyl | O | 1 | 1 | 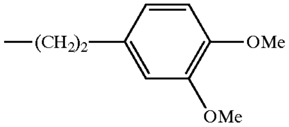 | $-(CH_2)_3CO_2Me$ | H |
| 44 | 4-bromophenyl | O | 1 | 1 | 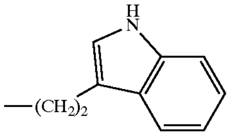 | $-(CH_2)_3CO_2Me$ | H |
| 45 | 4-bromophenyl | O | 1 | 1 | 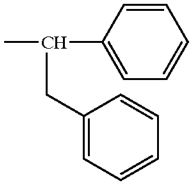 | $-(CH_2)_3CO_2Me$ | H |

-continued
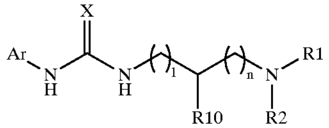
| CPD No. | Ar | X | l | n | R1 | R2 | R10 |
|---|---|---|---|---|---|---|---|
| 46 | 4-bromophenyl | O | 1 | 1 | 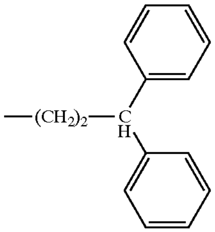 | $—(CH_2)_3CO_2Me$ | H |
| 47 | 4-bromophenyl | O | 1 | 1 | 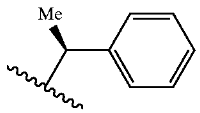 | $—(CH_2)_3CO_2Me$ | H |
| 48 | 4-bromophenyl | O | 1 | 1 | 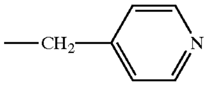 | $—(CH_2)_3CO_2Me$ | H |
| 49 | phenyl | O | 1 | 1 | 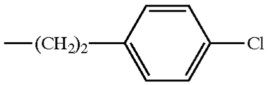 | $—(CH_2)_3CO_2Me$ | H |
| 50 | 4-bromophenyl | O | 1 | 0 | 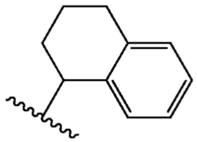 | $—(CH_2)_3CO_2Me$ | H |
| 51 | 3-chlorophenyl | O | 1 | 1 | 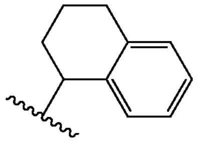 | $—(CH_2)_3CO_2Me$ | H |

-continued
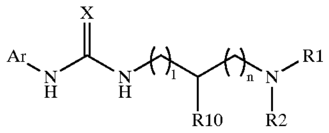
| CPD No. | Ar | X | l | n | R1 | R2 | R10 |
|---|---|---|---|---|---|---|---|
| 52 | 3-methylphenyl | O | 1 | 1 | 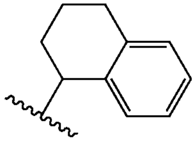 | —$(CH_2)_3CO_2Me$ | H |
| 53 | 4-chloro-3-(trifluoromethyl)phenyl | O | 1 | 1 | 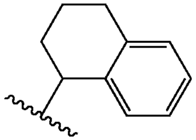 | —$(CH_2)_3CO_2Me$ | H |
| 54 | 2-biphenyl | O | 1 | 1 | 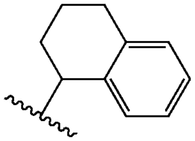 | —$(CH_2)_3CO_2Me$ | H |
| 55 | 2,4-dimethoxyphenyl | O | 1 | 1 | 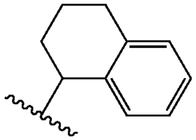 | —$(CH_2)_3CO_2Me$ | H |
| 56 | phenyl | O | 1 | 1 | 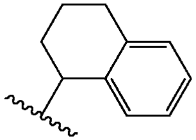 | —$(CH_2)_3CO_2Me$ | H |

-continued
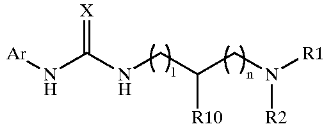
| CPD No. | Ar | X | l | n | R1 | R2 | R10 |
|---|---|---|---|---|---|---|---|
| 57 | 4-methoxyphenyl | O | 1 | 1 | 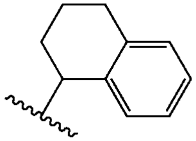 | $-(CH_2)_3CO_2Me$ | H |
| 58 | 4-phenoxyphenyl | O | 1 | 1 | 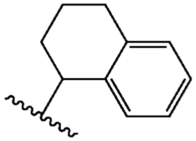 | $-(CH_2)_3CO_2Me$ | H |
| 59 | 1-naphthyl | O | 1 | 1 | 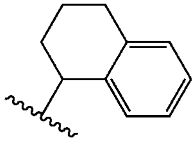 | $-(CH_2)_3CO_2Me$ | H |
| 60 | 4-bromophenyl | O | 1 | 1 | 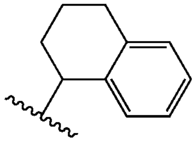 | $-(CH_2)_3CO_2H$ | H |
| 61 | 4-bromophenyl | O | 1 | 1 | 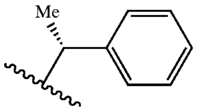 | $-(CH_2)_3CO_2H$ | H |
| 62 | 4-bromophenyl | O | 1 | 2 | 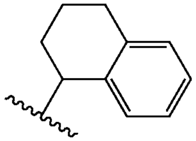 | $-(CH_2)_3CO_2H$ | H |

-continued
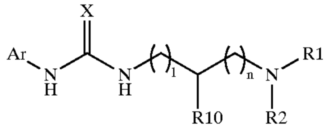
| CPD No. | Ar | X | l | n | R1 | R2 | R10 |
|---|---|---|---|---|---|---|---|
| 63 | 4-bromophenyl | O | 1 | 3 | 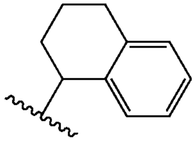 | —$(CH_2)_3CO_2H$ | H |
| 64 | 4-methylphenyl | O | 1 | 1 | 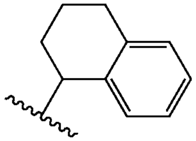 | —$(CH_2)_3CO_2H$ | H |
| 65 | 3,4-dichlorophenyl | O | 1 | 1 | 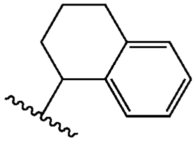 | —$(CH_2)_3CO_2H$ | H |
| 66 | 4-bromophenyl | O | 1 | 1 | 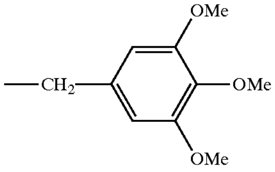 | —$(CH_2)_3CO_2H$ | H |
| 67 | 4-bromophenyl | O | 1 | 1 | 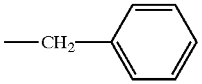 | —$(CH_2)_3CO_2H$ | H |
| 68 | 4-bromophenyl | O | 1 | 1 | 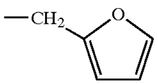 | —$(CH_2)_3CO_2H$ | H |

-continued
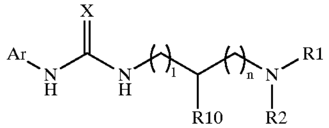
| CPD No. | Ar | X | l | n | R1 | R2 | R10 |
|---|---|---|---|---|---|---|---|
| 69 | 4-bromophenyl | O | 1 | 1 | 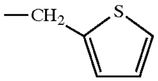 | $—(CH_2)_3CO_2H$ | H |
| 70 | 4-bromophenyl | O | 1 | 1 | 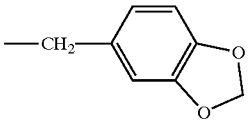 | $—(CH_2)_3CO_2H$ | H |
| 71 | 4-bromophenyl | O | 1 | 1 | 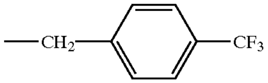 | $—(CH_2)_3CO_2H$ | H |
| 72 | 4-bromophenyl | O | 1 | 1 | 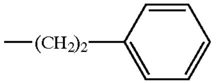 | $—(CH_2)_3CO_2H$ | H |
| 73 | 4-bromophenyl | O | 1 | 1 | 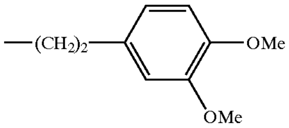 | $—(CH_2)_3CO_2H$ | H |
| 74 | 4-bromophenyl | O | 1 | 1 | 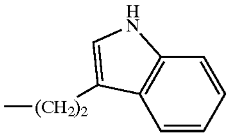 | $—(CH_2)_3CO_2H$ | H |

-continued
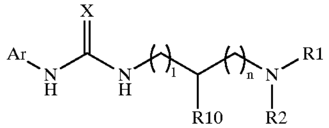
| CPD No. | Ar | X | l | n | R1 | R2 | R10 |
|---|---|---|---|---|---|---|---|
| 75 | 4-bromophenyl | O | 1 | 1 | 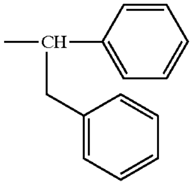 | $-(CH_2)_3CO_2H$ | H |
| 76 | 4-bromophenyl | O | 1 | 1 | 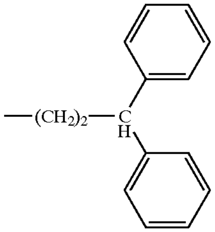 | $-(CH_2)_3CO_2H$ | H |
| 77 | 4-bromophenyl | O | 1 | 1 | 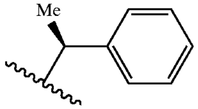 | $-(CH_2)_3CO_2H$ | H |
| 78 | 4-bromophenyl | O | 1 | 1 | 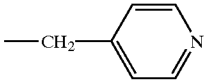 | $-(CH_2)_3CO_2H$ | H |
| 79 | 4-bromophenyl | O | 1 | 1 | 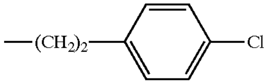 | $-(CH_2)_3CO_2H$ | H |
| 80 | phenyl | O | 1 | 1 | 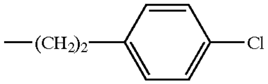 | $-(CH_2)_3CO_2H$ | H |

-continued
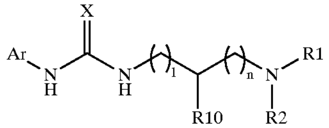
| CPD No. | Ar | X | l | n | R1 | R2 | R10 |
|---|---|---|---|---|---|---|---|
| 82 | 3-chlorophenyl | O | 1 | 1 | 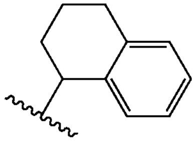 | $-(CH_2)_3CO_2H$ | H |
| 83 | 3-methylphenyl | O | 1 | 1 | 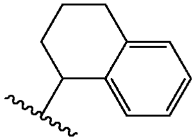 | $-(CH_2)_3CO_2H$ | H |
| 84 | 4-chloro-3-(trifluoromethyl)phenyl | O | 1 | 1 | 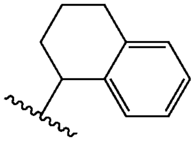 | $-(CH_2)_3CO_2H$ | H |
| 85 | 2-biphenyl | O | 1 | 1 | 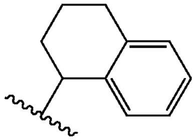 | $-(CH_2)_3CO_2H$ | H |
| 86 | 2,4-dimethoxyphenyl | O | 1 | 1 | 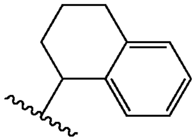 | $-(CH_2)_3CO_2H$ | H |

-continued
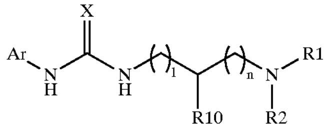
| CPD No. | Ar | X | l | n | R1 | R2 | R10 |
|---|---|---|---|---|---|---|---|
| 87 | phenyl | O | 1 | 1 | 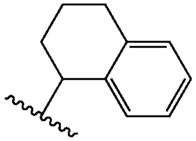 | $-(CH_2)_3CO_2H$ | H |
| 88 | 4-methoxyphenyl | O | 1 | 1 | 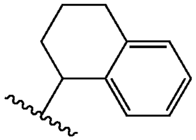 | $-(CH_2)_3CO_2H$ | H |
| 89 | 4-phenoxyphenyl | O | 1 | 1 | 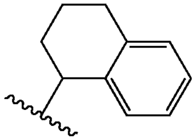 | $-(CH_2)_3CO_2H$ | H |
| 90 | 1-naphthyl | O | 1 | 1 | 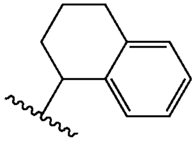 | $-(CH_2)_3CO_2H$ | H |
| 93 | 4-chloro-3-(trifluoromethyl)phenyl | O | 1 | 1 | 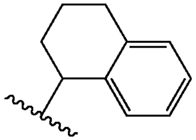 | ethyl | H |

-continued
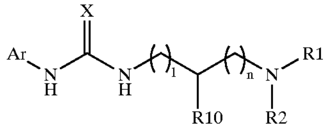
| CPD No. | Ar | X | l | n | R1 | R2 | R10 |
|---|---|---|---|---|---|---|---|
| 94 | 4-chloro-3-(trifluoromethyl)phenyl | O | 1 | 1 | 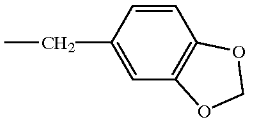 | $—(CH_2)_3SMe$ | H |
| 95 | 4-chloro-3-(trifluoromethyl)phenyl | O | 1 | 1 | 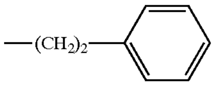 | $—CH_2CH(CH_3)_2$ | H |
| 96 | 4-chloro-3-(trifluoromethyl)phenyl | O | 1 | 1 | 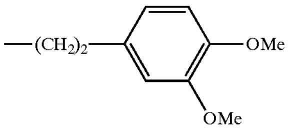 | $—CH_2CH(CH_3)_2$ | H |
| 97 | 4-chloro-3-(trifluoromethyl)phenyl | O | 1 | 1 | 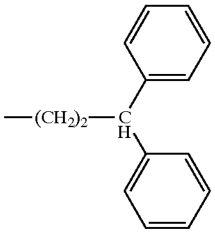 | $—(CH_2)_3CO_2H$ | H |
| 98 | 2-biphenyl | O | 1 | 1 | 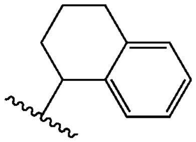 | 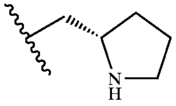 | H |

-continued
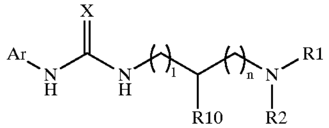
| CPD No. | Ar | X | l | n | R1 | R2 | R10 |
|---|---|---|---|---|---|---|---|
| 99 | 2-biphenyl | O | 1 | 1 | 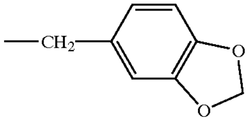 | $—(CH_2)_2CH(CH_3)_2$ | H |
| 100 | 2-biphenyl | O | 1 | 1 | 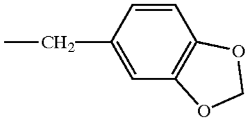 | $—(CH_2)_3SMe$ | H |
| 101 | 2-biphenyl | O | 1 | 1 | 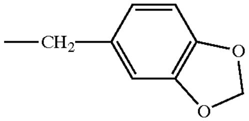 | $—(CH_2)_3CO_2H$ | H |
| 102 | 2-biphenyl | O | 1 | 1 | 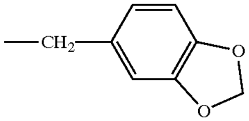 | 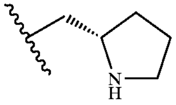 | H |
| 103 | 2-biphenyl | O | 1 | 1 | 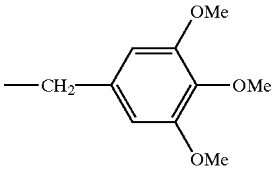 | $—(CH_2)_3SMe$ | H |

-continued
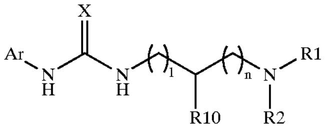
| CPD No. | Ar | X | l | n | R1 | R2 | R10 |
|---|---|---|---|---|---|---|---|
| 104 | 2-biphenyl | O | 1 | 1 | 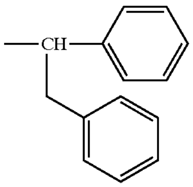 | $—CH_2CH(CH_3)_2$ | H |
| 105 | 2-biphenyl | O | 1 | 1 | 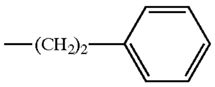 | $—(CH_2)_3SMe$ | H |
| 106 | 2-biphenyl | O | 1 | 1 | 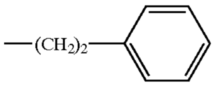 | $—(CH_2)_3CO_2Me$ | H |
| 107 | 2-biphenyl | O | 1 | 1 | 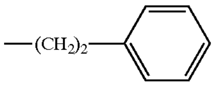 | 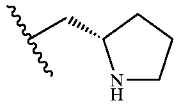 | H |
| 108 | 2-biphenyl | O | 1 | 1 | 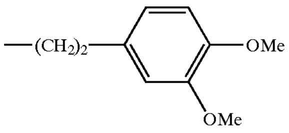 | $—CH_2CH(CH_3)_2$ | H |
| 109 | 2-biphenyl | O | 1 | 1 | 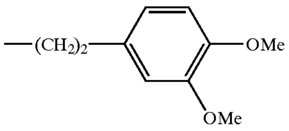 | 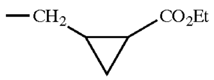 | H |

-continued
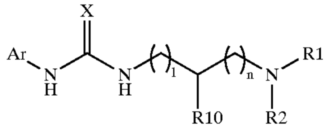
| CPD No. | Ar | X | l | n | R1 | R2 | R10 |
|---|---|---|---|---|---|---|---|
| 110 | 2-biphenyl | O | 1 | 1 | 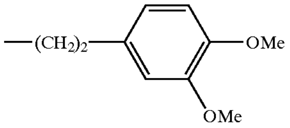 | 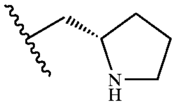 | H |
| 111 | 2-biphenyl | O | 1 | 1 | 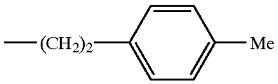 | $—CH_2CH(CH_3)_2$ | H |
| 112 | 2-biphenyl | O | 1 | 1 | 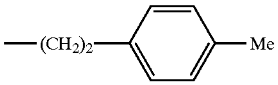 | 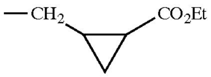 | H |
| 113 | 2-biphenyl | O | 1 | 1 | 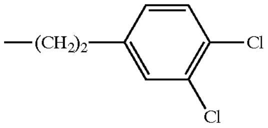 | $—CH_2CH(CH_3)_2$ | H |
| 114 | 2-biphenyl | O | 1 | 1 | 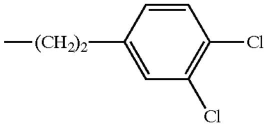 | 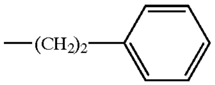 | H |
| 115 | 2-biphenyl | O | 1 | 1 | 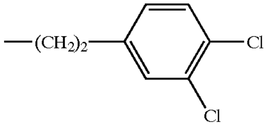 | 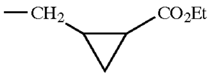 | H |
| 116 | 2-biphenyl | O | 1 | 1 | 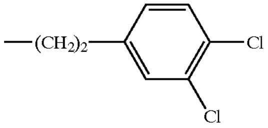 | 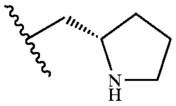 | H |

-continued
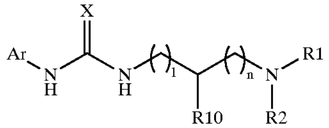
| CPD No. | Ar | X | l | n | R1 | R2 | R10 |
|---|---|---|---|---|---|---|---|
| 117 | 2-biphenyl | O | 1 | 1 | 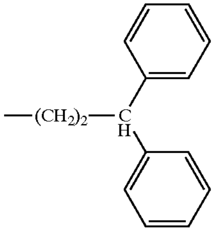 | $—CH_2CH(CH_3)_2$ | H |
| 118 | 4-bromophenyl | O | 1 | 1 | 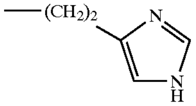 | $—CH_2CH(CH_3)_2$ | H |
| 119 | 4-bromophenyl | O | 1 | 1 | 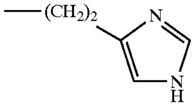 | $—(CH_2)_2CH(CH_3)_2$ | H |
| 120 | 4-bromophenyl | O | 1 | 1 | 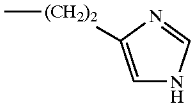 | 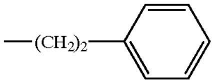 | H |
| 121 | 4-bromophenyl | O | 1 | 1 | 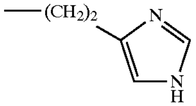 | 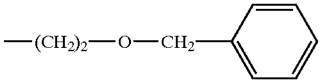 | H |

-continued
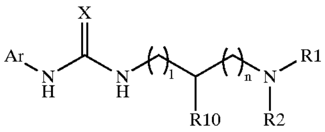
| CPD No. | Ar | X | l | n | R1 | R2 | R10 |
|---|---|---|---|---|---|---|---|
| 122 | 4-bromophenyl | O | 1 | 1 | 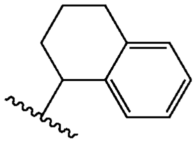 | $—CH_2CH(CH_3)_2$ | H |
| 123 | 4-bromophenyl | O | 1 | 1 | 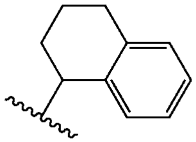 | 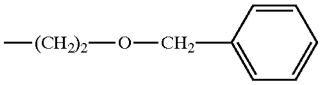 | H |
| 124 | 4-bromophenyl | O | 1 | 1 | 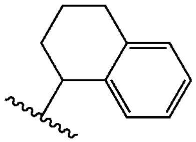 | $—(CH_2)_3SMe$ | H |
| 125 | 4-bromophenyl | O | 1 | 1 | 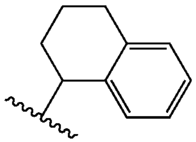 | 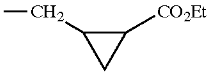 | H |
| 126 | 4-bromophenyl | O | 1 | 1 | 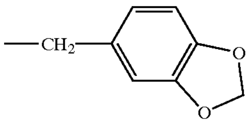 | $—CH_2CH(CH_3)_2$ | H |
| 127 | 4-bromophenyl | O | 1 | 1 | 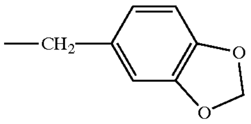 | 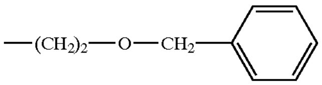 | H |

-continued
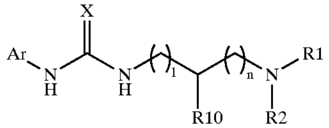
| CPD No. | Ar | X | l | n | R1 | R2 | R10 |
|---|---|---|---|---|---|---|---|
| 128 | 4-bromophenyl | O | 1 | 1 | 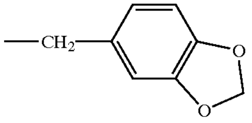 | 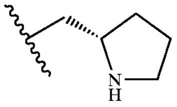 | H |
| 129 | 4-bromophenyl | O | 1 | 1 | 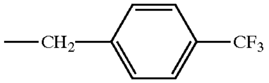 | $—CH_2CH(CH_3)_2$ | H |
| 130 | 4-bromophenyl | O | 1 | 1 | 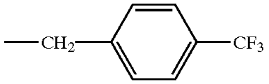 | $—(CH_2)_3SMe$ | H |
| 131 | 4-bromophenyl | O | 1 | 1 | 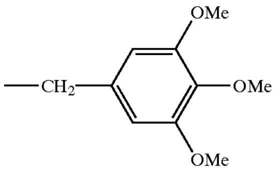 | $—(CH_2)_2CH(CH_3)_2$ | H |
| 132 | 4-bromophenyl | O | 1 | 1 | 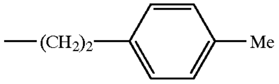 | $—(CH_2)_3CO_2H$ | H |
| 133 | 4-bromophenyl | O | 1 | 1 | 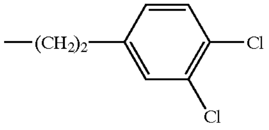 | $—(CH_2)_3CO_2H$ | H |

-continued
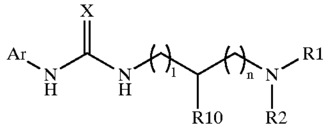
| CPD No. | Ar | X | l | n | R1 | R2 | R10 |
|---|---|---|---|---|---|---|---|
| 134 | 4-bromophenyl | O | 1 | 1 | 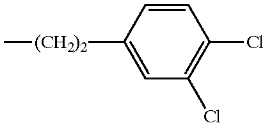 | 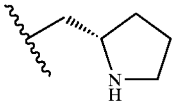 | H |
| 135 | 3-methylphenyl | O | 1 | 1 | 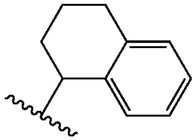 | 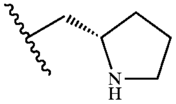 | H |
| 136 | 3-methylphenyl | O | 1 | 1 | 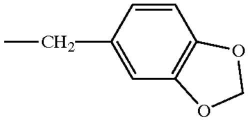 | $—CH_2CH(CH_3)_2$ | H |
| 137 | 3-methylphenyl | O | 1 | 1 | 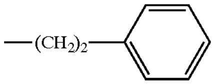 | ethyl | H |
| 138 | 3-methylphenyl | O | 1 | 1 | 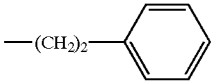 | 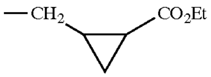 | H |
| 139 | 3-methylphenyl | O | 1 | 1 | 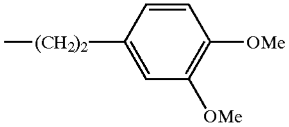 | $—(CH_2)_3SMe$ | H |

-continued
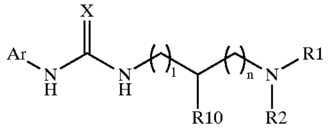
| CPD No. | Ar | X | l | n | R1 | R2 | R10 |
|---|---|---|---|---|---|---|---|
| 140 | 3-methylphenyl | O | 1 | 1 | 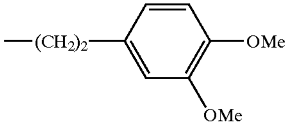 | $-(CH_2)_3CO_2H$ | H |
| 141 | 3-methylphenyl | O | 1 | 1 | 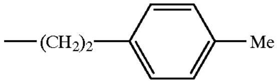 | $-(CH_2)_3SMe$ | H |
| 142 | 3-methylphenyl | O | 1 | 1 | 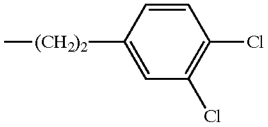 | $-(CH_2)_3SMe$ | H |
| 143 | 3-methylphenyl | O | 1 | 1 | 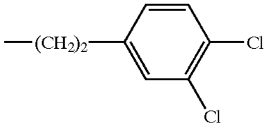 | 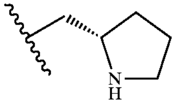 | H |
| 144 | 3-chlorophenyl | O | 1 | 1 | 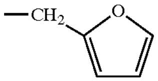 | 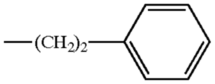 | H |
| 145 | 3-chlorophenyl | O | 1 | 1 | 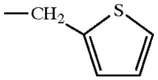 | $-(CH_2)_2CH(CH_3)_2$ | H |
| 146 | 3-chlorophenyl | O | 1 | 1 | 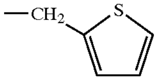 | 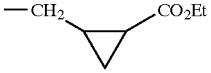 | H |

-continued
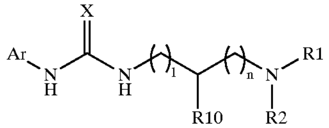
| CPD No. | Ar | X | l | n | R1 | R2 | R10 |
|---|---|---|---|---|---|---|---|
| 147 | 3-chlorophenyl | O | 1 | 1 | 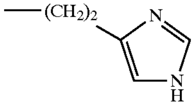 | 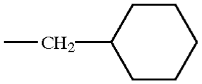 | H |
| 148 | 3-chlorophenyl | O | 1 | 1 | 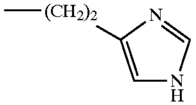 | 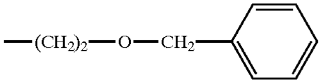 | H |
| 149 | 3-chlorophenyl | O | 1 | 1 | 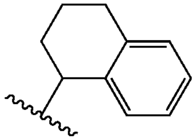 | 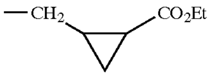 | H |
| 150 | 3-chlorophenyl | O | 1 | 1 | 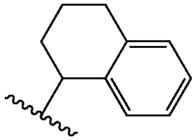 | 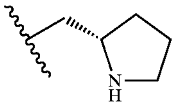 | H |
| 151 | 3-chlorophenyl | O | 1 | 1 | 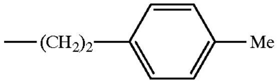 | $—CH_2CHCH_3)_2$ | H |
| 152 | 3-chlorophenyl | O | 1 | 1 | 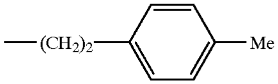 | 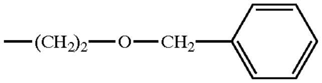 | H |
| 153 | 3-chlorophenyl | O | 1 | 1 | 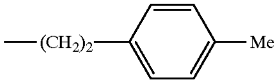 | 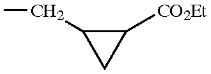 | H |

-continued
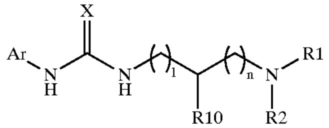
| CPD No. | Ar | X | l | n | R1 | R2 | R10 |
|---|---|---|---|---|---|---|---|
| 154 | 3-chlorophenyl | O | 1 | 1 | 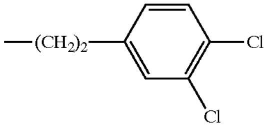 | 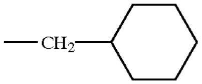 | H |
| 155 | 3-chlorophenyl | O | 1 | 1 | 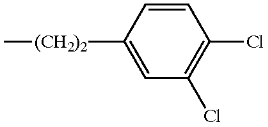 | 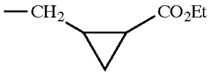 | H |
| 156 | 3-chlorophenyl | O | 1 | 1 | 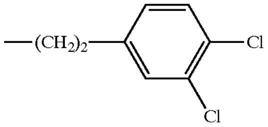 | $-(CH_2)_3CO_2Me$ | H |
| 157 | 2,4-dimethoxyphenyl | O | 1 | 1 | 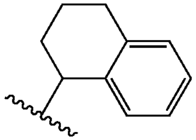 | $-(CH_2)_3SMe$ | H |
| 158 | 2,4-dimethoxyphenyl | O | 1 | 1 | 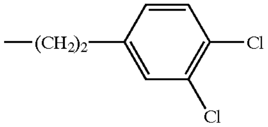 | $-(CH_2)_3SMe$ | H |
| 159 | 4-methoxyphenyl | O | 1 | 1 | 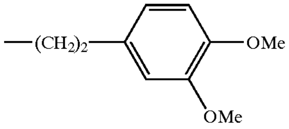 | 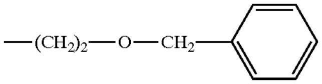 | H |

-continued
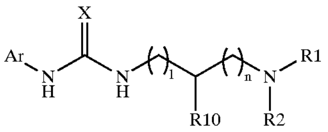
| CPD No. | Ar | X | l | n | R1 | R2 | R10 |
|---|---|---|---|---|---|---|---|
| 160 | 3,4-dichlorophenyl | O | 1 | 1 | 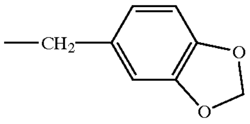 | $—(CH_2)_3CO_2Me$ | H |
| 161 | 1-naphthyl | O | 1 | 1 | 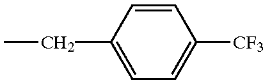 | $—(CH_2)_3CO_2H$ | H |
| 162 | 1-naphthyl | O | 1 | 1 | 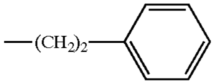 | 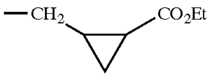 | H |
| 163 | phenyl | O | 1 | 1 | 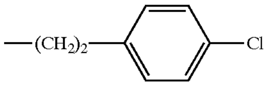 | ethyl | OH |
| 164 | 4-chlorophenyl | S | 1 | 1 | 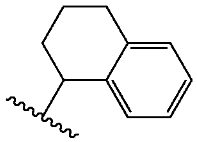 | $—(CH_2)_3CO_2H$ | H |
| 165 | 4-bromophenyl | O | 0 | 2 | 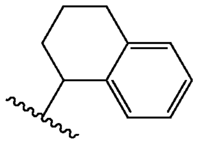 | $—(CH_2)_3CO_2H$ | 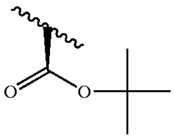 |
| 166 | 4-bromophenyl | O | 0 | 2 | 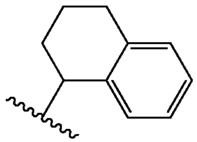 | $—(CH_2)_3CO_2H$ | 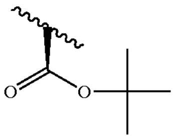 |

-continued
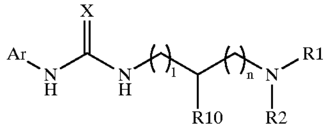
| CPD No. | Ar | X | l | n | R1 | R2 | R10 |
|---|---|---|---|---|---|---|---|
| 167 | 4-bromophenyl | O | 1 | 1 | 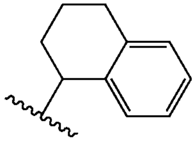 | $-(CH_2)_3CO_2H$ | OH |
| 168 | 4-methoxyphenyl | S | 1 | 1 | 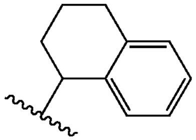 | $-(CH_2)_3CO_2H$ | H |
| 169 | 4-benzyloxyphenyl | S | 1 | 1 | 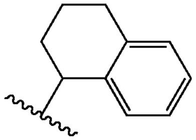 | $-(CH_2)_3CO_2H$ | H |
| 170 | 4-(trifluoromethoxy)phenyl | S | 1 | 1 | 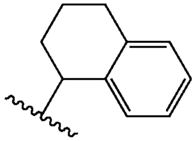 | $-(CH_2)_3CO_2H$ | H |
| 171 | 4-chlorophenyl | O | 1 | 1 | 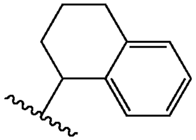 | $-(CH_2)_3CO_2H$ | H |

-continued
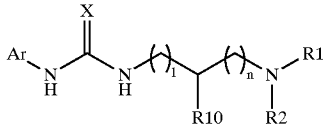
| CPD No. | Ar | X | l | n | R1 | R2 | R10 |
|---|---|---|---|---|---|---|---|
| 172 | 4-bromophenyl | O | 1 | 1 | 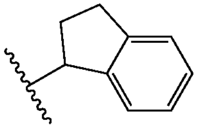 | —$(CH_2)_3CO_2Me$ | H |
| 173 | 4-bromophenyl | O | 1 | 1 | 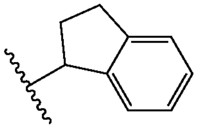 | —$(CH_2)_3CO_2H$ | H |
| 174 | 4-bromophenyl | O | 1 | 1 | 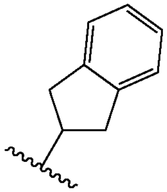 | —$(CH_2)_3CO_2Me$ | H |
| 175 | 4-bromophenyl | O | 1 | 1 | 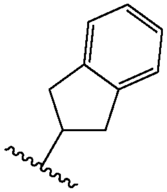 | —$(CH_2)_3CO_2H$ | H |
| 176 | 4-bromophenyl | O | 1 | 1 | 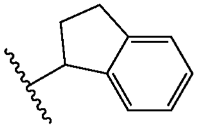 | —$(CH_2)_3CO_2Me$ | H |

-continued
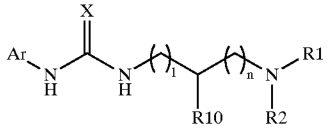
| CPD No. | Ar | X | l | n | R1 | R2 | R10 |
|---|---|---|---|---|---|---|---|
| 177 | 4-bromophenyl | O | 1 | 1 | 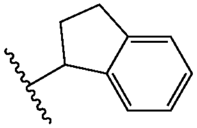 | $-(CH_2)_3CO_2H$ | H |
| 178 | 4-bromophenyl | O | 1 | 1 | 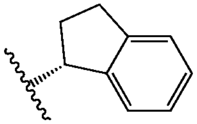 | $-(CH_2)_3CO_2Me$ | H |
| 179 | 4-bromophenyl | O | 1 | 1 | 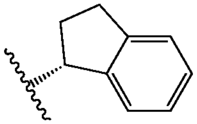 | $-(CH_2)_3CO_2H$ | H |
| 180 | 4-bromophenyl | O | 1 | 1 | 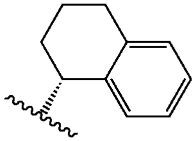 | $-(CH_2)_3CO_2Me$ | H |
| 181 | 4-bromophenyl | O | 1 | 1 | 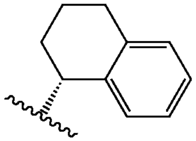 | $-(CH_2)_3CO_2H$ | H |
| 182 | 4-bromophenyl | O | 1 | 1 | 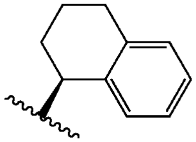 | $-(CH_2)_3CO_2Me$ | H |

-continued
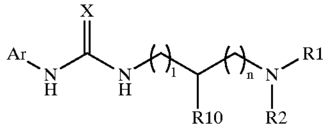
| CPD No. | Ar | X | l | n | R1 | R2 | R10 |
|---|---|---|---|---|---|---|---|
| 183 | 4-bromophenyl | O | 1 | 1 | 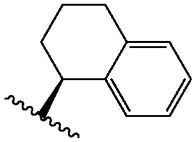 | $—(CH_2)_3CO_2H$ | H |
| 184 | 4-bromophenyl | O | 1 | 1 | 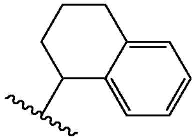 | $—(CH_2)_3CO_2Et$ | H |
| 185 | 4-chlorophenyl | O | 1 | 1 | 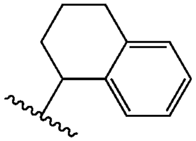 | $—(CH_2)_3CO_2Me$ | H |
| 186 | 4-bromophenyl | O | 1 | 1 | 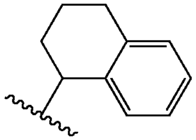 | $—CH_2CO_2H$ | H |
| 187 | 4-fluorophenyl | O | 1 | 1 | 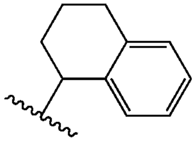 | $—(CH_2)_3CO_2Me$ | H |

-continued
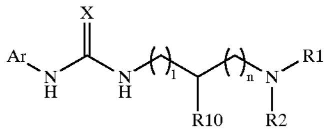
| CPD No. | Ar | X | l | n | R1 | R2 | R10 |
|---|---|---|---|---|---|---|---|
| 188 | 4-fluorophenyl | O | 1 | 1 | 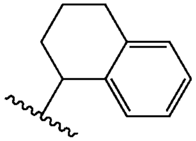 | $-(CH_2)_3CO_2H$ | H |
| 189 | 2-bromophenyl | O | 1 | 1 | 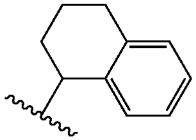 | $-(CH_2)_3CO_2Me$ | H |
| 190 | 2-bromophenyl | O | 1 | 1 | 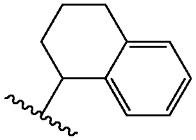 | $-(CH_2)_3CO_2H$ | H |
| 191 | 4-bromophenyl | O | 1 | 1 | 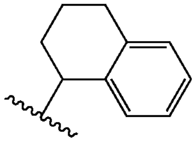 | ethyl | H |
| 192 | phenyl | O | 1 | 1 | 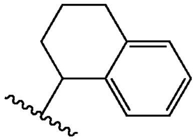 | ethyl | H |

-continued
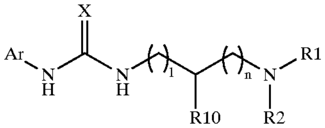
| CPD No. | Ar | X | l | n | R1 | R2 | R10 |
|---|---|---|---|---|---|---|---|
| 193 | 4-bromophenyl | O | 1 | 1 | 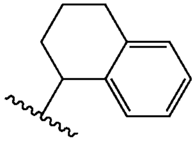 | $-(CH_2)_3CONH_2$ | H |
| 194 | 4-bromophenyl | O | 1 | 1 | 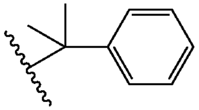 | $-(CH_2)_3CO_2Me$ | H |
| 195 | 4-bromophenyl | O | 1 | 1 | 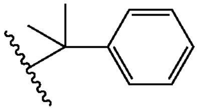 | $-(CH_2)_3CO_2H$ | H |
| 196 | 4-bromophenyl | O | 1 | 1 | 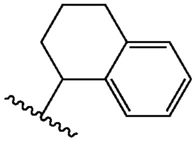 | 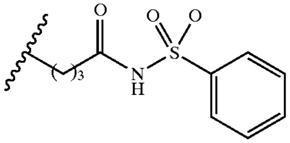 | H |
| 197 | 4-bromophenyl | O | 1 | 1 | 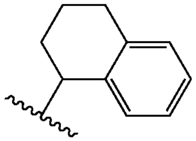 | 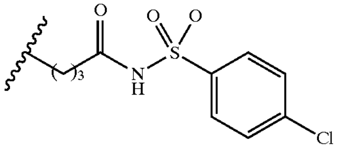 | H |
| 198 | 3-bromophenyl | O | 1 | 1 | 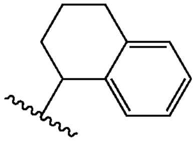 | $-(CH_2)_3CO_2Me$ | H |

-continued
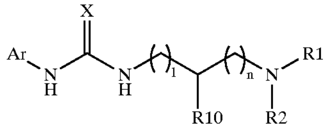
| CPD No. | Ar | X | l | n | R1 | R2 | R10 |
|---|---|---|---|---|---|---|---|
| 199 | 3-bromophenyl | O | 1 | 1 | 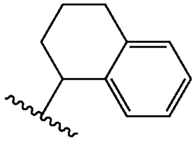 | $-(CH_2)_3CO_2H$ | H |
| 200 | 4-bromo-2-methylphenyl | O | 1 | 1 | 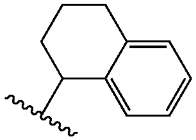 | $-(CH_2)_3CO_2Me$ | H |
| 201 | 4-bromo-2-methylphenyl | O | 1 | 1 | 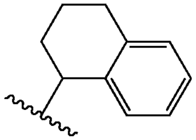 | $-(CH_2)_3CO_2H$ | H |
| 202 | 4-bromophenyl | O | 1 | 1 | 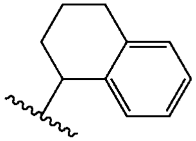 | $-(CH_2)_4OCOCH_3$ | H |
| 203 | 4-bromophenyl | O | 1 | 1 | 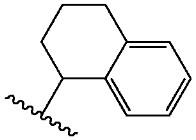 | $-(CH_2)_4OH$ | H |

-continued
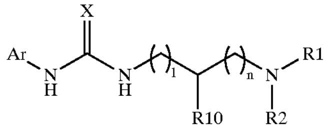
| CPD No. | Ar | X | l | n | R1 | R2 | R10 |
| --- | --- | --- | --- | --- | --- | --- | --- |
| 204 | 4-bromophenyl | O | 1 | 1 | 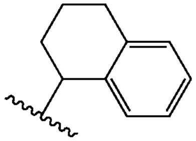 | $—(CH_2)_5OCOCH_3$ | H |
| 205 | 4-bromophenyl | O | 1 | 1 | 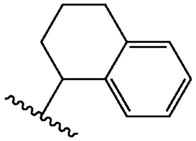 | $—(CH_2)_5OH$ | H |
| 206 | 4-bromophenyl | O | 1 | 1 | 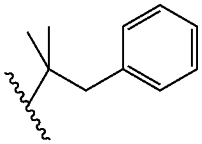 | $—(CH_2)_3CO_2Me$ | H |
| 207 | 4-bromophenyl | O | 1 | 1 | 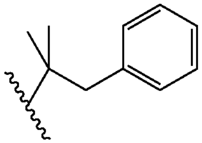 | $—(CH_2)_3CO_2H$ | H |
| 208 | 4-bromophenyl | O | 1 | 1 | 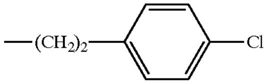 | $—(CH_2)_3CO_2Me$ | H |
| 209 | 4-bromophenyl | O | 1 | 1 | 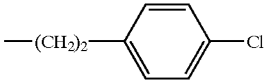 | $—(CH_2)_3CO_2H$ | H |

-continued
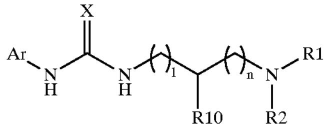
| CPD No. | Ar | X | l | n | R1 | R2 | R10 |
|---|---|---|---|---|---|---|---|
| 210 | 4-bromophenyl | O | 1 | 1 | 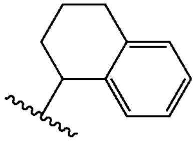 | 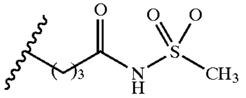 | H |
| 211 | 4-bromophenyl | O | 1 | 1 | 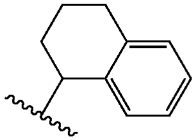 | —$(CH_2)_5CO_2H$ | H |
| 212 | 4-bromophenyl | O | 1 | 1 | 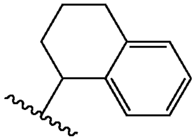 | 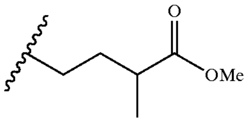 | H |
| 213 | 4-bromophenyl | O | 1 | 1 | 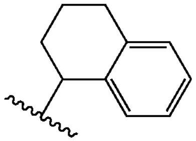 | —$(CH_2)_4CO_2Me$ | H |
| 214 | 4-bromophenyl | O | 1 | 1 | 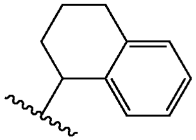 | —$(CH_2)_4CO_2H$ | H |

-continued
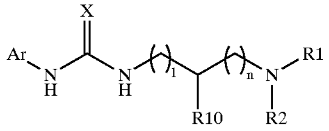
| CPD No. | Ar | X | l | n | R1 | R2 | R10 |
|---|---|---|---|---|---|---|---|
| 215 | 4-bromophenyl | O | 1 | 1 | 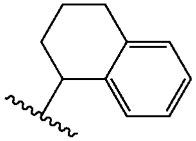 | $—(CH_2)_3OCOCH_3$ | H |
| 216 | 4-bromophenyl | O | 1 | 1 | 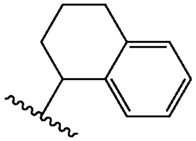 | $—(CH_2)_3OH$ | H |
| 217 | 4-bromophenyl | O | 1 | 1 | 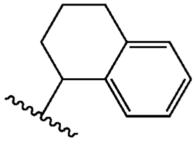 | 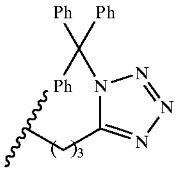 | H |
| 218 | 4-bromophenyl | O | 1 | 1 | 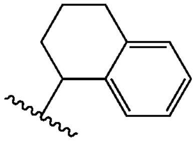 | 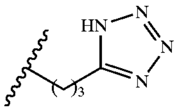 | H |
| 219 | phenyl | O | 1 | 1 | 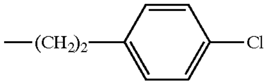 | $—(CH_2)_3OH$ | H |
| 220 | phenyl | O | 1 | 1 | 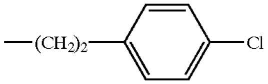 | $—CH_2CONH_2$ | H |

-continued
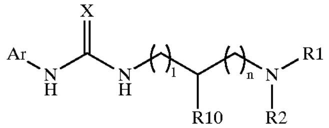
| CPD No. | Ar | X | l | n | R1 | R2 | R10 |
|---|---|---|---|---|---|---|---|
| 221 | phenyl | O | 1 | 1 | 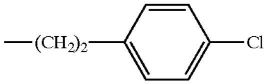 | —$CH_2CH$=$CH_2$ | H |
| 222 | 4-bromophenyl | O | 1 | 1 | 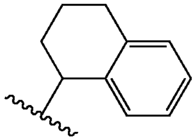 | 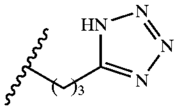 | H |
| 223 | 4-bromophenyl | O | 1 | 1 | 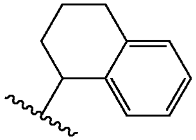 | 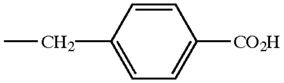 | H |
| 224 | 4-bromophenyl | O | 1 | 1 | 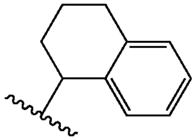 | 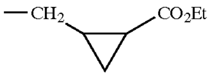 | H |
| 225 | 4-carboxyphenyl | O | 1 | 1 | 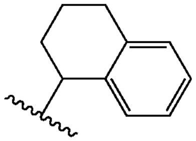 | —$(CH_2)_3CO_2Me$ | H |
| 226 | 4-bromophenyl | O | 1 | 1 | 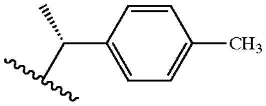 | —$(CH_2)_3CO_2H$ | H |

-continued
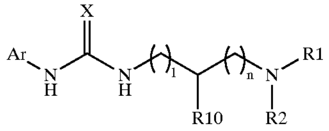
| CPD No. | Ar | X | l | n | R1 | R2 | R10 |
|---|---|---|---|---|---|---|---|
| 227 | 4-bromophenyl | O | 1 | 1 | 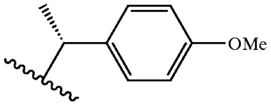 | $—(CH_2)_3CO_2H$ | H |
| 228 | 4-(ethoxycarbonyl)phenyl) | O | 1 | 1 | 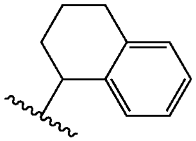 | $—(CH_2)_3CO_2H$ | H |
| 229 | 4-iodophenyl | O | 1 | 1 | 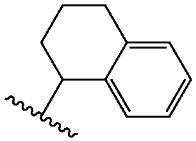 | $—(CH_2)_3CO_2H$ | H |
| 230 | phenyl | O | 1 | 1 | 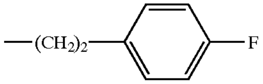 | ethyl | H |
| 231 | phenyl | O | 1 | 1 | 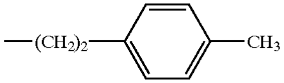 | ethyl | H |
| 232 | phenyl | O | 1 | 1 | 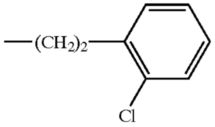 | ethyl | H |

-continued
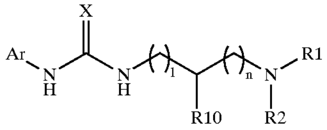
| CPD No. | Ar | X | l | n | R1 | R2 | R10 |
|---|---|---|---|---|---|---|---|
| 233 | phenyl | O | 1 | 1 | 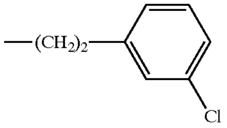 | ethyl | H |
| 234 | phenyl | O | 1 | 1 | 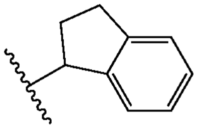 | ethyl | H |
| 235 | 4-carboxyphenyl | O | 1 | 1 | 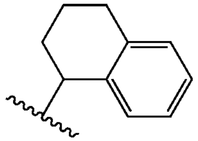 | $-(CH_2)_3CO_2H$ | H |
| 236 | 3-(ethoxycarbonyl)phenyl) | O | 1 | 1 | 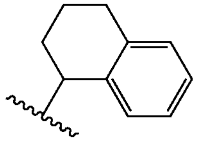 | $-(CH_2)_3CO_2H$ | H |
| 237 | 4-(n-butyloxycarbonyl)phenyl | O | 1 | 1 | 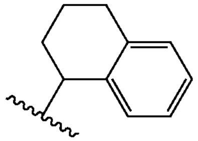 | $-(CH_2)_3CO_2H$ | H |
| 238 | phenyl | O | 1 | 1 | 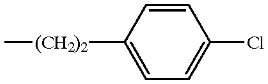 | 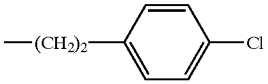 | H |

-continued
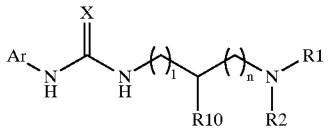
| CPD No. | Ar | X | l | n | R1 | R2 | R10 |
|---|---|---|---|---|---|---|---|
| 239 | phenyl | O | 1 | 1 | 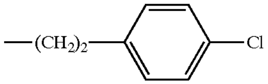 | $—CH_2CH(CH_3)_2$ | H |
| 240 | phenyl | O | 1 | 1 | 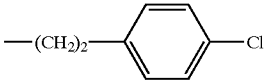 | 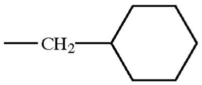 | H |
| 241 | phenyl | O | 1 | 1 | 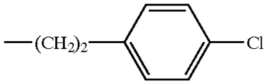 | $—(CH_2)_4CO_2Me$ | H |
| 242 | phenyl | O | 1 | 1 | 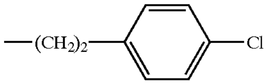 | $—(CH_2)_5CO_2Et$ | H |
| 243 | phenyl | O | 1 | 1 | 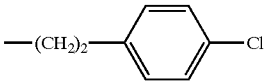 | $—(CH_2)_2CONH_2$ | H |
| 244 | phenyl | O | 1 | 1 | 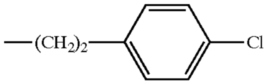 | $—(CH_2)_2OCOCH_3$ | H |
| 245 | phenyl | O | 1 | 1 | 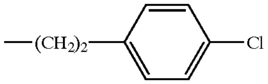 | $—CH_2CO_2Me$ | H |
| 246 | 4-bromophenyl | S | 1 | 1 | 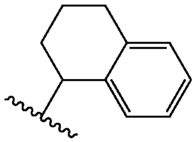 | $—(CH_2)_3CO_2H$ | H |

-continued
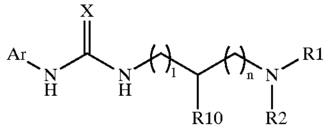
| CPD No. | Ar | X | l | n | R1 | R2 | R10 |
|---|---|---|---|---|---|---|---|
| 247 | 3-bromophenyl | S | 1 | 1 | 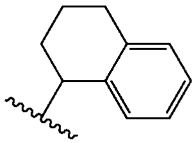 | —$(CH_2)_3CO_2H$ | H |
| 248 | 3-chlorophenyl | S | 1 | 1 | 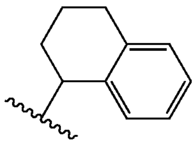 | —$(CH_2)_3CO_2H$ | H |
| 249 | 4-iodophenyl | S | 1 | 1 | 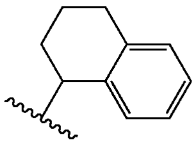 | —$(CH_2)_3CO_2H$ | H |
| 250 | 4-methylphenyl | S | 1 | 1 | 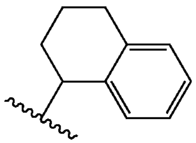 | —$(CH_2)_3CO_2H$ | H |
| 251 | 3,4-dichlorophenyl | S | 1 | 1 | 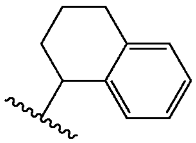 | —$(CH_2)_3CO_2H$ | H |

-continued
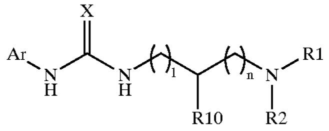
| CPD No. | Ar | X | l | n | R1 | R2 | R10 |
|---|---|---|---|---|---|---|---|
| 252 | 4-bromophenyl | S | 1 | 1 | 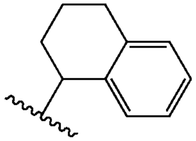 | $—(CH_2)_3CO_2Me$ | H |
| 253 | 3-bromophenyl | S | 1 | 1 | 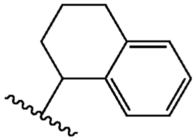 | $—(CH_2)_3CO_2Me$ | H |
| 254 | 3-chlorophenyl | S | 1 | 1 | 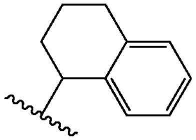 | $—(CH_2)_3CO_2Me$ | H |
| 255 | 4-iodophenyl | S | 1 | 1 | 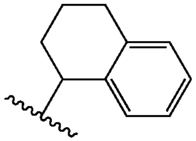 | $—(CH_2)_3CO_2Me$ | H |
| 256 | 3,4-dichlorophenyl | S | 1 | 1 | 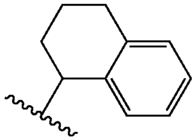 | $—(CH_2)_3CO_2Me$ | H |

-continued
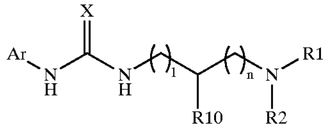
| CPD No. | Ar | X | l | n | R1 | R2 | R10 |
|---|---|---|---|---|---|---|---|
| 257 | 4-fluorophenyl | S | 1 | 1 | 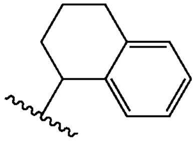 | $-(CH_2)_3CO_2H$ | H |
| 258 | 4-bromophenyl | O | 1 | 1 | 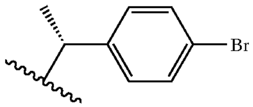 | $-(CH_2)_3CO_2H$ | H |
| 259 | 4-bromophenyl | O | 1 | 1 | 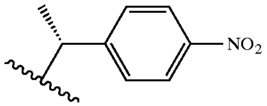 | $-(CH_2)_3CO_2H$ | H |
| 260 | 3-cyanophenyl | O | 1 | 1 | 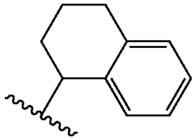 | $-(CH_2)_3CO_2H$ | H |
| 261 | 3-methoxyphenyl | O | 1 | 1 | 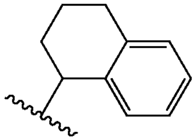 | $-(CH_2)_3CO_2H$ | H |
| 262 | 3-acetylphenyl | O | 1 | 1 | 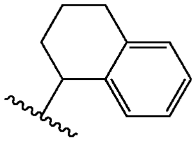 | $-(CH_2)_3CO_2H$ | H |

-continued
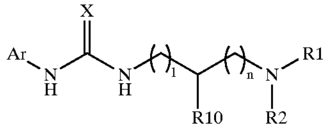
| CPD No. | Ar | X | l | n | R1 | R2 | R10 |
|---|---|---|---|---|---|---|---|
| 263 | 3-(methylthio)phenyl | O | 1 | 1 | 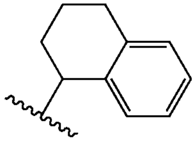 | $-(CH_2)_3CO_2H$ | H |
| 264 | 4-methylthiophenyl | O | 1 | 1 | 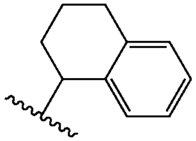 | $-(CH_2)_3CO_2H$ | H |
| 265 | 2-naphthyl | O | 1 | 1 | 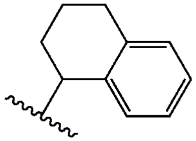 | $-(CH_2)_3CO_2H$ | H |
| 266 | 4-(trifluoromethoxy)phenyl | O | 1 | 1 | 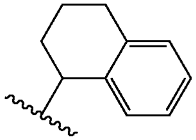 | $-(CH_2)_3CO_2H$ | H |
| 267 | 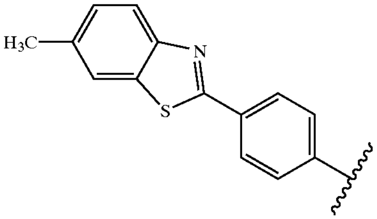 | O | 1 | 1 | 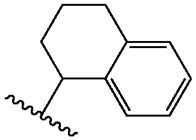 | $-(CH_2)_3CO_2H$ | H |

-continued
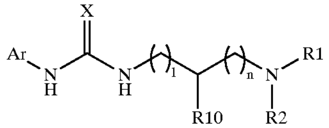
| CPD No. | Ar | X | l | n | R1 | R2 | R10 |
|---|---|---|---|---|---|---|---|
| 268 | 4-bromophenyl | O | 1 | 1 | 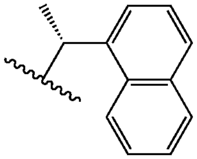 | $-(CH_2)_3CO_2H$ | H |
| 269 | 4-bromophenyl | O | 1 | 1 | 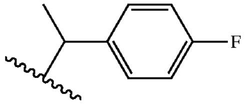 | $-(CH_2)_3CO_2H$ | H |
| 270 | 4-bromophenyl | O | 1 | 1 | 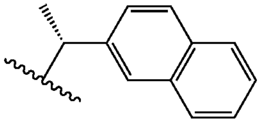 | $-(CH_2)_3CO_2H$ | H |
| 271 | 4-bromophenyl | O | 1 | 1 | 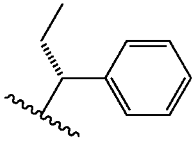 | $-(CH_2)_3CO_2H$ | H |
| 272 | 4-bromophenyl | O | 1 | 1 | 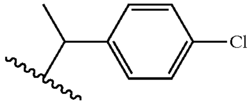 | $-(CH_2)_3CO_2H$ | H |
| 273 | 4-bromophenyl | O | 1 | 1 | 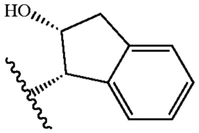 | $-(CH_2)_3CO_2H$ | H |

-continued
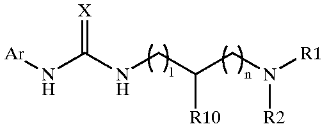
| CPD No. | Ar | X | l | n | R1 | R2 | R10 |
|---|---|---|---|---|---|---|---|
| 274 | phenyl | O | 1 | 1 | 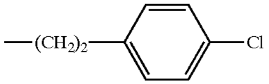 | $-(CH_2)_3CO_2Me$ | H |
| 275 | phenyl | O | 1 | 1 | 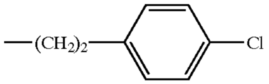 | $-(CH_2)_2OCH_3$ | H |
| 276 | phenyl | O | 1 | 1 | 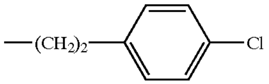 | $-CH(CH_3)_2$ | H |
| 277 | 4-biphenyl | O | 1 | 1 | 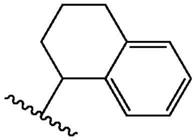 | $-(CH_2)_3CO_2H$ | H |
| 278 | 4-acetylphenyl | O | 1 | 1 | 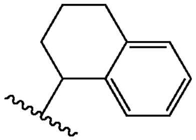 | $-(CH_2)_3CO_2H$ | H |
| 280 | phenyl | O | 1 | 1 | 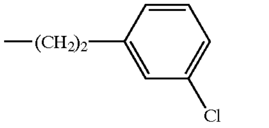 | 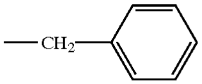 | H |
| 281 | 4-bromophenyl | O | 0 | 2 | 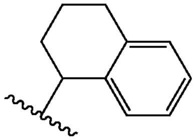 | $-(CH_2)_3CO_2Me$ | 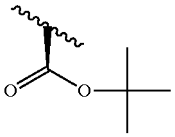 |

-continued
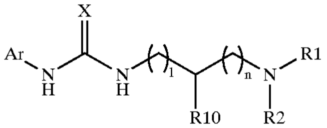
| CPD No. | Ar | X | l | n | R1 | R2 | R10 |
|---|---|---|---|---|---|---|---|
| 282 | 4-bromophenyl | O | 0 | 2 | 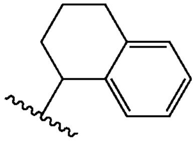 | $-(CH_2)_3CO_2Me$ | 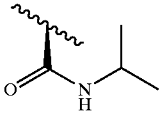 |
| 283 | 4-bromophenyl | O | 0 | 2 | 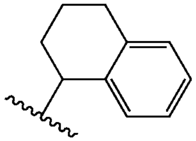 | $-(CH_2)_3CO_2Me$ | 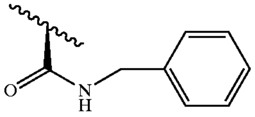 |
| 284 | 4-bromophenyl | O | 0 | 2 | 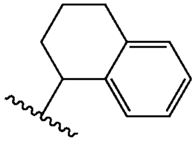 | $-(CH_2)_3CO_2H$ | 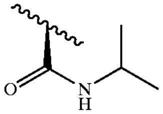 |
| 285 | 4-bromophenyl | O | 0 | 2 | 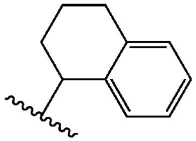 | $-(CH_2)_3CO_2H$ | 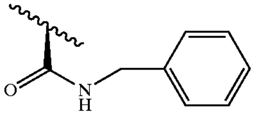 |

-continued
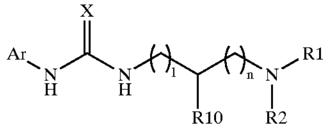
| CPD No. | Ar | X | l | n | R1 | R2 | R10 |
|---|---|---|---|---|---|---|---|
| 286 | 4-bromophenyl | O | 0 | 2 | 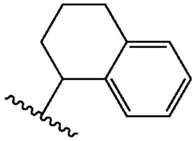 | $—(CH_2)_3CO_2H$ | 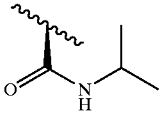 |
| 287 | 4-bromophenyl | O | 0 | 2 | 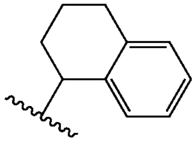 | $—(CH_2)_3CO_2H$ | 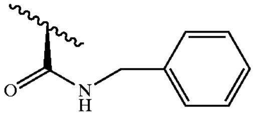 |
| 288 | 4-bromophenyl | S | 1 | 1 | 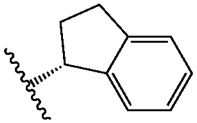 | $—(CH_2)_3CO_2H$ | H |
| 289 | 4-bromophenyl | S | 1 | 1 | 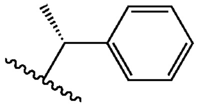 | $—(CH_2)_3CO_2H$ | H |

-continued
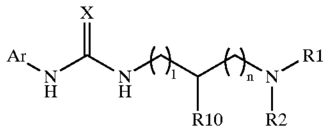
| CPD No. | Ar | X | l | n | R1 | R2 | R10 |
|---|---|---|---|---|---|---|---|
| 290 | 4-bromophenyl | S | 1 | 1 | 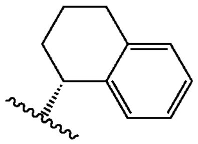 | $—(CH_2)_3CO_2H$ | H |
| 291 | phenyl | O | 1 | 1 | 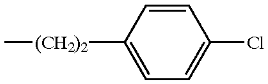 | 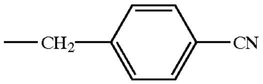 | H |
| 292 | phenyl | O | 1 | 1 | 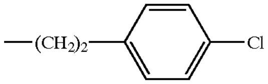 | 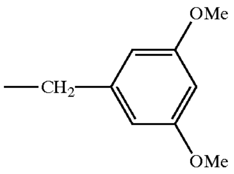 | H |
| 293 | 4-bromophenyl | O | 1 | 1 | 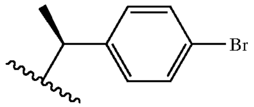 | $—(CH_2)_3CO_2H$ | H |

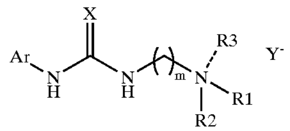
| CPD No. | Ar | X | m | R1 | R2 | R3 | Y |
|---|---|---|---|---|---|---|---|
| 91 | phenyl | O | 3 | 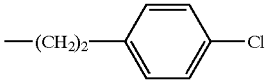 | ethyl | ethyl | I |
| 92 | 4-bromophenyl | O | 3 | 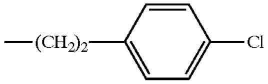 | ethyl | ethyl | I |
| 294 | 4-bromophenyl | O | 3 | 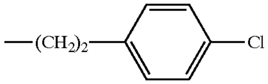 | n-butyl | ethyl | I |
| 295 | 4-bromophenyl | O | 3 | 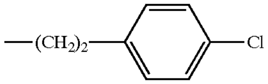 | n-propyl | ethyl | I |
| 296 | phenyl | O | 3 | 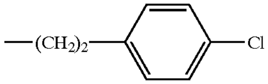 | 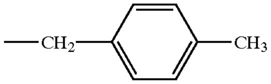 | 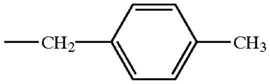 | Br |
| 297 | phenyl | O | 3 | 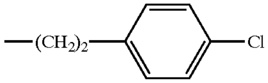 | 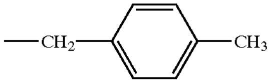 | ethyl | I |
| 298 | phenyl | O | 3 | 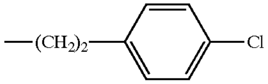 | 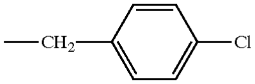 | ethyl | I |
| 299 | phenyl | O | 3 | 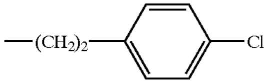 | $-(CH_2)_3OH$ | ethyl | I |

-continued
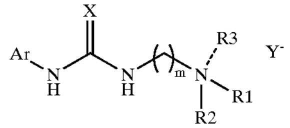
| CPD No. | Ar | X | m | R1 | R2 | R3 | Y |
|---|---|---|---|---|---|---|---|
| 300 | phenyl | O | 3 | 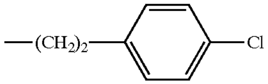 | $—CH_2CONH_2$ | ethyl | I |
| 301 | phenyl | O | 3 | 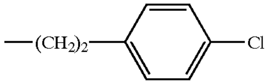 | $—CH_2CH{=}CH_2$ | ethyl | I |
| 302 | phenyl | O | 3 | 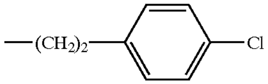 | 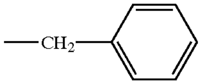 | ethyl | I |
| 303 | phenyl | O | 3 | 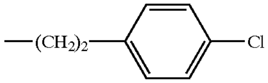 | 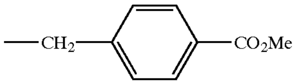 | ethyl | I |
| 304 | phenyl | O | 3 | 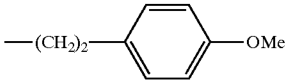 | ethyl | ethyl | I |
| 305 | phenyl | O | 3 | 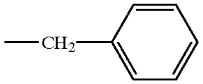 | ethyl | ethyl | I |
| 306 | phenyl | O | 3 | 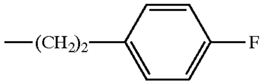 | ethyl | ethyl | I |
| 307 | phenyl | O | 3 | 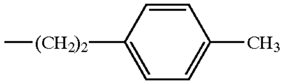 | ethyl | ethyl | I |

-continued
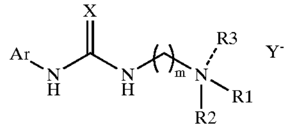
| CPD No. | Ar | X | m | R1 | R2 | R3 | Y |
|---|---|---|---|---|---|---|---|
| 308 | phenyl | O | 3 | 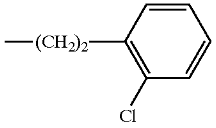 | ethyl | ethyl | I |
| 309 | phenyl | O | 3 | 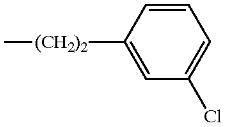 | ethyl | ethyl | I |
| 310 | phenyl | O | 3 | 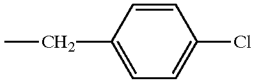 | ethyl | ethyl | I |
| 311 | phenyl | O | 3 | 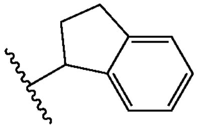 | ethyl | ethyl | I |
| 312 | 4-bromophenyl | O | 3 | 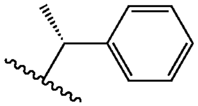 | $-(CH_2)_3CO_2Me$ | ethyl | I |
| 313 | 4-bromophenyl | O | 3 | 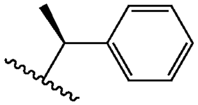 | $-(CH_2)_3CO_2Me$ | ethyl | I |

-continued
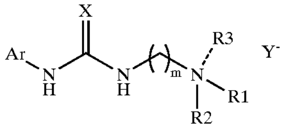
| CPD No. | Ar | X | m | R1 | R2 | R3 | Y |
|---|---|---|---|---|---|---|---|
| 314 | 4-bromophenyl | O | 3 | 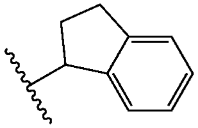 | $-(CH_2)_3CO_2Me$ | ethyl | I |
| 315 | 4-bromophenyl | O | 3 | 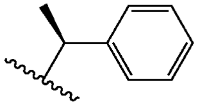 | $-(CH_2)_3CO_2H$ | ethyl | $CF_3COO$ |
| 316 | 4-bromophenyl | O | 3 | 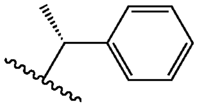 | $-(CH_2)_3CO_2H$ | ethyl | $CF_3COO$ |
| 317 | phenyl | O | 3 | 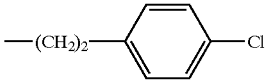 | 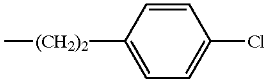 | ethyl | I |
| 318 | phenyl | O | 3 | 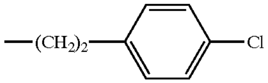 | $-CH_2CH(CH_3)_2$ | ethyl | I |
| 319 | phenyl | O | 3 | 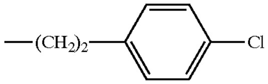 | 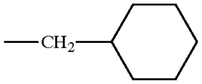 | ethyl | I |
| 320 | phenyl | O | 3 | 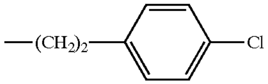 | $-(CH_2)_4CO_2Me$ | ethyl | I |
| 321 | phenyl | O | 3 | 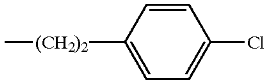 | $-(CH_2)_5CO_2Et$ | ethyl | I |

-continued
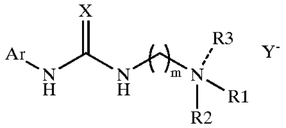
| CPD No. | Ar | X | m | R1 | R2 | R3 | Y |
|---|---|---|---|---|---|---|---|
| 322 | phenyl | O | 3 | 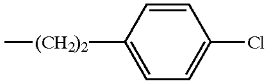 | 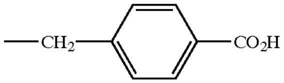 | ethyl | I |
| 323 | phenyl | O | 5 | 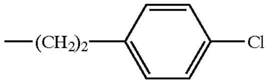 | ethyl | ethyl | I |
| 324 | 4-methoxyphenyl | O | 3 | 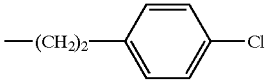 | 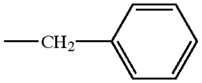 | ethyl | I |
| 325 | 3,4-dichlorophenyl | O | 3 | 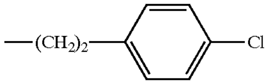 | 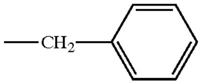 | ethyl | I |
| 326 | 4-cyanophenyl | O | 3 | 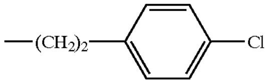 | 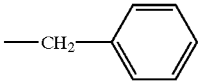 | ethyl | I |
| 327 | phenyl | O | 3 | 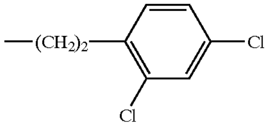 | 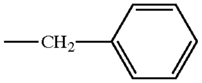 | ethyl | I |
| 328 | phenyl | O | 3 | 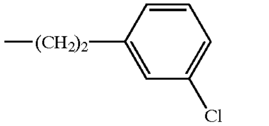 | 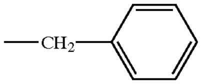 | ethyl | I |

-continued
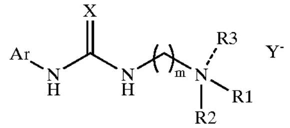
| CPD No. | Ar | X | m | R1 | R2 | R3 | Y |
|---|---|---|---|---|---|---|---|
| 329 | phenyl | O | 3 | 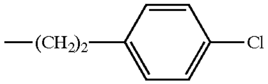 | 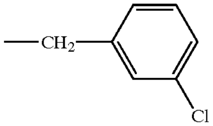 | ethyl | I |
| 330 | phenyl | O | 3 | 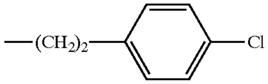 | 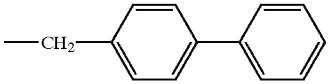 | ethyl | I |
| 331 | phenyl | O | 3 | 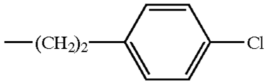 | 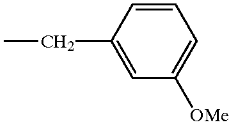 | ethyl | I |
| 332 | phenyl | O | 3 | 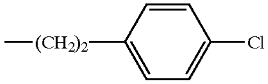 | 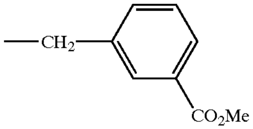 | ethyl | I |
| 333 | phenyl | O | 3 | 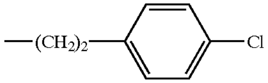 | 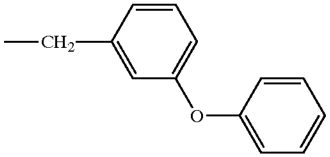 | ethyl | I |
| 334 | phenyl | O | 3 | 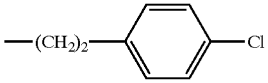 | 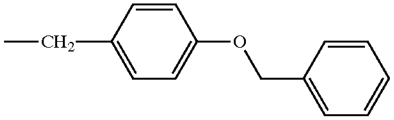 | ethyl | I |

-continued
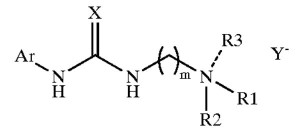
| CPD No. | Ar | X | m | R1 | R2 | R3 | Y |
|---|---|---|---|---|---|---|---|
| 335 | 4-bromophenyl | S | 3 | 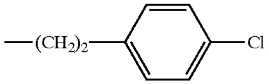 | ethyl | ethyl | I |
| 336 | phenyl | S | 3 | 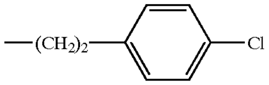 | ethyl | ethyl | I |
| 337 | phemyl | O | 3 | 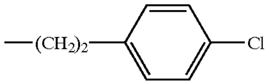 | 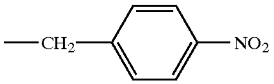 | ethyl | I |
| 338 | phenyl | O | 3 | 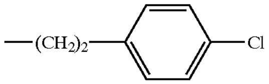 | 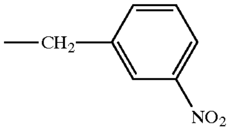 | ethyl | I |
| 339 | phenyl | O | 3 | 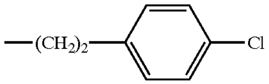 | 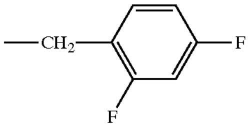 | ethyl | I |
| 340 | phenyl | O | 3 | 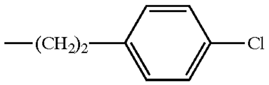 | 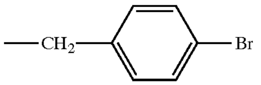 | ethyl | I |
| 341 | phenyl | O | 3 | 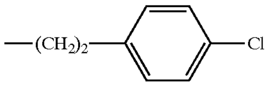 | 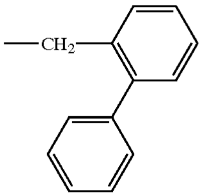 | ethyl | I |

-continued
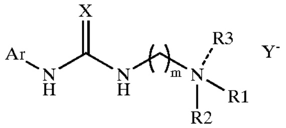
| CPD No. | Ar | X | m | R1 | R2 | R3 | Y |
|---|---|---|---|---|---|---|---|
| 342 | phenyl | O | 3 | 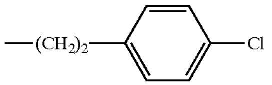 | 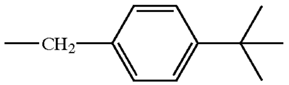 | ethyl | I |
| 343 | phenyl | O | 3 | 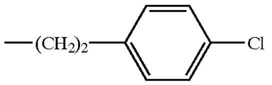 | 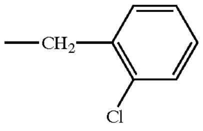 | ethyl | I |
| 344 | phenyl | O | 3 | 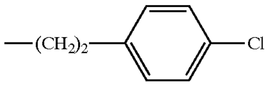 | 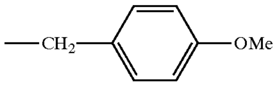 | ethyl | I |
| 345 | phenyl | O | 3 | 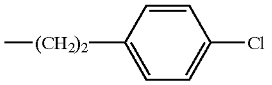 | 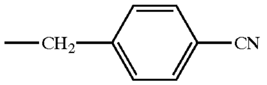 | ethyl | I |
| 346 | phenyl | O | 3 | 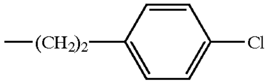 | 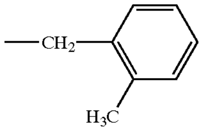 | ethyl | I |
| 347 | phenyl | O | 3 | 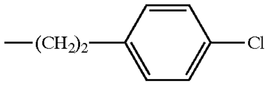 | 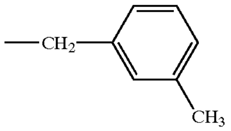 | ethyl | I |

-continued
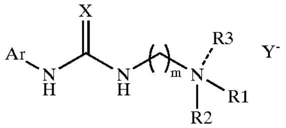
| CPD No. | Ar | X | m | R1 | R2 | R3 | Y |
|---|---|---|---|---|---|---|---|
| 348 | phenyl | O | 3 | 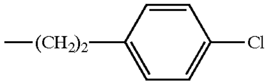 | 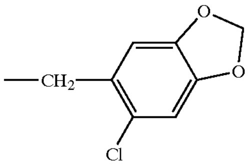 | ethyl | I |
| 349 | phenyl | O | 3 | 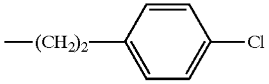 | 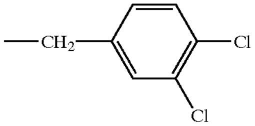 | ethyl | I |
| 350 | phenyl | O | 3 | 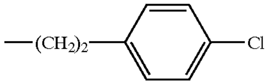 | 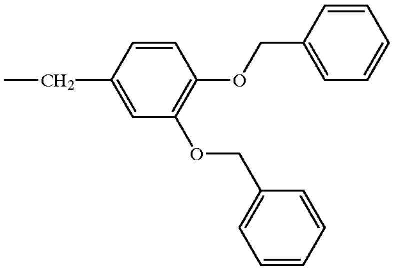 | ethyl | I |
| 351 | phenyl | O | 3 | 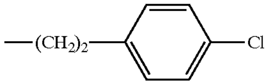 | 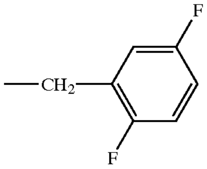 | ethyl | I |

-continued
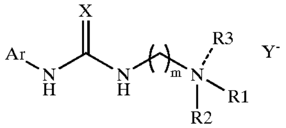
| CPD No. | Ar | X | m | R1 | R2 | R3 | Y |
|---|---|---|---|---|---|---|---|
| 352 | phenyl | O | 3 | 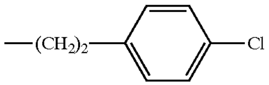 | 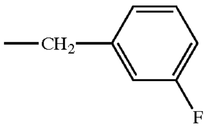 | ethyl | I |
| 353 | phenyl | O | 3 | 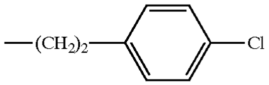 | 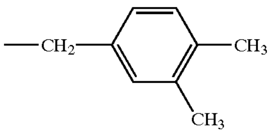 | ethyl | I |
| 354 | phenyl | O | 3 | 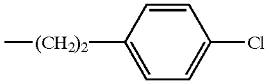 | 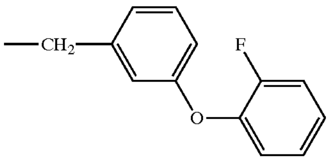 | ethyl | I |
| 355 | 3,4-dichlorophenyl | O | 3 | 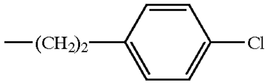 | $—(CH_2)_2O(CH_2)_2OMe$ | ethyl | I |
| 356 | 3,4-dichlorophenyl | O | 3 | 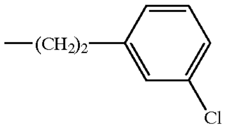 | $—(CH_2)_2O(CH_2)_2OMe$ | ethyl | I |
| 357 | 3,4-dichlorophenyl | O | 3 | 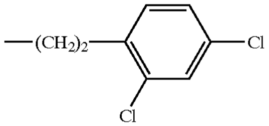 | $—(CH_2)_2O(CH_2)_2OMe$ | ethyl | I |

-continued
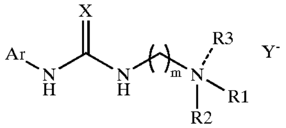
| CPD No. | Ar | X | m | R1 | R2 | R3 | Y |
|---|---|---|---|---|---|---|---|
| 358 | 3,4-dichlorophenyl | O | 3 | 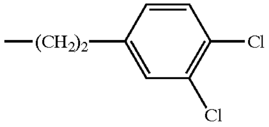 | $—(CH_2)_2O(CH_2)_2OMe$ | ethyl | I |
| 359 | 3,4-dichlorophenyl | O | 3 | 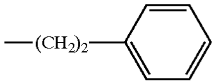 | $—(CH_2)_2O(CH_2)_2OMe$ | ethyl | I |
| 360 | 3,4-dichlorophenyl | O | 3 | 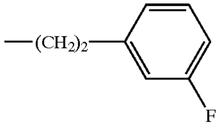 | $—(CH_2)_2O(CH_2)_2OMe$ | ethyl | I |
| 361 | 3,4-dichlorophenyl | O | 3 | 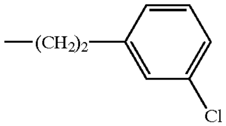 | 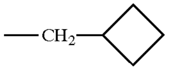 | ethyl | I |
| 362 | 3,4-dichlorophenyl | O | 3 | 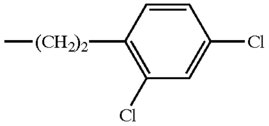 | 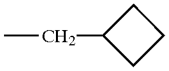 | ethyl | I |
| 363 | 3,4-dichlorophenyl | O | 3 | 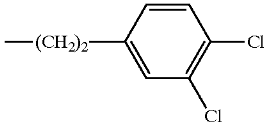 | 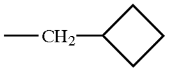 | ethyl | I |

-continued
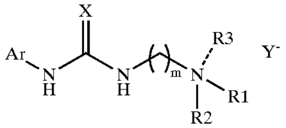
| CPD No. | Ar | X | m | R1 | R2 | R3 | Y |
|---|---|---|---|---|---|---|---|
| 364 | 3,4-dichlorophenyl | O | 3 | 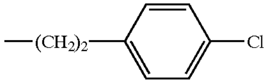 | 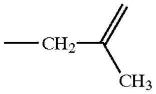 | ethyl | I |
| 365 | 3,4-dichlorophenyl | O | 3 | 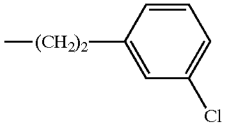 | 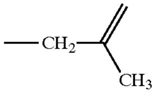 | ethyl | I |
| 366 | 3,4-dichlorophenyl | O | 3 | 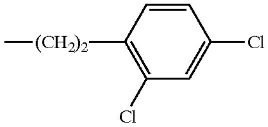 | 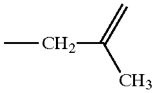 | ethyl | I |
| 367 | 3,4-dichlorophenyl | O | 3 | 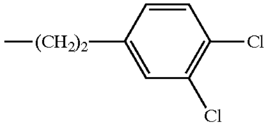 | 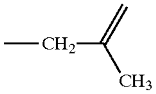 | ethyl | I |
| 368 | 3,4-dichlorophenyl | O | 3 | 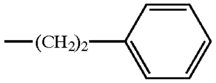 | 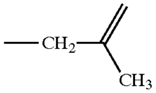 | ethyl | I |
| 369 | 3,4-dichlorophenyl | O | 3 | 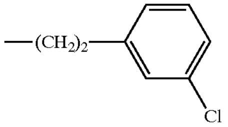 | —$(CH_2)_2F$ | ethyl | I |
| 370 | 3,4-dichlorophenyl | O | 3 | 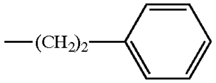 | —$(CH_2)_2F$ | ethyl | I |

-continued
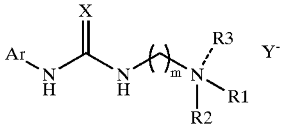
| CPD No. | Ar | X | m | R1 | R2 | R3 | Y |
|---|---|---|---|---|---|---|---|
| 371 | 3,4-dichlorophenyl | O | 3 | 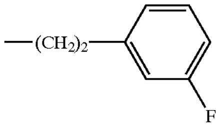 | $—(CH_2)_2F$ | ethyl | I |
| 372 | 4-bromophenyl | O | 3 | 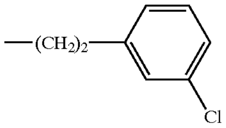 | $—CH_2CN$ | ethyl | I |
| 373 | 4-bromophenyl | O | 3 | 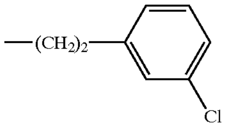 | $—(CH_2)_2O(CH_2)_2OMe$ | ethyl | I |
| 374 | 4-bromophenyl | O | 3 | 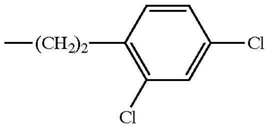 | $—(CH_2)_2O(CH_2)_2OMe$ | ethyl | I |
| 375 | 4-bromophenyl | O | 3 | 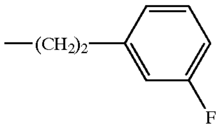 | $—(CH_2)_2O(CH_2)_2OMe$ | ethyl | I |
| 376 | 4-bromophenyl | O | 3 | 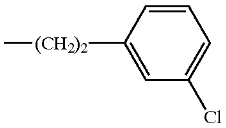 | 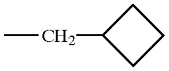 | ethyl | I |

-continued
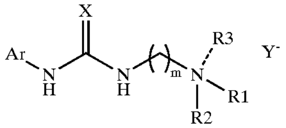
| CPD No. | Ar | X | m | R1 | R2 | R3 | Y |
|---|---|---|---|---|---|---|---|
| 377 | 4-bromophenyl | O | 3 | 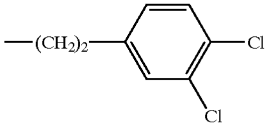 | 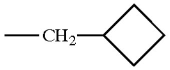 | ethyl | I |
| 378 | 4-bromophenyl | O | 3 | 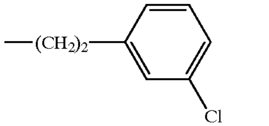 | 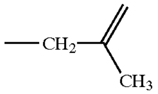 | ethyl | I |
| 379 | 4-bromophenyl | O | 3 | 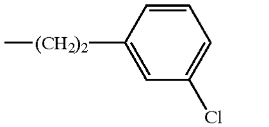 | $—CH_2CH(CH_2CH_3)_2$ | ethyl | I |
| 380 | 4-bromophenyl | O | 3 | 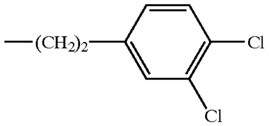 | $—CH_2CH(CH_2CH_3)_2$ | ethyl | I |
| 381 | 4-bromophenyl | O | 3 | 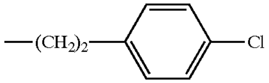 | $—(CH_2)_2F$ | ethyl | I |
| 382 | 4-bromophenyl | O | 3 | 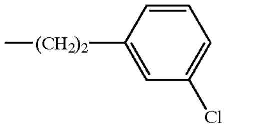 | $—(CH_2)_2F$ | ethyl | I |

-continued
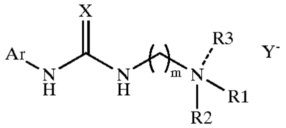
| CPD No. | Ar | X | m | R1 | R2 | R3 | Y |
|---|---|---|---|---|---|---|---|
| 383 | 4-bromophenyl | O | 3 | 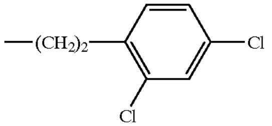 | $-(CH_2)_2F$ | ethyl | I |
| 384 | 4-bromophenyl | O | 3 | 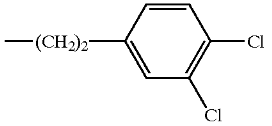 | $-(CH_2)_2F$ | ethyl | I |
| 385 | 4-bromophenyl | O | 3 | 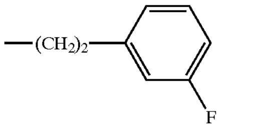 | $-(CH_2)_2F$ | ethyl | I |
| 386 | 4-(trifluoromethyl)phenyl | O | 3 | 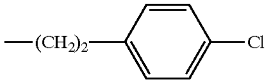 | $-(CH_2)_2O(CH_2)_2OMe$ | ethyl | I |
| 387 | 4-(trifluoromethyl)phenyl | O | 3 | 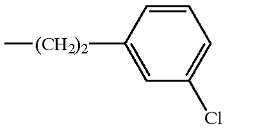 | $-(CH_2)_2O(CH_2)_2OMe$ | ethyl | I |
| 388 | 4-(trifluoromethyl)phenyl | O | 3 | 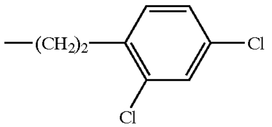 | $-(CH_2)_2O(CH_2)_2OMe$ | ethyl | I |

-continued
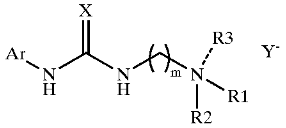
| CPD No. | Ar | X | m | R1 | R2 | R3 | Y |
|---|---|---|---|---|---|---|---|
| 389 | 4-(trifluoromethyl)phenyl | O | 3 | 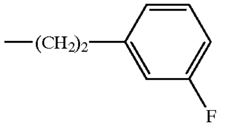 | $—(CH_2)_2O(CH_2)_2OMe$ | ethyl | I |
| 390 | 4-(trifluoromethyl)phenyl | O | 3 | 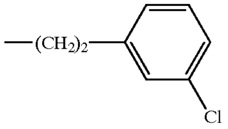 | 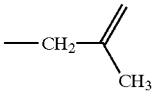 | ethyl | I |
| 391 | 4-(trifluoromethyl)phenyl | O | 3 | 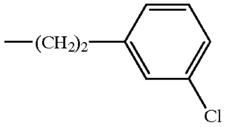 | $—(CH_2)_2F$ | ethyl | I |
| 392 | 4-cyanophenyl | O | 3 | 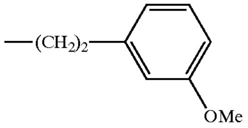 | $—(CH_2)_2O(CH_2)_2OMe$ | ethyl | I |
| 393 | 4-cyanophenyl | O | 3 | 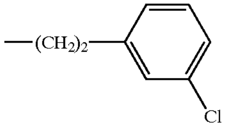 | $—(CH_2)_2CH(CH_3)_2$ | ethyl | I |
| 394 | 4-cyanophenyl | O | 3 | 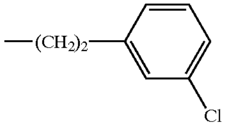 | $—(CH_2)_2O(CH_2)_2OMe$ | ethyl | I |

-continued
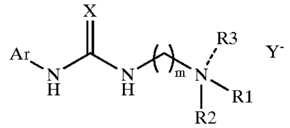
| CPD No. | Ar | X | m | R1 | R2 | R3 | Y |
|---|---|---|---|---|---|---|---|
| 395 | 4-cyanophenyl | O | 3 | 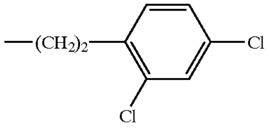 | $—(CH_2)_2O(CH_2)_2OMe$ | ethyl | I |
| 396 | 4-cyanophenyl | O | 3 | 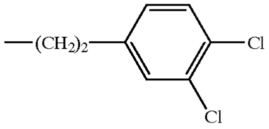 | $—(CH_2)_2O(CH_2)_2OMe$ | ethyl | I |
| 397 | 4-cyanophenyl | O | 3 | 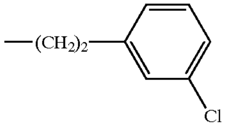 | 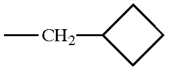 | ethyl | I |
| 398 | 4-cyanophenyl | O | 3 | 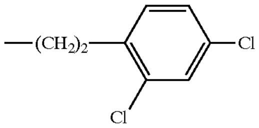 | 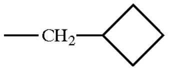 | ethyl | I |
| 399 | 4-cyanophenyl | O | 3 | 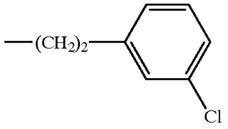 | 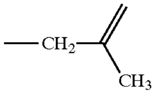 | ethyl | I |
| 400 | 4-cyanophenyl | O | 3 | 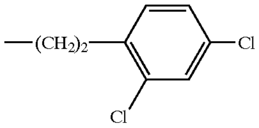 | 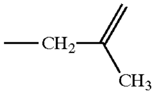 | ethyl | I |

-continued
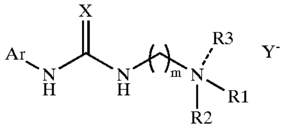
| CPD No. | Ar | X | m | R1 | R2 | R3 | Y |
|---|---|---|---|---|---|---|---|
| 401 | 4-cyanophenyl | O | 3 | 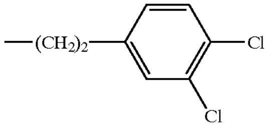 | 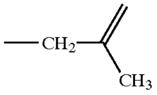 | ethyl | I |
| 402 | 4-cyanophenyl | O | 3 | 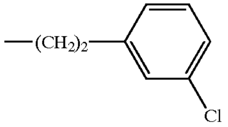 | $—CH_2CH(CH_2CH_3)_2$ | ethyl | I |
| 403 | 4-cyanophenyl | O | 3 | 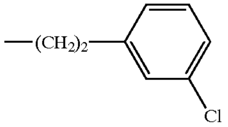 | $—(CH_2)_2F$ | ethyl | I |
| 404 | 4-cyanophenyl | O | 3 | 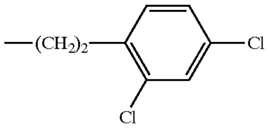 | $—(CH_2)_2F$ | ethyl | I |
| 405 | 4-cyanophenyl | O | 3 | 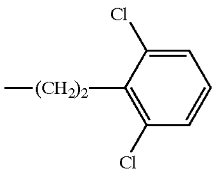 | $—(CH_2)_2F$ | ethyl | I |
| 406 | phenyl | O | 3 | 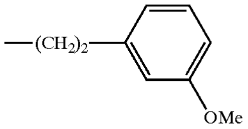 | $—(CH_2)_2O(CH_2)_2OMe$ | ethyl | I |

-continued
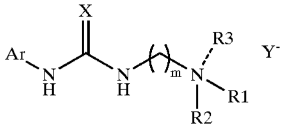
| CPD No. | Ar | X | m | R1 | R2 | R3 | Y |
|---|---|---|---|---|---|---|---|
| 407 | phenyl | O | 3 | 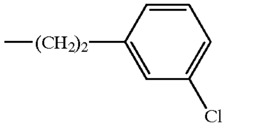 | $-(CH_2)_2CH(CH_3)_2$ | ethyl | I |
| 408 | phenyl | O | 3 | 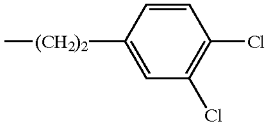 | $-(CH_2)_2CH(CH_3)_2$ | ethyl | I |
| 409 | phenyl | O | 3 | 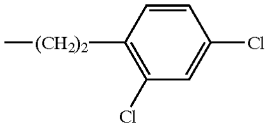 | $-CH_2CONH_2$ | ethyl | I |
| 410 | phenyl | O | 3 | 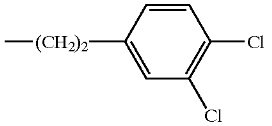 | $-CH_2CONH_2$ | ethyl | I |
| 411 | phenyl | O | 3 | 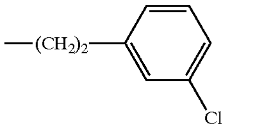 | $-CH_2CN$ | ethyl | I |
| 412 | phenyl | O | 3 | 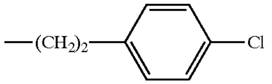 | $-(CH_2)_2O(CH_2)_2OMe$ | ethyl | I |

-continued
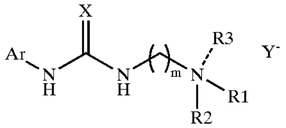
| CPD No. | Ar | X | m | R1 | R2 | R3 | Y |
|---|---|---|---|---|---|---|---|
| 413 | phenyl | O | 3 | 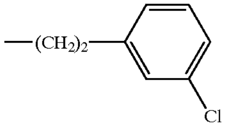 | $-(CH_2)_2O(CH_2)_2OMe$ | ethyl | I |
| 414 | phenyl | O | 3 | 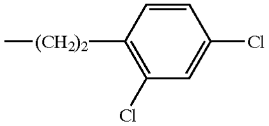 | $-(CH_2)_2O(CH_2)_2OMe$ | ethyl | I |
| 415 | phenyl | O | 3 | 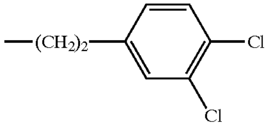 | $-(CH_2)_2O(CH_2)_2OMe$ | ethyl | I |
| 416 | phenyl | O | 3 | 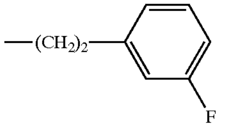 | $-(CH_2)_2O(CH_2)_2OMe$ | ethyl | I |
| 417 | phenyl | O | 3 | 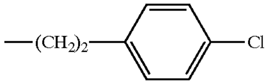 | 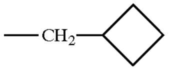 | ethyl | I |
| 418 | phenyl | O | 3 | 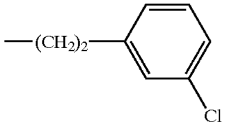 | 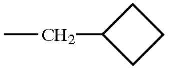 | ethyl | I |

-continued
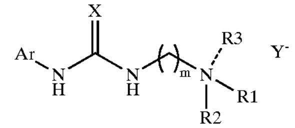
| CPD No. | Ar | X | m | R1 | R2 | R3 | Y |
|---|---|---|---|---|---|---|---|
| 419 | phenyl | O | 3 | 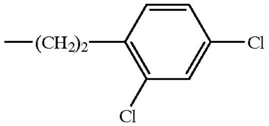 | 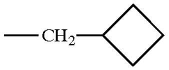 | ethyl | I |
| 420 | phenyl | O | 3 | 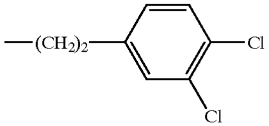 | 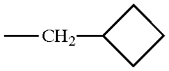 | ethyl | I |
| 421 | phenyl | O | 3 | 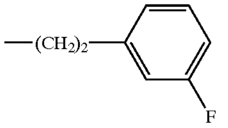 | 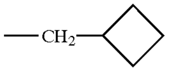 | ethyl | I |
| 422 | phenyl | O | 3 | 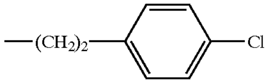 | 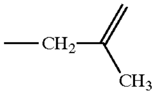 | ethyl | I |
| 423 | phenyl | O | 3 | 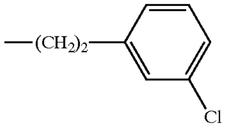 | 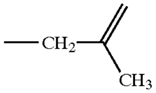 | ethyl | I |
| 424 | phenyl | O | 3 | 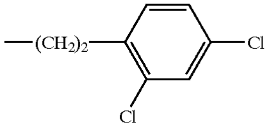 | 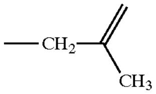 | ethyl | I |

-continued
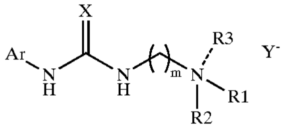
| CPD No. | Ar | X | m | R1 | R2 | R3 | Y |
|---|---|---|---|---|---|---|---|
| 425 | phenyl | O | 3 | 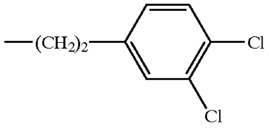 | 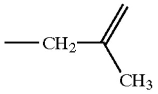 | ethyl | I |
| 426 | phenyl | O | 3 | 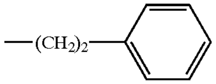 | 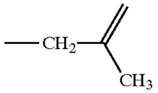 | ethyl | I |
| 427 | phenyl | O | 3 | 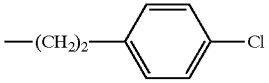 | $—CH_2CH(CH_2CH_3)_2$ | ethyl | I |
| 428 | phenyl | O | 3 | 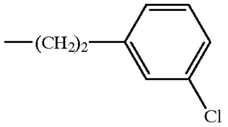 | $—CH_2CH(CH_2CH_3)_2$ | ethyl | I |
| 429 | phenyl | O | 3 | 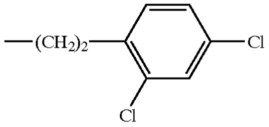 | $—CH_2CH(CH_2CH_3)_2$ | ethyl | I |
| 430 | phenyl | O | 3 | 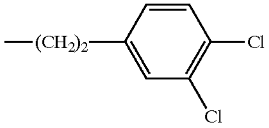 | $—CH_2CH(CH_2CH_3)_2$ | ethyl | I |

-continued
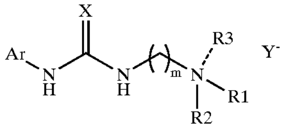
| CPD No. | Ar | X | m | R1 | R2 | R3 | Y |
|---|---|---|---|---|---|---|---|
| 431 | phenyl | O | 3 | 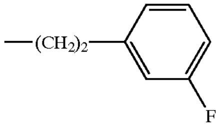 | $—CH_2CH(CH_2CH_3)_2$ | ethyl | I |
| 432 | phenyl | O | 3 | 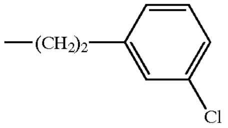 | $—(CH_2)_2F$ | ethyl | I |
| 433 | phenyl | O | 3 | 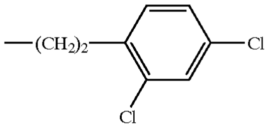 | $—(CH_2)_2F$ | ethyl | I |
| 434 | phenyl | O | 3 | 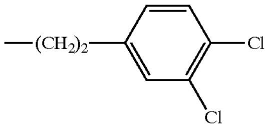 | $—(CH_2)_2F$ | ethyl | I |
| 435 | 4-methoxyphenyl | O | 3 | 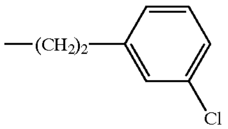 | $—CH_2CH(CH_3)_2$ | ethyl | I |
| 436 | 4-methoxyphenyl | O | 3 | 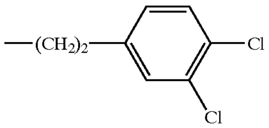 | $—CH_2CH(CH_3)_2$ | ethyl | I |

-continued
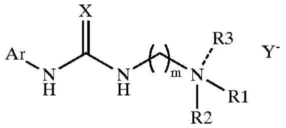
| CPD No. | Ar | X | m | R1 | R2 | R3 | Y |
|---|---|---|---|---|---|---|---|
| 437 | 4-methoxyphenyl | O | 3 | 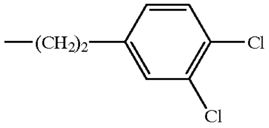 | $—CH_2CONH_2$ | ethyl | I |
| 438 | 4-methoxyphenyl | O | 3 | 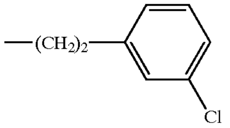 | $—(CH_2)_2O(CH_2)_2OMe$ | ethyl | I |
| 439 | 4-methoxyphenyl | O | 3 | 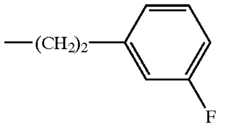 | $—(CH_2)_2O(CH_2)_2OMe$ | ethyl | I |
| 440 | 4-methoxyphenyl | O | 3 | 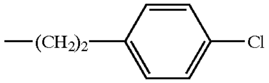 | 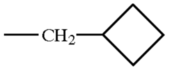 | ethyl | I |
| 441 | 4-methoxyphenyl | O | 3 | 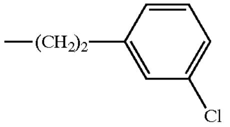 | 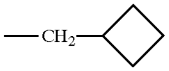 | ethyl | I |
| 442 | 4-methoxyphenyl | O | 3 | 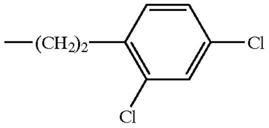 | 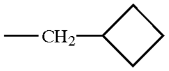 | ethyl | I |

-continued
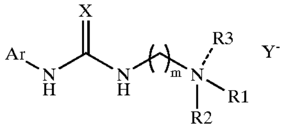
| CPD No. | Ar | X | m | R1 | R2 | R3 | Y |
|---|---|---|---|---|---|---|---|
| 443 | 4-methoxyphenyl | O | 3 | 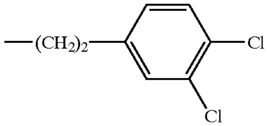 | 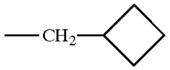 | ethyl | I |
| 444 | 4-methoxyphenyl | O | 3 | 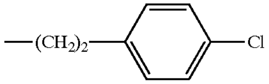 | 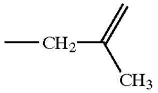 | ethyl | I |
| 445 | 4-methoxyphenyl | O | 3 | 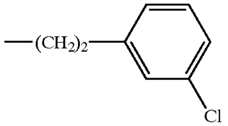 | 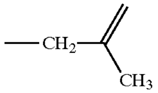 | ethyl | I |
| 446 | 4-methoxyphenyl | O | 3 | 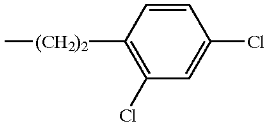 | 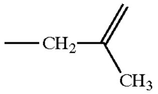 | ethyl | I |
| 447 | 4-methoxyphenyl | O | 3 | 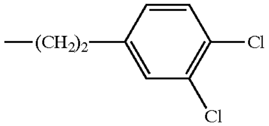 | 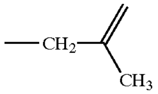 | ethyl | I |
| 448 | 4-methoxyphenyl | O | 3 | 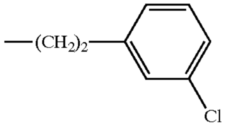 | $—CH_2CH(CH_2CH_3)_2$ | ethyl | I |

-continued
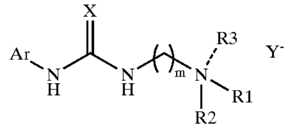
| CPD No. | Ar | X | m | R1 | R2 | R3 | Y |
|---|---|---|---|---|---|---|---|
| 449 | 4-methoxyphenyl | O | 3 | 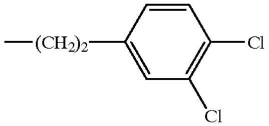 | $—CH_2CH(CH_2CH_3)_2$ | ethyl | I |
| 450 | 4-methoxyphenyl | O | 3 | 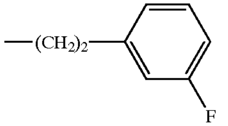 | $—CH_2CH(CH_2CH_3)_2$ | ethyl | I |
| 451 | 4-methoxyphenyl | O | 3 | 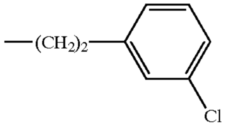 | $—(CH_2)_2F$ | ethyl | I |
| 452 | 4-methoxyphenyl | O | 3 | 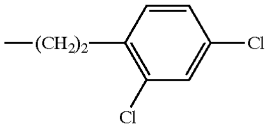 | $—(CH_2)_2F$ | ethyl | I |
| 453 | 4-methoxyphenyl | O | 3 | 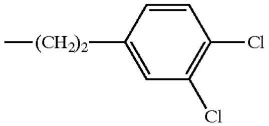 | $—(CH_2)_2F$ | ethyl | I. |

25. A pharmaceutical composition comprising a compound according to claim 1.

* * * * *